US008674077B2

(12) United States Patent
Sutherland et al.

(10) Patent No.: US 8,674,077 B2
(45) Date of Patent: Mar. 18, 2014

(54) PROCESSES FOR PRODUCING SILK DOPE

(75) Inventors: Tara D. Sutherland, Watson (AU);
Victoria S. Haritos, Kingsville (AU);
Alagacone Sriskantha, Nicholls (AU);
Sarah Weisman, Griffith (AU); Michael George Huson, Geelong (AU); Jeffrey Scott Church, Highton (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 13/392,054

(22) PCT Filed: Aug. 25, 2010

(86) PCT No.: PCT/AU2010/001095
§ 371 (c)(1),
(2), (4) Date: Aug. 3, 2012

(87) PCT Pub. No.: WO2011/022771
PCT Pub. Date: Mar. 3, 2011

(65) Prior Publication Data
US 2012/0302734 A1 Nov. 29, 2012

Related U.S. Application Data

(60) Provisional application No. 61/315,812, filed on Mar. 19, 2010, provisional application No. 61/237,156, filed on Aug. 26, 2009.

(51) Int. Cl.
*A61K 8/64* (2006.01)
*C09H 3/00* (2006.01)
*C09H 3/02* (2006.01)
*A61K 39/00* (2006.01)
*A61K 38/00* (2006.01)
*C07K 14/005* (2006.01)

(52) U.S. Cl.
USPC ............ 530/353; 530/355; 530/825; 530/826

(58) Field of Classification Search
None
See application file for complete search history.

(56) References Cited

U.S. PATENT DOCUMENTS

| | | | |
|---|---|---|---|
| 4,515,737 A | 5/1985 | Karino et al. | |
| 4,677,196 A | 6/1987 | Rausch et al. | |
| 4,766,224 A * | 8/1988 | Rausch | 530/412 |
| 4,943,674 A | 7/1990 | Houck et al. | |
| 5,232,611 A | 8/1993 | Ohashi et al. | |
| 5,856,451 A | 1/1999 | Olsen et al. | |
| 5,939,288 A | 8/1999 | Thornburg | |
| 5,981,718 A | 11/1999 | Olsen et al. | |
| 5,989,894 A | 11/1999 | Lewis et al. | |
| 6,013,250 A | 1/2000 | Cannell et al. | |
| 6,129,770 A | 10/2000 | Deutz et al. | |
| 6,139,851 A | 10/2000 | Omura et al. | |
| 6,175,053 B1 | 1/2001 | Tsubouchi | |
| 6,268,169 B1 | 7/2001 | Fahnestock | |
| 6,280,747 B1 | 8/2001 | Philippe et al. | |
| 6,284,246 B1 | 9/2001 | Weisgerber et al. | |
| 6,303,752 B1 | 10/2001 | Olsen et al. | |
| 6,358,501 B1 | 3/2002 | Dietz et al. | |
| 6,398,821 B1 | 6/2002 | Dias et al. | |
| 6,416,558 B1 | 7/2002 | Ona et al. | |
| 6,620,917 B1 * | 9/2003 | Mello et al. | 530/412 |
| 7,635,755 B2 * | 12/2009 | Kaplan et al. | 530/353 |
| 2003/0155670 A1 | 8/2003 | O'Brien | |
| 2003/0192077 A1 | 10/2003 | Yang | |
| 2003/0229212 A1 | 12/2003 | Fahrner et al. | |
| 2004/0005363 A1 | 1/2004 | Tsukada et al. | |
| 2004/0132978 A1 | 7/2004 | Fahnestock et al. | |
| 2004/0170590 A1 | 9/2004 | Fahnestock et al. | |
| 2004/0170827 A1 | 9/2004 | Crighton | |
| 2004/0199241 A1 | 10/2004 | Gravett et al. | |
| 2004/0210956 A1 | 10/2004 | Roth et al. | |
| 2004/0219630 A1 | 11/2004 | Tsubouchi | |
| 2004/0266992 A1 | 12/2004 | Migliaresi et al. | |
| 2005/0010035 A1 | 1/2005 | Lewis et al. | |
| 2005/0019297 A1 | 1/2005 | Philippe et al. | |
| 2005/0054830 A1 | 3/2005 | Islam et al. | |
| 2005/0055051 A1 | 3/2005 | Grafton | |
| 2005/0089552 A1 | 4/2005 | Altman et al. | |
| 2005/0130857 A1 | 6/2005 | Meesilpa et al. | |

(Continued)

FOREIGN PATENT DOCUMENTS

EP 0239400 8/1994
JP 2000139755 5/2000

(Continued)

OTHER PUBLICATIONS

Lawrence, B. et al "Processing methods to control silk fibroin film biomaterial features" 2008 J Mater Sci 43:6967-6985.*
Stellner, K. et al."Surfactant precipitation in aqueous solutions containing mixtures of anionic and nonionic surfactants" 1986 JAOCS 63:566-574.*
Sutherland, T. et al. "A highly divergent gene cluster in hiney bees encodes a novel silk family" 2006 Genome Research 16:1414-1421.*
Atkins (1967) "A Four-Strand Coiled-Coil Model for Some Insect Fibrous Proteins" *J Mol Biol* 24(1):139-141.
Bendtsen, et al. (2004) "Improved prediction of signal peptides: SignalP 3.0." *J Mol Biol.* 340(4):783-795.
Bini, et al., Mapping domain structures in silks from insects and spiders related to protein assembly, J Mol Biol. Jan. 2, 2004;335(1):27-40.

(Continued)

*Primary Examiner* — John S Brusca
*Assistant Examiner* — Gerard Lacourciere
(74) *Attorney, Agent, or Firm* — Carol L. Francis; Bozicevic, Field & Francis LLP

(57) ABSTRACT

The present invention relates to methods of producing silk dope comprising silk proteins with a coiled-coil structure such as honeybee silk proteins. The silk proteins are obtained from cells producing them, solubilizing the proteins by contacting them with a surfactant or an ionic liquid and concentrating the proteins to produce silk dope. The proteins can be used for a variety of purposes such as in the production of personal care products, plastics, textiles and biomedical products.

21 Claims, 4 Drawing Sheets

(56) References Cited

U.S. PATENT DOCUMENTS

Figure 1:
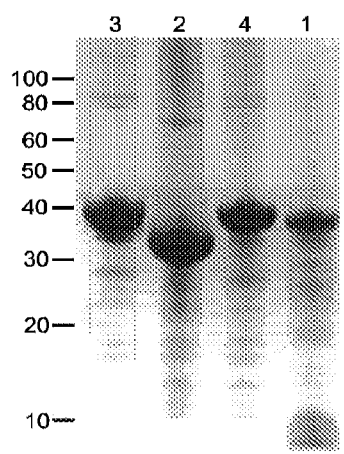

| | | |
|---|---|---|
| 2005/0161058 A1 | 7/2005 | Yerushalmy |
| 2005/0175825 A1 | 8/2005 | Hansen et al. |
| 2005/0266992 A1 | 12/2005 | Ohno et al. |
| 2005/0268443 A1 | 12/2005 | Ramkumar |
| 2010/0100975 A1* | 4/2010 | Sutherland et al. ............ 800/13 |
| 2012/0245103 A1 | 9/2012 | Sutherland et al. |

FOREIGN PATENT DOCUMENTS

| | | |
|---|---|---|
| JP | 2004284246 | 10/2004 |
| WO | WO 03020916 | 3/2003 |
| WO | WO 2005045122 | 1/2004 |
| WO | WO 2004016651 | 2/2004 |
| WO | WO 2005012606 | 2/2005 |
| WO | WO 2005017004 | 2/2005 |
| WO | WO 2007038837 | 4/2007 |

OTHER PUBLICATIONS

BugBuster® Protein Extraction Reagent Oct. 28, 2010, 5 pages, retrieved from the internet, http://www.ebiotrade.com/buyf/productsf/Novasen/70584-000.pdf.

Craig & Riekel (2002) "Comparative Architecture of Silks, Fibrous Proteins and Their Encoding Genes in Insects and Spiders" *Comp Biochem Physiol B Biochem Mol Biol* 133(4):493-507.

Database EMBL "JGI_CABJ9548.fwd NIH_XGC_tropSkil *Xenopus tropicalis* cDNA clone Image: 7874366 5', mRNA sequence." EBI Accession No. EM_EST: DT432295, dated Aug. 27, 2005.

Database EMBL "QL1 39 *Bombus terrestris* larval caste mRNA *Bombus terrestris* cDNA clone QL1 39, mRNA sequence." EBI Accession No. EM_EST: DN048371, dated Feb. 14, 2005.

Database Uniprot "SubName: Full=Mucin-associated surface protein (MASP), putative;" EBI Accession No. UNIPROT: Q4DU48, dated Sep. 13, 2005.

Database Uniprot "SubName: Full=Mucin-associated surface protein (MASP), putative;" EBI Accession No. UNIPROT: Q4DYV1, dated Sep. 13, 2005.

DeLorenzi & Speed (2002) "An HMM Model for Coiled-Coil Domains and a Comparison with PSSM-Based Predictions" *Bioinformatics* 18(4):617-625.

Deng, et al., Antiparallel Four-Stranded Coiled Coil Specified by a 3-3-1 Hydrophobic Heptad Repeat, Structure, vol. 14, Issue 2, 247-255, Feb. 2, 2006.

Dicko, et al.,Conformational Polymorphism, stability and aggregation in spider dragline silks proteins, International Journal of Biological Macromolecules, 36 (2005), 215-224.

Flower, et al., Studies on insect fibrous proteins: the larval silk of *Apis, Bombus* and *Vespa* (Hymenoptera: Aculeata), J R Microsc Soc. Feb. 1967;86(3):297-310.

Genbank Accession Nos. FJ235088 "*Apis mellifera* silk fibroin 1 mRNA, complete cds" dated Oct. 20, 2008.

Genbank Accession Nos. FJ235089 "*Apis mellifera* silk fibroin 2 mRNA, complete cds" dated Oct. 20, 2008.

Genbank Accession Nos. FJ235090 "*Apis mellifera* silk fibroin 3 mRNA, complete cds" dated Oct. 20, 2008.

Genbank Accession Nos. FJ235091 "*Apis mellifera* silk fibroin 4 mRNA, complete cds" dated Oct. 20, 2008.

Green & Kay the influence of organic solvents and enzymatic modification on the secondary structure of fetuin, The journal of biological chemistry, vol. 238, No. 11, Nov. 1963.

Harayama, et al., Artificial evolution by DNA shuffling, Trends in Biotechnology, vol. 16, Issue 2, 76-82, Feb. 1, 1998.

Heimburg, et al., FTIR-Spectroscopy of multistranded coiled coil proteins, Biochemistry. Sep. 28, 1999;38(39):12727-12734.

Hepburn, et al., Extensometric properties of insect fibroins: the green lacewing cross-β, honeybee α-helical and greater waxmoth parallel-β conformations. Insect Biochemistry and Molecular Biology 9:69-77, (1979).

Kennell (1971) "Principles and practices of nucleic acid hybridization" *Prog Nucleic Acid Res Mol Biol* 11:259-301.

Kohn et al. (1997) "α-Helical Protein Assembly Motifs" *J Biol Chem* 272(5):2583-2586.

Lamunyon, Craig, Hindgut Changes Preceding Pupation and Related Cocoon Structure in *Chrysoperla comanche* Banks (Neuroptera, Chrysopidae), Psyche vol. 95 (1988), Issue 3-4, pp. 203-209.

Lamunyon, et al., Use and Effect of an Anal Defensive Secretion in Larval *Chrysopidae* (Neuroptera), Annals of the Entomological Society of America, vol. 80, No. 6, Nov. 1987, pp. 804-808(5).

Lange et al. (2005) "Ionic Liquids as Refolding Additives: N'-alkyl and N'-(ω-Hydroxylalkyl_N-Methylimidazolium Chlorides" *Protein Sci* 14(10):2693-2701.

Lucas & Rudall (1968) "Extracellular Fibrous Proteins: The Silks" Elsevier Publ., New York, NY, USA, pp. 475-558.

Lucas, et al. (1960) "Comparative studies of fibroins. I. The amino acid composition of various fibroins and its significance in relation to their crystal structure and taxonomy" J Mol Biol. 2:339-349.

Lupas, et al., Predicting coiled coils from protein sequences, Science. May 24, 1991;252(5010):1162-1164.

Meng et al (2001) "Dissociation and unfolding of GCN4 leucine zipper in the presence of sodium dodecyl sulfate" Biochimie 83(10):953-956.

Needleman & Wunsch A general method applicable to the search for similarities in the amino acid sequence of two proteins, J Mol Biol. Mar. 1970;48(3):443-453.

New Zealand Examination Report for New Zealand Application No. 598555, dated Nov. 7, 2012.

Ngo et al. (1994) "Computational Complexity, Protein Structure Prediction, and the Levinthal Paradox" *The Protein Folding Problem and Tertiary Structure Prediction*, Ed. Merz, et al., Birkhauser Boston: Boston, MA, pp. 433and 492-495.

Otzen & Oliveberg (2001) "A simple way to measure protein refolding rates in water" J. Mol. Biol. 313(3):479-483.

Quicke, et al., Cocoon silk chemistry of non-cyclostome Braconidae, with remarks on phylogenetic relationships within the Microgastrinae (Hymenoptera: Braconidae), Journal of Natural History, 1464-5262, vol. 38, Issue 17, 2004, pp. 2167-2181.

Reiser, et al., Enzymatic and nonenzymatic cross-linking of collagen and elastin, The FASEB Journal, vol. 6, 2439-2449, Copyright 1992 by the Federation of American Societies for Experimental Biology.

Rost, et al., Prediction of protein secondary structure at better than 70% accuracy, J Mol Biol. Jul. 20, 1993;232(2):584-599.

Rost, et al., The PredictProtein server, Nucleic Acids Res. Jul. 1, 2004;32(Web Server issue):W321-326.

Rudall, et al., Arthropod Silks: The Problem of Fibrous Proteins in Animal Tissues, Annual Review of Entomology, vol. 16: 73-96 (Volume publication date Jan. 1971).

Rudinger (1976) "Characteristics of the Amino Acids as Components of a Peptide Hormone Sequence" *Peptide Hormones*, Ed. Parsons, University Park Press: Baltimore, MD, pp. 1-7.

Sezutzu et al. (2007) "Identification of four major hornet silk genes with a complex of alanine-rich and serine-rich sequences in *Vespa simillima* xanthoptera Cameron" Biosci. Biotechnol. Biochem. 71(11):2725-34.

Shi et al. (2008) "Identification, recombinant production and Structural Characterization of Four Silk Proteins from the Asiatic Honeybee *Apis cerana*" Biomaterials 29(18):2820-2828.

Silva-Zacarin, et al., Silk formation mechanisms in the larval salivary glands of *Apis mellifera* (Hymenoptera: Apidae), Journal of Biosciences, vol. 28, No. 6 / Dec. 2003, pp. 753-764.

Singh & Panda (2005) "Solubilization and Refolding of Bacterial Inclusion Body Proteins" *J Biosci Bioeng* 99(4):303-310.

Spiegler, Paul E., The Origin and Nature of the Adhesive Substance in Larvae of the Genus *Chrysopa* (Neuroptera: Chrysopidae), Annals of the Entomological Society of America, vol. 55, No. 1, Jan. 1962, pp. 69-77(9).

Sutherland et al. (2007) "Conservation of essential design features in coiled coil silks" Mol Biol Evol 24(11):2424-32.

Van Beek, et al., The molecular structure of spider dragline silk:Folding and orientation of the protein backbone, 10266-102871, PNAS, Aug. 6, 2002,vol. 99, No. 16.

Weisman et al. (2010) "Honeybee Silk: Recombinant Protein Production, Assembly and Fiber Spinning" *Biomaterials* 31(9):2695-2700.

(56) References Cited

OTHER PUBLICATIONS

Wilson, et al., Confrontational transitions in model silk peptides, Biophysical journal, vol. 78, May 2000, 2690-2701.

XP002504559, Database Uniprot, Jul. 19, 2004, Database accession No. Q6F986.

XP002504560, Database Uniprot, Nov. 1, 1999, Database accession No. Q9W6J8.

XP002504561, Database Uniprot, Jul. 5, 2004, Database accession No. Q6PYY3.

XP002504562, Database Uniprot, Jun. 1, 2003, Database accession No. Q871k9.

XP002504563, Database Uniprot, Nov. 6, 2003, Database accession No. ADA15988.

XP002504564, Database EMBL, Feb. 14, 2005, Database accession No. DN048371.

XP002504565, Database EMBL, Aug. 30, 2001, Database accession No. BI508270.

XP002504566, Database EMBL, Mar. 27, 2004, Database accession No. CK631883.

Yamada, et al., A novel asparagine-rich fibrous protein (Xenofibron) from the cocoons of the parasitic wasp *Cotesia* (=*Apanteles*) *glomerata*, Int J Wild Silkmoths Silk, vol. 9;No.;p. 61-66(2004).

Yu, et al. (1996) "Conformation Transition of Silk Fibroin" Chemical Journal of Chinese Universities 17(2):323-325.

\* cited by examiner

```
SEQUENCE LISTING

<160> NUMBER OF SEQ ID NOS: 108

<210> SEQ ID NO 1
<211> LENGTH: 314
<212> TYPE: PRT
<213> ORGANISM: Apis mellifera

<400> SEQUENCE: 1

Gly Leu Glu Gly Pro Gly Asn Ser Leu Pro Glu Leu Val Lys Gly Ser
1               5                   10                  15

Ala Ser Ala Thr Ala Ser Thr Ala Val Thr Ala Arg Ser Gly Leu Arg
            20                  25                  30

Ala Gly Gln Val Ala Leu Ala Ser Gln Lys Asp Ala Val Leu Gln Ala
        35                  40                  45

Gln Ala Ala Ala Ser Ala Ala Ser Glu Ala Arg Ala Ala Ala Asp Leu
    50                  55                  60

Thr Ala Lys Leu Ser Gln Glu Ser Ala Ser Val Gln Ser Gln Ala Ala
65                  70                  75                  80
```

Ala Lys Gly Lys Glu Thr Glu Ala Ala Val Gly Gln Ala Arg Ala
            85                  90                  95

Gly Leu Glu Ser Val Ser Met Ala Ala Ser Ala Thr Ser Ala Ala Lys
            100                 105                 110

Glu Ala Ser Thr Ala Ala Lys Ala Ala Ser Ala Leu Ser Thr Ala
            115                 120                 125

Val Val Gln Ala Lys Ile Ala Glu Arg Ala Ala Lys Ala Glu Ala Val
130                 135                 140

Ala Ser Asp Glu Ala Lys Ala Lys Ala Ile Ala Ala Asn Leu Ala
145                 150                 155                 160

Ala Glu Ala Ser Val Ala Ala Glu Ala Ala Leu Lys Ala Glu Lys Val
            165                 170                 175

Ala Glu Glu Ala Ile Ala Arg Ala Ala Ser Ala Lys Ala Ala Arg
            180                 185                 190

Ala Ala Ala Ala Ala Leu Ala Ser Ser Lys Glu Ala Ala Thr Ala Ser
            195                 200                 205

Ala Arg Asn Ala Ala Glu Ser Glu Ala Arg Asn Glu Val Ala Val Leu
            210                 215                 220

Ile Ala Glu Ile Asp Lys Lys Ser Arg Glu Ile Asp Ala Ala Ser Ser
225                 230                 235                 240

Leu Asn Ala Arg Ala Ala Lys Ala Ser Ser Arg Asn Val Glu Thr
            245                 250                 255

Ala Thr Ile Gly Ala Asn Ile Asn Ser Ser Lys Gln Val Val Ser Ile
            260                 265                 270

Pro Val Glu Ile Lys Lys Phe Ser Glu Pro Glu Val Ser Thr Ser Trp
            275                 280                 285

Arg Glu Asp Glu Glu Val Thr Lys Glu Lys Lys Glu His Ile Asn Leu
            290                 295                 300

Asn Asp Phe Asp Leu Lys Ser Asn Val Phe
305                 310

<210> SEQ ID NO 2
<211> LENGTH: 333
<212> TYPE: PRT
<213> ORGANISM: Apis mellifera

<400> SEQUENCE: 2

Met Lys Ile Pro Val Leu Leu Ala Thr Cys Leu Tyr Leu Cys Gly Phe
1               5                   10                  15

Ala Ser Ala Gly Leu Glu Gly Pro Gly Asn Ser Leu Pro Glu Leu Val
            20                  25                  30

Lys Gly Ser Ala Ser Ala Thr Ala Ser Thr Ala Val Thr Ala Arg Ser
            35                  40                  45

Gly Leu Arg Ala Gly Gln Val Ala Leu Ala Ser Gln Lys Asp Ala Val
        50                  55                  60

Leu Gln Ala Gln Ala Ala Ala Ser Ala Ala Ser Glu Ala Arg Ala Ala
65                  70                  75                  80

Ala Asp Leu Thr Ala Lys Leu Ser Gln Glu Ser Ala Ser Val Gln Ser
            85                  90                  95

Gln Ala Ala Ala Lys Gly Lys Glu Thr Glu Ala Ala Val Gly Gln
            100                 105                 110

Ala Arg Ala Gly Leu Glu Ser Val Ser Met Ala Ala Ser Ala Thr Ser
            115                 120                 125

Ala Ala Lys Glu Ala Ser Thr Ala Ala Lys Ala Ala Ser Ala Leu
130                 135                 140

Ser Thr Ala Val Val Gln Ala Lys Ile Ala Glu Arg Ala Ala Lys Ala
145                 150                 155                 160

Glu Ala Val Ala Ser Asp Glu Ala Lys Ala Lys Ala Ile Ala Ala Ala
                165                 170                 175

Asn Leu Ala Ala Glu Ala Ser Val Ala Glu Ala Ala Leu Lys Ala
            180                 185                 190

Glu Lys Val Ala Glu Ala Ile Ala Arg Ala Ala Ser Ala Lys Ala
        195                 200                 205

Ala Ala Arg Ala Ala Ala Ala Leu Ala Ser Ser Lys Glu Ala Ala
    210                 215                 220

Thr Ala Ser Ala Arg Asn Ala Ala Glu Ser Glu Ala Arg Asn Glu Val
225                 230                 235                 240

Ala Val Leu Ile Ala Glu Ile Asp Lys Lys Ser Arg Glu Ile Asp Ala
                245                 250                 255

Ala Ser Ser Leu Asn Ala Arg Ala Ala Ala Lys Ala Ser Ser Arg Asn
                260                 265                 270

Val Glu Thr Ala Thr Ile Gly Ala Asn Ile Asn Ser Ser Lys Gln Val
            275                 280                 285

Val Ser Ile Pro Val Glu Ile Lys Lys Phe Ser Glu Pro Glu Val Ser
        290                 295                 300

Thr Ser Trp Arg Glu Asp Glu Glu Val Thr Lys Glu Lys Lys Glu His
305                 310                 315                 320

Ile Asn Leu Asn Asp Phe Asp Leu Lys Ser Asn Val Phe
                325                 330

<210> SEQ ID NO 3
<211> LENGTH: 290
<212> TYPE: PRT
<213> ORGANISM: Apis mellifera

<400> SEQUENCE: 3

Arg Val Ile Asn His Glu Ser Leu Lys Thr Ser Glu Asp Ile Gln Gly
1               5                   10                  15

Gly Tyr Ser Ala Gly Ile Val Gly Asp Gly Ser Asp Ala Leu Gly Ser
            20                  25                  30

Ser Ile Glu Asn Ala Gln Lys Val Ala Arg Ala Ala Glu Asn Val Gly
        35                  40                  45

Leu Asn Leu Glu Leu Gly Ala Gly Ala Arg Ala Ala Ser Val Ala Ala
    50                  55                  60

Ala Ala Gln Ala Lys Asn Thr Glu Ala Ala Glu Ala Gly Ala Asn Ala
65                  70                  75                  80

Ala Leu Ala Ala Ala Ile Ala Lys Arg Glu Glu Ala Ile Lys Ala Ser
                85                  90                  95

Glu Ile Ala Asn Gln Leu Leu Thr Asn Ala Lys Ala Ala Glu Ala
            100                 105                 110

Thr Val Ser Ala Thr Lys Arg Ala Ala Gln Leu Thr Ala Ala Ala Lys
        115                 120                 125

Glu Ala Thr Arg Ala Ser Ala Ala Ala Glu Ala Ala Thr Glu Ala
    130                 135                 140

Gln Val Lys Ala Asn Ala Asp Ser Ile Ile Thr Lys Arg Ala Ala Ile
145                 150                 155                 160

Ala Glu Ala Gln Ala Ala Ala Glu Ala Gln Val Lys Ala Ala Ile Ala
                165                 170                 175

Arg Lys Ser Ala Ala Asn Phe Leu Ala Lys Ala Gln Ile Ala Ala Ala
            180                 185                 190

```
Ala Glu Ser Glu Ala Thr Lys Leu Ala Ala Glu Ala Val Ala Leu
            195                 200                 205

Thr Asn Ala Glu Val Ala Val Asn Gln Ala Arg Asn Ala Gln Ala Asn
210                 215                 220

Ala Ser Thr Gln Ala Ser Met Ala Val Arg Val Asp Ser Gln Ala Ala
225                 230                 235                 240

Asn Ala Glu Ala Ala Val Ala Gln Ala Glu Thr Leu Leu Val Thr
            245                 250                 255

Ala Glu Ala Val Ala Ala Glu Ala Glu Val Ala Asn Lys Ala Ala
            260                 265                 270

Thr Phe Ala Lys Gln Ile Val Asn Glu Lys Lys Ile His Val Ala Lys
    275                 280                 285

Leu Glu
    290

<210> SEQ ID NO 4
<211> LENGTH: 309
<212> TYPE: PRT
<213> ORGANISM: Apis mellifera

<400> SEQUENCE: 4

Met Lys Ile Pro Ala Ile Phe Val Thr Ser Leu Leu Val Trp Gly Leu
1               5                   10                  15

Ala Glu Gly Arg Val Ile Asn His Glu Ser Leu Lys Thr Ser Glu Asp
            20                  25                  30

Ile Gln Gly Gly Tyr Ser Ala Gly Ile Val Gly Asp Gly Ser Asp Ala
        35                  40                  45

Leu Gly Ser Ser Ile Glu Asn Ala Gln Lys Val Ala Arg Ala Ala Glu
    50                  55                  60

Asn Val Gly Leu Asn Leu Glu Leu Gly Ala Gly Ala Arg Ala Ala Ser
65                  70                  75                  80

Val Ala Ala Ala Ala Gln Ala Lys Asn Thr Glu Ala Ala Glu Ala Gly
                85                  90                  95

Ala Asn Ala Ala Leu Ala Ala Ile Ala Lys Arg Glu Glu Ala Ile
            100                 105                 110

Lys Ala Ser Glu Ile Ala Asn Gln Leu Leu Thr Asn Ala Ala Lys Ala
        115                 120                 125

Ala Glu Ala Thr Val Ser Ala Thr Lys Arg Ala Ala Gln Leu Thr Ala
    130                 135                 140

Ala Ala Lys Glu Ala Thr Arg Ala Ser Ala Ala Ala Glu Ala Ala
145                 150                 155                 160

Thr Glu Ala Gln Val Lys Ala Asn Ala Asp Ser Ile Ile Thr Lys Arg
                165                 170                 175

Ala Ala Ile Ala Glu Ala Gln Ala Ala Glu Ala Gln Val Lys Ala
            180                 185                 190

Ala Ile Ala Arg Lys Ser Ala Ala Asn Phe Leu Ala Lys Ala Gln Ile
        195                 200                 205

Ala Ala Ala Ala Glu Ser Glu Ala Thr Lys Leu Ala Ala Glu Ala Val
    210                 215                 220

Val Ala Leu Thr Asn Ala Glu Val Ala Val Asn Gln Ala Arg Asn Ala
225                 230                 235                 240

Gln Ala Asn Ala Ser Thr Gln Ala Ser Met Ala Val Arg Val Asp Ser
                245                 250                 255

Gln Ala Ala Asn Ala Glu Ala Ala Val Ala Gln Ala Glu Thr Leu
            260                 265                 270
```

```
Leu Val Thr Ala Glu Ala Val Ala Ala Glu Ala Glu Val Ala Asn
        275                 280                 285

Lys Ala Ala Thr Phe Ala Lys Gln Ile Val Asn Glu Lys Lys Ile His
        290                 295                 300

Val Ala Lys Leu Glu
305

<210> SEQ ID NO 5
<211> LENGTH: 316
<212> TYPE: PRT
<213> ORGANISM: Apis mellifera

<400> SEQUENCE: 5

Gly Val Glu Glu Phe Lys Ser Ser Ala Thr Glu Glu Val Ile Ser Lys
  1               5                  10                  15

Asn Leu Glu Val Asp Leu Leu Lys Asn Val Asp Thr Ser Ala Lys Arg
                 20                  25                  30

Arg Glu Asn Gly Ala Pro Val Leu Gly Lys Asn Thr Leu Gln Ser Leu
             35                  40                  45

Glu Lys Ile Lys Thr Ser Ala Ser Val Asn Ala Lys Ala Ala Ala Val
         50                  55                  60

Val Lys Ala Ser Ala Leu Ala Leu Ala Glu Ala Tyr Leu Arg Ala Ser
 65                  70                  75                  80

Ala Leu Ser Ala Ala Ala Ser Ala Lys Ala Ala Ala Ala Leu Lys Asn
                 85                  90                  95

Ala Gln Gln Ala Gln Leu Asn Ala Gln Glu Lys Ser Leu Ala Ala Leu
            100                 105                 110

Lys Ala Gln Ser Glu Glu Glu Ala Ala Ser Ala Arg Ala Asn Ala Ala
        115                 120                 125

Thr Ala Ala Thr Gln Ser Ala Leu Glu Arg Ala Gln Ala Ser Ser Arg
130                 135                 140

Leu Ala Thr Val Ala Gln Asn Val Ala Ser Asp Leu Gln Lys Arg Thr
145                 150                 155                 160

Ser Thr Lys Ala Ala Ala Glu Ala Ala Thr Leu Arg Gln Leu Gln
                165                 170                 175

Asp Ala Glu Arg Thr Lys Trp Ser Ala Asn Ala Ala Leu Glu Val Ser
            180                 185                 190

Ala Ala Ala Ala Ala Glu Thr Lys Thr Thr Ala Ser Ser Glu Ala
        195                 200                 205

Ala Asn Ala Ala Ala Lys Lys Ala Ala Ile Ala Ser Asp Ala Asp
        210                 215                 220

Gly Ala Glu Arg Ser Ala Ser Thr Glu Ala Gln Ser Ala Ala Lys Ile
225                 230                 235                 240

Glu Ser Val Ala Ala Glu Gly Ser Ala Asn Ser Ala Ser Glu Asp
                245                 250                 255

Ser Arg Ala Ala Gln Leu Glu Ala Ser Thr Ala Ala Arg Ala Asn Val
            260                 265                 270

Ala Ala Ala Val Gly Asp Gly Ala Ile Ile Gly Leu Gly Glu Glu Ala
        275                 280                 285

Gly Ala Ala Ala Gln Leu Leu Ala Gln Ala Lys Ala Leu Ala Glu Val
        290                 295                 300

Ser Ser Lys Ser Glu Asn Ile Glu Asp Lys Lys Phe
305                 310                 315

<210> SEQ ID NO 6
```

```
<211> LENGTH: 335
<212> TYPE: PRT
<213> ORGANISM: Apis mellifera

<400> SEQUENCE: 6

Met Gln Ile Pro Thr Phe Val Ala Ile Cys Leu Leu Thr Ser Gly Leu
1               5                   10                  15

Val His Ala Gly Val Glu Glu Phe Lys Ser Ser Ala Thr Glu Glu Val
            20                  25                  30

Ile Ser Lys Asn Leu Glu Val Asp Leu Leu Lys Asn Val Asp Thr Ser
        35                  40                  45

Ala Lys Arg Arg Glu Asn Gly Ala Pro Val Leu Gly Lys Asn Thr Leu
    50                  55                  60

Gln Ser Leu Glu Lys Ile Lys Thr Ser Ala Ser Val Asn Ala Lys Ala
65                  70                  75                  80

Ala Ala Val Val Lys Ala Ser Ala Leu Ala Leu Ala Glu Ala Tyr Leu
                85                  90                  95

Arg Ala Ser Ala Leu Ser Ala Ala Ser Ala Lys Ala Ala Ala
            100                 105                 110

Leu Lys Asn Ala Gln Gln Ala Gln Leu Asn Ala Gln Glu Lys Ser Leu
            115                 120                 125

Ala Ala Leu Lys Ala Gln Ser Glu Glu Glu Ala Ala Ser Ala Arg Ala
    130                 135                 140

Asn Ala Ala Thr Ala Ala Thr Gln Ser Ala Leu Glu Arg Ala Gln Ala
145                 150                 155                 160

Ser Ser Arg Leu Ala Thr Val Ala Gln Asn Val Ala Ser Asp Leu Gln
                165                 170                 175

Lys Arg Thr Ser Thr Lys Ala Ala Ala Glu Ala Ala Thr Leu Arg
            180                 185                 190

Gln Leu Gln Asp Ala Glu Arg Thr Lys Trp Ser Ala Asn Ala Ala Leu
            195                 200                 205

Glu Val Ser Ala Ala Ala Ala Ala Glu Thr Lys Thr Thr Ala Ser
    210                 215                 220

Ser Glu Ala Ala Asn Ala Ala Lys Lys Ala Ala Ile Ala Ser
225                 230                 235                 240

Asp Ala Asp Gly Ala Glu Arg Ser Ala Ser Thr Glu Ala Gln Ser Ala
                245                 250                 255

Ala Lys Ile Glu Ser Val Ala Ala Glu Gly Ser Ala Asn Ser Ala
            260                 265                 270

Ser Glu Asp Ser Arg Ala Ala Gln Leu Glu Ala Ser Thr Ala Ala Arg
            275                 280                 285

Ala Asn Val Ala Ala Val Gly Asp Gly Ala Ile Ile Gly Leu Gly
    290                 295                 300

Glu Glu Ala Gly Ala Ala Ala Gln Leu Leu Ala Gln Ala Lys Ala Leu
305                 310                 315                 320

Ala Glu Val Ser Ser Lys Ser Glu Asn Ile Glu Asp Lys Lys Phe
                325                 330                 335

<210> SEQ ID NO 7
<211> LENGTH: 323
<212> TYPE: PRT
<213> ORGANISM: Apis mellifera

<400> SEQUENCE: 7

Ala Arg Glu Glu Val Glu Thr Arg Asp Lys Thr Lys Thr Ser Thr Val
1               5                   10                  15
```

```
Val Lys Ser Glu Lys Val Glu Val Ala Pro Ala Lys Asp Glu Leu
         20                  25                  30
Lys Leu Thr Ser Glu Pro Ile Phe Gly Arg Arg Val Gly Thr Gly Ala
     35                  40                  45
Ser Glu Val Ala Ser Ser Gly Glu Ala Ile Ala Ile Ser Leu Gly
 50                  55                  60
Ala Gly Gln Ser Ala Ala Glu Ser Gln Ala Leu Ala Ala Ser Gln Ser
 65                  70                  75                  80
Lys Thr Ala Ala Asn Ala Ala Ile Gly Ala Ser Glu Leu Thr Asn Lys
                 85                  90                  95
Val Ala Ala Leu Val Ala Gly Ala Thr Gly Ala Gln Ala Arg Ala Thr
             100                 105                 110
Ala Ala Ser Ser Ser Ala Leu Lys Ala Ser Leu Ala Thr Glu Glu Ala
         115                 120                 125
Ala Glu Glu Ala Glu Ala Ala Val Ala Asp Ala Lys Ala Ala Ala Glu
     130                 135                 140
Lys Ala Glu Ser Leu Ala Lys Asn Leu Ala Ser Ser Ala Arg Ala
145                 150                 155                 160
Ala Leu Ser Ser Glu Arg Ala Asn Glu Leu Gln Ala Glu Ser Ala
                 165                 170                 175
Ala Ala Ala Glu Ala Gln Ala Lys Thr Ala Ala Ala Lys Ala Ala
             180                 185                 190
Glu Ile Ala Leu Lys Val Ala Glu Ile Ala Val Lys Ala Glu Ala Asp
         195                 200                 205
Ala Ala Ala Ala Val Ala Ala Ala Lys Ala Arg Ala Val Ala Asp
     210                 215                 220
Ala Ala Ala Ala Arg Ala Ala Ala Val Asn Ala Ile Ala Lys Ala Glu
225                 230                 235                 240
Glu Glu Ala Ser Ala Gln Ala Glu Asn Ala Gly Val Leu Gln Ala
                 245                 250                 255
Ala Ala Ser Ala Ala Ala Glu Ser Arg Ala Ala Ala Ala Ala Ala
             260                 265                 270
Ala Thr Ser Glu Ala Ala Ala Glu Ala Gly Pro Leu Ala Gly Glu Met
         275                 280                 285
Lys Pro Pro His Trp Lys Trp Glu Arg Ile Pro Val Lys Lys Glu Glu
     290                 295                 300
Trp Lys Thr Ser Thr Lys Glu Glu Trp Lys Thr Thr Asn Glu Glu Trp
305                 310                 315                 320
Glu Val Lys

<210> SEQ ID NO 8
<211> LENGTH: 342
<212> TYPE: PRT
<213> ORGANISM: Apis mellifera

<400> SEQUENCE: 8

Met Lys Ile Pro Ser Ile Leu Ala Val Ser Leu Leu Ile Trp Gly Leu
1               5                   10                  15
Ala Ser Gly Ala Arg Glu Glu Val Glu Thr Arg Asp Lys Thr Lys Thr
             20                  25                  30
Ser Thr Val Val Lys Ser Glu Lys Val Glu Val Ala Pro Ala Lys
         35                  40                  45
Asp Glu Leu Lys Leu Thr Ser Glu Pro Ile Phe Gly Arg Arg Val Gly
     50                  55                  60
Thr Gly Ala Ser Glu Val Ala Ser Ser Ser Gly Glu Ala Ile Ala Ile
```

```
                65                  70                  75                  80
Ser Leu Gly Ala Gly Gln Ser Ala Ala Glu Ser Gln Ala Leu Ala Ala
                    85                  90                  95
Ser Gln Ser Lys Thr Ala Ala Asn Ala Ala Ile Gly Ala Ser Glu Leu
                100                 105                 110
Thr Asn Lys Val Ala Ala Leu Val Ala Gly Ala Thr Gly Ala Gln Ala
                115                 120                 125
Arg Ala Thr Ala Ala Ser Ser Ala Leu Lys Ala Ser Leu Ala Thr
            130                 135                 140
Glu Glu Ala Ala Glu Ala Glu Ala Val Ala Asp Ala Lys Ala
145                 150                 155                 160
Ala Ala Glu Lys Ala Glu Ser Leu Ala Lys Asn Leu Ala Ser Ala Ser
                165                 170                 175
Ala Arg Ala Ala Leu Ser Ser Glu Arg Ala Asn Glu Leu Ala Gln Ala
                180                 185                 190
Glu Ser Ala Ala Ala Glu Ala Gln Ala Lys Thr Ala Ala Ala Ala
                195                 200                 205
Lys Ala Ala Glu Ile Ala Leu Lys Val Ala Glu Ile Ala Val Lys Ala
                210                 215                 220
Glu Ala Asp Ala Ala Ala Ala Val Ala Ala Ala Lys Ala Arg Ala
225                 230                 235                 240
Val Ala Asp Ala Ala Ala Arg Ala Ala Ala Val Asn Ala Ile Ala
                245                 250                 255
Lys Ala Glu Glu Glu Ala Ser Ala Gln Ala Glu Asn Ala Ala Gly Val
                260                 265                 270
Leu Gln Ala Ala Ala Ser Ala Ala Ala Glu Ser Arg Ala Ala Ala Ala
                275                 280                 285
Ala Ala Ala Ala Thr Ser Glu Ala Ala Ala Glu Ala Gly Pro Leu Ala
                290                 295                 300
Gly Glu Met Lys Pro Pro His Trp Lys Trp Glu Arg Ile Pro Val Lys
305                 310                 315                 320
Lys Glu Glu Trp Lys Thr Ser Thr Lys Glu Glu Trp Lys Thr Thr Asn
                325                 330                 335
Glu Glu Trp Glu Val Lys
            340

<210> SEQ ID NO 9
<211> LENGTH: 942
<212> TYPE: DNA
<213> ORGANISM: Apis mellifera

<400> SEQUENCE: 9
ggtttggagg ggccgggcaa ctcgttgccc gagctcgtga aaggtagcgc atcggccacc    60
gcgtcgaccg ctgtgaccgc tagatcagga cttagagccg acaagtagc tttagcttcg    120 cagaaggatg ccgtactcca agctcaagct gctgcatccg ccgcgtcaga ggcgcgcgct   180
gctgccgatc tgacggctaa acttagccaa gaatcggcat cagtgcaatc gcaggctgcc   240
gccaaaggga aggaaacgga ggaggcagct gttggtcaag ctagggctgg cctcgagtcg   300
gtgtccatgg ccgcatcagc cacatctgct gccaagaag catcgaccgc cgccaaagcc   360
gcagcatccg cactatccac agccgtggtg caagcgaaaa tagctgagag gcagccaaa   420 gctgaagctg ttgcctcgga cgaagccaag gccaaggcga ttgcagcagc caacttggcg   480
gctgaggcca gtgtagccgc agaagcagct ctcaaggccg agaaagtggc cgaagaagcc   540
atcgcaagag cggcctctgc aaaggctgcc gcaagagctg ctgctgccgc tctagcctcc   600
```

| tcgaaggaag cagccacggc cagcgcaaga acgccgcgg aatccgaggc caggaacgaa | 660 |
| gtagctgtat tgatcgccga gattgataaa aagagtaggg aaatcgacgc agccagttcg | 720 |
| cttaatgcgc gtgccgctgc caaggcaagc tccaggaacg tagaaacggc gacaatcggg | 780 |
| gccaacatca actcttcgaa acaagtcgtg tcaattccag tggaaataaa gaaattctcg | 840 |
| gagccggaag tgtcaacatc atggagagaa gatgaagagg ttacgaaaga gaagaaggag | 900 |
| cacataaatc tgaacgactt cgacttgaag agcaacgtat tt | 942 |

<210> SEQ ID NO 10
<211> LENGTH: 999
<212> TYPE: DNA
<213> ORGANISM: Apis mellifera
<400> SEQUENCE: 10

| atgaagattc cagtattgct tgcaacgtgc tctacctttt gcggatttgc gtccgccggt | 60 |
| ttggagggc cgggcaactc gttgcccgag ctcgtgaaag gtagcgcatc ggccaccgcg | 120 |
| tcgaccgctg tgaccgctag atcaggactt agagccggac aagtagcttt agcttcgcag | 180 |
| aaggatgccg tactccaagc tcaagctgct gcatccgccg cgtcagaggc gcgcgctgct | 240 |
| gccgatctga cggctaaact tagccaagaa tcggcatcag tgcaatcgca ggctgccgcc | 300 |
| aaagggaagg aaacggagga ggcagctgtt ggtcaagcta gggctggcct cgagtcggtg | 360 |
| tccatggccg catcagccac atctgctgcc aaagaagcat cgaccgccgc caaagccgca | 420 |
| gcatccgcac tatccacagc cgtggtgcaa gcgaaaatag ctgagagggc agccaaagct | 480 |
| gaagctgttg cctcggacga agccaaggcc aaggcgattg cagcagccaa cttggcggct | 540 |
| gaggccagtg tagccgcaga agcagctctc aaggccgaga agtggccga agaagccatc | 600 |
| gcaagagcgg cctctgcaaa ggctgccgca agagctgctg ctgccgctct agcctcctcg | 660 |
| aaggaagcag ccacggccag cgcaagaaac gccgcgaat ccgaggccag gaacgaagta | 720 |
| gctgtattga tcgccgagat tgataaaaag agtagggaaa tcgacgcagc cagttcgctt | 780 |
| aatgcgcgtg ccgctgccaa ggcaagctcc aggaacgtag aaacggcgac aatcggggcc | 840 |
| aacatcaact cttcgaaaca gtcgtgtca attccagtgg aaataaagaa attctcggag | 900 |
| ccggaagtgt caacatcatg gagagaagat gaagaggtta cgaaagagaa gaaggagcac | 960 |
| ataaatctga acgacttcga cttgaagagc aacgtattt | 999 |

<210> SEQ ID NO 11
<211> LENGTH: 870
<212> TYPE: DNA
<213> ORGANISM: Apis mellifera
<400> SEQUENCE: 11

| cgcgtgatta atcacgagtc cctgaagacg agcgaggata ttcaaggagg atattcagca | 60 |
| ggaatagtcg gtgatggatc tgacgcgctt ggctcctcca tagaaaacgc ccaaaaagtc | 120 |
| gctcgagcgg ctgaaaacgt gggcttgaat ctggaattgg cgcaggcgc gcgtgctgcc | 180 |
| agtgttgccg ctgctgccca ggccaaaaac acagaggctg cggaagcagg agcaaacgcc | 240 |
| gctctggccg ccgccattgc caaacgggag gaagcgatta agccagcga gatagcaaac | 300 |
| caattgttga ccaatgcagc aaaagcggca gaagcgactg tatcggcaac gaagagggca | 360 |
| gcacaattga cggctgcagc gaaagaagca accagagctt ctgcagccgc tgctgaagct | 420 |
| gctacggagg cccaggtaaa ggctaacgcc gattcaatca tcacgaagag ggctgcgatt | 480 |
| gccgaggctc aagctgcggc ggaagctcaa gttaaggcgg caatcgccag aaaatcggca | 540 |

```
gcgaatttttt tggctaaggc tcaaatagcg gctgccgcgg aatccgaggc cacgaaactc    600
gcggccgaag ctgtagtggc actaacaaac gccgaagtcg ccgtgaacca ggctagaaac    660
gcacaggcaa acgcctcgac tcaagcttcc atggctgtta gggtagattc tcaagcagcg    720
aacgctgaag cagccgctgt agcgcaagcc gaaactctct tggttacggc agaagctgtc    780
gcagctgcgg aggctgaggt tgcgaacaaa gccgccacat ttgcaaaaca gatcgtcaac    840
gagaagaaaa tacatgtagc aaagttggaa                                     870

<210> SEQ ID NO 12
<211> LENGTH: 927
<212> TYPE: DNA
<213> ORGANISM: Apis mellifera

<400> SEQUENCE: 12
atgaagattc cagcaatatt cgtcacgtct ctgctggtct ggggattggc cgagggccgc     60
gtgattaatc acgagtccct gaagacgagc gaggatattc aaggaggata ttcagcagga    120
atagtcggtg atggatctga cgcgcttggc tcctccatag aaaacgccca aaaagtcgct    180
cgagcggctg aaaacgtggg cttgaatctg gaattgggcg caggcgcgcg tgctgccagt    240
gttgccgctg ctgcccaggc caaaaacaca gaggctgcgg aagcaggagc aaacgccgct    300
ctggccgccg ccattgccaa acgggaggaa gcgattaaag ccagcgagat agcaaaccaa    360
ttgttgacca atgcagcaaa agcggcagaa gcgactgtat cggcaacgaa gagggcagca    420
caattgacgg ctgcagcgaa agaagcaacc agagcttctg cagccgctgc tgaagctgct    480
acggaggccc aggtaaaggc taacgccgat tcaatcatca cgaagagggc tgcgattgcc    540
gaggctcaag ctgcggcgga agctcaagtt aaggcggcaa cgccagaaa  tcggcagcg    600 aattttttgg ctaaggctca aatagcggct gccgcggaat ccgaggccac gaaactcgcg    660
gccgaagctg tagtggcact aacaaacgcc gaagtcgccg tgaaccaggc tagaaacgca    720
caggcaaacg cctcgactca agcttccatg gctgttaggg tagattctca agcagcgaac    780
gctgaagcag ccgctgtagc gcaagccgaa actctcttgg ttacggcaga agctgtcgca    840
gctgcggagg ctgaggttgc gaacaaagcc gccacatttg caaaacagat cgtcaacgag    900
aagaaaatac atgtagcaaa gttggaa                                       927

<210> SEQ ID NO 13
<211> LENGTH: 949
<212> TYPE: DNA
<213> ORGANISM: Apis mellifera

<400> SEQUENCE: 13
ggcgtcgagg aattcaagtc ctcggcaacc gaggaggtga tcagcaaaaa cttagaagtc     60
gacctgttga aaaatgtgga cactagcgcg aaacgaagag agaacggcgc cccggtgctc    120
ggcaagaaca cacttcaatc cctggagaag atcaagacgt cggcgagcgt gaatgccaaa    180
gcagcagccg tggtgaaagc gtccgctctg gctcttgcag aggcctattt gcgagcgtcc    240
gcattgtcag ccgccgcttc agccaaggca gccgccgccc tgaaaaatgc tcaacaagcg    300
caattaaacg cccaggaaaa gtctttggcc gcgttgaaag ctcagtccga ggaagaggca    360
gcttctgctc gtgcaaacgc agcaaccgcc gcgacacagt cggcactgga acgcgctcaa    420
gcctcctcca ggttagcaac ggtcgcccaa aacgtagcca gcgacttgca gaaacggacc    480
agcaccaagg ccgcggctga agccgctgcc accctcagac aattacagga gcggaacga     540 acgaaatgga gtgccaacgc tgccttagaa gtctccgccg ctgcagctgc cgcagaaacc    600
```

```
aagaccactg cctcctcgga ggccgccaac gccgccgcca aaaaggcggc cgcgatagct    660
tctgacgcgg acggcgcgga aaggtcggca tctaccgagg cacaatcagc tgcgaagatc    720
gagagtgtgg cagccgccga gggatccgcc aactcggcct ctgaggattc ccgggccgct    780
caattggaag cctccaccgc ggcgagagcc aacgtggccg cagctgtcgg ggatggagcg    840
attataggac ttggagagga gcgggtgccg cggctcagt tgcttgcaca ggcgaaggca    900
ttggccgaag ttagctcgaa atccgaaaat attgaggata aaaattt                  949
```

<210> SEQ ID NO 14
<211> LENGTH: 1006
<212> TYPE: DNA
<213> ORGANISM: Apis mellifera

<400> SEQUENCE: 14

```
atgcagatcc caacgtttgt cgccatatgc ttgctcacat cgggcttggt gcacgcaggc     60
gtcgaggaat tcaagtcctc ggcaaccgag gaggtgatca gcaaaaactt agaagtcgac    120
ctgttgaaaa atgtggacac tagcgcgaaa cgaagagaga cggcgcccc ggtgctcggc     180 aagaacacac ttcaatccct ggagaagatc aagacgtcgg cgagcgtgaa tgccaaagca    240
gcagccgtgg tgaaagcgtc cgctctggct cttgcagagg cctatttgcg agcgtccgca    300
ttgtcagccg ccgcttcagc caaggcagcc gccgccctga aaaatgctca acaagcgcaa    360
ttaaacgccc aggaaaagtc tttggccgcg ttgaaagctc agtccgagga gaggcagct    420 tctgctcgtg caaacgcagc aaccgccgcg cacagtcgg cactggaacg cgctcaagcc    480
tcctccaggt tagcaacggt cgcccaaaac gtagccagcg acttgcagaa acggaccagc    540
accaaggccg cggctgaagc cgctgccacc ctcagacaat tacaggacgc ggaacgaacg    600
aaatggagtg ccaacgctgc cttagaagtc tccgccgctg cagctgccgc agaaaccaag    660
accactgcct cctcggaggc cgccaacgcc gccgccaaaa aggcggccgc gatagcttct    720
gacgcggacg gcgcggaaag gtcggcatct accgaggcac aatcagctgc gaagatcgag    780
agtgtggcag ccgccgaggg atccgccaac tcggcctctg aggattccg ggccgctcaa    840 ttggaagcct ccaccgcggc gagagccaac gtggccgcag ctgtcgggga tggagcgatt    900
ataggacttg gagaggaagc gggtgccgcg gctcagttgc ttgcacaggc gaaggcattg    960
gccgaagtta gctcgaaatc gaaaatatt gaggataaaa aattt                    1006
```

<210> SEQ ID NO 15
<211> LENGTH: 969
<212> TYPE: DNA
<213> ORGANISM: Apis mellifera

<400> SEQUENCE: 15

```
gcaagggaag aggtggagac acgggacaag accaagacct cgacagtggt gaaaagcgag     60
aaagtggaag tcgttgctcc cgctaaggat gaacttaaat taacgagcga gcctatcttt    120
ggaagaagag tgggaactgg agcatccgag gtggcatcta gcagcggtga agccatcgcg    180
ataagtcttg gagcagggca gtcagcggca gagtctcagg ccttggccgc ctcgcaatcc    240
aaaacggcag cgaacgccgc cataggcgcg agcgagctta ccaacaaagt tgctgctcta    300
gttgctggcg cgactggtgc gcaggcgaga gctacggccg cctcctcgag cgcgttgaag    360
gccagcttgg cgaccgaaga agcggcgaa gaggccgagg cggccgtggc tgacgccaag    420 gctgccgcg aaaaggccga atccctggcg aaaaatctcg cgtcggcgag cgctcgcgcg    480
gccctctcct ccgaaagggc gaacgaattg gctcaagctg agagcgctgc agcggccgag    540
```

-continued

```
gcgcaggcca agacagcagc cgccgccaaa gcagcggaaa tcgcccttaa ggtcgctgag      600
atagcggtga aggcggaagc ggacgcagca gctgccgccg tggcagctgc aaaggcaaga      660
gccgtggcag acgcggccgc tgcccgtgcc gcagccgtga acgccatcgc caaggcggaa      720
gaggaggcct cggcccaagc agagaacgcc gccggtgttt tgcaagcagc cgcctccgcc      780
gcggcggaat cgcgagccgc tgcagctgcc gccgctgcta cctcggaggc agcggctgaa      840
gctggcccgt tggcaggtga gatgaaacca ccgcactgga aatgggaacg gattcctgtg      900
aagaaggagg agtggaaaac gtcaacgaag gaagaatgga aaacgacgaa tgaagaatgg      960
gaggtgaag                                                              969
```

<210> SEQ ID NO 16
<211> LENGTH: 1026
<212> TYPE: DNA
<213> ORGANISM: Apis mellifera

<400> SEQUENCE: 16

```
atgaagatcc catccatact cgcggtttcc ctgctgatct ggggtttggc aagcggcgca      60
agggaagagg tggagacacg ggacaagacc aagacctcga cagtggtgaa aagcgagaaa      120
gtggaagtcg ttgctcccgc taaggatgaa cttaaattaa cgagcgagcc tatctttgga      180
agaagagtgg gaactggagc atccgaggtg gcatctagca gcggtgaagc catcgcgata      240
agtcttggag cagggcagtc agcggcagag tctcaggcct tggccgcctc gcaatccaaa      300
acggcagcga acgccgccat aggcgcgagc gagcttacca caaagttgcc tgctctagtt      360
gctggcgcga ctggtgcgca ggcgagagct acggccgcct cctcgagcgc gttgaaggcc      420
agcttggcga ccgaagaagc ggcggaagag gccgaggcgg ccgtggctga cgccaaggct      480
gccgcggaaa aggccgaatc cctggcgaaa atctcgcgt cggcgagcgc tcgcgcggcc      540
ctctcctccg aaagggcgaa cgaattggct caagctgaga gcgctgcagc ggccgaggcg      600
caggccaaga cagcagccgc cgccaaagca gcggaaatcg cccttaaggt cgctgagata      660
gcggtgaagg cggaagcgga cgcagcagct gccgccgtgg cagctgcaaa ggcaagagcc      720
gtggcagacg cggccgctgc ccgtgccgca gccgtgaacg ccatcgccaa ggcggaagag      780
gaggcctcgg cccaagcaga gaacgccgcc ggtgttttgc aagcagccgc tccgccgcg      840 gcggaatcgc gagccgctgc agctgccgcc gctgctacct cggaggcagc ggctgaagct      900
ggcccgttgg caggtgagat gaaaccaccg cactggaaat gggacggat tcctgtgaag      960 aaggaggagt ggaaaacgtc aacgaaggaa gaatggaaaa cgacgaatga agaatgggag     1020
gtgaag                                                                1026
```

<210> SEQ ID NO 17
<211> LENGTH: 308
<212> TYPE: PRT
<213> ORGANISM: Bombus terrestris

<400> SEQUENCE: 17

```
Gly Gln Ser Ser Pro Leu Leu Glu Ile Val Gln Gly Ser Ala Ser Ala
1               5                   10                  15

Thr Ala Ser Thr Ala Val Thr Ala Arg Ser Gly Leu Arg Ala Gly Gln
            20                  25                  30

Val Ala Val Ala Ser Gln Lys Asp Ala Thr Leu Gln Ala Asp Ala Ser
        35                  40                  45

Ala Ala Ala Ala Ala Ala Ala Arg Ala Ser Ala Asp Gln Ser Ala Ser
    50                  55                  60
```

Leu Ala Gln Gln Ser Ala Ser Leu Gln Ser Lys Ala Ala Arg Ala
65                  70                  75                  80

Lys Ser Ala Glu Glu Ser Ala Ala Thr Ala Lys Ala Glu Leu Gln
            85                  90                  95

Ala Glu Ser Ile Ala Ala Ser Ala Ser Asn Ala Arg Glu Ala Ala
            100                 105                 110

Ala Ser Ala Lys Ala Ser Ala Ser Ala Met Ser Ser Ala Ala Val Gln
            115                 120                 125

Ala Lys Leu Ala Glu Lys Thr Ala Lys Asn Gln Ala Leu Ala Ser Glu
            130                 135                 140

Glu Ala Lys Leu Lys Ala Ala Ala Ala Ser Ala Ala Ala Ala
145                 150                 155                 160

Ser Ala Ala Ala Glu Ala Ala Leu Lys Ala Glu Arg Ile Ala Glu
            165                 170                 175

Ala Ile Ala Lys Ala Ala Ala Lys Ala Ala Arg Ala Ala Ala
            180                 185                 190

Ala Ala Leu Asn Ser Ala Lys Glu Ala Ala Thr Ser Ser Ala Arg Ser
            195                 200                 205

Ala Ala Glu Ala Glu Ala Lys Ser Glu Val Ala Ile Leu Ile Ser Glu
            210                 215                 220

Leu Asp Lys Lys Ser Arg Glu Val Ala Ala Ser Ala Ser Ala Lys Ala
225                 230                 235                 240

Arg Ala Ala Ala Ala Ser Ser Arg Asn Ala Glu Thr Ala Val Ile
            245                 250                 255

Gly Ala Asn Ile Asn Val Ala Lys Glu Val Leu Ala Ile Pro Ile Glu
            260                 265                 270

Pro Lys Lys Leu Pro Glu Pro Glu Leu Ala Leu Lys Glu Glu Asn Val
            275                 280                 285

Ala Val Ala Ser Ser Glu Ser Glu Val Lys Val Glu Thr Ser Ser Glu
            290                 295                 300

Ala Trp Ser Ile
305

<210> SEQ ID NO 18
<211> LENGTH: 327
<212> TYPE: PRT
<213> ORGANISM: Bombus terrestris

<400> SEQUENCE: 18

Met Lys Ile Pro Ala Leu Leu Val Thr Cys Leu Tyr Leu Trp Gly Phe
1               5                   10                  15

Ala Ser Ala Gly Gln Ser Ser Pro Leu Leu Glu Ile Val Gln Gly Ser
            20                  25                  30

Ala Ser Ala Thr Ala Ser Thr Ala Val Thr Ala Arg Ser Gly Leu Arg
            35                  40                  45

Ala Gly Gln Val Ala Val Ala Ser Gln Lys Asp Ala Thr Leu Gln Ala
        50                  55                  60

Asp Ala Ser Ala Ala Ala Ala Ala Arg Ala Ser Ala Asp Gln
65                  70                  75                  80

Ser Ala Ser Leu Ala Gln Gln Ser Ala Ser Leu Gln Ser Lys Ala Ala
            85                  90                  95

Ala Arg Ala Lys Ser Ala Glu Glu Ser Ala Ala Thr Ala Lys Ala
            100                 105                 110

Glu Leu Gln Ala Glu Ser Ile Ala Ala Ser Ala Ser Ser Asn Ala Arg
            115                 120                 125

```
Glu Ala Ala Ala Ser Ala Lys Ala Ser Ala Met Ser Ser Ala
    130                 135                 140

Ala Val Gln Ala Lys Leu Ala Glu Lys Thr Ala Lys Asn Gln Ala Leu
145                 150                 155                 160

Ala Ser Glu Glu Ala Lys Leu Lys Ala Ala Ala Ala Ser Ala Ala
                165                 170                 175

Ala Ala Ala Ser Ala Ala Ala Glu Ala Ala Leu Lys Ala Glu Arg Ile
            180                 185                 190

Ala Glu Glu Ala Ile Ala Lys Ala Ala Ala Lys Ala Ala Ala Arg
        195                 200                 205

Ala Ala Ala Ala Ala Leu Asn Ser Ala Lys Glu Ala Ala Thr Ser Ser
    210                 215                 220

Ala Arg Ser Ala Ala Glu Ala Glu Ala Lys Ser Glu Val Ala Ile Leu
225                 230                 235                 240

Ile Ser Glu Leu Asp Lys Lys Ser Arg Glu Val Ala Ala Ser Ala Ser
                245                 250                 255

Ala Lys Ala Arg Ala Ala Ala Ala Ser Ser Arg Asn Ala Glu Thr
            260                 265                 270

Ala Val Ile Gly Ala Asn Ile Asn Val Ala Lys Glu Val Leu Ala Ile
        275                 280                 285

Pro Ile Glu Pro Lys Lys Leu Pro Glu Pro Glu Leu Ala Leu Lys Glu
    290                 295                 300

Glu Asn Val Ala Val Ala Ser Ser Glu Ser Glu Val Lys Val Glu Thr
305                 310                 315                 320

Ser Ser Glu Ala Trp Ser Ile
                325

<210> SEQ ID NO 19
<211> LENGTH: 293
<212> TYPE: PRT
<213> ORGANISM: Bombus terrestris

<400> SEQUENCE: 19

His Val Val Lys Arg Asp Lys Glu Leu Lys Ala Pro Ala Leu Pro Glu
1               5                   10                  15

Leu Leu Gly Asp Gly Ser Asp Thr Leu Gly Ala Ser Met Glu Asn Gly
                20                  25                  30

Ile Lys Val Ala Arg Ala Ser Gln Asn Val Gly Leu Arg Thr Glu Leu
            35                  40                  45

Asn Ala Ala Arg Ala Ala Ala Ala Ala Thr Lys Gln Ala Lys
        50                  55                  60

Asp Thr Glu Ala Ala Glu Ala Gly Ala Ala Ala Ile Ala Ile Ala
65                  70                  75                  80

Ile Ala Lys Arg Glu Glu Ala Ile Lys Ala Ser Glu Leu Ala Ser Lys
                85                  90                  95

Leu Leu Thr Ala Ala Gly Ser Ser Glu Ala Ala Val Ser Ala Thr
                100                 105                 110

Val Arg Ala Ala Gln Leu Thr Ala Ala Ser Ala Ala Ala Lys Ala
            115                 120                 125

Ser Ala Ser Ala Ser Glu Ala Ser Ala Glu Ala Gln Val Arg Ala Asn
    130                 135                 140

Ala Glu Ala Asn Ile Ala Lys Lys Ala Ser Ala Ala Glu Ala Lys Ala
145                 150                 155                 160

Ala Ala Glu Ala Gln Val Lys Ala Glu Leu Ala Lys Lys Ala Ala Ala
                165                 170                 175
```

Gly Phe Leu Ala Lys Ala Arg Leu Ala Ala Ser Ala Glu Ser Glu Ala
                180                 185                 190

Thr Lys Leu Ala Ala Glu Ala Glu Val Ala Leu Ala Lys Ala Arg Val
            195                 200                 205

Ala Val Asp Gln Ser Gln Ser Ala Gln Ala Thr Ala Thr Ala Gln Ala
        210                 215                 220

Ala Thr Ala Val Gln Leu Gln Ser Gln Ala Ala Asn Ala Glu Ala Ser
225                 230                 235                 240

Ala Val Ala Gln Ala Glu Thr Leu Leu Val Thr Ala Glu Ala Val Ser
                245                 250                 255

Ala Ala Glu Ala Glu Ala Ala Thr Lys Ala Thr Ser Trp Gly Glu Glu
            260                 265                 270

Cys His Gln Arg Glu Lys Val Thr Phe Ser Glu Asp Arg Leu Asn Glu
        275                 280                 285

Arg Gln Asp Asn Trp
    290

<210> SEQ ID NO 20
<211> LENGTH: 313
<212> TYPE: PRT
<213> ORGANISM: Bombus terrestris

<400> SEQUENCE: 20

Met Lys Ile Pro Ala Ile Leu Val Thr Ser Leu Leu Val Trp Gly Gly
1               5                   10                  15

Leu Ala Glu Gly His Val Val Lys Arg Asp Lys Glu Leu Lys Ala Pro
                20                  25                  30

Ala Leu Pro Glu Leu Leu Gly Asp Gly Ser Asp Thr Leu Gly Ala Ser
            35                  40                  45

Met Glu Asn Gly Ile Lys Val Ala Arg Ala Ser Gln Asn Val Gly Leu
        50                  55                  60

Arg Thr Glu Leu Asn Ala Ala Arg Ala Ala Ala Ala Ala Ala Ala Thr
65                  70                  75                  80

Lys Gln Ala Lys Asp Thr Glu Ala Ala Glu Ala Gly Ala Ala Ala Ala
                85                  90                  95

Ile Ala Ile Ala Ile Ala Lys Arg Glu Glu Ala Ile Lys Ala Ser Glu
            100                 105                 110

Leu Ala Ser Lys Leu Leu Thr Ala Ala Ala Gly Ser Ser Glu Ala Ala
        115                 120                 125

Val Ser Ala Thr Val Arg Ala Ala Gln Leu Thr Ala Ala Ser Ala
130                 135                 140

Ala Ala Lys Ala Ser Ala Ser Ala Ser Glu Ala Ser Ala Glu Ala Gln
145                 150                 155                 160

Val Arg Ala Asn Ala Glu Ala Asn Ile Ala Lys Lys Ala Ser Ala Ala
                165                 170                 175

Glu Ala Lys Ala Ala Ala Glu Ala Gln Val Lys Ala Glu Leu Ala Lys
            180                 185                 190

Lys Ala Ala Ala Gly Phe Leu Ala Lys Ala Arg Leu Ala Ala Ser Ala
        195                 200                 205

Glu Ser Glu Ala Thr Lys Leu Ala Ala Glu Ala Glu Val Ala Leu Ala
    210                 215                 220

Lys Ala Arg Val Ala Val Asp Gln Ser Gln Ser Ala Gln Ala Thr Ala
225                 230                 235                 240

Thr Ala Gln Ala Ala Thr Ala Val Gln Leu Gln Ser Gln Ala Ala Asn
                245                 250                 255

```
Ala Glu Ala Ser Ala Val Ala Gln Ala Glu Thr Leu Leu Val Thr Ala
            260                 265                 270

Glu Ala Val Ser Ala Ala Glu Ala Glu Ala Ala Thr Lys Ala Thr Ser
        275                 280                 285

Trp Gly Glu Glu Cys His Gln Arg Glu Lys Val Thr Phe Ser Glu Asp
    290                 295                 300

Arg Leu Asn Glu Arg Gln Asp Asn Trp
305                 310

<210> SEQ ID NO 21
<211> LENGTH: 313
<212> TYPE: PRT
<213> ORGANISM: Bombus terrestris

<400> SEQUENCE: 21

Gly Ser Val Glu Leu Gly Ala Pro Lys Gln Glu Ser Val Leu Val Glu
1               5                   10                  15

Gln Leu Leu Lys Asn Val Glu Thr Ser Ala Lys Arg Lys Glu Asn
            20                  25                  30

Gly Ala Pro Lys Leu Gly Glu Ser Thr Ala Ala Ala Leu Ala Ser Thr
        35                  40                  45

Lys Ala Thr Ala Ala Ala Glu Ala Lys Ala Ser Ala Lys Val Lys Ala
50                  55                  60

Ser Ala Leu Ala Leu Glu Ala Phe Leu Arg Ala Ser Ala Ala Phe
65                  70                  75                  80

Ala Ala Ala Ser Ala Lys Ala Ala Ala Val Lys Glu Ala Thr Gln
                85                  90                  95

Ala Gln Leu Leu Ala Gln Glu Lys Ala Leu Ile Ala Leu Lys Thr Gln
            100                 105                 110

Ser Glu Gln Gln Ala Ala Ser Ala Arg Ala Asp Ala Ala Ala Ala
        115                 120                 125

Ala Val Ser Ala Leu Glu Arg Ala Gln Ala Ser Ser Arg Ala Ala Thr
130                 135                 140

Thr Ala Gln Asp Ile Ser Ser Asp Leu Glu Lys Arg Val Ala Thr Ser
145                 150                 155                 160

Ala Ala Ala Glu Ala Gly Ala Thr Leu Arg Ala Glu Gln Ser Ala Ala
                165                 170                 175

Gln Ser Lys Trp Ser Ala Ala Leu Ala Ala Gln Thr Ala Ala Ala
            180                 185                 190

Ala Ala Ile Glu Ala Lys Ala Thr Ala Ser Ser Glu Ser Thr Ala Ala
        195                 200                 205

Ala Thr Ser Lys Ala Ala Val Leu Thr Ala Asp Thr Ser Ser Ala Glu
210                 215                 220

Ala Ala Ala Ala Glu Ala Gln Ser Ala Ser Arg Ile Ala Gly Thr
225                 230                 235                 240

Ala Ala Thr Glu Gly Ser Ala Asn Trp Ala Ser Glu Asn Ser Arg Thr
                245                 250                 255

Ala Gln Leu Glu Ala Ser Ala Ser Ala Lys Ala Thr Ala Ala Ala
            260                 265                 270

Val Gly Asp Gly Ala Ile Ile Gly Leu Ala Arg Asp Ala Ser Ala Ala
        275                 280                 285

Ala Gln Ala Ala Ala Glu Val Lys Leu Glu Ala Ser Ala Ser
290                 295                 300

Leu Gly Ala Ser Glu Lys Asp Lys Lys
305                 310
```

<210> SEQ ID NO 22
<211> LENGTH: 332
<212> TYPE: PRT
<213> ORGANISM: Bombus terrestris

<400> SEQUENCE: 22

Met Gln Ile Pro Ala Ile Phe Val Thr Cys Leu Leu Thr Trp Gly Leu
1               5                   10                  15

Val His Ala Gly Ser Val Glu Leu Gly Ala Pro Lys Gln Glu Ser Val
            20                  25                  30

Leu Val Glu Gln Leu Leu Leu Lys Asn Val Thr Ser Ala Lys Arg
        35                  40                  45

Lys Glu Asn Gly Ala Pro Lys Leu Gly Glu Ser Thr Ala Ala Leu
50                  55                  60

Ala Ser Thr Lys Ala Thr Ala Ala Glu Ala Lys Ala Ser Ala Lys
65                  70                  75                  80

Val Lys Ala Ser Ala Leu Ala Leu Ala Glu Ala Phe Leu Arg Ala Ser
            85                  90                  95

Ala Ala Phe Ala Ala Ala Ser Ala Lys Ala Ala Ala Val Lys Glu
            100                 105                 110

Ala Thr Gln Ala Gln Leu Leu Ala Gln Glu Lys Ala Leu Ile Ala Leu
            115                 120                 125

Lys Thr Gln Ser Glu Gln Gln Ala Ser Ala Arg Ala Asp Ala Ala
130                 135                 140

Ala Ala Ala Ala Val Ser Ala Leu Glu Arg Ala Gln Ala Ser Ser Arg
145                 150                 155                 160

Ala Ala Thr Thr Ala Gln Asp Ile Ser Ser Asp Leu Glu Lys Arg Val
            165                 170                 175

Ala Thr Ser Ala Ala Ala Glu Ala Gly Ala Thr Leu Arg Ala Glu Gln
            180                 185                 190

Ser Ala Ala Gln Ser Lys Trp Ser Ala Leu Ala Ala Gln Thr Ala
            195                 200                 205

Ala Ala Ala Ala Ala Ile Glu Ala Lys Ala Thr Ala Ser Ser Glu Ser
210                 215                 220

Thr Ala Ala Ala Thr Ser Lys Ala Ala Val Leu Thr Ala Asp Thr Ser
225                 230                 235                 240

Ser Ala Glu Ala Ala Ala Ala Glu Ala Gln Ser Ala Ser Arg Ile
            245                 250                 255

Ala Gly Thr Ala Ala Thr Glu Gly Ser Ala Asn Trp Ala Ser Glu Asn
            260                 265                 270

Ser Arg Thr Ala Gln Leu Glu Ala Ser Ala Ser Ala Lys Ala Thr Ala
            275                 280                 285

Ala Ala Ala Val Gly Asp Gly Ala Ile Ile Gly Leu Ala Arg Asp Ala
            290                 295                 300

Ser Ala Ala Gln Ala Ala Ala Glu Val Lys Ala Leu Ala Glu Ala
305                 310                 315                 320

Ser Ala Ser Leu Gly Ala Ser Glu Lys Asp Lys Lys
            325                 330

<210> SEQ ID NO 23
<211> LENGTH: 338
<212> TYPE: PRT
<213> ORGANISM: Bombus terrestris

<400> SEQUENCE: 23

Gly Lys Pro Leu Ile Ala Asn Ala Gln Ile Gly Lys Val Lys Thr Glu
1               5                   10                  15

Thr Ser Ser Ser Ser Glu Ile Glu Thr Leu Val Ser Gly Ser Gln Thr
            20                  25                  30

Leu Val Ala Gly Ser Glu Thr Leu Ala Ser Glu Ser Glu Ala Leu Ala
        35                  40                  45

Ser Lys Ser Glu Ala Leu Thr Ser Glu Ala Glu Ile Ala Ser Val Thr
50                  55                  60

Thr Lys Asp Glu Leu Ile Leu Lys Gly Glu Ala Ile Thr Gly Lys Lys
65                  70                  75                  80

Leu Gly Thr Gly Ala Ser Glu Val Ala Ala Ala Ser Gly Glu Ala Ile
                85                  90                  95

Ala Thr Thr Leu Gly Ala Gly Gln Ala Ala Glu Ala Gln Ala Ala
            100                 105                 110

Ala Ala Ala Gln Ala Lys Ser Ala Ala Ala Ala Ala Asn Ala Gly
            115                 120                 125

Glu Ser Ser Asn Ser Ala Ala Ala Leu Val Ala Ala Ala Ala Ala
            130                 135                 140

Gln Gly Lys Ala Ala Ala Ala Ala Ala Thr Lys Ala Ser Leu
145                 150                 155                 160

Glu Ala Ala Asp Ala Ala Glu Glu Ala Glu Ser Ala Val Ala Leu Ala
                165                 170                 175

Arg Ala Ala Ser Ala Lys Ala Glu Ala Leu Ala Ser Thr Ala Ala Ala
            180                 185                 190

Ala Asn Thr Arg Ala Ala Leu Gln Ala Glu Lys Ser Asn Glu Leu Ala
            195                 200                 205

Gln Ala Glu Ala Ala Ala Ala Glu Ala Gln Ala Lys Ala Ala
210                 215                 220

Ala Ala Lys Ala Thr Gln Leu Ala Leu Lys Val Ala Glu Thr Ala Val
225                 230                 235                 240

Lys Thr Glu Ala Asp Ala Ala Ala Ala Val Ala Ala Ala Lys Ala
                245                 250                 255

Arg Ala Val Ala Asp Ala Ala Ser Arg Ala Thr Ala Val Asn Ala
            260                 265                 270

Ile Ala Glu Ala Glu Glu Arg Asp Ser Ala Gln Ala Glu Asn Thr Ala
275                 280                 285

Gly Val Ala Gln Ala Ala Leu Ala Ala Ala Glu Ala Gln Asp Ser Cys
            290                 295                 300

Ile Gly Ala Ala Ala Thr Pro Arg His Ser Ser Ser Tyr Ala Trp Trp
305                 310                 315                 320

Lys Leu Arg Ile Thr Ser Leu Ile Val Ile Leu Ser Pro Arg Asn Arg
                325                 330                 335

Arg Thr

<210> SEQ ID NO 24
<211> LENGTH: 357
<212> TYPE: PRT
<213> ORGANISM: Bombus terrestris

<400> SEQUENCE: 24

Met Lys Ile Pro Ser Ile Leu Ala Val Ser Leu Leu Val Trp Gly Leu
1               5                   10                  15

Ala Ser Ala Gly Lys Pro Leu Ile Ala Asn Ala Gln Ile Gly Lys Val
            20                  25                  30

Lys Thr Glu Thr Ser Ser Ser Ser Glu Ile Glu Thr Leu Val Ser Gly

```
                35                    40                    45
Ser Gln Thr Leu Val Ala Gly Ser Glu Thr Leu Ala Ser Glu Ser Glu
 50                  55                  60
Ala Leu Ala Ser Lys Ser Glu Ala Leu Thr Ser Glu Ala Glu Ile Ala
 65                  70                  75                  80
Ser Val Thr Thr Lys Asp Glu Leu Ile Leu Lys Gly Glu Ala Ile Thr
                 85                  90                  95
Gly Lys Lys Leu Gly Thr Gly Ala Ser Glu Val Ala Ala Ser Gly
                100                 105                 110
Glu Ala Ile Ala Thr Thr Leu Gly Ala Gly Gln Ala Ala Glu Ala
            115                 120                 125
Gln Ala Ala Ala Ala Gln Ala Lys Ser Ala Ala Ala Ala Ala
130                 135                 140
Asn Ala Gly Glu Ser Ser Asn Ser Ala Ala Ala Leu Val Ala Ala Ala
145                 150                 155                 160
Ala Ala Ala Gln Gly Lys Ala Ala Ala Ala Ala Ala Ala Thr Lys
                165                 170                 175
Ala Ser Leu Glu Ala Ala Asp Ala Ala Glu Glu Ala Glu Ser Ala Val
            180                 185                 190
Ala Leu Ala Arg Ala Ala Ser Ala Lys Ala Glu Ala Leu Ala Ser Thr
            195                 200                 205
Ala Ala Ala Asn Thr Arg Ala Ala Leu Gln Ala Glu Lys Ser Asn
            210                 215                 220
Glu Leu Ala Gln Ala Glu Ala Ala Ala Ala Glu Ala Gln Ala Lys
225                 230                 235                 240
Ala Ala Ala Ala Ala Lys Ala Thr Gln Leu Ala Leu Lys Val Ala Glu
                245                 250                 255
Thr Ala Val Lys Thr Glu Ala Asp Ala Ala Ala Ala Val Ala Ala
                260                 265                 270
Ala Lys Ala Arg Ala Val Ala Asp Ala Ala Ala Ser Arg Ala Thr Ala
            275                 280                 285
Val Asn Ala Ile Ala Glu Ala Glu Glu Arg Asp Ser Ala Gln Ala Glu
            290                 295                 300
Asn Thr Ala Gly Val Ala Gln Ala Ala Leu Ala Ala Ala Glu Ala Gln
305                 310                 315                 320
Asp Ser Cys Ile Gly Ala Ala Ala Thr Pro Arg His Ser Ser Ser Tyr
                325                 330                 335
Ala Trp Trp Lys Leu Arg Ile Thr Ser Leu Ile Val Ile Leu Ser Pro
                340                 345                 350
Arg Asn Arg Arg Thr
            355
```

<210> SEQ ID NO 25
<211> LENGTH: 927
<212> TYPE: DNA
<213> ORGANISM: Bombus terrestris

<400> SEQUENCE: 25

```
ggccagagct cacctctgct cgagatcgtg cagggtagcg cgtcggccac cgcatccacc    60
gctgtgaccg ctagatccgg acttcgtgcc ggtcaggtag ccgtggcctc gcagaaggat   120
gccacacttc aggcagatgc ctcagcggcc gccgcggccg ctgcacgcgc ttccgccgac   180
cagtcggcca gtctagccca acagtcggcg tctttgcagt ccaaagctgc cgccagagca   240
aaatcagccg aggagtcagc ggcagctacg gccaaagccg agttgcaggc agaatccatt   300
```

```
gctgcatctg ccagttccaa tgccagagag gctgcagcgt ccgcaaaagc ctccgcatcc    360
gcgatgtcat cggctgccgt gcaggcgaaa ctcgctgaaa agacggccaa gaatcaagct    420
ctggcttccg aagaagccaa actcaaggct gccgccgctg ccagcgcagc agcagcagcc    480
agcgccgccg ccgaggcagc cctgaaagct gagagaatag cggaagaagc catcgccaag    540
gcggccgctg ccaaagcagc cgccagagcc gctgcagccg cgttaaactc cgcgaaggaa    600
gccgccacga gcagcgcaag gagcgccgcc gaagccgaag ctaagagcga agtcgctata    660
ctgatcagcg aactcgacaa gaagagcagg gaagtcgccg cttccgcgtc cgccaaggca    720
cgcgctgctg ctgcggctag ctccagaaac gcagaaacgg ctgttatcgg agctaacatc    780
aatgtggcca agaggtcttt ggcgattccc atcgagccaa agaaacttcc ggagccagag    840
ctggcgttga agaagagaaa tgtcgcggtc gcgagctcag agagtgaagt gaaggtagaa    900
acgagcagcg aagcatggtc aatttaa                                         927

<210> SEQ ID NO 26
<211> LENGTH: 984
<212> TYPE: DNA
<213> ORGANISM: Bombus terrestris

<400> SEQUENCE: 26
atgaagattc cagcactgct cgtaacgtgc ctctacctttt ggggcttcgc gtccgccggc     60
cagagctcac ctctgctcga gatcgtgcag ggtagcgcgt cggccaccgc atccaccgct    120
gtgaccgcta gatccggact tcgtgccggt caggtagccg tggcctcgca gaaggatgcc    180
acacttcagg cagatgcctc agcggccgcc gcggccgctg cacgcgcttc cgccgaccag    240
tcggccagtc tagcccaaca gtcggcgtct ttgcagtcca agctgccgc cagagcaaaa    300 tcagccgagg agtcagcggc agctacggcc aaagccgagt tgcaggcaga atccattgct    360
gcatctgcca gttccaatgc cagagaggct gcagcgtccg caaaagcctc cgcatccgcg    420
atgtcatcgg ctgccgtgca ggcgaaactc gctgaaaaga cggccaagaa tcaagctctg    480
gcttccgaag aagccaaact caaggctgcc gccgctgcca gcagcagc agcagccagc    540 gccgccgccg aggcagccct gaaagctgag agaatagcgg aagaagccat cgccaaggcg    600
gccgctgcca aagcagccgc cagagccgct gcagccgcgt taaactccgc gaaggaagcc    660
gccacgagca gcgcaaggag cgccgccgaa gccgaagcta agagcgaagt cgctatactg    720
atcagcgaac tcgacaagaa gagcagggaa gtcgccgctt ccgcgtccgc caaggcacgc    780
gctgctgctg cggctagctc cagaaacgca gaaacgctg ttatcggagc taacatcaat    840
gtggccaaag aggtcttggc gattcccatc gagccaaaga aacttccgga gccagagctg    900
gcgttgaaga agagaatgt cgcggtcgcg agctcagaga gtgaagtgaa ggtagaaacg    960
agcagcgaag catggtcaat ttaa                                             984

<210> SEQ ID NO 27
<211> LENGTH: 882
<212> TYPE: DNA
<213> ORGANISM: Bombus terrestris

<400> SEQUENCE: 27
cacgtggtga agcgcgacaa ggagctcaag gccccggctt taccggaact actcggtgat     60
gggtctgaca cgctcggtgc ctcgatggag aacgggatca agtcgccag agcatcgcag    120 aatgtgggtc tgagaacaga gttgaatgca ccgcgcggg ctgcagccgc tgctgcgacc    180
aagcaggcca aagacacaga ggccgcggaa gctggagcgg ccgctgcgat tgccatcgct    240
```

```
atcgccaagc gtgaagaagc tatcaaagca agcgaattag ccagcaagtt gttgacagcc    300
gcggctgggt ccagcgaagc tgccgtgtca gcgacggtga gggcggcgca attgacggcc    360
gcagctagcg cagctgccaa agcttctgca tccgcctctg aggcttctgc cgaagcccag    420
gtgagggcca acgccgaagc aaacatcgcc aagaaagctt cggcagctga agcaaaagcc    480
gcagccgaag cccaggttaa ggcggaactc gccaagaaag cggccgccgg tttcttagct    540
aaggctagac tagcggccag cgccgaatcc gaggccacta actcgcagc cgaagctgaa    600 gtagcactgg ctaaggccag agtcgccgtc gaccagtcgc agagcgcaca ggcaaccgct    660
accgctcaag ctgccacagc cgttcagctg cagtctcaag cagctaacgc ggaagcctcc    720
gctgtagcac aggctgaaac tctgctggtc acggcggaag ccgtctctgc cgcggaagcc    780
gaagccgcga ccaaagctac cagttggggc gaagaatgtc atcaacgaga aaaagttacg    840
tttagcgaag atcgattaaa cgagagacaa gacaattggt ag                      882

<210> SEQ ID NO 28
<211> LENGTH: 942
<212> TYPE: DNA
<213> ORGANISM: Bombus terrestris

<400> SEQUENCE: 28
atgaagattc cagcaatact ggttacgtct ctgctggtct ggggtggtct ggccgagggc     60
cacgtggtga agcgcgacaa ggagctcaag gccccggctt taccggaact actcggtgat    120
gggtctgaca cgctcggtgc ctcgatggag aacgggatca agtcgccag agcatcgcag    180 aatgtgggtc tgagaacaga gttgaatgca gccgcgcggg ctgcagccgc tgctgcgacc    240
aagcaggcca agacacaga ggccgcggaa gctggagcgg ccgctgcgat tgccatcgct    300
atcgccaagc gtgaagaagc tatcaaagca agcgaattag ccagcaagtt gttgacagcc    360
gcggctgggt ccagcgaagc tgccgtgtca gcgacggtga gggcggcgca attgacggcc    420
gcagctagcg cagctgccaa agcttctgca tccgcctctg aggcttctgc cgaagcccag    480
gtgagggcca acgccgaagc aaacatcgcc aagaaagctt cggcagctga agcaaaagcc    540
gcagccgaag cccaggttaa ggcggaactc gccaagaaag cggccgccgg tttcttagct    600
aaggctagac tagcggccag cgccgaatcc gaggccacta actcgcagc cgaagctgaa    660 gtagcactgg ctaaggccag agtcgccgtc gaccagtcgc agagcgcaca ggcaaccgct    720
accgctcaag ctgccacagc cgttcagctg cagtctcaag cagctaacgc ggaagcctcc    780
gctgtagcac aggctgaaac tctgctggtc acggcggaag ccgtctctgc cgcggaagcc    840
gaagccgcga ccaaagctac cagttggggc gaagaatgtc atcaacgaga aaaagttacg    900
tttagcgaag atcgattaaa cgagagacaa gacaattggt ag                      942

<210> SEQ ID NO 29
<211> LENGTH: 942
<212> TYPE: DNA
<213> ORGANISM: Bombus terrestris

<400> SEQUENCE: 29
ggtagcgtgg aactcggtgc ccccaagcag gagtctgtcc tcgtggagca gctcctattg     60
aagaacgtgg agactagtgc gaagcgaaag gagaacggcg caccgaaaact cggcgagagc    120 acagctgcgg ctctggctag taccaaggca actgcagccg cagaggctaa ggcatccgcc    180
aaagtgaaag cttctgcctt ggccctcgct gaggctttct tgcgtgcgtc ggcagcgttt    240
gctgctgctt cagccaaagc tgctgccgct gtaaaggaag caacgcaggc acagttgctg    300
```

| | |
|---|---|
| gcacaggaga aggctttgat agcgttgaaa actcaatctg agcaacaagc tgcctctgct | 360 |
| cgcgcggacg ccgcggctgc cgcagccgta tccgcgctag aacgcgccca ggcctcctcc | 420 |
| agagcagcca cgaccgccca agacatctcc agcgatctgg agaaacgtgt cgccacctca | 480 |
| gccgctgctg aagcaggtgc caccctcaga gcggaacaat ccgccgcgca atcgaaatgg | 540 |
| tccgccgcac tggccgccca aaccgccgct gctgcagccg ctatagaagc aaaggccacc | 600 |
| gcttcctcag aaagcaccgc tgccgctact agtaaggccg ccgtgttgac cgctgacact | 660 |
| agcagcgcag aagctgccgc tgcagcggag gcacaatccg cttcgcggat cgcaggtaca | 720 |
| gcagccaccg agggatccgc caactgggct agcgagaact cgcgtaccgc acaactggaa | 780 |
| gcttccgcct cagcgaaggc caccgcagcc gcagctgtcg agatggagc tattatagga | 840 |
| cttgcacggg acgctagtgc cgcagctcag gcagccgcag aagttaaagc cttagctgaa | 900 |
| gctagtgcca gcttaggtgc ttcagaaaag gacaagaaat ga | 942 |

<210> SEQ ID NO 30
<211> LENGTH: 999
<212> TYPE: DNA
<213> ORGANISM: Bombus terrestris

<400> SEQUENCE: 30

| | |
|---|---|
| atgcagatcc cagcgatttt cgtcacgtgc ctgctcacat ggggcctggt gcacgcaggt | 60 |
| agcgtggaac tcggtgcccc caagcaggag tctgtcctcg tggagcagct cctattgaag | 120 |
| aacgtggaga ctagtgcgaa gcgaaaggag aacggcgcac cgaaactcgg cgagagcaca | 180 |
| gctgcggctc tggctagtac caaggcaact gcagccgcag aggctaaggc atccgccaaa | 240 |
| gtgaaagctt ctgccttggc cctcgctgag gcttcttgc gtgcgtcggc agcgtttgct | 300 |
| gctgcttcag ccaaagctgc tgccgctgta aggaagcaa cgcaggcaca gttgctggca | 360 |
| caggagaagg ctttgatagc gttgaaaact caatctgagc aacaagctgc ctctgctcgc | 420 |
| gcggacgccg cggctgccgc agccgtatcc gcgctagaac gcgcccaggc ctcctccaga | 480 |
| gcagccacga ccgcccaaga catctccagc gatctggaga acgtgtcgc cacctcagcc | 540 |
| gctgctgaag caggtgccac cctcagagcg gaacaatccg ccgcgcaatc gaaatggtcc | 600 |
| gccgcactgg ccgcccaaac cgccgctgct gcagccgcta tagaagcaaa ggccaccgct | 660 |
| tcctcagaaa gcaccgctgc cgctactagt aaggccgccg tgttgaccgc tgacactagc | 720 |
| agcgcagaag ctgccgctgc agcggaggca caatccgctt cgcggatcgc aggtacagca | 780 |
| gccaccgagg gatccgccaa ctgggctagc gagaactcgc gtaccgcaca actggaagct | 840 |
| tccgcctcag cgaaggccac cgcagccgca gctgtcggag atggagctat tataggactt | 900 |
| gcacgggacg ctagtgccgc agctcaggca gccgcagaag ttaaagcctt agctgaagct | 960 |
| agtgccagct taggtgcttc agaaaaggac aagaaatga | 999 |

<210> SEQ ID NO 31
<211> LENGTH: 1017
<212> TYPE: DNA
<213> ORGANISM: Bombus terrestris

<400> SEQUENCE: 31

| | |
|---|---|
| ggcaaaccac tcattgccaa tgcgcaaata gggaaggtca agaccgaaac gtcatcgtct | 60 |
| tcagagattg agacgttggt atcaggaagc cagacattgg tggcaggaag tgagacattg | 120 |
| gcttcagaaa gcgaggcatt ggcgtcaaaa agcgaggcat tgacgtcaga gccgagata | 180 |
| gcgagcgtga caacgaagga cgagctcata ctaaagggcg aagctatcac tggaaagaaa | 240 |

-continued

```
ctaggaaccg gggcgtcgga agtagcggcg gcctctgggg aggctatcgc aactaccctt      300
ggcgcgggac aagctgcagc agaggcacaa gcagccgccg ccgcgcaagc aaaatcagca      360
gcggcagctg ccgcgaatgc aggtgaatcc agcaacagtg ctgctgcgtt ggttgctgct      420
gcagctgcag cacaaggaaa agcggctgcc gccgcagcag ccgcgacgaa ggctagctta      480
gaggccgcag acgctgctga ggaagctgag tcggccgtgg ccttggctag gctgcctcc      540 gcaaaggcgg aagcgctcgc atcgaccgcc gctgctgcga tacccgtgc tgctctccaa      600 gcggaaaaat cgaacgagct ggcgcaagct gaggctgcag ccgccgccga agcccaggct      660
aaagccgccg ctgctgccaa gcaacacaa ctcgcccta aagttgccga aactgcggtg       720
aaaacggaag cagatgcagc agctgccgcc gttgcggccg caaaagccag agcagtcgca      780
gacgcagccg cgtctcgtgc gaccgcagtg aacgccattg ctgaagcgga agaaagagac      840
tctgcacagg cggagaacac cgctggtgta gcacaagcag cgctcgctgc tgcggaagca     900
caagactcct gcatcggcgc tgccgcgact cctaggcatt cgtcgagcta tgcatggtgg      960
aagcttagga taacatcctt gatcgtcatt ctatcgccac gcaatcgacg tacttaa       1017
```

<210> SEQ ID NO 32
<211> LENGTH: 1074
<212> TYPE: DNA
<213> ORGANISM: Bombus terrestris

<400> SEQUENCE: 32

```
atgaagattc catcgatact cgcggtgtcc ctgctggttt ggggtctggc cagcgcaggc       60
aaaccactca ttgccaatgc gcaaataggg aaggtcaaga ccgaaacgtc atcgtcttca      120
gagattgaga cgttggtatc aggaagccag acattggtgg caggaagtga gacattggct      180
tcagaaagcg aggcattggc gtcaaaaagc gaggcattga cgtcagaagc cgagatagcg      240
agcgtgacaa cgaaggacga gctcatacta aagggcgaag ctatcactgg aaagaaacta      300
ggaaccgggg cgtcggaagt agcggcggcc tctggggagg ctatcgcaac tacccttggc      360
gcgggacaag ctgcagcaga ggcacaagca gccgccgccg cgcaagcaaa atcagcagcg      420
gcagctgccg cgaatgcagg tgaatccagc aacagtgctg ctgcgttggt tgctgctgca      480
gctgcagcac aaggaaaagc ggctgccgcc gcagcagccg cgacgaaggc tagcttagag      540
gccgcagacg ctgctgagga agctgagtcg gccgtggcct ggctagggc tgcctccgca      600 aaggcggaag cgctcgcatc gaccgccgct gctgcgaata cccgtgctgc tctccaagcg      660
gaaaaatcga acgagctggc gcaagctgag gctgcagccg ccgccgaagc ccaggctaaa      720
gccgccgctg ctgccaaggc aacacaactc gcccttaaag ttgccgaaac tgcggtgaaa      780
acggaagcag atgcagcagc tgccgccgtt gcggccgcaa aagccagagc agtcgcagac      840
gcagccgcgt ctcgtgcgac gcagtgaac gccattgctg aagcggaaga aagagactct      900
gcacaggcgg agaacaccgc tggtgtagca caagcagcgc tcgctgctgc ggaagcacaa      960
gactcctgca tcggcgctgc cgcgactcct aggcattcgt cgagctatgc atggtggaag     1020
cttaggataa catccttgat cgtcattcta tcgccacgca atcgacgtac ttaa           1074
```

<210> SEQ ID NO 33
<211> LENGTH: 403
<212> TYPE: PRT
<213> ORGANISM: Myrmecia forficata

<400> SEQUENCE: 33

```
Ser Gly Pro Arg Leu Leu Gly Gly Arg Ser Ala Ala Ser Ala Ser Ala
1               5                   10                  15
```

Ser Ala Ser Ala Glu Ala Ser Ala Gly Gly Trp Arg Lys Ser Gly Ala
            20                  25                  30

Ser Ala Ser Ala Ser Lys Ala Gly Ser Ser Asn Ile Leu Ser Arg
        35                  40                  45

Val Gly Ala Ser Arg Ala Ala Thr Leu Val Ser Ala Ala Val
 50                  55                  60

Glu Ala Lys Ala Gly Leu Arg Ala Gly Lys Ala Thr Ala Glu Glu Gln
 65                  70                  75                  80

Arg Glu Ala Leu Glu Met Leu Thr Leu Ser Ala Asp Lys Asn Ala Glu
                 85                  90                  95

Ala Arg Ile Leu Ala Asp Asp Thr Ala Val Leu Val Gln Gly Ser Ala
                100                 105                 110

Glu Ala Gln Ser Val Ala Ala Lys Thr Val Ala Val Glu Glu Glu
                115                 120                 125

Ser Ala Ser Leu Asp Ala Ala Val Glu Ala Glu Val Ala Ala Ala
130                 135                 140

Thr Ser Lys Ser Ser Ala Gly Gln Ala Leu Gln Ser Ala Gln Thr Ala
145                 150                 155                 160

Ala Ser Ala Leu Arg Thr Ser Ala Arg Ser Ala Leu Thr Ala Leu Lys
                165                 170                 175

Leu Ala Arg Leu Gln Gly Ala Ala Ser Ser Asn Ala Ala Arg Met Met
                180                 185                 190

Glu Lys Ala Leu Ala Ala Thr Gln Asp Ala Asn Ala Ala Gln Gln
                195                 200                 205

Ala Met Ala Ala Glu Ser Ala Ala Glu Ala Ala Ile Ala Ala
        210                 215                 220

Ala Lys Gln Ser Glu Ala Arg Asp Ala Gly Ala Glu Ala Lys Ala Ala
225                 230                 235                 240

Met Ala Ala Leu Ile Thr Ala Gln Arg Asn Leu Val Gln Ala Asn Ala
                245                 250                 255

Arg Ala Glu Met Ala Ser Glu Glu Ala Glu Leu Asp Ser Lys Ser Arg
                260                 265                 270

Ala Ser Asp Ala Lys Val Asn Ala Val Ala Arg Ala Ala Ser Lys Ser
                275                 280                 285

Ser Ile Arg Arg Asp Glu Leu Ile Glu Ile Gly Ala Glu Phe Gly Lys
                290                 295                 300

Ala Ser Gly Glu Val Ile Ser Thr Gly Thr Arg Ser Asn Gly Gly Gln
305                 310                 315                 320

Asp Ala Ile Ala Thr Ala Glu Ala Ser Ser Ser Ala Ser Ala Val Gly
                325                 330                 335

Ile Lys Lys Thr Ser Gly His Trp Gly Ser Gly Lys Trp Ser Arg Val
                340                 345                 350

Ser Lys Gly Lys Gly Trp Ala Ser Ser Asn Ala Asp Ala Asp Ala Ser
                355                 360                 365

Ser Ser Ser Ile Ile Ile Gly Gly Leu Lys Arg Gly Gly Leu Gly Ser
        370                 375                 380

Glu Ala Ser Ala Ala Ala Ser Ala Glu Ala Ala Ser Ala Gly Thr
385                 390                 395                 400

Leu Leu Leu

<210> SEQ ID NO 34
<211> LENGTH: 422
<212> TYPE: PRT
<213> ORGANISM: Myrmecia forficata

<400> SEQUENCE: 34

```
Met Lys Ile Pro Ala Ile Ile Ala Thr Ser Leu Leu Leu Trp Gly Phe
1               5                   10                  15

Ala Ser Ala Ser Gly Pro Arg Leu Leu Gly Gly Arg Ser Ala Ala Ser
            20                  25                  30

Ala Ser Ala Ser Ala Ser Ala Glu Ala Ser Ala Gly Gly Trp Arg Lys
        35                  40                  45

Ser Gly Ala Ser Ala Ser Ala Ser Ala Lys Ala Gly Ser Ser Asn Ile
    50                  55                  60

Leu Ser Arg Val Gly Ala Ser Arg Ala Ala Thr Leu Val Ala Ser
65                  70                  75                  80

Ala Ala Val Glu Ala Lys Ala Gly Leu Arg Ala Gly Lys Ala Thr Ala
                85                  90                  95

Glu Glu Gln Arg Glu Ala Leu Glu Met Leu Thr Leu Ser Ala Asp Lys
            100                 105                 110

Asn Ala Glu Ala Arg Ile Leu Ala Asp Asp Thr Ala Val Leu Val Gln
        115                 120                 125

Gly Ser Ala Glu Ala Gln Ser Val Ala Ala Lys Thr Val Ala Val
130                 135                 140

Glu Glu Glu Ser Ala Ser Leu Asp Ala Ala Val Glu Ala Glu Val
145                 150                 155                 160

Ala Ala Ala Thr Ser Lys Ser Ser Ala Gly Gln Ala Leu Gln Ser Ala
                165                 170                 175

Gln Thr Ala Ala Ser Ala Leu Arg Thr Ser Ala Arg Ser Ala Leu Thr
            180                 185                 190

Ala Leu Lys Leu Ala Arg Leu Gln Gly Ala Ala Ser Ser Asn Ala Ala
        195                 200                 205

Arg Met Met Glu Lys Ala Leu Ala Ala Thr Gln Asp Ala Asn Ala Ala
    210                 215                 220

Ala Gln Gln Ala Met Ala Ala Glu Ser Ala Ala Ala Glu Ala Ala Ala
225                 230                 235                 240

Ile Ala Ala Ala Lys Gln Ser Glu Ala Arg Asp Ala Gly Ala Glu Ala
                245                 250                 255

Lys Ala Ala Met Ala Ala Leu Ile Thr Ala Gln Arg Asn Leu Val Gln
            260                 265                 270

Ala Asn Ala Arg Ala Glu Met Ala Ser Glu Glu Ala Glu Leu Asp Ser
        275                 280                 285

Lys Ser Arg Ala Ser Asp Ala Lys Val Asn Ala Val Ala Arg Ala Ala
    290                 295                 300

Ser Lys Ser Ser Ile Arg Arg Asp Glu Leu Ile Glu Ile Gly Ala Glu
305                 310                 315                 320

Phe Gly Lys Ala Ser Gly Glu Val Ile Ser Thr Gly Thr Arg Ser Asn
                325                 330                 335

Gly Gly Gln Asp Ala Ile Ala Thr Ala Glu Ala Ser Ser Ala Ser
            340                 345                 350

Ala Val Gly Ile Lys Lys Thr Ser Gly His Trp Gly Ser Gly Lys Trp
        355                 360                 365

Ser Arg Val Ser Lys Gly Lys Gly Trp Ala Ser Ser Asn Ala Asp Ala
    370                 375                 380

Asp Ala Ser Ser Ser Ile Ile Ile Gly Gly Leu Lys Arg Gly Gly
385                 390                 395                 400

Leu Gly Ser Glu Ala Ser Ala Ala Ser Ala Glu Ala Glu Ala Ser
                405                 410                 415
```

Ala Gly Thr Leu Leu Leu
            420

<210> SEQ ID NO 35
<211> LENGTH: 392
<212> TYPE: PRT
<213> ORGANISM: Myrmecia forficata

<400> SEQUENCE: 35

Arg Val Ile Glu Ser Ser Ser Ala Ser Gln Ala Ser Ala Ser
1               5                   10                  15

Ala Gly Ser Arg Gly Leu Leu Gly Lys Arg Pro Ile Gly Lys Leu Glu
            20                  25                  30

Trp Gly Lys Glu Glu Lys Lys Leu Glu Glu Leu Asp Glu Glu Ser Leu
        35                  40                  45

Asn Glu Ala Ala Leu Lys Val Gly Ile Lys Asn Gly Gly Leu Asp Val
    50                  55                  60

Ala Lys Gly Ala Ala Val Leu Glu Ala Ala Met Ser Asp Val Ala Thr
65                  70                  75                  80

Leu Thr Asp Gln Arg Ser Leu Val Asp Leu Gly Leu Gly Pro Val Ala
                85                  90                  95

Asn Glu Ala Glu Ile Leu Ala Glu Ala Gln Ala Ala Thr Ser Ala Gln
            100                 105                 110

Ala Gly Ala Val Ala Asn Ser Ala Ala Glu Arg Ala Ile Ala Ala Met
        115                 120                 125

Glu Met Ala Asp Arg Thr Glu Tyr Ile Ala Ala Leu Val Thr Thr Lys
    130                 135                 140

Ala Ala Lys Ala Ala Glu Ala Thr Met Ala Ala Thr Ala Arg Ala Thr
145                 150                 155                 160

Ala Ala Ala Ser Ala Ser Lys Ile Ser Ser Gln Glu Ser Ala Ala Ser
                165                 170                 175

Ala Ala Asn Ala Ala Asn Ala Glu Ala Lys Ala Asn Ala Ala Ser Ile
            180                 185                 190

Ile Ala Asn Lys Ala Asn Ala Val Leu Ala Glu Ala Ala Ala Val Leu
        195                 200                 205

Ala Ala Thr Ala Ala Lys Ala Lys Glu Ser Ala Met Lys Ser Leu Ser
    210                 215                 220

Ala Ala Gln Ala Ala Ala Lys Ala Gln Ala Arg Asn Ala Glu Ala Ser
225                 230                 235                 240

Ala Glu Ala Gln Ile Lys Leu Ser Gln Ala Arg Ala Ala Val Ala Arg
                245                 250                 255

Ala Ala Ala Asp Gln Ala Val Cys Ser Ser Gln Ala Gln Ala Ala Ser
            260                 265                 270

Gln Ile Gln Ser Arg Ala Ser Ala Ser Glu Ser Ala Ala Ser Ala Gln
        275                 280                 285

Ser Glu Thr Asn Thr Ala Ala Ala Glu Ala Val Ala Thr Ala Asp Ala
    290                 295                 300

Glu Ala Ala Ala Gln Ala Glu Ala Trp Val Met Ser Leu Lys Asn Asp
305                 310                 315                 320

Leu Trp Leu His Leu Asn Met Lys Gly Glu Ala Lys Ala Glu Gly Glu
                325                 330                 335

Ala Val Ser Ile Ser Lys Gly His Arg Gly Gly Ile Arg Ser Gly Ser
            340                 345                 350

Ile Ser Glu Ala Ser Ala Glu Ala Ser Ser Asn Val Ser Met Gly Gly
        355                 360                 365

```
Arg His Gly Arg Lys Asp Leu Val Ser Glu Ala Leu Ala Gly Ala Ser
        370                 375                 380

Ala Gly Ser Ser Ala Asp Ser Leu
385                 390

<210> SEQ ID NO 36
<211> LENGTH: 411
<212> TYPE: PRT
<213> ORGANISM: Myrmecia forficata

<400> SEQUENCE: 36

Met Lys Ile Pro Ala Ile Leu Val Thr Ser Leu Leu Ala Trp Gly Leu
1               5                   10                  15

Ala Ser Gly Arg Val Ile Glu Ser Ser Ser Ala Ser Ala Gln Ala
            20                  25                  30

Ser Ala Ser Ala Gly Ser Arg Gly Leu Leu Gly Lys Arg Pro Ile Gly
            35                  40                  45

Lys Leu Glu Trp Gly Lys Glu Glu Lys Lys Leu Glu Leu Asp Glu
    50                  55                  60

Glu Ser Leu Asn Glu Ala Ala Leu Lys Val Gly Ile Lys Asn Gly Gly
65                  70                  75                  80

Leu Asp Val Ala Lys Gly Ala Ala Val Leu Glu Ala Ala Met Ser Asp
                85                  90                  95

Val Ala Thr Leu Thr Asp Gln Arg Ser Leu Val Asp Leu Gly Leu Gly
                100                 105                 110

Pro Val Ala Asn Glu Ala Glu Ile Leu Ala Glu Ala Gln Ala Ala Thr
                115                 120                 125

Ser Ala Gln Ala Gly Ala Val Ala Asn Ser Ala Ala Glu Arg Ala Ile
            130                 135                 140

Ala Ala Met Glu Met Ala Asp Arg Thr Glu Tyr Ile Ala Ala Leu Val
145                 150                 155                 160

Thr Thr Lys Ala Ala Lys Ala Glu Ala Thr Met Ala Ala Thr Ala
                165                 170                 175

Arg Ala Thr Ala Ala Ser Ala Ser Lys Ile Ser Ser Gln Glu Ser
                180                 185                 190

Ala Ala Ser Ala Ala Asn Ala Ala Asn Ala Glu Ala Lys Ala Asn Ala
            195                 200                 205

Ala Ser Ile Ile Ala Asn Lys Ala Asn Ala Val Leu Ala Glu Ala Ala
    210                 215                 220

Ala Val Leu Ala Ala Thr Ala Ala Lys Ala Lys Glu Ser Ala Met Lys
225                 230                 235                 240

Ser Leu Ser Ala Ala Gln Ala Ala Lys Ala Gln Ala Arg Asn Ala
                245                 250                 255

Glu Ala Ser Ala Glu Ala Gln Ile Lys Leu Ser Gln Ala Arg Ala Ala
                260                 265                 270

Val Ala Arg Ala Ala Asp Gln Ala Val Cys Ser Ser Gln Ala Gln
    275                 280                 285

Ala Ala Ser Gln Ile Gln Ser Arg Ala Ser Ala Ser Glu Ser Ala Ala
            290                 295                 300

Ser Ala Gln Ser Glu Thr Asn Thr Ala Ala Glu Ala Val Ala Thr
305                 310                 315                 320

Ala Asp Ala Glu Ala Ala Ala Gln Ala Glu Ala Trp Val Met Ser Leu
                325                 330                 335

Lys Asn Asp Leu Trp Leu His Leu Asn Met Lys Gly Glu Ala Lys Ala
                340                 345                 350
```

```
Glu Gly Glu Ala Val Ser Ile Ser Lys Gly His Arg Gly Gly Ile Arg
            355                 360                 365

Ser Gly Ser Ile Ser Glu Ala Ser Ala Glu Ala Ser Ser Asn Val Ser
        370                 375                 380

Met Gly Gly Arg His Gly Arg Lys Asp Leu Val Ser Glu Ala Leu Ala
385                 390                 395                 400

Gly Ala Ser Ala Gly Ser Ser Ala Asp Ser Leu
            405                 410

<210> SEQ ID NO 37
<211> LENGTH: 375
<212> TYPE: PRT
<213> ORGANISM: Myrmecia forficata

<400> SEQUENCE: 37

Asn Leu Leu Lys Glu Ser Lys Ala Ser Ala Ser Ala Ser Ala Ser Ala
1               5                   10                  15

Ser Ala Arg Ala Ser Gly Lys Lys Asn Leu His Val Leu Pro Leu Pro
            20                  25                  30

Lys Lys Ser Glu His Gly Ile Val Ile Asp Lys Ser Val Phe Asp Ile
        35                  40                  45

Lys Asp Val Val Leu Ser Ala Val Asp Glu Ile Asn Gly Ala Pro Lys
50                  55                  60

Leu Gly Leu Gly Trp Lys Lys Val Ser Met Gly Val Glu Arg Ala Glu
65                  70                  75                  80

Ala Asn Ala Ala Ala Ala Glu Ala Leu Ala Met Ile Lys Lys Ile
                85                  90                  95

Ala Met Ala Arg Ser Ser Ala Tyr Val Gln Ala Trp Ala Ser Ala
            100                 105                 110

Gln Ala Ser Ala Asp Ala Leu Ala Ser Ala Arg Val Ala Gln Ala Ser
            115                 120                 125

Gln Glu Ala Ala Glu Ala Lys Gly Arg Ala Ala Ser Glu Ala Leu Ser
    130                 135                 140

Arg Ala Ile Glu Ala Ser Ser Arg Ala Asp Ala Ala Ala Ala Ala Thr
145                 150                 155                 160

Leu Asp Ala Met Asp Arg Thr Met Glu Asn Ala Arg Ala Ala Asn Ala
                165                 170                 175

Ala Gln Thr Gln Ala Ser Gly Gln Ala Glu Asn Ala Asn Arg Ser Ala
            180                 185                 190

Ala Ala Ile Leu Ala Ala Leu Leu Arg Ile Ala Glu Ala Ser Ala Leu
            195                 200                 205

Asn Asn Glu Ala Ala Val Asn Ala Ala Ala Ala Ala Ala Ala Ser
    210                 215                 220

Ala Leu Gln Ala Lys Ala Asn Ala Ala Ser Gln Ala Thr Ala Arg Ala
225                 230                 235                 240

Ala Gly Gln Ala Ser Thr Ala Ala Glu Glu Ala Gln Ser Ala Gln Glu
                245                 250                 255

Ala Ala Asp Lys Asn Ala Glu Leu Thr Thr Val Met Leu Glu Lys Ala
            260                 265                 270

Ser Ala Asp Gln Gln Ala Ala Ser Ala Arg Ala Asp Tyr Tyr Thr Ala
            275                 280                 285

Ser Thr Glu Ala Glu Ala Ala Ala Gln Ala Ser Ala Ile Asn Ala Leu
    290                 295                 300

Arg Asp Gly Ile Val Val Gly Met Gly Asn Asp Ala Gly Ala Ser Ala
305                 310                 315                 320
```

Gln Ala Met Ala Gln Val Glu Ala Leu Ala Arg Ala Ser Glu His Lys
            325                 330                 335

Ala Leu Gly Glu Lys Lys Gly Leu Val Trp Gly Tyr Gly Ser Lys
        340                 345                 350

Gly Ser Ser Ala Ser Ala Ser Ala Ser Ala Glu Ala Ser
        355                 360                 365

Ser Arg Leu Gly Lys Asp Trp
        370                 375

<210> SEQ ID NO 38
<211> LENGTH: 394
<212> TYPE: PRT
<213> ORGANISM: Myrmecia forficata

<400> SEQUENCE: 38

Met Lys Ile Pro Ala Ile Leu Val Thr Ser Phe Leu Ala Trp Gly Leu
1               5                   10                  15

Ala Ser Gly Asn Leu Leu Lys Glu Ser Lys Ala Ser Ala Ser Ala Ser
            20                  25                  30

Ala Ser Ala Ser Ala Arg Ala Ser Gly Lys Lys Asn Leu His Val Leu
        35                  40                  45

Pro Leu Pro Lys Lys Ser Glu His Gly Ile Val Ile Asp Lys Ser Val
50                  55                  60

Phe Asp Ile Lys Asp Val Val Leu Ser Ala Val Asp Glu Ile Asn Gly
65                  70                  75                  80

Ala Pro Lys Leu Gly Leu Gly Trp Lys Lys Val Ser Met Gly Val Glu
            85                  90                  95

Arg Ala Glu Ala Asn Ala Ala Ala Ala Glu Ala Leu Ala Met Ile
        100                 105                 110

Lys Lys Ile Ala Met Ala Arg Ser Ser Ala Tyr Val Gln Ala Ala Trp
        115                 120                 125

Ala Ser Ala Gln Ala Ser Ala Asp Ala Leu Ala Ser Ala Arg Val Ala
        130                 135                 140

Gln Ala Ser Gln Glu Ala Ala Glu Ala Lys Gly Arg Ala Ala Ser Glu
145                 150                 155                 160

Ala Leu Ser Arg Ala Ile Glu Ala Ser Ser Arg Ala Asp Ala Ala
            165                 170                 175

Ala Thr Leu Asp Ala Met Asp Arg Thr Met Glu Asn Ala Arg Ala
        180                 185                 190

Ala Asn Ala Ala Gln Thr Gln Ala Ser Gly Gln Ala Glu Asn Ala Asn
        195                 200                 205

Arg Ser Ala Ala Ile Leu Ala Ala Leu Leu Arg Ile Ala Glu Ala
        210                 215                 220

Ser Ala Leu Asn Asn Glu Ala Ala Val Asn Ala Ala Ala Ala Ala
225                 230                 235                 240

Ala Ala Ser Ala Leu Gln Ala Lys Ala Asn Ala Ala Ser Gln Ala Thr
            245                 250                 255

Ala Arg Ala Ala Gly Gln Ala Ser Thr Ala Ala Glu Glu Ala Gln Ser
        260                 265                 270

Ala Gln Glu Ala Ala Asp Lys Asn Ala Glu Leu Thr Thr Val Met Leu
        275                 280                 285

Glu Lys Ala Ser Ala Asp Gln Gln Ala Ala Ser Ala Arg Ala Asp Tyr
        290                 295                 300

Tyr Thr Ala Ser Thr Glu Ala Glu Ala Ala Ala Gln Ala Ser Ala Ile
305                 310                 315                 320

```
Asn Ala Leu Arg Asp Gly Ile Val Val Gly Met Gly Asn Asp Ala Gly
                325                 330                 335

Ala Ser Ala Gln Ala Met Ala Gln Val Glu Ala Leu Ala Arg Ala Ser
            340                 345                 350

Glu His Lys Ala Leu Gly Glu Lys Lys Gly Leu Val Trp Gly Tyr
        355                 360                 365

Gly Ser Lys Gly Ser Ser Ala Ser Ala Ser Ala Ser Ala
370                 375                 380

Glu Ala Ser Ser Arg Leu Gly Lys Asp Trp
385                 390

<210> SEQ ID NO 39
<211> LENGTH: 422
<212> TYPE: PRT
<213> ORGANISM: Myrmecia forficata

<400> SEQUENCE: 39

Ser Glu Leu Glu Ser Glu Ala Ser Ala Ala Ser Ala Gln Ala Glu
1               5                   10                  15

Ala Ser Ser Ser Gly Arg Ser Gly Lys Leu Ser Ala Ser Gln Ala Ser
            20                  25                  30

Ala Ser Ala Ser Ala Ser Ala Gly Ser Arg Gly Gly Ser Lys
            35                  40                  45

Gly Gly Trp Gly Gln Leu Arg Arg Gly Asp Val Lys Ser Glu Ala Lys
50                  55                  60

Ser Ala Ala Ala Ile Ala Val Glu Gly Ala Lys Ile Gly Thr Gly Ile
65                  70                  75                  80

Gly Asn Thr Ala Ser Ser Ala Glu Ala Leu Ser Arg Gly Leu Gly
            85                  90                  95

Ile Gly Gln Ala Ala Glu Ala Gln Ala Ala Ala Gly Gln Ala
            100                 105                 110

Glu Val Ala Ala Lys Ser Cys Glu Leu Ala Asp Lys Thr Thr Ala Lys
            115                 120                 125

Ala Val Ala Met Val Glu Ala Ala Ala Glu Ala Glu Ile Glu Val Ala
            130                 135                 140

Asn Gln Glu Val Ala Ala Val Lys Leu Ser Thr Trp Ala Ala Lys Ala
145                 150                 155                 160

Ala Arg Ile Val Glu Glu Asp Ser Ala Ala Val Arg Ala Ala Gly
            165                 170                 175

Lys Leu Leu Leu Ala Ala Arg Ala Ala Ala Ala Glu Arg Arg Ala
            180                 185                 190

Asn Glu Glu Ser Glu Ala Ala Asn Glu Leu Ala Gln Ala Ser Ser Ala
            195                 200                 205

Ala Ala Ala Glu Ala Glu Ala Lys Ala Asn Ala Gly Arg Glu Ala Ala
            210                 215                 220

Ala Ala Ala Leu Ala Ile Ala Glu Ala Ala Val Ala Ile Glu Gln Glu
225                 230                 235                 240

Ala Val Ile Leu Ala Arg Lys Ala Gln Asp Ala Arg Leu Asn Ala Glu
            245                 250                 255

Ala Ala Ala Ala Ala Ala Met Asn Ala Arg Val Ile Ala Ser Ala Glu
            260                 265                 270

Ser Glu Ala Ser Glu Asp Leu Glu Asn Arg Ala Ser Val Ala Arg Ala
            275                 280                 285

Ser Ala Ala Gly Ala Ala Glu Ala Lys Ala Ile Ala Thr Asp Ala Gly
            290                 295                 300
```

Ala Thr Ala Glu Ile Ala Ala Tyr Ser Trp Ala Lys Lys Gly Glu Leu
305                 310                 315                 320

Ile Asn Pro Gly Pro Leu Pro Lys Ile Ile Ser Val Asn Ala Asp Leu
            325                 330                 335

Ser Lys Ser Glu Val Glu Ala Met Lys Ile Thr Arg Gly Gln Val Gln
            340                 345                 350

Glu Val Lys Lys Ile Ser Thr His Lys Gly Gly Trp Gly Trp Gly Lys
        355                 360                 365

Glu Gly Arg Ser Lys Val Ser Ser Asn Ala Ser Ala Arg Ala Ser Ala
        370                 375                 380

Ser Ala Asn Ala Ala Ala Gly Ser Leu Gly Ser Lys Trp Gly Arg Gln
385                 390                 395                 400

Leu Ser Ala Ser Ser Ala Ser Ala Asp Ala Asn Ala Glu Ala Asp Ser
            405                 410                 415

Gln Leu Leu Lys Val Trp
            420

<210> SEQ ID NO 40
<211> LENGTH: 441
<212> TYPE: PRT
<213> ORGANISM: Myrmecia forficata

<400> SEQUENCE: 40

Met Lys Ile Pro Ala Ile Leu Ala Thr Ser Leu Leu Ile Trp Gly Leu
1               5                   10                  15

Val Gly Ala Ser Glu Leu Glu Ser Glu Ala Ser Ala Ala Ala Ser Ala
            20                  25                  30

Gln Ala Glu Ala Ser Ser Ser Gly Arg Ser Gly Lys Leu Ser Ala Ser
        35                  40                  45

Gln Ala Ser Ala Ser Ala Ser Ala Ser Ala Gly Ser Arg Gly
    50                  55                  60

Gly Ser Lys Gly Gly Trp Gly Gln Leu Arg Arg Gly Asp Val Lys Ser
65                  70                  75                  80

Glu Ala Lys Ser Ala Ala Ile Ala Val Glu Gly Ala Lys Ile Gly
                85                  90                  95

Thr Gly Ile Gly Asn Thr Ala Ser Ala Ser Ala Glu Ala Leu Ser Arg
            100                 105                 110

Gly Leu Gly Ile Gly Gln Ala Ala Glu Ala Gln Ala Ala Ala
        115                 120                 125

Gly Gln Ala Glu Val Ala Ala Lys Ser Cys Glu Leu Ala Asp Lys Thr
    130                 135                 140

Thr Ala Lys Ala Val Ala Met Val Glu Ala Ala Glu Ala Glu Ile
145                 150                 155                 160

Glu Val Ala Asn Gln Glu Val Ala Ala Val Lys Leu Ser Thr Trp Ala
                165                 170                 175

Ala Lys Ala Ala Arg Ile Val Glu Glu Asp Ser Ala Ala Val Arg Ala
            180                 185                 190

Ala Ala Gly Lys Leu Leu Leu Ala Ala Arg Ala Ala Ala Ala Glu
        195                 200                 205

Arg Arg Ala Asn Glu Glu Ser Glu Ala Ala Asn Glu Leu Ala Gln Ala
    210                 215                 220

Ser Ser Ala Ala Ala Glu Ala Glu Ala Lys Ala Asn Ala Gly Arg
225                 230                 235                 240

Glu Ala Ala Ala Ala Leu Ala Ile Ala Glu Ala Ala Val Ala Ile
                245                 250                 255

```
Glu Gln Glu Ala Val Ile Leu Ala Arg Lys Ala Gln Asp Ala Arg Leu
            260                 265                 270

Asn Ala Glu Ala Ala Ala Ala Ala Met Asn Ala Arg Val Ile Ala
        275                 280                 285

Ser Ala Glu Ser Glu Ala Ser Glu Asp Leu Glu Asn Arg Ala Ser Val
        290                 295                 300

Ala Arg Ala Ser Ala Ala Gly Ala Ala Glu Ala Lys Ala Ile Ala Thr
305                 310                 315                 320

Asp Ala Gly Ala Thr Ala Glu Ile Ala Ala Tyr Ser Trp Ala Lys Lys
                325                 330                 335

Gly Glu Leu Ile Asn Pro Gly Pro Leu Pro Lys Ile Ile Ser Val Asn
            340                 345                 350

Ala Asp Leu Ser Lys Ser Glu Val Glu Ala Met Lys Ile Thr Arg Gly
            355                 360                 365

Gln Val Gln Glu Val Lys Lys Ile Ser Thr His Lys Gly Gly Trp Gly
        370                 375                 380

Trp Gly Lys Glu Gly Arg Ser Lys Val Ser Ser Asn Ala Ser Ala Arg
385                 390                 395                 400

Ala Ser Ala Ser Ala Asn Ala Ala Ala Gly Ser Leu Gly Ser Lys Trp
                405                 410                 415

Gly Arg Gln Leu Ser Ala Ser Ser Ala Ser Ala Asp Ala Asn Ala Glu
            420                 425                 430

Ala Asp Ser Gln Leu Leu Lys Val Trp
            435                 440

<210> SEQ ID NO 41
<211> LENGTH: 1212
<212> TYPE: DNA
<213> ORGANISM: Myrmecia forficata

<400> SEQUENCE: 41
agcgggccgc gcttactcgg cggcagatcg gccgcgtccg cgtcggcttc cgcttcggct        60
gaggcgtcgg cgggcggttg gaggaaaagc ggcgcatccg cttccgcttc gctaaggct       120 ggtagcagca acatcctcag ccgcgtggga gcttcgaggg cggccgcgac gttggtcgct      180
tccgccgcgg tggaggccaa ggcgggtctc cgtgccggca aggcaaccgc cgaggagcag      240
agggaggctt tggaaatgct caccttgtcc gccgacaaga atgccgaggc gcgtatcctg      300
gccgacgaca cggccgttct ggttcaaggc agcgccgagg cacagtcggt cgccgccgcg      360
aagaccgtcg cggtcgagga agagtccgct tccttggatg cggccgcagt tgaagcggag      420
gtcgcagccg ccacgtcgaa atcgtcggct ggccaagcac tccagtccgc acagaccgcc      480
gcatctgctc tcagaacttc cgccaggagc gccttgacgg ccctcaagct ggcacgcctc      540
caaggcgcgg cttctagcaa cgctgccagg atgatggaaa aggcgctggc cgccacccag      600
gacgcaaatg ccgccgccca gcaagctatg gcggccgaga gtgcagccgc agaagcagcg      660
gctatcgcgg cagcgaaaca atcggaggcg agagacgccg gcgccgaggc caaggccgcc      720
atggcagcac tcatcaccgc ccagaggaat ctcgtgcagg ccaatgccag gcggaaatg       780 gcaagcgagg aagccgaatt ggattcgaag tctagagcgt ccgacgccaa ggtgaacgcc      840
gttgctcgtg cggcctccaa gtccagcata cgcagagatg aacttatcga gatcggcgct      900
gagttcggca aggccagcgg cgaggtgatt tccaccggca cgcgttccaa cggcggtcaa      960
gacgccatcg ccaccgccga ggcatcgagt agcgcgtccg ccgtcggcat caagaaaaca     1020
agcggacact gggggagcgg aaaatggagt cgtgtctcca agggtaaagg atgggcttcc     1080
```

```
tcgaatgcgg acgctgacgc cagcagcagc agcatcatca tcggcggtct caaacgcggc    1140
ggcctcggtt cggaagcctc tgcggcagct tccgcagaag cggaagcttc cgccggcaca    1200
ctcctgctgt aa                                                        1212

<210> SEQ ID NO 42
<211> LENGTH: 1269
<212> TYPE: DNA
<213> ORGANISM: Myrmecia forficata

<400> SEQUENCE: 42
atgaagatcc cagcgataat cgcaacgtcc cttctcctct ggggtttcgc cagcgccagc     60
gggccgcgct tactcggcgg cagatcggcc gcgtccgcgt cggcttccgc ttcggctgag    120
gcgtcggcgg gcggttggag gaaaagcggc gcatccgctt ccgcttccgc taaggctggt    180
agcagcaaca tcctcagccg cgtgggagct cgagggcgg ccgcgacgtt ggtcgcttcc    240
gccgcggtgg aggccaaggc gggtctccgt gccggcaagg caaccgccga ggagcagagg    300
gaggctttgg aaatgctcac cttgtccgcc gacaagaatg ccgaggcgcg tatcctggcc    360
gacgacacgc ccgttctggt tcaaggcagc gccgaggcac agtcggtcgc cgccgcgaag    420
accgtcgcgg tcgaggaaga gtccgcttcc ttggatgcgg ccgcagttga gcggaggtc    480 gcagccgcca cgtcgaaatc gtcggctggc caagcactcc agtccgcaca accgccgca    540 tctgctctca gaacttccgc caggagcgcc ttgacggccc tcaagctggc acgcctccaa    600
ggcgcggctt ctagcaacgc tgccaggatg atggaaaagg cgctggccgc cacccaggac    660
gcaaatgccg ccgcccagca agctatggcg gccgagagtg cagccgcaga agcagcggct    720
atcgcggcag cgaaacaatc ggaggcgaga gacgccggcg ccgaggccaa ggccgccatg    780
gcagcactca tcaccgccca gaggaatctc gtgcaggcca atgccagggc ggaaatggca    840
agcgaggaag ccgaattgga ttcgaagtct agagcgtccg acgccaaggt gaacgccgtt    900
gctcgtgcgg cctccaagtc cagcatacgc agagatgaac ttatcgagat cggcgctgag    960
ttcggcaagg ccagcggcga ggtgatttcc accggcacgc gttccaacgg cggtcaagac   1020
gccatcgcca ccgccgaggc atcgagtagc gcgtccgccg tcggcatcaa gaaaacaagc   1080
ggacactggg ggagcggaaa atggagtcgt gtctccaagg gtaaaggatg gcttcctcg    1140 aatgcggacg ctgacgccag cagcagcagc atcatcatcg gcggtctcaa acgcggcggc   1200
ctcggttcgg aagcctctgc ggcagcttcc gcagaagcgg aagcttccgc cggcacactc   1260
ctgctgtaa                                                            1269

<210> SEQ ID NO 43
<211> LENGTH: 1179
<212> TYPE: DNA
<213> ORGANISM: Myrmecia forficata

<400> SEQUENCE: 43
cgggtcatcg agtccagctc gtcggcttcc gcacaggcgt cggcatcggc cggctcgaga     60
ggcctgctcg gtaaacggcc gattggcaag ctcgagtggg gcaaggagga gaagaaactc    120
gaagaactcg acgaggaatc gctcaatgag gccgctctga aggtcggcat caagaacggc    180
ggattggatg tcgcgaaggg cgcggcagtc ctcgaggcag cgatgagcga cgtcgcgacc    240
cttacggatc agcgttctct tgtggatctc ggtctcggcc ggtcgcgaa cgaggccgag    300 atcctggcg aggcgcaggc cgccacgagc gcccaagctg gcgctgtcgc taatagcgcc    360
gcggagcgtg cgatcgcggc gatggagatg ccgacagaa ccgaatatat tgcggcactt    420
```

```
gtcaccacca aagccgccaa agctgccgag ccactatgg ccgctactgc cgtgccacc       480 gccgccgcct cagcctccaa gatatccagt caggaatcag ccgcatcggc cgctaacgcc      540
gccaacgccg aagccaaggc caacgccgct tccataatcg ctaacaaggc gaacgccgtc      600
ctggctgagg ccgccgccgt actcgcagcc actgctgcca aggccaagga atcggcgatg      660
aaatcgctta gcgccgctca ggccgccgcc aaggcacaag ccaggaacgc cgaggcctcc      720
gccgaagctc agatcaaact tcccaggcc agggccgccg tggcacgcgc tgcagccgat       780
caggccgtct gttcctccca ggctcaggcc gcaagtcaga taatcgag gcatccgca        840 tccgaatccg cggcatcggc acaatcagag accaacaccg ccgcggccga agcggtcgcc     900
accgctgacg ccgaagcggc cgcgcaagct gaagcgtggg tcatgtcgct gaagaacgat     960
ctgtggctgc atctcaacat gaagggtgag gccaaggccg aaggcgaggc cgtttcgatc    1020
agcaaaggac atcgcggcgg tatcaggtcg ggcagcatct cggaagccag cgccgaggca    1080
agcagcaacg tttccatggg cggacgtcat ggacggaagg acctcgtctc tgaagcgtta    1140
gcgggagcat cagcgggcag cagtgccgac tcccttga                            1179

<210> SEQ ID NO 44
<211> LENGTH: 1236
<212> TYPE: DNA
<213> ORGANISM: Myrmecia forficata

<400> SEQUENCE: 44
atgaagattc cagcgatact cgtgacgtct ctcctcgcct ggggattagc cagcggccgg     60
gtcatcgagt ccagctcgtc ggcttccgca caggcgtcgg catcggccgg ctcgagaggc    120
ctgctcggta acggccgat tggcaagctc gagtggggca aggaggagaa gaaactcgaa     180
gaactcgacg aggaatcgct caatgaggcc gctctgaagg tcggcatcaa gaacggcgga    240
ttggatgtcg cgaagggcgc ggcagtcctc gaggcagcga tgagcgacgt cgcgaccctt    300
acggatcagc gttctcttgt ggatctcggt ctcggcccgg tcgcgaacga ggccgagatc    360
ctggcggagg cgcaggccgc cacgagcgcc caagctggcg ctgtcgctaa tagcgccgcg    420
gagcgtgcga tcgcggcgat ggagatggcc gacagaaccg aatatattgc ggcacttgtc    480
accaccaaag ccgccaaagc tgccgaggcc actatgcccg ctactgcccg tgccaccgcc    540
gccgcctcag cctccaagat atccagtcag gaatcagccg catcggccgc taacgccgcc    600
aacgccgaag ccaaggccaa cgccgcttcc ataatcgcta acaaggcgaa cgccgtcctg    660
gctgaggccg ccgccgtact cgcagccact gctgccaagg ccaaggaatc ggcgatgaaa    720
tcgcttagcg ccgctcaggc cgccgccaag gcacaagcca ggaacgccga ggcctccgcc    780
gaagctcaga tcaaactttc ccaggccagg ccgccgtgg cacgcgctgc agccgatcag     840
gccgtctgtt cctcccaggc tcaggccgca agtcagatac aatcgagggc atccgcatcc    900
gaatccgcgg catcggcaca atcagagacc aacaccgccg cggccgaagc ggtcgccacc    960
gctgacgccg aagcggccgc gcaagctgaa gcgtgggtca tgtcgctgaa gaacgatctg   1020
tggctgcatc tcaacatgaa gggtgaggcc aaggccgaag cgaggccgt ttcgatcagc    1080 aaaggacatc gcggcggtat caggtcgggc agcatctcgg aagccagcgc cgaggcaagc    1140
agcaacgttt ccatgggcgg acgtcatgga cggaaggacc tcgtctctga agcgttagcg    1200
ggagcatcag cgggcagcag tgccgactcc ctttga                             1236

<210> SEQ ID NO 45
<211> LENGTH: 1128
```

```
<212> TYPE: DNA
<213> ORGANISM: Myrmecia forficata

<400> SEQUENCE: 45
aatctcctta aggagtcgaa agcttccgcg tccgcgtccg cgtccgcttc cgcgagggcc      60
agcggcaaga agaatcttca cgtgttgcca ttaccgaaga aaagcgagca tggcatcgtg     120
atcgacaagt cggtgttcga catcaaggat gtagtgctga gcgcggtcga cgagatcaac     180
ggcgccccga aactcggcct gggatggaag aaggtcagca tggggtgga gcgcgccgag      240
gcgaacgcag ccgctgccgc cgaggcattg gcgatgatca agaagattgc catggcccgc     300
agcagtgcat acgtccaggc ggcctgggca tcggcccagg catcagctga cgcattggct     360
agcgccaggg tggcacaggc gtctcaggag gctgcggagg caagggtag agcggcttcc      420
gaggcgctct ccagagccat cgaagcatcc tcgcgagccg atgcggcagc cgctgcgacg     480
ctggacgcga tggaccgcac catggagaac gcgagggcgg caaatgccgc gcaaacgcag     540
gccagcggcc aagctgagaa cgcaaatcgc agcgctgctg ccatcctcgc agctctgcta     600
cgtatcgcgg aggcatccgc gttgaacaac gaggccgcgg tcaacgcggc cgcggccgca     660
gccgcagcgt ctgcccttca ggccaaggct aacgcggctt ctcaagcaac cgccagagcc     720
gcaggacagg cgtcgacggc cgccgaagag gcgcaatccg cccaagaagc cgccgataag     780
aacgcggagc tgaccacggt catgctcgaa aaggctagtg ctgatcaaca ggcggcatcc     840
gctagggctg actactacac cgcctcaacc gaggccgaag ccgctgcaca ggcgtctgct     900
atcaacgcac tcagggacgg aatagttgtc ggaatgggaa atgacgctgg cgcatcggcc     960
caagcgatgg cacaggtaga agctctcgct cgcgccagcg agcacaaggc gttaggcgag    1020
aagaagaagg gcctggtttg gggctacgga agcaagggca gtagctccgc cagcgcatcc    1080
gccagcgcct ccgccgaagc atcctcgaga ctcggaaagg actggtag                 1128

<210> SEQ ID NO 46
<211> LENGTH: 1185
<212> TYPE: DNA
<213> ORGANISM: Myrmecia forficata

<400> SEQUENCE: 46
atgaagatac cagcgatact cgtgacgtcc ttcctcgcct ggggactggc cagcgggaat      60
ctccttaagg agtcgaaagc ttccgcgtcc gcgtccgcgt ccgcttccgc gagggccagc     120
ggcaagaaga atcttcacgt gttgccatta ccgaagaaaa gcgagcatgg catcgtgatc     180
gacaagtcgg tgttcgacat caaggatgta gtgctgagcg cggtcgacga gatcaacggc     240
gccccgaaac tcggcctggg atggaagaag gtcagcatgg gggtggagcg cgccgaggcg     300
aacgcagccg ctgccgccga ggcattggcg atgatcaaga gattgccat ggcccgcagc      360
agtgcatacg tccaggcggc ctgggcatcg gcccaggcat cagctgacgc attggctagc     420
gccagggtgg cacaggcgtc tcaggagget gcggaggcaa agggtagagc ggcttccgag     480
gcgctctcca gagccatcga agcatcctcg cgagccgatg cggcagccgc tgcgacgctg     540
gacgcgatgg accgcaccat ggagaacgcg agggcggcaa atgccgcgca aacgcaggcc     600
agcggccaag ctgagaacgc aaatcgcagc gctgctgcca tcctcgcagc tctgctacgt     660
atcgcggagg catccgcgtt gaacaacgag gccgcggtca acgcggccgc ggccgcagcc     720
gcagcgtctg cccttcaggc caaggctaac gcggcttctc aagcaaccgc cagagccgca     780
ggacaggcgt cgacggccgc cgaagaggcg caatccgccc aagaagccgc cgataagaac     840
gcggagctga ccacggtcat gctcgaaaag gctagtgctg atcaacaggc ggcatccgct     900
```

```
agggctgact actacaccgc ctcaaccgag gccgaagccg ctgcacaggc gtctgctatc    960
aacgcactca gggacggaat agttgtcgga atgggaaatg acgctggcgc atcggcccaa   1020
gcgatggcac aggtagaagc tctcgctcgc gccagcgagc acaaggcgtt aggcgagaag   1080
aagaagggcc tggtttgggg ctacggaagc aagggcagta gctccgccag cgcatccgcc   1140
agcgcctccg ccgaagcatc ctcgagactc ggaaaggact ggtag                   1185
```

<210> SEQ ID NO 47
<211> LENGTH: 1269
<212> TYPE: DNA
<213> ORGANISM: Myrmecia forficata

<400> SEQUENCE: 47

```
agcgagctcg aatcggaagc gagtgcggcg gcgtctgcgc aagcggaagc gtcctcgtct     60
ggtcgctccg gcaaactgtc cgcgtctcag gcttccgcca gcgcgtccgc cagcgcgtca    120
gccggcagca gaggtggcag caaaggtggc tggggccagc tccgccgtgg tgatgttaag    180
agcgaggcga agagcgccgc cgcgatcgcg gtcgaaggag ctaaaatcgg caccggaatc    240
ggaaataccg cgtccgcatc cgcggaggcg ctctcacgag gactcggcat cggacaggcg    300
gccgcggagg cgcaagccgc agccgcaggt caggcagagg tcgccgcgaa atcgtgcgaa    360
cttgccgaca agaccaccgc caaagcggtc gccatggtcg aagcggcagc cgaggccgaa    420
atcgaggtgg ccaatcagga ggtcgcagcc gtcaaattat cgacttgggc cgctaaagca    480
gcaaggatag tcgaggaaga cagcgccgcc gtgagggcgg ctgccggcaa attgcttttg    540
gccgcgagag ctgccgccgc cgccgagaga cgcgccaacg aggaatccga ggcggccaac    600
gaacttgctc aagcgtcatc tgccgctgcc gccgaggccg aagccaaagc gaacgccggc    660
cgtgaggccg ctgccgctgc cttggctatc gccgaggccg ccgtcgccat cgaacaagaa    720
gccgtcattt tggctcgcaa ggcacaagat gcccgtttga atgctgaagc cgcagccgcc    780
gctgcgatga acgcccgtgt catcgcttcc gccgaatccg aggccagtga agatctggag    840
aatcgcgcta gtgtggcgcg tgccagtgcg gccggtgccg ctgaggcaaa ggctatcgcc    900
accgatgccg gcgccactgc cgagatcgcg gcctacagtt gggccaagaa gggcgaactg    960
atcaaccccg gcccgttgcc gaagatcatc agcgtcaacg ccgatctgtc caagagcgag   1020
gtcgaggcca tgaagatcac ccggggtcaa gtacaggaag tcaagaaaat cagcactcac   1080
aaaggtggct ggggatgggg aaaggaagga aggtcgaagg tatcttccaa cgctagtgcc   1140
agagctagtg ccagcgccaa tgcagccgcc ggtagcctcg gcagcaaatg gggaagacaa   1200
ctatccgcat catccgcgtc ggctgacgcc aacgccgaag ccgacagcca gttgctgaaa   1260
gtgtggtga                                                           1269
```

<210> SEQ ID NO 48
<211> LENGTH: 1326
<212> TYPE: DNA
<213> ORGANISM: Myrmecia forficata

<400> SEQUENCE: 48

```
atgaagattc cagcgatact tgcgacgtcc ctcctcatct ggggtcttgt cggcgccagc     60
gagctcgaat cggaagcgag tgcggcggcg tctgcgcaag cggaagcgtc ctcgtctggt    120
cgctccggca aactgtccgc gtctcaggct tccgccagcg cgtccgccag cgcgtcagcc    180
ggcagcagag gtggcagcaa aggtggctgg ggccagctcc gccgtggtga tgttaagagc    240
gaggcgaaga gcgccgccgc gatcgcggtc gaaggagcta aaatcggcac cggaatcgga    300
```

```
aataccgcgt ccgcatccgc ggaggcgctc tcacgaggac tcggcatcgg acaggcggcc      360
gcggaggcgc aagccgcagc cgcaggtcag gcagaggtcg ccgcgaaatc gtgcgaactt      420
gccgacaaga ccaccgccaa agcggtcgcc atggtcgaag cggcagccga ggccgaaatc      480
gaggtggcca atcaggaggt cgcagccgtc aaattatcga cttgggccgc taaagcagca      540
aggatagtcg aggaagacag cgccgccgtg agggcggctg ccggcaaatt gcttttggcc      600
gcgagagctg ccgccgccgc cgagagacgc gccaacgagg aatccgaggc ggccaacgaa      660
cttgctcaag cgtcatctgc cgctgccgcc gaggccgaag ccaaagcgaa cgccggccgt      720
gaggccgctg ccgctgcctt ggctatcgcc gaggccgccg tcgccatcga acaagaagcc      780
gtcattttgg ctcgcaaggc acaagatgcc cgtttgaatg ctgaagccgc agccgccgct      840
gcgatgaacg cccgtgtcat cgcttccgcc gaatccgagg ccagtgaaga tctggagaat      900
cgcgctagtg tggcgcgtgc cagtgcggcc ggtgccgctg aggcaaaggc tatcgccacc      960
gatgccggcg ccactgccga gatcgcggcc tacagttggg ccaagaaggg cgaactgatc     1020
aaccccggcc cgttgccgaa gatcatcagc gtcaacgccg atctgtccaa gagcgaggtc     1080
gaggccatga agatcacccg gggtcaagta caggaagtca agaaaatcag cactcacaaa     1140
ggtggctggg gatggggaaa ggaaggaagg tcgaaggtat cttccaacgc tagtgccaga     1200
gctagtgcca cgccaatgc agccgccggt agcctcggca gcaaatgggg aagacaacta     1260
tccgcatcat ccgcgtcggc tgacgccaac gccgaagccg acagccagtt gctgaaagtg     1320
tggtga                                                                1326
```

<210> SEQ ID NO 49
<211> LENGTH: 372
<212> TYPE: PRT
<213> ORGANISM: Oecophylla smaragdina

<400> SEQUENCE: 49

```
Ser Lys Ser Tyr Leu Leu Gly Ser Ser Ala Ser Ala Ser Ala
1               5                   10                  15

Ser Ala Ser Ala Ser Ala Gly Gly Ser Thr Gly Gly Val Gly Val Gly
            20                  25                  30

Ser Val Ile Ser Gly Gly Asn Asn Ile Ile Arg Gly Ala Ser Thr Thr
        35                  40                  45

Ser Val Thr Leu Ala Ala Ala Ala Glu Ala Lys Ala Ala Leu Asn
    50                  55                  60

Ala Gly Lys Ala Thr Val Glu Glu Gln Arg Glu Ala Leu Gln Leu Leu
65                  70                  75                  80

Thr Ala Ser Ala Glu Lys Asn Ala Glu Ala Arg Ser Leu Ala Asp Asp
                85                  90                  95

Ala Ala Val Leu Val Gln Gly Ala Ala Glu Ala Gln Ser Val Ala Ala
            100                 105                 110

Ala Lys Thr Val Ala Val Glu Gln Gly Ser Asn Ser Leu Asp Ala Ala
        115                 120                 125

Ala Ala Glu Ala Glu Ala Ala Ala Ala Ser Arg Val Ser Ala Gln
    130                 135                 140

Gln Ala Leu Gln Ala Ala Gln Thr Ser Ala Ala Ile Gln Thr Ala
145                 150                 155                 160

Ala Gly Ser Ala Leu Thr Ala Leu Lys Leu Ala Arg Lys Gln Glu Ala
                165                 170                 175

Glu Ser Asn Asn Ala Ala Glu Gln Ala Asn Lys Ala Leu Ala Leu Ser
            180                 185                 190
```

```
Arg Ala Ala Ser Ala Ala Thr Gln Arg Ala Val Ala Ala Gln Asn Ala
            195                 200                 205

Ala Ala Ala Ser Ala Ala Ser Ala Gly Ala Ala Gln Ala Glu Ala Arg
    210                 215                 220

Asn Ala Tyr Ala Lys Ala Lys Ala Ala Ile Ala Ala Leu Thr Ala Ala
225                 230                 235                 240

Gln Arg Asn Tyr Ala Ala Lys Ala Ser Ala Ser Ala Gly Ser Val
            245                 250                 255

Val Ala Glu Gln Asp Ala Gln Ser Arg Ala Ala Asp Ala Glu Val Asn
            260                 265                 270

Ala Val Ala Gln Ala Ala Ala Arg Ala Ser Val Arg Asn Gln Glu Ile
    275                 280                 285

Val Glu Ile Gly Ala Glu Phe Gly Asn Ala Ser Gly Gly Val Ile Ser
            290                 295                 300

Thr Gly Thr Arg Ser Ser Gly Gly Lys Gly Val Ser Val Thr Ala Gly
305                 310                 315                 320

Ala Gln Ala Ser Ala Ser Ala Ser Ala Thr Ser Ser Ser Ser Ser Ser
            325                 330                 335

Ser Gly Ile Asn Lys Gly His Pro Arg Trp Gly His Asn Trp Gly Leu
            340                 345                 350

Gly Ser Ser Glu Ala Ser Ala Asn Ala Glu Ala Glu Ser Ser Ala Ser
            355                 360                 365

Ser Tyr Ser Ser
    370

<210> SEQ ID NO 50
<211> LENGTH: 391
<212> TYPE: PRT
<213> ORGANISM: Oecophylla smaragdina

<400> SEQUENCE: 50

Met Lys Ile Pro Ala Ile Ile Ala Thr Thr Leu Leu Leu Trp Gly Phe
1               5                   10                  15

Ala Asp Ala Ser Lys Ser Tyr Leu Leu Gly Ser Ser Ala Ser Ala Ser
            20                  25                  30

Ala Ser Ala Ser Ala Ser Ala Ser Ala Gly Gly Ser Thr Gly Gly Val
    35                  40                  45

Gly Val Gly Ser Val Ile Ser Gly Gly Asn Asn Ile Ile Arg Gly Ala
    50                  55                  60

Ser Thr Thr Ser Val Thr Leu Ala Ala Ala Ala Glu Ala Lys Ala
65                  70                  75                  80

Ala Leu Asn Ala Gly Lys Ala Thr Val Glu Glu Gln Arg Glu Ala Leu
            85                  90                  95

Gln Leu Leu Thr Ala Ser Ala Glu Lys Asn Ala Glu Ala Arg Ser Leu
            100                 105                 110

Ala Asp Asp Ala Ala Val Leu Val Gln Gly Ala Ala Glu Ala Gln Ser
    115                 120                 125

Val Ala Ala Ala Lys Thr Val Ala Val Glu Gln Gly Ser Asn Ser Leu
    130                 135                 140

Asp Ala Ala Ala Glu Ala Glu Ala Ala Ala Ala Ser Arg Val
145                 150                 155                 160

Ser Ala Gln Gln Ala Leu Gln Ala Ala Gln Thr Ser Ala Ala Ile
            165                 170                 175

Gln Thr Ala Ala Gly Ser Ala Leu Thr Ala Leu Lys Leu Ala Arg Lys
            180                 185                 190
```

-continued

Gln Glu Ala Glu Ser Asn Asn Ala Ala Glu Gln Ala Asn Lys Ala Leu
          195                 200                 205

Ala Leu Ser Arg Ala Ala Ser Ala Ala Thr Gln Arg Ala Val Ala Ala
  210                 215                 220

Gln Asn Ala Ala Ala Ala Ser Ala Ala Ser Ala Gly Ala Ala Gln Ala
225                 230                 235                 240

Glu Ala Arg Asn Ala Tyr Ala Lys Ala Ala Ile Ala Ala Leu
              245                 250                 255

Thr Ala Ala Gln Arg Asn Tyr Ala Ala Ala Lys Ala Ser Ala Ser Ala
              260                 265                 270

Gly Ser Val Val Ala Glu Gln Asp Ala Gln Ser Arg Ala Ala Asp Ala
          275                 280                 285

Glu Val Asn Ala Val Ala Gln Ala Ala Arg Ala Ser Val Arg Asn
          290                 295                 300

Gln Glu Ile Val Glu Ile Gly Ala Glu Phe Gly Asn Ala Ser Gly Gly
305                 310                 315                 320

Val Ile Ser Thr Gly Thr Arg Ser Ser Gly Gly Lys Gly Val Ser Val
              325                 330                 335

Thr Ala Gly Ala Gln Ala Ser Ala Ser Ala Ser Ala Thr Ser Ser Ser
              340                 345                 350

Ser Ser Ser Ser Gly Ile Asn Lys Gly His Pro Arg Trp Gly His Asn
          355                 360                 365

Trp Gly Leu Gly Ser Ser Glu Ala Ser Ala Asn Ala Glu Ala Glu Ser
  370                 375                 380

Ser Ala Ser Ser Tyr Ser Ser
385                 390

<210> SEQ ID NO 51
<211> LENGTH: 381
<212> TYPE: PRT
<213> ORGANISM: Oecophylla smaragdina

<400> SEQUENCE: 51

Gly Val Ile Gly Pro Asp Thr Ser Ser Ser Gln Ala Ser Ala Ser
1               5                   10                  15

Ala Ser Ala Ser Ala Ser Ala Ser Ser Ala Ser Ile Gly
          20                  25                  30

Tyr Asn Glu Leu His Lys Ser Ile Asn Ala Pro Ala Leu Ala Val Gly
              35                  40                  45

Val Lys Asn Gly Gly Val Asp Val Ala Lys Gly Ala Ala Val Val Glu
  50                  55                  60

Ser Ala Ile Ser Asp Val Ser Thr Leu Thr Asp Asp Arg Thr Leu Asn
65                  70                  75                  80

Gly Leu Ala Ile Ile Gly Asn Ser Ala Glu Ser Leu Ala Arg Ala Gln
              85                  90                  95

Ala Ser Ser Ser Ala Ser Ala Gly Ala Lys Ala Asn Ala Leu Ile Lys
          100                 105                 110

Gln Ser Ile Ala Ala Ile Glu Ile Thr Glu Lys Ala Glu Tyr Leu Ala
          115                 120                 125

Ser Ile Val Ala Thr Lys Ala Ala Lys Ala Ala Glu Ala Thr Ala Ala
  130                 135                 140

Ala Thr Ala Arg Ala Thr Ala Val Ala Glu Ala Ala Lys Val Ser Ser
145                 150                 155                 160

Glu Gln Phe Ala Ala Glu Ala Arg Ala Ala Ala Asp Ala Glu Ala Lys
              165                 170                 175

-continued

```
Ala Asn Ala Ala Ser Ile Ile Ala Asn Lys Ala Asn Ala Val Leu Ala
                180                 185                 190

Glu Ala Ala Thr Gly Leu Ser Ala Ser Ala Gly Lys Ala Gln Gln Ser
            195                 200                 205

Ala Thr Arg Ala Leu Gln Ala Arg Ala Ala Lys Ala Gln Ala
        210                 215                 220

Glu Leu Thr Gln Lys Ala Ala Gln Ile Leu Val Leu Ile Ala Glu Ala
225                 230                 235                 240

Lys Ala Ala Val Ser Arg Ala Ser Ala Asp Gln Ser Val Cys Thr Ser
                245                 250                 255

Gln Ala Gln Ala Ala Ser Gln Ile Gln Ser Arg Ala Ser Ala Ala Glu
                260                 265                 270

Ser Ala Ala Ser Ala Gln Ser Glu Ala Asn Thr Ile Ala Ala Glu Ala
                275                 280                 285

Val Ala Arg Ala Asp Ala Glu Ala Ser Gln Ala Gln Ala Trp Ala
            290                 295                 300

Glu Ser Phe Lys Arg Glu Leu Ser Ser Val Val Leu Glu Ala Glu Ala
305                 310                 315                 320

Asn Ala Ser Ala Ser Ala Gly Ala Leu Ala Ser Gly Ser Ser
                325                 330                 335

Ser Ser Gly Ala Ser Ser Ala Asp Ala Ser Ala Gly Ala Ser Ser
                340                 345                 350

Tyr Gly Ser Leu Gly Gly Tyr Arg His Gly Gly Ser Phe Ser Glu Ala
                355                 360                 365

Ser Ala Ala Ser Ala Ala Ser Arg Ala Glu Ala Ala
            370                 375                 380

<210> SEQ ID NO 52
<211> LENGTH: 400
<212> TYPE: PRT
<213> ORGANISM: Oecophylla smaragdina

<400> SEQUENCE: 52

Met Lys Ile Pro Ala Ile Phe Val Thr Ser Leu Leu Ala Trp Gly Leu
1               5                   10                  15

Ala Ser Gly Gly Val Ile Gly Pro Asp Thr Ser Ser Ser Ser Gln Ala
                20                  25                  30

Ser Ala Ser Ala Ser Ala Ser Ala Ser Ala Ser Ser Ser Ala
            35                  40                  45

Ser Ile Gly Tyr Asn Glu Leu His Lys Ser Ile Asn Ala Pro Ala Leu
        50                  55                  60

Ala Val Gly Val Lys Asn Gly Val Asp Val Ala Lys Gly Ala Ala
65                  70                  75                  80

Val Val Glu Ser Ala Ile Ser Asp Val Ser Thr Leu Thr Asp Asp Arg
                85                  90                  95

Thr Leu Asn Gly Leu Ala Ile Ile Gly Asn Ser Ala Glu Ser Leu Ala
            100                 105                 110

Arg Ala Gln Ala Ser Ser Ser Ala Ser Ala Gly Ala Lys Ala Asn Ala
            115                 120                 125

Leu Ile Lys Gln Ser Ile Ala Ala Ile Glu Ile Thr Glu Lys Ala Glu
        130                 135                 140

Tyr Leu Ala Ser Ile Val Ala Thr Lys Ala Lys Ala Ala Glu Ala
145                 150                 155                 160

Thr Ala Ala Ala Thr Ala Arg Ala Thr Ala Val Ala Glu Ala Ala Lys
                165                 170                 175
```

```
Val Ser Ser Glu Gln Phe Ala Ala Glu Ala Arg Ala Ala Asp Ala
        180                 185                 190

Glu Ala Lys Ala Asn Ala Ala Ser Ile Ile Ala Asn Lys Ala Asn Ala
        195                 200                 205

Val Leu Ala Glu Ala Ala Thr Gly Leu Ser Ala Ser Ala Gly Lys Ala
210                 215                 220

Gln Gln Ser Ala Thr Arg Ala Leu Gln Ala Ala Arg Ala Ala Lys
225                 230                 235                 240

Ala Gln Ala Glu Leu Thr Gln Lys Ala Ala Gln Ile Leu Val Leu Ile
            245                 250                 255

Ala Glu Ala Lys Ala Ala Val Ser Arg Ala Ser Ala Asp Gln Ser Val
            260                 265                 270

Cys Thr Ser Gln Ala Gln Ala Ala Ser Gln Ile Gln Ser Arg Ala Ser
            275                 280                 285

Ala Ala Glu Ser Ala Ala Ser Ala Gln Ser Glu Ala Asn Thr Ile Ala
            290                 295                 300

Ala Glu Ala Val Ala Arg Ala Asp Ala Glu Ala Ala Ser Gln Ala Gln
305                 310                 315                 320

Ala Trp Ala Glu Ser Phe Lys Arg Glu Leu Ser Ser Val Val Leu Glu
                325                 330                 335

Ala Glu Ala Asn Ala Ser Ala Ser Ala Ser Ala Gly Ala Leu Ala Ser
            340                 345                 350

Gly Ser Ser Ser Ser Gly Ala Ser Ser Ala Asp Ala Ser Ala Gly
            355                 360                 365

Ala Ser Ser Tyr Gly Ser Leu Gly Gly Tyr Arg His Gly Gly Ser Phe
        370                 375                 380

Ser Glu Ala Ser Ala Ala Ala Ser Ala Ala Ser Arg Ala Glu Ala Ala
385                 390                 395                 400

<210> SEQ ID NO 53
<211> LENGTH: 376
<212> TYPE: PRT
<213> ORGANISM: Oecophylla smaragdina

<400> SEQUENCE: 53

Gly Val Pro Lys Glu Leu Gly Thr Ser Ile Ser Ser Ala Ser Ala Ser
1               5                   10                  15

Ala Ser Ala Ser Ala Ser Ala Thr Ala Ser Ser Ser Ser Lys Asn Val
            20                  25                  30

His Leu Leu Pro Leu Lys Ser Glu His Gly Ile Val Ile Asp Lys Ser
        35                  40                  45

Lys Phe Asn Ile Arg Lys Val Val Leu Ser Ala Ile Asp Glu Ile Asn
    50                  55                  60

Gly Ala Pro Asn Ile Gly Leu Gly Leu Lys Gln Val Ser Leu Ala Leu
65                  70                  75                  80

Ala Lys Ala Gln Ala Ser Ala Gln Ser Ser Ala Glu Ala Leu Ala Ile
                85                  90                  95

Ile Lys Lys Ile Val Ala Leu Leu Ile Ser Ala Tyr Val Arg Ala Ala
            100                 105                 110

Glu Ala Ala Ala Arg Ala Ser Ala Glu Ala Leu Ala Thr Val Arg Ala
        115                 120                 125

Ala Glu Gln Ala Gln Lys Ile Ala Glu Ala Lys Gly Arg Ala Ala Ala
    130                 135                 140

Glu Ala Leu Ser Glu Leu Val Glu Ala Ser Gln Lys Ala Asp Ala Ala
145                 150                 155                 160
```

```
Ala Ala Gly Thr Thr Asp Ala Ile Glu Arg Thr Tyr Gln Asp Ala Arg
                165                 170                 175

Ala Ala Thr Ser Ala Gln Thr Lys Ala Ser Gly Glu Ala Glu Asn Ala
            180                 185                 190

Asn Arg Asn Ala Ala Ala Thr Leu Ala Ala Val Leu Ser Ile Ala Lys
        195                 200                 205

Ala Ala Ser Gly Gln Gly Gly Thr Arg Ala Ala Val Asp Ala Ala Ala
    210                 215                 220

Ala Ala Ala Ala Ala Ala Leu His Ala Lys Ala Asn Ala Val Ser
225                 230                 235                 240

Gln Ala Thr Ser Lys Ala Ala Glu Ala Arg Val Ala Ala Glu Glu
                245                 250                 255

Ala Ala Ser Ala Gln Ala Ser Ala Ser Ala Gln Leu Thr Ala
            260                 265                 270

Gln Leu Glu Glu Lys Val Ser Ala Asp Gln Gln Ala Ala Ser Ala Ser
        275                 280                 285

Thr Asp Thr Ser Ala Ala Ile Ala Glu Ala Glu Ala Ala Ala Leu Ala
    290                 295                 300

Ser Thr Val Asn Ala Ile Asn Asp Gly Val Val Ile Gly Leu Gly Asn
305                 310                 315                 320

Thr Ala Ser Ser Ala Gln Ala Ser Ala Gln Ala Ser Ala Leu Ala
                325                 330                 335

Arg Ala Lys Asn Ala Arg Pro Lys Ile Lys Gly Trp Tyr Lys Ile Gly
            340                 345                 350

Gly Ala Thr Ser Ala Ser Ala Ser Ala Ser Ala Ser Ala Gln
        355                 360                 365

Ser Ser Ser Gln Gly Leu Val Tyr
    370                 375

<210> SEQ ID NO 54
<211> LENGTH: 395
<212> TYPE: PRT
<213> ORGANISM: Oecophylla smaragdina

<400> SEQUENCE: 54

Met Lys Ile Pro Ala Ile Leu Val Thr Ser Phe Leu Ala Trp Gly Leu
1               5                   10                  15

Ala Ser Gly Gly Val Pro Lys Glu Leu Gly Thr Ser Ile Ser Ser Ala
            20                  25                  30

Ser Ala Ser Ala Ser Ala Ser Ala Thr Ala Ser Ser Ser Ser
        35                  40                  45

Lys Asn Val His Leu Leu Pro Leu Lys Ser Glu His Gly Ile Val Ile
    50                  55                  60

Asp Lys Ser Lys Phe Asn Ile Arg Lys Val Val Leu Ser Ala Ile Asp
65                  70                  75                  80

Glu Ile Asn Gly Ala Pro Asn Ile Gly Leu Gly Leu Lys Gln Val Ser
                85                  90                  95

Leu Ala Leu Ala Lys Ala Gln Ser Ala Gln Ser Ser Ala Glu Ala
            100                 105                 110

Leu Ala Ile Ile Lys Lys Ile Val Ala Leu Leu Ile Ser Ala Tyr Val
        115                 120                 125

Arg Ala Ala Glu Ala Ala Ala Arg Ser Ala Glu Ala Leu Ala Thr
    130                 135                 140

Val Arg Ala Ala Glu Gln Ala Gln Lys Ile Ala Glu Ala Lys Gly Arg
145                 150                 155                 160
```

```
Ala Ala Ala Glu Ala Leu Ser Glu Leu Val Glu Ala Ser Gln Lys Ala
            165                 170                 175

Asp Ala Ala Ala Gly Thr Thr Asp Ala Ile Glu Arg Thr Tyr Gln
            180                 185                 190

Asp Ala Arg Ala Ala Thr Ser Ala Gln Thr Lys Ala Ser Gly Glu Ala
            195                 200                 205

Glu Asn Ala Asn Arg Asn Ala Ala Ala Thr Leu Ala Ala Val Leu Ser
210                 215                 220

Ile Ala Lys Ala Ala Ser Gly Gln Gly Gly Thr Arg Ala Ala Val Asp
225                 230                 235                 240

Ala Ala Ala Ala Ala Ala Ala Ala Leu His Ala Lys Ala Asn
            245                 250                 255

Ala Val Ser Gln Ala Thr Ser Lys Ala Ala Glu Ala Arg Val Ala
            260                 265                 270

Ala Glu Glu Ala Ala Ser Ala Gln Ala Ser Ala Ser Ala Gln
            275                 280                 285

Leu Thr Ala Gln Leu Glu Glu Lys Val Ser Ala Asp Gln Gln Ala Ala
            290                 295                 300

Ser Ala Ser Thr Asp Thr Ser Ala Ala Ile Ala Glu Ala Glu Ala Ala
305                 310                 315                 320

Ala Leu Ala Ser Thr Val Asn Ala Ile Asn Asp Gly Val Val Ile Gly
            325                 330                 335

Leu Gly Asn Thr Ala Ser Ser Ala Gln Ala Ser Ala Gln Ala Ser
            340                 345                 350

Ala Leu Ala Arg Ala Lys Asn Ala Arg Pro Lys Ile Lys Gly Trp Tyr
            355                 360                 365

Lys Ile Gly Gly Ala Thr Ser Ala Ser Ala Ser Ala Ser Ala
370                 375                 380

Ser Ala Gln Ser Ser Ser Gln Gly Leu Val Tyr
385                 390                 395

<210> SEQ ID NO 55
<211> LENGTH: 424
<212> TYPE: PRT
<213> ORGANISM: Oecophylla smaragdina

<400> SEQUENCE: 55

Ser Glu Leu Val Gly Ser Asp Ala Ser Ala Thr Ala Ser Ala Glu Ala
1               5                   10                  15

Ser Ala Ser Ser Ala Tyr Gly Ser Lys Tyr Gly Ile Gly Ser Gly
            20                  25                  30

Ala Val Ser Gly Ala Ser Ala Ser Ala Ser Ala Ser Ala Ser
            35                  40                  45

Ala Ser Ala Ser Ser Ala Pro Ala Ile Glu Gly Val Asn Val Gly Thr
50                  55                  60

Gly Val Ser Asn Thr Ala Ser Ala Ser Ala Glu Ala Leu Ser Arg Gly
65                  70                  75                  80

Leu Gly Ile Gly Gln Ala Ala Glu Ala Gln Ala Ala Ala Gly
            85                  90                  95

Gln Ala Ala Ile Ala Ala Lys Ser Cys Ala Leu Ala Ala Lys Ser Thr
            100                 105                 110

Ala Gln Ala Val Ala Leu Val Glu Lys Val Ala Arg Ala Glu Val Asp
            115                 120                 125

Leu Ala Glu Ser Ala Arg Lys Ala Thr Arg Leu Ser Ala Glu Ala Ala
130                 135                 140
```

Lys Ala Ala Ala Glu Val Glu Lys Asp Leu Val Gly Leu Arg Gly Ala
145                 150                 155                 160

Ala Gly Lys Leu Asn Leu Ala Ala Arg Ala Gly Ser Lys Ala Gln Glu
            165                 170                 175

Arg Ala Asn Glu Asp Ser Ile Glu Asn Glu Leu Ala Gln Ala Thr
                180                 185                 190

Ala Ala Ala Gly Ala Glu Ala Glu Ala Lys Ala Asn Ala Ala Gln Glu
                195                 200                 205

Ala Gly Ala Ser Ala Leu Ala Ile Ala Gln Ala Leu Asn Ile Glu
        210                 215                 220

Gln Glu Thr Val Lys Leu Thr Arg Gln Ala Gln Asn Thr Arg Leu Arg
225                 230                 235                 240

Ser Glu Asn Ile Leu Ala Ala Ser Asn Ala Arg Ala Ile Ala Ser
                245                 250                 255

Ala Glu Ala Glu Ala Ser Ser Asp Leu Asn Asn Arg Ala Asn Ala Ala
                260                 265                 270

Arg Ser Asn Ala Arg Ala Ala Glu Thr Arg Ala Val Ala Thr Glu
        275                 280                 285

Ala Ala Ser Thr Ala Glu Ile Ala Ala Tyr Ser Ser Glu Lys Gly
        290                 295                 300

Glu Ile Thr Asn Pro Gly Pro Leu Pro Lys Ile Val Ser Val Thr Ala
305                 310                 315                 320

Gly Leu Thr Gln Asn Glu Ile Ala Gly Ser Gly Ala Ala Ala Ser Ala
                325                 330                 335

Ser Ala Ser Ala Leu Ala Ser Ala Ser Ala Gly Ala Gly Ala Gly Ala
                340                 345                 350

Gly Ala Gly Ala Gly Ala Ser Ala Gly Ala Gly Ala Val Ala Gly Ala
        355                 360                 365

Gly Ala Gly Ala Gly Ala Gly Ala Ser Ala Gly Ala Ser Ala Gly Ala
        370                 375                 380

Asn Ala Gly Ala Gly Ala Ser Ser Leu Leu Leu Pro Gln Ser Lys Leu
385                 390                 395                 400

His Pro Ile Ser Arg Ser Ser Ala Ser Ala Ser Ala Ser Ala Glu Ala
                405                 410                 415

Glu Ala Asn Ser Ser Ala Tyr Ala
            420

<210> SEQ ID NO 56
<211> LENGTH: 443
<212> TYPE: PRT
<213> ORGANISM: Oecophylla smaragdina

<400> SEQUENCE: 56

Met Lys Ile Pro Ala Ile Leu Ala Thr Ser Leu Phe Val Trp Gly Leu
1               5                   10                  15

Val Gly Ala Ser Glu Leu Val Gly Ser Asp Ala Ser Ala Thr Ala Ser
                20                  25                  30

Ala Glu Ala Ser Ala Ser Ser Ser Ala Tyr Gly Ser Lys Tyr Gly Ile
            35                  40                  45

Gly Ser Gly Ala Val Ser Gly Ala Ser Ala Ser Ala Ser Ala
        50                  55                  60

Ser Ala Ser Ala Ser Ala Ser Ser Ala Pro Ala Ile Glu Gly Val Asn
65                  70                  75                  80

Val Gly Thr Gly Val Ser Asn Thr Ala Ser Ala Ser Ala Glu Ala Leu
                85                  90                  95

Ser Arg Gly Leu Gly Ile Gly Gln Ala Ala Glu Ala Gln Ala Ala
            100                 105                 110

Ala Ala Gly Gln Ala Ala Ile Ala Ala Lys Ser Cys Ala Leu Ala Ala
            115                 120                 125

Lys Ser Thr Ala Gln Ala Val Ala Leu Val Glu Lys Val Ala Arg Ala
130                 135                 140

Glu Val Asp Leu Ala Glu Ser Ala Arg Lys Ala Thr Arg Leu Ser Ala
145                 150                 155                 160

Glu Ala Ala Lys Ala Ala Ala Glu Val Glu Lys Asp Leu Val Gly Leu
                165                 170                 175

Arg Gly Ala Ala Gly Lys Leu Asn Leu Ala Ala Arg Ala Gly Ser Lys
            180                 185                 190

Ala Gln Glu Arg Ala Asn Glu Asp Ser Ile Glu Ala Asn Glu Leu Ala
            195                 200                 205

Gln Ala Thr Ala Ala Ala Gly Ala Glu Ala Glu Ala Lys Ala Asn Ala
            210                 215                 220

Ala Gln Glu Ala Gly Ala Ser Ala Leu Ala Ile Ala Gln Ala Ala Leu
225                 230                 235                 240

Asn Ile Glu Gln Glu Thr Val Lys Leu Thr Arg Gln Ala Gln Asn Thr
                245                 250                 255

Arg Leu Arg Ser Glu Asn Ile Leu Ala Ala Ser Asn Ala Arg Ala
            260                 265                 270

Ile Ala Ser Ala Glu Ala Glu Ala Ser Ser Asp Leu Asn Asn Arg Ala
            275                 280                 285

Asn Ala Ala Arg Ser Asn Ala Arg Ala Ala Glu Thr Arg Ala Val
            290                 295                 300

Ala Thr Glu Ala Ala Ser Thr Ala Glu Ile Ala Ala Tyr Ser Ser Ser
305                 310                 315                 320

Glu Lys Gly Glu Ile Thr Asn Pro Gly Pro Leu Pro Lys Ile Val Ser
                325                 330                 335

Val Thr Ala Gly Leu Thr Gln Asn Glu Ile Ala Gly Ser Gly Ala Ala
            340                 345                 350

Ala Ser Ala Ser Ala Ser Ala Leu Ala Ser Ala Ser Ala Gly Ala Gly
            355                 360                 365

Ala Gly Ala Gly Ala Gly Ala Gly Ala Ser Ala Gly Ala Gly Ala Val
            370                 375                 380

Ala Gly Ala Gly Ala Gly Ala Gly Ala Gly Ser Ala Gly Ala Ser
385                 390                 395                 400

Ala Gly Ala Asn Ala Gly Ala Gly Ala Ser Ser Leu Leu Leu Pro Gln
                405                 410                 415

Ser Lys Leu His Pro Ile Ser Arg Ser Ser Ala Ser Ala Ser Ala Ser
            420                 425                 430

Ala Glu Ala Glu Ala Asn Ser Ser Ala Tyr Ala
            435                 440

<210> SEQ ID NO 57
<211> LENGTH: 1119
<212> TYPE: DNA
<213> ORGANISM: Oecophylla smaragdina

<400> SEQUENCE: 57
agcaagtcgt acctcttagg ctcatccgcg tctgcttccg cttccgcttc cgcctcggca      60
tcagcgggag gaagcaccgg cggcgtcggc gtcggatctg taatatccgg tggcaacaac     120
atcatcagag gagcttcgac cacatccgtg acattggcag ccgccgcagc ggaggccaag     180

```
gcagctctga atgctggaaa agcgactgtc gaagagcaaa gggaagcgtt acagttgctc      240
accgcgtccg ctgaaaaaaa cgccgaggcg cgttccttgg ccgacgatgc ggccgttcta      300
gttcagggtg ccgctgaggc gcaatcggtc gccgccgcga agacggtcgc ggtcgagcaa      360
ggatccaact ctctggatgc agctgcagcc gaagcggaag ccgccgccgc cgcatccagg      420
gtatcggccc agcaggcact ccaggccgcg cagacctccg ccgccgctat tcaaaccgct      480
gccggtagcg ccctgacggc tctcaaattg gcacgcaaac aggaagcgga atccaataat      540
gccgccgaac aggcaaataa agcattggcc ttaagtcgcg cagccagcgc tgccactcaa      600
cgagccgtgg cagctcagaa cgcggctgcc gcatcagcgg cttcggctgg agccgcacaa      660
gctgaggcaa ggaacgccta cgccaaagcc aaagcagcga tagctgctct tacgccgcc       720 caaagaaatt acgccgcggc caaggctagc gcaagcgcgg gtagcgtggt ggccgaacaa      780
gatgctcaat ctagagcggc cgatgccgag gtgaacgccg ttgcccaagc cgctgcccga      840
gccagcgttc gcaatcagga gatcgttgaa atcggcgcg aattcggcaa cgccagcggc       900
ggagtgatct cgaccggcac acgttcttcc ggaggcaagg gtgtctccgt taccgctgga      960
gctcaggcta gcgcgtccgc ttccgcgacc tcctcctcct cctcctcctc cggcatcaac     1020
aaaggacatc ccagatgggg gcacaattgg ggtttaggtt cttcggaagc gtcagcaaac     1080
gctgaagccg aaagcagcgc ttcctcttat tcatcttaa                            1119
```

<210> SEQ ID NO 58
<211> LENGTH: 1176
<212> TYPE: DNA
<213> ORGANISM: Oecophylla smaragdina

<400> SEQUENCE: 58

```
atgaagatcc cagcgataat cgcaacgacc ctccttctct ggggtttcgc cgacgccagc       60
aagtcgtacc tcttaggctc atccgcgtct gcttccgctt ccgcttccgc ctcggcatca      120
gcgggaggaa gcaccggcgg cgtcggcgtc ggatctgtaa tatccggtgg caacaacatc      180
atcagaggag cttcgaccac atccgtgaca ttggcagccg ccgcagcgga ggccaaggca      240
gctctgaatg ctggaaaagc gactgtcgaa gagcaaaggg aagcgttaca gttgctcacc      300
gcgtccgctg aaaaaaacgc cgaggcgcgt tccttggccg acgatgcggc cgttctagtt      360
cagggtgccg ctgaggcgca atcggtcgcc gccgcgaaga cggtcgcggt cgagcaagga      420
tccaactctc tggatgcagc tgcagccgaa gcggaagccg ccgccgccgc atccagggta      480
tcggcccagc aggcactcca ggccgcgcag acctccgccg ccgctattca aaccgctgcc      540
ggtagcgccc tgacggctct caaattggca cgcaaacagg aagcggaatc caataatgcc      600
gccgaacagg caaataaagc attggcctta agtcgcgcag ccagcgctgc cactcaacga      660
gccgtggcag ctcagaacgc ggctgccgca tcagcggctt cggctggagc cgcacaagct      720
gaggcaagga acgcctacgc caaagccaaa gcagcgatag ctgctcttac ggccgcccaa      780
agaaattacg ccgcggccaa ggctagcgca agcgcgggta gcgtggtggc cgaacaagat      840
gctcaatcta gagcggccga tgccgaggtg aacgccgttg cccaagccgc tgcccgagcc      900
agcgttcgca atcaggagat cgttgaaatc ggcgcggaat tcggcaacgc cagcggcgga      960
gtgatctcga ccggcacacg ttcttccgga ggcaagggtg tctccgttac cgctggagct     1020
caggctagcg cgtccgcttc cgcgacctcc tcctcctcct cctccgg catcaacaaa        1080 ggacatccca gatgggggca caattggggt ttaggttctt cggaagcgtc agcaaacgct     1140
gaagccgaaa gcagcgcttc ctcttattca tcttaa                               1176
```

<210> SEQ ID NO 59
<211> LENGTH: 1146
<212> TYPE: DNA
<213> ORGANISM: Oecophylla smaragdina

<400> SEQUENCE: 59

| | | | | | |
|---|---|---|---|---|---|
| ggagtcatag | gtcccgacac | gtcctcatcg | tcccaggcat | cggcatcggc | atcggcgtca | 60 |
| gcatcggcgt | cggcatcatc | gtcggcatcg | atcggttaca | acgaactcca | taaatcgatc | 120 |
| aatgcgcccg | ccttggcggt | cggcgtcaag | aacggcggag | tggatgtcgc | caagggcgcg | 180 |
| gccgttgtcg | aatcagcgat | atccgacgta | tcgactctaa | ccgatgatcg | tacgttgaac | 240 |
| ggtctcgcta | tcatcgggaa | tagcgccgag | agtctggcaa | gagcacaggc | ttcctcgagc | 300 |
| gccagcgccg | gcgcaaaagc | caatgctctc | atcaaacaat | cgatagcggc | tatagagatc | 360 |
| accgaaaagg | cagagtacct | tgcgtcgatc | gtcgccacca | aggcagcgaa | ggccgccgag | 420 |
| gccacagcgg | ccgcgaccgc | tcgcgccact | gccgtcgccg | aggctgccaa | ggtttccagc | 480 |
| gagcaattcg | cggccgaggc | acgcgcggcc | gccgacgccg | aagccaaggc | caacgccgct | 540 |
| tccatcatcg | ccaacaaagc | gaacgccgtc | ctcgcggagg | cagccaccgg | acttagcgcc | 600 |
| agcgctggca | agcccaaca | atcggcgacc | agggcgttgc | aagccgcacg | agctgccgct | 660 |
| aaggctcaag | ccgaacttac | ccagaaagcc | gctcaaatct | tagtcctcat | tgctgaagcc | 720 |
| aaagccgccg | tgagccgagc | aagcgccgat | caatccgtct | gtacgtccca | ggcacaagcc | 780 |
| gccagtcaga | ttcaatcgag | agcctccgcg | gccgaatccg | cggcatcggc | tcaatcggaa | 840 |
| gccaacacca | ttgcggccga | ggcggtcgct | agagctgacg | ccgaggcggc | cagtcaagct | 900 |
| caagcgtggg | ccgaatcctt | caaacgcgaa | ctctcgagtg | tcgttttgga | ggccgaggcc | 960 |
| aatgcctcgg | ctagtgcctc | ggctggtgcc | ctggccagtg | gtagcagcag | ctcgggcgcg | 1020 |
| agttccagcg | cggatgccag | cgccggagcg | agcagctatg | gatccttggg | cggatatcga | 1080 |
| cacggcggaa | gcttcagcga | ggcatcggca | gccgcgtcag | cggccagtcg | cgccgaggct | 1140 |
| gcgtaa | | | | | | 1146 |

<210> SEQ ID NO 60
<211> LENGTH: 1203
<212> TYPE: DNA
<213> ORGANISM: Oecophylla smaragdina

<400> SEQUENCE: 60

| | | | | | |
|---|---|---|---|---|---|
| atgaagattc | cagcgatatt | cgtgacgtct | ctgctcgcct | ggggactcgc | cagcggcgga | 60 |
| gtcataggtc | ccgacacgtc | ctcatcgtcc | caggcatcgg | catcggcatc | ggcgtcagca | 120 |
| tcggcgtcgg | catcatcgtc | ggcatcgatc | ggttacaacg | aactccataa | atcgatcaat | 180 |
| gcgcccgcct | tggcggtcgg | cgtcaagaac | ggcggagtgg | atgtcgccaa | gggcgcggcc | 240 |
| gttgtcgaat | cagcgatatc | cgacgtatcg | actctaaccg | atgatcgtac | gttgaacggt | 300 |
| ctcgctatca | tcgggaatag | cgccgagagt | ctggcaagag | cacaggcttc | ctcgagcgcc | 360 |
| agcgccggcg | caaaagccaa | tgctctcatc | aaacaatcga | tagcggctat | agagatcacc | 420 |
| gaaaaggcag | agtaccttgc | gtcgatcgtc | gccaccaagg | cagcgaaggc | cgccgaggcc | 480 |
| acagcggccg | cgaccgctcg | cgccactgcc | gtcgccgagg | ctgccaaggt | tccagcgag | 540 |
| caattcgcgg | ccgaggcacg | cgccgccgcc | gacgccgaag | ccaaggccaa | cgccgcttcc | 600 |
| atcatcgcca | acaaagcgaa | cgccgtcctc | gcggaggcag | ccaccggact | tagcgccagc | 660 |
| gctggcaaag | cccaacaatc | ggcgaccagg | gcgttgcaag | ccgcacgagc | tgccgctaag | 720 |

```
gctcaagccg aacttaccca gaaagccgct caaatcttag tcctcattgc tgaagccaaa    780
gccgccgtga gccgagcaag cgccgatcaa tccgtctgta cgtcccaggc acaagccgcc    840
agtcagattc aatcgagagc ctccgcggcc gaatccgcgg catcggctca atcggaagcc    900
aacaccattg cggccgaggc ggtcgctaga gctgacgccg aggcggccag tcaagctcaa    960
gcgtgggccg aatccttcaa acgcgaactc tcgagtgtcg ttttggaggc cgaggccaat   1020
gcctcggcta gtgcctcggc tggtgccctg gccagtggta gcagcagctc gggcgcgagt   1080
tccagcgcgg atgccagcgc cggagcgagc agctatggat ccttgggcgg atatcgacac   1140
ggcggaagct tcagcgaggc atcggcagcc gcgtcagcgg ccagtcgcgc cgaggctgcg   1200
taa                                                                 1203
```

<210> SEQ ID NO 61
<211> LENGTH: 1131
<212> TYPE: DNA
<213> ORGANISM: Oecophylla smargdina

<400> SEQUENCE: 61

```
ggtgtcccta aagagttggg aacttccatt tcttccgcgt ccgcatccgc atccgcatcc     60
gcatccgcga ccgcgtcctc cagtagcaag aatgttcact tattaccatt gaaaagcgag    120
catggcatcg taattgacaa gtcaaaattc aacatcagaa aggtagtgtt gagcgcaatc    180
gatgagatca acggcgcgcc caacatcggt ctgggattga acaggtcag tttggcgctc     240 gcaaaagccc aggctagtgc tcaatcgagc gccgaggcat tggcaatcat caagaaaatc    300
gtcgcgctcc tcatctcggc ctacgtcaga gcagccgagg ccgcggctcg agcatccgcc    360
gaagctttag ctaccgttag ggctgcggaa caagcgcaaa aaattgctga gcgaagggt     420 agagcggctg ctgaggcgct ctccgagtta gtcgaggcgt cccagaaggc cgatgcggcg    480
gccgcgggaa cgacggacgc gatcgaacgc acctaccagg atgccagagc ggccacttcc    540
gcacagacca aggccagcgg cgaagccgag aatgctaatc gcaatgctgc cgccaccctc    600
gcggcggtct tgagcatcgc taaggccgcc tccggtcaag gaggcactcg agccgctgtc    660
gatgcagctg ctgccgctgc cgccgcagcc gctctgcatg ctaaagctaa cgcggtttcg    720
caagctacca gcaaagcagc cgctgaagct agagtcgcgg ctgaggaggc agcatccgcc    780
caggcatccg cctcagcaag cgcacagctg accgcacaat tagaggagaa agtcagcgcc    840
gatcaacaag cagcctccgc cagtactgat acctccgctg ctatagccga ggctgaagct    900
gccgcgttag cgtccaccgt caacgcgatc aacgacggag tggtcatcgg attaggaaat    960
accgccagtt cttctgccca agcttccgca caggccagtg ctctcgctcg cgcaaaaaat   1020
gcgcgcccta aaataaaggg ctggtacaaa atcggaggcg cgacttccgc ttctgcaagc   1080
gcatcggcca gcgcttccgc ccagtcatcc tcgcaaggac tggtatacta g            1131
```

<210> SEQ ID NO 62
<211> LENGTH: 1188
<212> TYPE: DNA
<213> ORGANISM: Oecophylla smaragdina

<400> SEQUENCE: 62

```
atgaagattc agcgatact cgtgacgtcc ttcctcgcct ggggactggc cagcgggggt      60
gtccctaaag agttgggaac ttccatttct tccgcgtccg catccgcatc cgcatccgca    120
tccgcgaccg cgtcctccag tagcaagaat gttcacttat taccattgaa aagcgagcat    180
ggcatcgtaa ttgacaagtc aaaattcaac atcagaaagg tagtgttgag cgcaatcgat    240
```

```
gagatcaacg gcgcgcccaa catcggtctg ggattgaaac aggtcagttt ggcgctcgca    300
aaagcccagg ctagtgctca atcgagcgcc gaggcattgg caatcatcaa gaaaatcgtc    360
gcgctcctca tctcggccta cgtcagagca gccgaggccg cggctcgagc atccgccgaa    420
gctttagcta ccgttagggc tgcggaacaa gcgcaaaaaa ttgctgaagc gaagggtaga    480
gcggctgctg aggcgctctc cgagttagtc gaggcgtccc agaaggccga tgcggcggcc    540
gcgggaacga cggacgcgat cgaacgcacc taccaggatg ccagagcggc cacttccgca    600
cagaccaagg ccagcggcga agccgagaat gctaatcgca atgctgccgc caccctcgcg    660
gcggtcttga gcatcgctaa ggccgcctcc ggtcaaggag gcactcgagc cgctgtcgat    720
gcagctgctg ccgctgccgc cgcagccgct ctgcatgcta aagctaacgc ggtttcgcaa    780
gctaccagca aagcagccgc tgaagctaga gtcgcggctg aggaggcagc atccgcccag    840
gcatccgcct cagcaagcgc acagctgacc gcacaattag aggagaaagt cagcgccgat    900
caacaagcag cctccgccag tactgatacc tccgctgcta tagccgaggc tgaagctgcc    960
gcgttagcgt ccaccgtcaa cgcgatcaac gacggagtgg tcatcggatt aggaaatacc   1020
gccagttctt ctgcccaagc ttccgcacag gccagtgctc tcgctcgcgc aaaaaatgcg   1080
cgccctaaaa taaagggctg gtacaaaatc ggaggcgcga cttccgcttc tgcaagcgca   1140
tcggccagcg cttccgccca gtcatcctcg caaggactgg tatactag                1188

<210> SEQ ID NO 63
<211> LENGTH: 1275
<212> TYPE: DNA
<213> ORGANISM: Oecophylla smaragdina

<400> SEQUENCE: 63
agcgaactcg tcggatcgga cgcgagcgcg acggcatctg ctgaagcgtc agcatcgtca     60
tccgcatacg gtagcaagta tggtattggt agtggtgctg tctccggtgc atcagccagc    120
gcctctgcca gcgcgtctgc tagcgcatca gccagcagtg ctcccgcgat cgaaggagta    180
aacgttggca ccggagtcag taacaccgct tcccgcgtccg cagaagctct ctcccgtgga    240
ctcggcatcg gacaagcggc tgccgaagcg caagccgctg ccgctggcca agcggcgatc    300
gctgcgaaat cgtgcgcgct agcggccaag agcaccgctc aagcggttgc cctggttgag    360
aaagtggccc gcgccgaggt agatctggcc gaaagcgcga gaaaggctac aagattatcg    420
gcagaagcag ccaaggcagc ggcggaagtc gagaaggacc tcgtcggtct gagaggggct    480
gccggtaaac tgaatctggc tgcgagagcc ggttctaaag cccaagaacg cgccaacgaa    540
gactctatag aggctaacga acttgcccaa gcaacggccg ccgccggtgc cgaggctgaa    600
gccaaggcga atgccgccca ggaggcaggc gcctccgctt tggccatcgc ccaagccgcc    660
cttaacatcg agcaagagac tgttaaattg acccgccagg cccagaatac tcgtctcaga    720
tctgaaaata ttctcgccgc ggccagcaat gcccgcgcca tcgcttccgc tgaggccgag    780
gccagtagtg atttgaataa tcgtgcgaat gcagcgcgtt ccaatgcccg agctgctgcc    840
gagaccagag ccgtagctac cgaagccgct tctaccgccg agatcgcagc ttatagttca    900
tccgagaaag gcgagatcac caatcccggt cctctgccca agatcgtcag tgttaccgca    960
ggtctgaccc agaacgaaat agcgggatca ggagcggccg ctagtgctag tgccagtgct   1020
cttgccagtg ccagtgccgg tgccggtgcc ggtgcaggtg caggagccgg tgcaagtgca   1080
ggagccggtg cagttgcagg tgcagagcc ggtgcaggag ccgtgctag tgccggagcg    1140 agtgccggag cgaatgccgg tgccggtgcc agcagtttac tcttgccgca gagtaaactc   1200
```

```
catccaatct ccaggtcttc cgcctctgcc tccgcttccg ccgaggccga agctaacagt   1260
tcggcgtatg cgtaa                                                    1275

<210> SEQ ID NO 64
<211> LENGTH: 1332
<212> TYPE: DNA
<213> ORGANISM: Oecophylla smaragdina

<400> SEQUENCE: 64
atgaagattc cagcgatact tgcgacgtcc cttttcgtct ggggtcttgt cggcgccagc     60
gaactcgtcg gatcggacgc gagcgcgacg gcatctgctg aagcgtcagc atcgtcatcc    120
gcatacggta gcaagtatgg tattggtagt ggtgctgtct ccggtgcatc agccagcgcc    180
tctgccagcg cgtctgctag cgcatcagcc agcagtgctc ccgcgatcga aggagtaaac    240
gttggcaccg gagtcagtaa caccgcttcc gcgtccgcag aagctctctc ccgtggactc    300
ggcatcggac aagcggctgc cgaagcgcaa gccgctgccg ctggccaagc ggcgatcgct    360
gcgaaatcgt gcgcgctagc ggccaagagc accgctcaag cggttgccct ggttgagaaa    420
gtggcccgcg ccgaggtaga tctggccgaa agcgcgagaa aggctacaag attatcggca    480
gaagcagcca aggcagcggc ggaagtcgag aaggacctcg tcggtctgag aggggctgcc    540
ggtaaactga atctggctgc gagagccggt tctaaagccc aagaacgcgc caacgaagac    600
tctatagagg ctaacgaact tgcccaagca acggccgccg ccggtgccga ggctgaagcc    660
aaggcgaatg ccgcccagga ggcaggcgcc tccgctttgg ccatcgccca agccgccctt    720
aacatcgagc aagagactgt taaattgacc cgccaggccc agaatactcg tctcagatct    780
gaaaatattc tcgccgcggc cagcaatgcc cgcgccatcg cttccgctga ggccgaggcc    840
agtagtgatt tgaataatcg tgcgaatgca gcgcgttcca atgcccgagc tgctgccgag    900
accagagccg tagctaccga agccgcttct accgccgaga tcgcagctta tagttcatcc    960
gagaaaggcg agatcaccaa tcccggtcct ctgcccaaga tcgtcagtgt taccgcaggt   1020
ctgacccaga acgaaatagc gggatcagga gcggccgcta gtgctagtgc cagtgctctt   1080
gccagtgcca gtgccggtgc cggtgccggt gcaggtgcag gagccggtgc aagtgcagga   1140
gccggtgcag ttgcaggtgc aggagccggt gcaggagccg tgctagtgc cggagcgagt   1200 gccggagcga atgccggtgc cggtgccagc agtttactct tgccgcagag taaactccat   1260
ccaatctcca ggtcttccgc ctctgcctcc gcttccgccg aggccgaagc taacagttcg   1320
gcgtatgcgt aa                                                      1332

<210> SEQ ID NO 65
<211> LENGTH: 461
<212> TYPE: PRT
<213> ORGANISM: Vespa simillima xanthoptera

<400> SEQUENCE: 65

Phe Ala Thr Ala Ala Glu Ser Ser Ser Ser Ser Ala Ala Ser Ser
1               5                   10                  15

Ala Ser Ser Ser Ser Ser Glu Ser Arg Gly Gln Leu Leu Leu Pro Leu
                20                  25                  30

Glu Arg Ser Ser Thr Arg Ser Leu Leu Asp Leu Val Ser Ser Ala Arg
            35                  40                  45

Ser Asn Thr Ala Ile Thr Ala Ser Ser Ala Ala Ala Lys Ala Thr
        50                  55                  60

Leu Arg Ala Ile Lys Ala Ala Asn Ser Ala Gln Gly Glu Ala Leu Ala
```

```
                65                  70                  75                  80
        Gln Ala Thr Ala Ser Ala Ala Ser Asn Ala Lys Ala Arg Ala Thr Ala
                        85                  90                  95
        Ala Ala Ala Ala Gln Ala Thr Asn Ala Ala Val Asn Ala Gln Gly Lys
                       100                 105                 110
        Ala Ser Ala Gln Ala Ile Ala Thr Ala Glu Ala Ala Glu Ala Leu Thr
                       115                 120                 125
        Lys Ser Ala Leu Gln Ala Gln Ser Ala Ala Ser Ser Lys Ser Glu
                130                 135                 140
        Ala Ala Gln Ala Ser Thr Ser Ala Asn Ala Gly Ala Gly Ala Leu Ala
        145                 150                 155                 160
        Thr Ala Ser Ala Gln Ala Leu Ser Ala Lys Lys Ala Ala Leu Ala Tyr
                       165                 170                 175
        Ala Ser Ala Ala Ala Asp Ala Ser Thr Ala Ala Lys Ala Arg Ala
                       180                 185                 190
        Ala Val Ala Ala Ala Glu Ala Ala Thr Arg Thr Ala Val Gln Ala Glu
                       195                 200                 205
        Arg Asp Ser Thr Asn Ala Ala Ser Leu Ala Ala Lys Ala Gln Ala Glu
                210                 215                 220
        Ala Arg Ala Ala Ala Ala Ala Ala Ala Ala Arg Leu Ala Ala Ser
        225                 230                 235                 240
        Ala Ala Ala Asp Ala Ser Ala Gln Ala Asp Ala Arg Val Arg Thr Ala
                       245                 250                 255
        Ser Ile Glu Ala Ala Ala Ser Ala Arg Thr Lys Ala Ser Asn Ala Gln
                       260                 265                 270
        Ala Thr Ala Glu Ala Ala Ala Ile Ala Arg Ser Ser Arg Asp Ala
                       275                 280                 285
        Gln Ala Asn Trp Val Asp Asn Arg Ser Ser Ser Ser Ser Ser Ala
                290                 295                 300
        Ser Ala Ser Ala Ser Val Ser Ala Ser Ala Ser Gly Glu Ala Asp Ser
        305                 310                 315                 320
        Glu Ala Asp Ser Asp Ala Ser Ala Ser Ala Arg Ser Ala Ala Asp Ser
                       325                 330                 335
        Asn Ala Gly Ser Ser Gly Leu Ala Ala Asp Ser Ala Ala Asp Thr
                       340                 345                 350
        Ala Ala Gly Ser Thr Ala Gly Ser Ala Ala Arg Leu Ser Ala Gly Ser
                       355                 360                 365
        Ala Ala Gly Ser Ile Ala Arg Ser Ala Ala Gly Ser Thr Ala Gly Ser
                       370                 375                 380
        Ser Thr Gly Ser Gly Ala Gly Ala Ser Ala Glu Gly Ser Ser Asn Ala
        385                 390                 395                 400
        Ser Ser Gly Thr Ser Ala Gly Ala Ser Ser Gly Ala Ser Thr Gly Ala
                       405                 410                 415
        Ser Ala Gly Ala Ser Ala Thr Ala Ser Ala Asp Asn Ser Ala Asp Asn
                       420                 425                 430
        Ser Ala Glu Ala Leu Ser Ser Ser Ala Glu Ser Ser Ser Ser Ser
                       435                 440                 445
        Trp Ser Ser Ser Ser Gln Asn Ile Trp Ser Gln Asp Trp
            450                 455                 460

<210> SEQ ID NO 66
<211> LENGTH: 476
<212> TYPE: PRT
<213> ORGANISM: Vespa simillima xanthoptera
```

<400> SEQUENCE: 66

```
Met Asn Ile Leu Thr Ile Leu Ala Thr Thr Leu Leu Leu Ser Gly Phe
1               5                   10                  15

Ala Thr Ala Ala Glu Ser Ser Ser Ser Ser Ala Ala Ser Ser Ala
            20                  25                  30

Ser Ser Ser Ser Ser Glu Ser Arg Gly Gln Leu Leu Leu Pro Leu Glu
        35                  40                  45

Arg Ser Ser Thr Arg Ser Leu Leu Asp Leu Val Ser Ser Ala Arg Ser
    50                  55                  60

Asn Thr Ala Ile Thr Ala Ser Ser Ala Ala Ala Lys Ala Thr Leu
65              70                  75                  80

Arg Ala Ile Lys Ala Ala Asn Ser Ala Gln Gly Glu Ala Leu Ala Gln
                85                  90                  95

Ala Thr Ala Ser Ala Ala Ser Asn Ala Lys Ala Arg Ala Thr Ala Ala
            100                 105                 110

Ala Ala Ala Gln Ala Thr Asn Ala Ala Val Asn Ala Gln Gly Lys Ala
        115                 120                 125

Ser Ala Gln Ala Ile Ala Thr Ala Glu Ala Ala Glu Ala Leu Thr Lys
    130                 135                 140

Ser Ala Leu Gln Ala Gln Ser Ala Ala Ser Ser Ser Lys Ser Glu Ala
145                 150                 155                 160

Ala Gln Ala Ser Thr Ser Ala Asn Ala Gly Ala Gly Ala Leu Ala Thr
            165                 170                 175

Ala Ser Ala Gln Ala Leu Ser Ala Lys Lys Ala Ala Leu Ala Tyr Ala
        180                 185                 190

Ser Ala Ala Ala Asp Ala Ser Thr Ala Ala Lys Ala Arg Ala Ala
    195                 200                 205

Val Ala Ala Ala Glu Ala Ala Thr Arg Thr Ala Val Gln Ala Glu Arg
    210                 215                 220

Asp Ser Thr Asn Ala Ala Ser Leu Ala Ala Lys Ala Gln Ala Glu Ala
225                 230                 235                 240

Arg Ala Ala Ala Ala Ala Ala Ala Ala Arg Leu Ala Ala Ser Ala
            245                 250                 255

Ala Ala Asp Ala Ser Gln Ala Asp Ala Arg Val Arg Thr Ala Ser
        260                 265                 270

Ile Glu Ala Ala Ala Ser Ala Arg Thr Lys Ala Ser Asn Ala Gln Ala
    275                 280                 285

Thr Ala Glu Ala Ala Ile Ala Arg Ser Ser Ser Arg Asp Ala Gln
290                 295                 300

Ala Asn Trp Val Asp Asn Arg Ser Ser Ala Ser Ser Ser Ala Ser
305                 310                 315                 320

Ala Ser Ala Ser Val Ser Ala Ser Ala Ser Gly Glu Ala Asp Ser Glu
            325                 330                 335

Ala Asp Ser Asp Ala Ser Ala Ser Ala Arg Ser Ala Ala Asp Ser Asn
        340                 345                 350

Ala Gly Ser Ser Ser Gly Leu Ala Ala Asp Ser Ala Ala Asp Thr Ala
    355                 360                 365

Ala Gly Ser Thr Ala Gly Ser Ala Ala Arg Leu Ser Ala Gly Ser Ala
    370                 375                 380

Ala Gly Ser Ile Ala Arg Ser Ala Ala Gly Ser Thr Ala Gly Ser Ser
385                 390                 395                 400

Thr Gly Ser Gly Ala Gly Ala Ser Ala Glu Gly Ser Ser Asn Ala Ser
            405                 410                 415
```

```
Ser Gly Thr Ser Ala Gly Ala Ser Ser Gly Ala Ser Thr Gly Ala Ser
            420                 425                 430

Ala Gly Ala Ser Ala Thr Ala Ser Ala Asp Asn Ser Ala Asp Asn Ser
            435                 440                 445

Ala Glu Ala Leu Ser Ser Ser Ala Glu Ser Ser Ser Ser Trp
            450                 455                 460

Ser Ser Ser Ser Gln Asn Ile Trp Ser Gln Asp Trp
465                 470                 475

<210> SEQ ID NO 67
<211> LENGTH: 486
<212> TYPE: PRT
<213> ORGANISM: Vespa simillima xanthoptera

<400> SEQUENCE: 67

Asp Arg Ser Trp Ala Ala Ser Asp Ala Asn Ala Glu Ala Ser Ala Ala
1               5                   10                  15

Val Glu Ser Pro Ser Leu Trp Glu Asp Ser Ser Ala Ser Ala Gly
            20                  25                  30

Ala Ser Asn Ala Ala Glu Ser Ser Leu Trp Glu Asp Ser Ser
            35                  40                  45

Glu Asn Thr Gly Ala Ser Thr Ala Ala Glu Ser Ser Ser Leu Trp Glu
50                  55                  60

Asp Ser Ser Ser Ala Ser Ala Arg Ala Ser Thr Ala Ala Gly Ser Ser
65                  70                  75                  80

Ser Ala Trp Glu Asp Ser Ser Ile Thr Asn Ala Arg Glu Ser Gly Ala
                85                  90                  95

Ser Gly Ser Leu Ser Ser Trp Glu Asp Ser Ser Ala Ser Ala Ser
            100                 105                 110

Ser Ser Thr Ser Ala Ser Ala Ser Ser Ser Ser Ser Ser Ser Ser
            115                 120                 125

Ile Ser Ser Ser Ala Ser Ser Ser Ser Ala Ser Ala Ser Ala Ser
            130                 135                 140

Thr Glu Ala Ser Asn Glu Ser Arg Arg Gly Ile Ala Ile Glu Gly Ala
145                 150                 155                 160

Leu Val Gly Thr Gly Ala Ala Ser Thr Ala Ala Ser Ala Glu Met
            165                 170                 175

Leu Ser Asp Thr Leu Gly Leu Gly Gln Ser Ala Leu Gln Ala Gln Thr
            180                 185                 190

Ala Ser Val Thr Gln Ala Asn Ile Ala Ser Asp Ala Ser Asn Gln Ala
            195                 200                 205

Asn Arg Leu Ala Ala Ala Ala Ala Ala Met Ser Ala Ala Ala Ser
210                 215                 220

Ala Gln Glu Asn Ala Ala Ser Leu Ala Arg Ala Ser Ala Ser Ala Ser
225                 230                 235                 240

Glu Ser Ala Ala Ser Ala Ser Ser Lys Ala Glu Ala Ser Ala Glu Ala
            245                 250                 255

Ala Lys Ser Ser Ala Glu Lys Cys Leu Leu Leu Ala Gln Asn Ser Ala
            260                 265                 270

Gln Ala Gln Ala Arg Ala Thr Glu Gln Ser Glu Ser Ser Asn Arg Asp
            275                 280                 285

Ser Ala Ala Asn Ala Ala Ala Ala Glu Ala Glu Arg Lys Ala Thr
            290                 295                 300

Leu Ala Leu Lys Ala Ile Ala Asp Ala Lys Ala Lys Ala Gly Val Ala
305                 310                 315                 320
```

```
Val Ala Ala Gln Ser Glu Ala Ala Ala Ala Ala Ala Ala Ala Lys
            325                 330                 335

Ala Arg Ala Asp Ala Glu Ala Gly Ala Asn Leu Ala Ala Ala Arg
            340                 345                 350

Ala Val Ala Ala Ala Glu Ala Ala Ser Arg Arg Asn Asp Arg Gln
            355                 360                 365

Ala Gly Ile Ala Gln Ala Gly Ala Ser Ala Ala Glu Thr Arg Ala
            370                 375                 380

Leu Ala Ser Ser Ala Ala Ala Thr Ala Lys Ala Ala Tyr Ala Asn
385                 390                 395                 400

Ala Asp Ile Arg Ala Leu Ser Ala Ala Leu Glu Ser Ser Ile Ser
            405                 410                 415

Ser Ser Ser Ser Thr Ser Ala Ser Ala Ser Ser Ser Ala Ser Ser
            420                 425                 430

Gly Ala Ser Ser Asp Ser Ser Gly Ala Ser Ser Gly Ala Ser Ser
            435                 440                 445

Asp Ser Ser Ser Asn Ser Ser Ser Asp Ser Ser Ser Leu Leu Gly Asp
            450                 455                 460

Asp Ala Ser Thr Ser Ala Ser Ser Thr Ala Glu Ala Glu Ser Arg Thr
465                 470                 475                 480

Ser Ser Leu Ile Leu Asn
            485

<210> SEQ ID NO 68
<211> LENGTH: 508
<212> TYPE: PRT
<213> ORGANISM: Vespa simillima xanthoptera

<400> SEQUENCE: 68

Met Lys Ser Leu Ser Thr Leu Val Ser Ser Leu Leu Leu Gly Ala Cys
1               5                   10                  15

Val Leu Ser Val His Ala Asp Arg Ser Trp Ala Ala Ser Asp Ala Asn
            20                  25                  30

Ala Glu Ala Ser Ala Ala Val Glu Ser Pro Ser Leu Trp Glu Asp Ser
            35                  40                  45

Ser Ser Ala Ser Ala Gly Ala Ser Asn Ala Ala Glu Ser Ser Ser Leu
        50                  55                  60

Trp Glu Asp Ser Ser Glu Asn Thr Gly Ala Ser Thr Ala Ala Glu
65                  70                  75                  80

Ser Ser Ser Leu Trp Glu Asp Ser Ser Ser Ala Ser Ala Arg Ala Ser
            85                  90                  95

Thr Ala Ala Gly Ser Ser Ser Ala Trp Glu Asp Ser Ser Ile Thr Asn
            100                 105                 110

Ala Arg Glu Ser Gly Ala Ser Gly Ser Leu Ser Ser Trp Glu Asp Ser
            115                 120                 125

Ser Ser Ala Ser Ala Ser Ser Thr Ser Ala Ser Ala Ser Ser Ser
            130                 135                 140

Ser Ser Ser Ser Ser Ser Ile Ser Ser Ser Ala Ser Ser Ser Ser
145                 150                 155                 160

Ala Ser Ala Ser Ala Ser Thr Glu Ala Ser Asn Glu Ser Arg Arg Gly
            165                 170                 175

Ile Ala Ile Glu Gly Ala Leu Val Gly Thr Ala Ala Ser Thr Ala
            180                 185                 190

Ala Ala Ser Ala Glu Met Leu Ser Asp Thr Leu Gly Leu Gly Gln Ser
            195                 200                 205
```

-continued

```
Ala Leu Gln Ala Gln Thr Ala Ser Val Thr Gln Ala Asn Ile Ala Ser
        210                 215                 220

Asp Ala Ser Asn Gln Ala Asn Arg Leu Ala Ala Ala Ala Ala Ala Ala
225                 230                 235                 240

Met Ser Ala Ala Ser Ala Gln Glu Asn Ala Ala Ser Leu Ala Arg
                245                 250                 255

Ala Ser Ala Ser Ala Ser Glu Ser Ala Ala Ser Ala Ser Ser Lys Ala
                260                 265                 270

Glu Ala Ser Ala Glu Ala Ala Lys Ser Ser Ala Glu Lys Cys Leu Leu
            275                 280                 285

Leu Ala Gln Asn Ser Ala Gln Ala Gln Ala Arg Ala Thr Glu Gln Ser
        290                 295                 300

Glu Ser Ser Asn Arg Asp Ser Ala Ala Asn Ala Ala Ala Ala Glu
305                 310                 315                 320

Ala Glu Arg Lys Ala Thr Leu Ala Leu Lys Ala Ile Ala Asp Ala Lys
                325                 330                 335

Ala Lys Ala Gly Val Ala Val Ala Ala Gln Ser Glu Ala Ala Ala Ala
            340                 345                 350

Ala Ala Ala Ala Ala Lys Ala Arg Ala Asp Ala Glu Ala Gly Ala Asn
        355                 360                 365

Leu Ala Ala Ala Arg Ala Val Ala Ala Glu Ala Ala Ala Ser
370                 375                 380

Arg Arg Asn Asp Arg Gln Ala Gly Ile Ala Gln Ala Gly Ala Ser Ala
385                 390                 395                 400

Ala Ala Glu Thr Arg Ala Leu Ala Ser Ser Ala Ala Thr Ala Lys
                405                 410                 415

Ala Ala Ala Tyr Ala Asn Ala Asp Ile Arg Ala Leu Ser Ala Ala Ala
            420                 425                 430

Leu Glu Ser Ser Ile Ser Ser Ser Ser Thr Ser Ala Ser Ser Ala
        435                 440                 445

Ser Ser Ser Ala Ser Ser Gly Ala Ser Ser Asp Ser Ser Ser Gly Ala
    450                 455                 460

Ser Ser Gly Ala Ser Ser Asp Ser Ser Asn Ser Ser Ser Asp Ser
465                 470                 475                 480

Ser Ser Leu Leu Gly Asp Asp Ala Ser Thr Ser Ala Ser Ser Thr Ala
                485                 490                 495

Glu Ala Glu Ser Arg Thr Ser Ser Leu Ile Leu Asn
            500                 505

<210> SEQ ID NO 69
<211> LENGTH: 359
<212> TYPE: PRT
<213> ORGANISM: Vespa simillima xanthoptera

<400> SEQUENCE: 69

Leu Ala Ala Gly Ser Ser Ser Ser Ala Glu Ser Ser Ala Ser Ala
1               5                  10                  15

Thr Ala Ser Ser Asp Ala Ser Trp Ser Ala Ser Ser Arg Ser Ser Ala
                20                  25                  30

Thr Gly Arg Ala Pro Asn Val Ile Leu Asn Arg Ala Pro Gln Leu Gly
            35                  40                  45

Ala Ser Ala Ala Ala Ile Ala Ser Ala Arg Ala Ser Thr Ser Ala Asn
        50                  55                  60

Ala Ala Ser Asp Glu Lys Ser Ala Arg Glu Thr Arg Ala Thr Ala Leu
65                  70                  75                  80
```

```
Ala Arg Ser Arg Ala Ala Val Thr Ala Ala Ala Arg Ala Ala Ala Arg
                85                  90                  95

Thr Gln Glu Ala Val Ala Ala Ala Lys Ala Ala Ser Arg Ala Gln Ala
            100                 105                 110

Leu Ala Ala Ala Lys Ser Ser Ala Ala Ile Ser Ala Leu Ala Ala Gly
        115                 120                 125

Glu Ala Ala Ala Gln Lys Ala Asp Ala Ala Leu Ala Ala Leu Ala
    130                 135                 140

Ala Asn Gln Arg Ser Val Lys Ala Ala Glu Asn Gly Leu Ala Val Gln
145                 150                 155                 160

Asn Arg Ala Asn Gly Glu Ala Glu Gln Ala Ser Arg Ala Ala Ala
                165                 170                 175

Asn Leu Ala Ala Ala Ile Arg Thr Arg Asp Asn Ala Leu Glu Thr Arg
                180                 185                 190

Arg Glu Ala Ala Arg Leu Lys Ala Leu Ala Thr Ala Ala Ala Asn Ala
            195                 200                 205

Asn Asn Lys Ala Thr Ser Leu Ala Glu Ala Ser Ala Asn Gln Ala Ala
210                 215                 220

Glu Ala Ser Ser Ala Ala Glu Asp Thr Ser Ser Ala Gln Ser Ala Ala
225                 230                 235                 240

Val Ala Gln Ala Glu Ala Ala Glu Thr Leu Asn Val Asn Leu Ala Ile
                245                 250                 255

Leu Glu Ser Thr Gln Ser Ser Arg Gln Asp Ser Asn Val Ala Lys Ala
                260                 265                 270

Glu Ala Ser Ala Ala Ala Lys Ala Ser Pro Gly Thr Ala Thr Arg Asp
            275                 280                 285

Gly Val Asn Leu Gly Leu Ala Ser Asp Ala Gly Ala Ala Ala Gln Leu
            290                 295                 300

Lys Ala Gln Ala Ala Ala Leu Ala Arg Ala Ser Ser Arg Ile Ser Ser
305                 310                 315                 320

Gly Pro Ala Leu Ser Ala Trp Lys Trp Arg Asn Glu Asp Ser Ser Glu
                325                 330                 335

Ser Ser Thr Ser Ala Ile Ala Ser Ser Ser Ala Ser Ser Ser Ser Ser
                340                 345                 350

Ser Arg Ser Ala Ser Gly Asn
            355

<210> SEQ ID NO 70
<211> LENGTH: 374
<212> TYPE: PRT
<213> ORGANISM: Vespa simillima xanthoptera

<400> SEQUENCE: 70

Met Lys Ile Pro Ser Ile Leu Val Thr Cys Leu Phe Thr Trp Gly Leu
1               5                   10                  15

Ala Ala Gly Ser Ser Ser Ser Ala Glu Ser Ala Ser Ala Ser Ala Thr
                20                  25                  30

Ala Ser Ser Asp Ala Ser Trp Ser Ala Ser Ser Arg Ser Ser Ala Thr
            35                  40                  45

Gly Arg Ala Pro Asn Val Ile Leu Asn Arg Ala Pro Gln Leu Gly Ala
        50                  55                  60

Ser Ala Ala Ala Ile Ala Ser Ala Arg Ala Ser Thr Ser Ala Asn Ala
65                  70                  75                  80

Ala Ser Asp Glu Lys Ser Ala Arg Glu Thr Arg Ala Thr Ala Leu Ala
                85                  90                  95
```

```
Arg Ser Arg Ala Ala Val Thr Ala Ala Ala Ala Ala Arg Thr
            100                 105                 110

Gln Glu Ala Val Ala Ala Lys Ala Ala Ser Arg Ala Gln Ala Leu
            115                 120                 125

Ala Ala Ala Lys Ser Ser Ala Ala Ile Ser Ala Leu Ala Ala Gly Glu
        130                 135                 140

Ala Ala Ala Gln Lys Ala Asp Ala Ala Leu Ala Ala Leu Ala Ala
145                 150                 155                 160

Asn Gln Arg Ser Val Lys Ala Ala Glu Asn Gly Leu Ala Val Gln Asn
                165                 170                 175

Arg Ala Asn Gly Glu Ala Glu Gln Ala Ser Arg Ala Ala Ala Asn
        180                 185                 190

Leu Ala Ala Ala Ile Arg Thr Arg Asp Asn Ala Leu Glu Thr Arg Arg
        195                 200                 205

Glu Ala Ala Arg Leu Lys Ala Leu Ala Thr Ala Ala Ala Asn Ala Asn
210                 215                 220

Asn Lys Ala Thr Ser Leu Ala Glu Ala Ser Ala Asn Gln Ala Ala Glu
225                 230                 235                 240

Ala Ser Ser Ala Ala Glu Asp Thr Ser Ser Ala Gln Ser Ala Ala Val
                245                 250                 255

Ala Gln Ala Glu Ala Ala Glu Thr Leu Asn Val Asn Leu Ala Ile Leu
            260                 265                 270

Glu Ser Thr Gln Ser Ser Arg Gln Asp Ser Asn Val Ala Lys Ala Glu
        275                 280                 285

Ala Ser Ala Ala Ala Lys Ala Ser Pro Gly Thr Ala Thr Arg Asp Gly
290                 295                 300

Val Asn Leu Gly Leu Ala Ser Asp Ala Gly Ala Ala Gln Leu Lys
305                 310                 315                 320

Ala Gln Ala Ala Ala Leu Ala Arg Ala Ser Ser Arg Ile Ser Ser Gly
                325                 330                 335

Pro Ala Leu Ser Ala Trp Lys Trp Arg Asn Glu Asp Ser Ser Glu Ser
            340                 345                 350

Ser Thr Ser Ala Ile Ala Ser Ser Ala Ser Ser Ser Ser Ser
        355                 360                 365

Arg Ser Ala Ser Gly Asn
    370

<210> SEQ ID NO 71
<211> LENGTH: 359
<212> TYPE: PRT
<213> ORGANISM: Vespa simillima xanthoptera

<400> SEQUENCE: 71

Ser Val Ala Gln Gly Gly Pro Ser Arg Leu Ser Glu Thr Ser Asp Ser
1               5                   10                  15

Ser Ala Ala Ser Trp Ser Ser Ser Ser Ser Ser Ser Leu Ser
            20                  25                  30

Ser Ser Leu Ala Ser Asp Ser Ala Ser Ser Ala Ser Gly Ser Ala
        35                  40                  45

Ser Ala Ser Ala Ser Ala Ser Ala Ser Ala Ser Ser Arg Asn
    50                  55                  60

Asp Asn Ser Arg Val Lys Ala Trp Lys Lys Gly Arg Gly Gly Ser Asp
65                  70                  75                  80

Ser Leu Val Leu Ser Ser Asp Ser Ser Glu Asp Ser Lys Ala Arg Glu
                85                  90                  95
```

```
Leu Leu Glu Thr Asp Ala Gly Leu Gly Ala Ala Ala Leu Ala Arg
            100                 105                 110

Ala Thr Ala Asp Ala Gln Ala Arg Thr Ala Ala Ser Ala Asp Ala Thr
        115                 120                 125

Ala Asn Lys Ala Thr Ala Lys Ala Leu Val Leu Ala Glu Ala Ala Val
    130                 135                 140

Arg Ala Glu Asn Ala Ala Ile Val Arg Ile Arg Arg Ala Leu Ser Ala
145                 150                 155                 160

Ala Gln Ala Leu Val Ser Ala Ser Asn Arg Ala Lys Ala Ala Ala Arg
                165                 170                 175

Ala Ala Arg Glu Ala Ala Ala Asn Ser Ala Ala Ala Ala Lys Ala
            180                 185                 190

Ser Thr Asn Gln Val Lys Ala Asn Ala Asp Ser Leu Val Ala Asn Arg
        195                 200                 205

Ala Ala Ala Ala Leu Leu Ala Ala Glu Glu Ala Leu Gln Lys Ala
    210                 215                 220

Ser Ala Ser Gln Asn Ala Ala Glu Ala Ala Lys Ala Arg Ala
225                 230                 235                 240

Ala Ala Asn Ala Asn Ala Ala Thr Thr Arg Ala Ala Ser Ala Ile
            245                 250                 255

Leu Ala Glu Ala Arg Ala Arg Thr Ala Ile Thr Lys Ala Leu Ala Ala
        260                 265                 270

Gln Ser Thr Ala Ser Gln Ala Ser Ser Ser Gln Val Gln Asn
    275                 280                 285

Arg Ala Asn Asn Leu Gln Ala Glu Thr Ala Ser Leu Ala Gln Ser Arg
        290                 295                 300

Ala Glu Ala Ala Ile Ala Ala Ala Ala Gln Ala Ala Leu Ala
305                 310                 315                 320

Glu Ala Asn Ala Gln Leu Ala Arg Leu Ser Lys Ala Ser Ala Gly Ala
                325                 330                 335

Ser Ser Glu Gly Ser Ala Ser Ala Ser Ala Ser Ala Ser Ala
        340                 345                 350

Ser Ser Ser Ser Ser Ser Ala
        355

<210> SEQ ID NO 72
<211> LENGTH: 375
<212> TYPE: PRT
<213> ORGANISM: Vespa simillima xanthoptera

<400> SEQUENCE: 72

Met Asn Val Gln Ala Thr Leu Val Leu Cys Leu Leu Ala Leu Phe Gly
1               5                   10                  15

Ser Val Ala Gln Gly Gly Pro Ser Arg Leu Ser Glu Thr Ser Asp Ser
            20                  25                  30

Ser Ala Ala Ser Trp Ser Ser Ser Ser Ser Ser Ser Ser Leu Ser
        35                  40                  45

Ser Ser Leu Ala Ser Asp Ser Ala Ser Ser Ala Ser Gly Ser Ala
    50                  55                  60

Ser Ala Ser Ala Ser Ala Ser Ala Ser Ala Ser Ser Arg Asn
65                  70                  75                  80

Asp Asn Ser Arg Val Lys Ala Trp Lys Lys Gly Arg Gly Gly Ser Asp
                85                  90                  95

Ser Leu Val Leu Ser Ser Asp Ser Ser Glu Asp Ser Lys Ala Arg Glu
            100                 105                 110
```

```
Leu Leu Glu Thr Asp Ala Gly Leu Gly Ala Ala Ala Leu Ala Arg
        115                 120                 125

Ala Thr Ala Asp Ala Gln Arg Thr Ala Ala Ser Ala Asp Ala Thr
    130                 135                 140

Ala Asn Lys Ala Thr Ala Lys Ala Leu Val Leu Ala Glu Ala Ala Val
145                 150                 155                 160

Arg Ala Glu Asn Ala Ala Ile Val Arg Ile Arg Ala Leu Ser Ala
                165                 170                 175

Ala Gln Ala Leu Val Ser Ala Ser Asn Arg Ala Lys Ala Ala Ala Arg
                180                 185                 190

Ala Ala Arg Glu Ala Ala Ala Asn Ser Ala Ala Ala Ala Lys Ala
            195                 200                 205

Ser Thr Asn Gln Val Lys Ala Asn Ala Asp Ser Leu Val Ala Asn Arg
210                 215                 220

Ala Ala Ala Ala Leu Leu Ala Ala Glu Glu Ala Leu Gln Lys Ala
225                 230                 235                 240

Ser Ala Ser Gln Asn Ala Ala Glu Ala Ala Lys Ala Arg Ala
                245                 250                 255

Ala Ala Asn Ala Asn Ala Ala Thr Thr Arg Ala Ala Ser Ala Ile
            260                 265                 270

Leu Ala Glu Ala Arg Ala Arg Thr Ala Ile Thr Lys Ala Leu Ala Ala
                275                 280                 285

Gln Ser Thr Ala Ser Ala Gln Ala Ser Ser Ser Gln Val Gln Asn
        290                 295                 300

Arg Ala Asn Asn Leu Gln Ala Glu Thr Ala Ser Leu Ala Gln Ser Arg
305                 310                 315                 320

Ala Glu Ala Ala Ile Ala Ala Ala Ala Gln Ala Ala Leu Ala
                325                 330                 335

Glu Ala Asn Ala Gln Leu Ala Arg Leu Ser Lys Ala Ser Ala Gly Ala
                340                 345                 350

Ser Ser Glu Gly Ser Ala Ser Ala Ser Ala Ser Ala Ser Ala
        355                 360                 365

Ser Ser Ser Ser Ser Ser Ala
        370                 375

<210> SEQ ID NO 73
<211> LENGTH: 1386
<212> TYPE: DNA
<213> ORGANISM: Vespa simillima xanthoptera

<400> SEQUENCE: 73
ttcgccacgg cagcagaaag ctcaagctca agctccgcgg catcttcggc ttcatcatca    60
tcctcagaga gtagaggaca gttgttgctt ccgttagaaa ggagttctac cagaagctta   120
ctggatttgg tgagcagtgc taggagcaat actgcgataa ccgcatcgtc cgcagccgct   180
gcaaaggcaa ctcttcgagc gattaaagct gcgaattccg ctcaaggaga agctttggca   240
caggcgactg cttctgcggc ttcgaatgca aaggcacgcg caaccgcggc cgctgcagcg   300
caagccacta acgcagccgt taacgcgcaa gggaaggctt ccgcgcaagc tattgcaacg   360
gcagaagcag cagaagcttt gactaaatcg gcactccaag cccagtccgc tgcgagcagc   420
tctaaatcag aggcagccca agcttcaacc tcagctaatg ccggagccgg tgctcttgcg   480
actgcttctg ctcaggcctt atccgcgaag aaggcagcct agcctacgc ctccgctgcc   540 gctgacgcaa gcaccgcagc ggccaaggct cgtgccgcga ttgctgctgc agaagcagcc   600
actcgtacag ccgtacaagc cgaaagagac tccacaaacg cagcctctct cgcagctaaa   660
```

```
gcccaagctg aagccagagc tgctgcagcc gctgctgcag cagcgagact cgccgcatca    720
gctgccgccg atgccagcgc tcaagccgat gcaagagtca gaaccgcttc tattgaagct    780
gccgccagcg ctcgtaccaa agcatccaat gctcaagcca cagccgaggc tgcagccata    840
gccaggagca gctccaggga cgcacaagca aactgggttg acaacaggtc ttctgcgtca    900
tcgtccagtg catcggccag tgcatcggtt agtgcatcag ccagtgggaga agccgattca    960 gaagccgatt cagatgctag tgcatcagct cgttcagcag ccgattctaa tgctggttca   1020
tcttccggtt tagccgccga ttcagcggcc gatacagccg ccggttcaac cgccggttca   1080 gctgccgtt  taagtgctgg ttctgcagcc ggttcaatag cacgttcagc tgccggttct   1140
acagccggct catcaactgg ttcaggagcc ggtgcatcag ctgaaggttc ctccaatgcc   1200
tcctccggta cctccgccgg tgcatcctcc ggtgcctcca ccggagcttc tgctggtgcc   1260
tccgccactg cttctgccga taattccgcc gataattctg ccgaagctct ttctagctcc   1320
tccgccgagt cttcgtcgtc ctcctggtct tcttccagcc agaatatctg gtcccaggat   1380
tggtag                                                              1386

<210> SEQ ID NO 74
<211> LENGTH: 1431
<212> TYPE: DNA
<213> ORGANISM: Vespa simillima xanthoptera

<400> SEQUENCE: 74
atgaacatcc taacgatact cgcgacaaca cttcttctga gtggcttcgc cacggcagca     60
gaaagctcaa gctcaagctc cgcggcatct tcggcttcat catcatcctc agagagtaga    120
ggacagttgt tgcttccgtt agaaaggagt tctaccagaa gcttactgga tttggtgagc    180
agtgctagga gcaatactgc gataaccgca tcgtccgcag ccgctgcaaa ggcaactctt    240
cgagcgatta aagctgcgaa ttccgctcaa ggagaagctt tggcacaggc gactgcttct    300
gcggcttcga atgcaaaggc acgcgcaacc gcggccgctg cagcgcaagc cactaacgca    360
gccgttaacg cgcaagggaa ggcttccgcg caagctattg caacggcaga agcagcagaa    420
gctttgacta aatcggcact ccaagcccag tccgctgcga gcagctctaa atcagaggca    480
gcccaagctt caacctcagc taatgccgga gccggtgctc ttgcgactgc ttctgctcag    540
gccttatccg cgaagaaggc agccttagcc tacgcctccg ctgccgctga cgcaagcacc    600
gcagcggcca aggctcgtgc cgcagttgct gctgcagaag cagccactcg tacagccgta    660
caagccgaaa gagactccac aaacgcagcc tctctcgcag ctaaagccca agctgaagcc    720
agagctgctg cagccgctgc tgcagcagcg agactcgccg catcagctgc cgccgatgcc    780
agcgctcaag ccgatgcaag agtcagaacc gcttctattg aagctgccgc cagcgctcgt    840
accaaagcat ccaatgctca agccacagcc gaggctgcag ccatagccag gagcagctcc    900
agggacgcac aagcaaactg ggttgacaac aggtcttctg cgtcatcgtc cagtgcatcg    960
gccagtgcat cggttagtgc atcagccagt ggagaagccg attcagaagc cgattcagat   1020
gctagtgcat cagctcgttc agcagccgat tctaatgctg gttcatcttc cggtttagcc   1080
gccgattcag cggccgatac agccgccggt tcaaccgccg gttcagctgc ccgtttaagt   1140
gctggttctg cagccggttc aatagcacgt tcagctgccg gttctacagc cggctcatca   1200
actggttcag gagccggtgc atcagctgaa ggttcctcca atgcctcctc cggtacctcc   1260
gccggtgcat cctccggtgc ctccaccgga gcttctgctg gtgcctccgc cactgcttct   1320
gccgataatt ccgccgataa ttctgccgaa gctctttcta gctcctccgc cgagtcttcg   1380
```

```
tcgtcctcct ggtcttcttc cagccagaat atctggtccc aggattggta g        1431
```

<210> SEQ ID NO 75
<211> LENGTH: 1461
<212> TYPE: DNA
<213> ORGANISM: Vespa simillima xanthoptera

<400> SEQUENCE: 75

```
gacagatcgt gggcagcatc ggatgcaaat gctgaagcgt cagccgcagt ggaatcgcct    60
tctctttggg aagattcatc cagtgcaagc gcgggagcgt caaacgcagc ggaatcgtca   120
tctctttggg aagattcatc cagtgaaaac acggagcgt caaccgcagc ggaatcgtca    180
tctctttggg aagattcatc cagtgcaagc gcgagagcgt caaccgcagc gggatcttca   240
tctgcttggg aagattcatc catcacaaac gcgagagaat caggggcatc gggatcgtta   300
tctagctggg aagattcatc cagtgcaagc gctagctcta gcacaagcgc aagcgctagc   360
tctagctcaa gttctagctc tagcattagc tccagcgcta gctctagctc tagtgctagt   420
gccagcgcta gtacagaagc atcaacgaa tcaagaaggg gtatcgccat tgagggagcc    480
cttgtaggta cggggggctgc aagtacggct gcggcatccg cagaaatgct ttcggacacc   540
ttgggattgg gtcaatctgc tcttcaagca caaacagcat ccgtaacgca ggctaacatt    600
gccagcgatg ccagcaacca agctaatcga ttggcggctg ccgcagcagc agcgatgtca    660
gccgcagctt ccgctcaaga gaacgccgcg tcgttagctc gagcttcggc cagtgcgtct    720
gaaagtgcgg ctagtgcctc atcgaaggcc gaggcgagcg ccgaagcggc caaatcgtct    780
gcggaaaaat gtttattgct cgcgcaaaac tccgcacaag cgcaagctcg cgcgactgaa    840
caatcagagt cctcgaacag agactcggct gccaacgcgg ccgccgccgc ggaagccgaa    900
aggaaggcca ctttggctct aaaagctata gctgatgcca aggccaaggc cggtgtagcc    960
gttgccgctc agtcggaggc tgctgcggca gccgcagccg ctgcaaaagc acgcgccgat   1020
gccgaagcag gtgctaatttt ggccgcagca gcgcgtgccg tcgccgcagc cgaagctgct   1080
gcttccagac gaaatgatcg tcaagctggt atagctcaag ccggagcatc cgccgcagcc   1140
gagaccagag cgcttgcatc ctccgccgca gccaccgcta aagcagccgc ttacgctaat   1200
gccgatatcc gagcactttc cgcagctgct ctagaatcct ccatatcttc gtcctctagc   1260
actagtgctt ccagtgcatc ctcatccgcc agcagcggtg ccagcagcga ttccagcagc   1320
ggtgccagca gcggtgccag cagcgattct agcagcaatt ccagcagcga ttccagtagc   1380
ctcctaggag atgatgcttc aaccagtgcc agcagcacag ctgaagccga gagtagaact   1440
agctcgctga tcttaaacta a                                            1461
```

<210> SEQ ID NO 76
<211> LENGTH: 1527
<212> TYPE: DNA
<213> ORGANISM: Vespa simillima xanthoptera

<400> SEQUENCE: 76

```
atgaagtctc tctcaacgct cgtgtcgtcg ctcttgttgg gagcctgtgt gctcagtgtc    60
catgccgaca gatcgtgggc agcatcggat gcaaatgctg aagcgtcagc cgcagtggaa   120
tcgccttctc tttgggaaga ttcatccagt gcaagcgcgg gagcgtcaaa cgcagcggaa   180
tcgtcatctc tttgggaaga ttcatccagt gaaaacacgg gagcgtcaac cgcagcggaa   240
tcgtcatctc tttgggaaga ttcatccagt gcaagcgcga gagcgtcaac cgcagcggga   300
tcttcatctg cttgggaaga ttcatccatc acaaacgcga gagaatcagg ggcatcggga   360
```

```
tcgttatcta gctgggaaga ttcatccagt gcaagcgcta gctctagcac aagcgcaagc      420
gctagctcta gctcaagttc tagctctagc attagctcca gcgctagctc tagctctagt      480
gctagtgcca gcgctagtac agaagcatct aacgaatcaa gaaggggtat cgccattgag      540
ggagcccttg taggtacggg ggctgcaagt acggctgcgg catccgcaga aatgctttcg      600
gacaccttgg gattgggtca atctgctctt caagcacaaa cagcatccgt aacgcaggct      660
aacattgcca gcgatgccag caaccaagct aatcgattgg cggctgccgc agcagcagcg      720
atgtcagccg cagcttccgc tcaagagaac gccgcgtcgt tagctcgagc ttcggccagt      780
gcgtctgaaa gtgcggctag tgcctcatcg aaggccgagc gagcgccga agcggccaaa      840 tcgtctgcgg aaaaatgttt attgctcgcg caaaactccg cacaagcgca agctcgcgcg      900
actgaacaat cagagtcctc gaacagagac tcggctgcca acgcggccgc cgccgcggaa      960
gccgaaagga aggccacttt ggctctaaaa gctatagctg atgccaaggc caaggccggt     1020
gtagccgttg ccgctcagtc ggaggctgct gcggcagccg cagccgctgc aaaagcacgc     1080
gccgatgccg aagcaggtgc taatttggcc gcagcagcgc gtgccgtcgc cgcagccgaa     1140
gctgctgctt ccagacgaaa tgatcgtcaa gctggtatag ctcaagcgg agcatccgcc      1200 gcagccgaga ccagagcgct tgcatcctcc gccgcagcca ccgctaaagc agccgcttac     1260
gctaatgcca atatccgagc actttccgca gctgctctag aatcctccat atcttcgtcc     1320
tctagcacta gtgcttccag tgcatcctca tccgccagca gcggtgccag cagcgattcc     1380
agcagcggtg ccagcagcgg tgccagcagc gattctagca gcaattccag cagcgattcc     1440
agtagcctcc taggagatga tgcttcaacc agtgccagca gcacagctga agccgagagt     1500
agaactagct cgctgatctt aaactaa                                          1527

<210> SEQ ID NO 77
<211> LENGTH: 1080
<212> TYPE: DNA
<213> ORGANISM: Vespa simillima xanthoptera

<400> SEQUENCE: 77
ttggctgccg ggagtagcag ctcgtccgcg gaatcttcgg catcggcgac agcgtcttca       60
gatgcgtcct ggagcgcgtc ctcgagatcg tcagctaccg gtagagcacc gaacgtgatt      120
ttgaataggg cacctcaatt aggagctagc gcggcagcga tcgcatcggc tcgagccagt      180
acctcagcaa atgctgcatc agacgaaaaa tctgcccgag aaacgcgagc gaccgctttg      240
gcccgatcaa gagctgctgt tacggcggca gcacgagcag ccgcaaggac gcaagaagcc      300
gtcgcggcag caaaagccgc aagtagggcc caagcgcttg ctgctgctaa atcttcggcg      360
gcaatttctg cattggccgc tggagaggct gccgcccaaa aggcggacgc cgcagctctc      420
gccgcattag ctgctaatca gagatctgtc aaagccgcag aaaatggtct agcagtgcag      480
aatcgtgcga atggagaagc ggaacaggca agtcgtgcgg ctgctgctaa ccttgccgcg      540
gccatccgta cccagacaa tgctctcgaa acgagaagag aagcagctcg attgaaggca      600
ctagccacag ctgccgctaa cgctaataac aaagcgacca gtcttgccga agcttctgcg      660
aaccaagcag ctgaagcaag ctccgctgcc gaggatactt cttccgctca atctgctgcg      720
gtcgctcaag ctgaggccgc tgaaacgctc aacgtaaatc tcgctatact cgaaagtacc      780
caatcctcca gacaggactc caacgtggcc aaagctgagg cttccgccgc agccaaggcc      840
tcgcctggca ctgccacaag agacggagtc aaccttggtc tcgcctctga tgctggtgca      900
gctgctcaac taaaagccca agccgcagca ttggcacgag caagtagcag aattagttcc      960
```

```
ggccctgcgt tatccgcatg gaaatggagg aacgaagatt cttcagaatc gtcaacctct    1020
gcaatcgcca gctctagcgc cagttccagc tccagttctc gcagcgcatc cggaaactaa    1080

<210> SEQ ID NO 78
<211> LENGTH: 1125
<212> TYPE: DNA
<213> ORGANISM: Vespa simillima xanthoptera

<400> SEQUENCE: 78
atgaagatcc cctcgattct cgtaacgtgc cttttacct ggggcttggc tgccgggagt      60
agcagctcgt ccgcggaatc ttcggcatcg gcgacagcgt cttcagatgc gtcctggagc    120
gcgtcctcga gatcgtcagc taccggtaga gcaccgaacg tgattttgaa tagggcacct    180
caattaggag ctagcgcggc agcgatcgca tcggctcgag ccagtacctc agcaaatgct    240
gcatcagacg aaaaatctgc ccgagaaacg cgagcgaccg ctttggcccg atcaagagct    300
gctgttacgg cggcagcacg agcagccgca aggacgcaag aagccgtcgc ggcagcaaaa    360
gccgcaagta gggcccaagc gcttgctgct gctaaatctt cggcggcaat ttctgcattg    420
gccgctggag aggctgccgc ccaaaaggcg gacgccgcag ctctcgccgc attagctgct    480
aatcagagat ctgtcaaagc cgcagaaaat ggtctagcag tgcagaatcg tgcgaatgga    540
gaagcggaac aggcaagtcg tgcggctgct gctaaccttg ccgcggccat ccgtacccga    600
gacaatgctc tcgaaacgag aagagaagca gctcgattga aggcactagc cacagctgcc    660
gctaacgcta ataacaaagc gaccagtctt gccgaagctt ctgcgaacca agcagctgaa    720
gcaagctccg ctgccgagga tacttcttcc gctcaatctg ctgcggtcgc tcaagctgag    780
gccgctgaaa cgctcaacgt aaatctcgct atactcgaaa gtacccaatc ctccagacag    840
gactccaacg tggccaaagc tgaggcttcc gccgcagcca aggcctcgcc tggcactgcc    900
acaagagacg gagtcaacct tggtctcgcc tctgatgctg gtgcagctgc tcaactaaaa    960
gcccaagccg cagcattggc acgagcaagt agcagaatta gttccggccc tgcgttatcc    1020
gcatggaaat ggaggaacga agattcttca gaatcgtcaa cctctgcaat cgccagctct    1080
agcgccagtt ccagctccag ttctcgcagc gcatccggaa actaa                   1125

<210> SEQ ID NO 79
<211> LENGTH: 1080
<212> TYPE: DNA
<213> ORGANISM: Vespa simillima xanthoptera

<400> SEQUENCE: 79
agcgtggccc aaggtgggcc atcaaggttg tctgaaacca gtgattcgtc cgcagcatct      60
tggtcctcga gttcgtcttc aagctcgtcc ttgtcctcat ctctggcttc ggattctgct    120
tcttcttctg cttcgggttc ggcttcggct tcggcttcgg cttcggcttc ggcttcagca    180
agttcgagaa acgataacag tagagttaag gcatggaaga agggtagagg aggtagcgac    240
agcttggtac tgtcgagtga ttcatcagaa gattcaaaag ccagggagct cctcgagaca    300
gacgccggat taggtgcggc cgctgcgtta gcaagagcta ccgcggatgc ccaagctaga    360
acagcagcaa gcgccgatgc tacggctaat aaggcaactg caaaggctct tgtattagcc    420
gaggctgctg taagggcgga aaatgcagcg attgtaagga tccgtagggc tttatcggca    480
gcgcaagctc tcgtctcggc atccaatcgt gcaaaggccg cagctagagc tgcgagggaa    540
gctgctgcga actctgccgc tgctgccgca aaagcttcca ctaatcaagt gaaagccaac    600
gctgactcgc ttgtcgccaa cagagctgca gccgcccttc ttgctgctgc cgaggaagcc    660
```

-continued

```
ctccagaaag ccagtgcttc gcagaatgca gcagctgaag ctgctgcgaa agctcgtgcc      720
gcagctaacg cgaatgccgc aaccaccaga gccgcggcct cggccatact cgccgaagct      780
cgtgccagaa cagctatcac gaaagcactt gccgctcaat caacggcctc cgctcaggct      840
tcttccgcct ctcaagtaca aaatcgtgca ataacctac aagccgaaac cgcttcttta       900
gcccaatcca gggcagaagc cgcaatagct gcagctgcgg cacaagctgc cgctctcgca      960
gaagctaacg ctcaactcgc tcgtctcagc aaagcatctg caggtgcttc cagcgagggt     1020
tcggcttcag cctcggcatc agcctcggca tcagcctctt cgagtagtag cagcgcctaa     1080
```

<210> SEQ ID NO 80
<211> LENGTH: 1128
<212> TYPE: DNA
<213> ORGANISM: Vespa simillima xanthoptera

<400> SEQUENCE: 80

```
atgaacgtac aagcgacact cgtgctttgc ctgctcgcat tgttcggcag cgtggcccaa       60
ggtgggccat caaggttgtc tgaaaccagt gattcgtccg cagcatcttg gtcctcgagt      120
tcgtcttcaa gctcgtcctt gtcctcatct ctggcttcgg attctgcttc ttcttctgct      180
tcgggttcgg cttcggcttc ggcttcggct tcggcttcgg cttcagcaag ttcgagaaac      240
gataacagta gagttaaggc atggaagaag ggtagaggag gtagcgacag cttggtactg      300
tcgagtgatt catcagaaga ttcaaaagcc agggagctcc tcgagacaga cgccggatta      360
ggtgcggccg ctgcgttagc aagagctacc gcggatgccc aagctagaac agcagcaagc      420
gccgatgcta cggctaataa ggcaactgca aaggctcttg tattagccga ggctgctgta      480
agggcggaaa atgcagcgat tgtaaggatc cgtagggctt tatcggcagc gcaagctctc      540
gtctcggcat ccaatcgtgc aaaggccgca gctagagctg cgagggaagc tgctgcgaac      600
tctgccgctg ctgccgcaaa agcttccact aatcaagtga agccaacgc tgactcgctt       660 gtcgccaaca gagctgcagc cgcccttctt gctgctgccg aggaagccct ccagaaagcc      720
agtgcttcgc agaatgcagc agctgaagct gctgcgaaag ctcgtgccgc agctaacgcg      780
aatgccgcaa ccaccagagc cgcggcctcg gccatactcg ccgaagctcg tgccagaaca      840
gctatcacga aagcacttgc cgctcaatca acggcctccg ctcaggcttc ttccgcctct      900
caagtacaaa atcgtgcaaa taacctacaa gccgaaaccg cttctttagc ccaatccagg      960
gcagaagccg caatagctgc agctgcggca caagctgccg ctctcgcaga agctaacgct     1020
caactcgctc gtctcagcaa agcatctgca ggtgcttcca gcgagggttc ggcttcagcc     1080
tcggcatcag cctcggcatc agcctcttcg agtagtagca gcgcctaa                  1128
```

<210> SEQ ID NO 81
<211> LENGTH: 314
<212> TYPE: PRT
<213> ORGANISM: Apis cerana

<400> SEQUENCE: 81

Gly Leu Glu Gly Ser Gly Asn Pro Leu Pro Glu Leu Val Lys Gly Ser
1               5                   10                  15

Ala Ser Ala Thr Ala Ser Thr Ala Val Thr Ala Arg Ser Gly Leu Arg
            20                  25                  30

Val Gly Gln Val Ala Leu Ala Ser Gln Lys Asp Ala Val Leu Gln Ala
        35                  40                  45

Glu Ala Ala Ala Ser Ala Ala Ser Glu Ala Arg Ala Ala Ala Asp Leu
    50                  55                  60

Thr Ala Lys Leu Ser Gln Glu Ser Ala Ser Val Gln Ser Gln Ala Ala
65                  70                  75                  80

Ala Lys Gly Lys Glu Thr Glu Ala Ala Val Gly Gln Ala Arg Ala
            85                  90                  95

Gly Leu Glu Ser Val Ser Ile Ala Ala Ser Ala Thr Ser Ala Ala Lys
                100                 105                 110

Glu Ala Ser Thr Ala Ala Arg Ala Ala Ser Ala Leu Ser Thr Ala
            115                 120                 125

Thr Val Gln Ala Lys Ile Ala Glu Arg Ala Ala Lys Ala Glu Ala Val
            130                 135                 140

Ala Ser Glu Glu Ala Lys Ala Lys Ala Ile Ala Ala Asn Leu Ala
145                 150                 155                 160

Ala Ala Ala Ser Glu Ala Ala Glu Thr Ala Leu Lys Ala Glu Lys Val
                165                 170                 175

Ala Glu Glu Ala Ile Ala Arg Ala Ala Ser Ala Lys Ala Ala Arg
            180                 185                 190

Ala Ala Ala Ala Leu Ala Ser Ser Lys Glu Ala Ala Thr Ala Ser
            195                 200                 205

Ala Arg Asn Ala Ala Glu Ser Glu Ala Arg Asn Glu Val Ala Val Leu
            210                 215                 220

Ile Ala Glu Ile Asp Lys Lys Ser Arg Glu Ile Asp Ala Ala Thr Ser
225                 230                 235                 240

Leu Asn Ala Arg Ala Ala Lys Ala Ser Ser Arg Asn Val Glu Thr
                245                 250                 255

Ala Thr Ile Gly Ala Asn Ile Asp Ser Ser Lys Gln Val Val Ser Ile
            260                 265                 270

Pro Val Glu Ile Lys Lys Phe Pro Glu Pro Glu Leu Ser Thr Ser Trp
            275                 280                 285

Arg Glu Asp Glu Glu Val Thr Lys Gly Lys Lys Glu Asp Ile Asn Leu
290                 295                 300

Asn Ser Phe Glu Leu Lys Ser Asn Val Phe
305                 310

<210> SEQ ID NO 82
<211> LENGTH: 333
<212> TYPE: PRT
<213> ORGANISM: Apis cerana

<400> SEQUENCE: 82

Met Lys Ile Pro Val Leu Leu Ala Thr Cys Leu Tyr Leu Cys Gly Phe
1               5                   10                  15

Ala Ser Ala Gly Leu Glu Gly Ser Gly Asn Pro Leu Pro Glu Leu Val
            20                  25                  30

Lys Gly Ser Ala Ser Ala Thr Ala Ser Thr Ala Val Thr Ala Arg Ser
            35                  40                  45

Gly Leu Arg Val Gly Gln Val Ala Leu Ala Ser Gln Lys Asp Ala Val
        50                  55                  60

Leu Gln Ala Glu Ala Ala Ser Ala Ala Ser Glu Ala Arg Ala Ala
65                  70                  75                  80

Ala Asp Leu Thr Ala Lys Leu Ser Gln Glu Ser Ala Ser Val Gln Ser
                85                  90                  95

Gln Ala Ala Ala Lys Gly Lys Glu Thr Glu Ala Ala Val Gly Gln
            100                 105                 110

Ala Arg Ala Gly Leu Glu Ser Val Ser Ile Ala Ala Ser Ala Thr Ser
            115                 120                 125

```
Ala Ala Lys Glu Ala Ser Thr Ala Ala Arg Ala Ala Ser Ala Leu
    130                 135                 140

Ser Thr Ala Thr Val Gln Ala Lys Ile Ala Glu Arg Ala Ala Lys Ala
145                 150                 155                 160

Glu Ala Val Ala Ser Glu Ala Lys Lys Ala Ile Ala Ala Ala
                165                 170                 175

Asn Leu Ala Ala Ala Ser Glu Ala Ala Glu Thr Ala Leu Lys Ala
                180                 185                 190

Glu Lys Val Ala Glu Glu Ala Ile Ala Arg Ala Ala Ser Ala Lys Ala
                195                 200                 205

Ala Ala Arg Ala Ala Ala Ala Leu Ala Ser Ser Lys Glu Ala Ala
    210                 215                 220

Thr Ala Ser Ala Arg Asn Ala Ala Glu Ser Glu Ala Arg Asn Glu Val
225                 230                 235                 240

Ala Val Leu Ile Ala Glu Ile Asp Lys Lys Ser Arg Glu Ile Asp Ala
                245                 250                 255

Ala Thr Ser Leu Asn Ala Arg Ala Ala Lys Ala Ser Ser Arg Asn
                260                 265                 270

Val Glu Thr Ala Thr Ile Gly Ala Asn Ile Asp Ser Ser Lys Gln Val
                275                 280                 285

Val Ser Ile Pro Val Glu Ile Lys Lys Phe Pro Glu Pro Glu Leu Ser
    290                 295                 300

Thr Ser Trp Arg Glu Asp Glu Glu Val Thr Lys Gly Lys Lys Glu Asp
305                 310                 315                 320

Ile Asn Leu Asn Ser Phe Glu Leu Lys Ser Asn Val Phe
                325                 330

<210> SEQ ID NO 83
<211> LENGTH: 288
<212> TYPE: PRT
<213> ORGANISM: Apis cerana

<400> SEQUENCE: 83

Arg Val Ile Asn His Glu Ser Leu Lys Thr Asn Val Asp Ile Gln Val
1               5                   10                  15

Thr Pro Gly Gln Val Gly Asp Gly Ser Asp Ala Thr Ser Ser Ser Ile
                20                  25                  30

Glu Asn Ala Leu Lys Val Ala Arg Ala Ser Glu Asn Val Gly Leu Asn
            35                  40                  45

Leu Glu Leu Asn Ala Gly Ala His Ala Ala Ser Val Ala Ala Ala Ala
    50                  55                  60

Gln Ala Lys Asn Thr Glu Ala Ala Glu Val Gly Ala Asn Ala Ala Leu
65              70                  75                  80

Ala Ala Ala Ile Ala Lys Arg Glu Glu Ala Ile Lys Ala Ser Glu Ile
                85                  90                  95

Ala Ser Gln Leu Leu Thr Asn Ala Ala Lys Ala Ala Glu Ala Thr Val
            100                 105                 110

Ser Ala Thr Lys Arg Ala Ala Gln Leu Thr Ala Ala Lys Glu Ala
            115                 120                 125

Thr Arg Ala Ser Ala Ala Ala Glu Ala Ala Thr Glu Ala Gln Val
    130                 135                 140

Lys Ala Asn Ala Asp Ser Ile Ile Thr Lys Arg Thr Ala Ile Ala Glu
145                 150                 155                 160

Ala Gln Ala Ala Ala Glu Ala Gln Val Lys Ala Ala Ile Ala Arg Lys
                165                 170                 175
```

```
Ala Ala Ala Asn Phe Leu Ala Lys Ala Gln Ile Ala Ala Ala Glu
            180                 185                 190

Ser Glu Ala Thr Lys Leu Ala Ala Glu Ala Thr Val Ala Leu Ser Asn
        195                 200                 205

Ala Glu Val Ala Val Asn Gln Ala Arg Asn Ala Gln Ala Thr Ala Ser
    210                 215                 220

Thr Gln Ala Ser Ala Ala Val Arg Val Asp Ser Gln Ala Ala Asn Ala
225                 230                 235                 240

Glu Ala Ala Ala Val Ala Gln Ala Glu Thr Leu Leu Val Thr Ala Glu
            245                 250                 255

Ala Ile Ala Ala Ala Glu Ala Glu Ala Ala Ser Lys Ala Ala Ser Phe
            260                 265                 270

Ala Lys Lys Ile Val Asp Glu Lys Lys Ile His Val Glu Lys Leu Glu
            275                 280                 285

<210> SEQ ID NO 84
<211> LENGTH: 307
<212> TYPE: PRT
<213> ORGANISM: Apis cerana

<400> SEQUENCE: 84

Met Lys Ile Pro Ala Ile Phe Val Thr Ser Leu Leu Val Trp Gly Leu
1               5                   10                  15

Ala Glu Gly Arg Val Ile Asn His Glu Ser Leu Lys Thr Asn Val Asp
            20                  25                  30

Ile Gln Val Thr Pro Gly Gln Val Gly Asp Gly Ser Asp Ala Thr Ser
        35                  40                  45

Ser Ser Ile Glu Asn Ala Leu Lys Val Ala Arg Ala Ser Glu Asn Val
50                  55                  60

Gly Leu Asn Leu Glu Leu Asn Ala Gly Ala His Ala Ala Ser Val Ala
65                  70                  75                  80

Ala Ala Ala Gln Ala Lys Asn Thr Glu Ala Ala Glu Val Gly Ala Asn
                85                  90                  95

Ala Ala Leu Ala Ala Ile Ala Lys Arg Glu Glu Ala Ile Lys Ala
            100                 105                 110

Ser Glu Ile Ala Ser Gln Leu Leu Thr Asn Ala Ala Lys Ala Ala Glu
        115                 120                 125

Ala Thr Val Ser Ala Thr Lys Arg Ala Ala Gln Leu Thr Ala Ala Ala
    130                 135                 140

Lys Glu Ala Thr Arg Ala Ser Ala Ala Ala Glu Ala Ala Thr Glu
145                 150                 155                 160

Ala Gln Val Lys Ala Asn Ala Asp Ser Ile Ile Thr Lys Arg Thr Ala
                165                 170                 175

Ile Ala Glu Ala Gln Ala Ala Glu Ala Gln Val Lys Ala Ala Ile
            180                 185                 190

Ala Arg Lys Ala Ala Ala Asn Phe Leu Ala Lys Ala Gln Ile Ala Ala
        195                 200                 205

Ala Ala Glu Ser Glu Ala Thr Lys Leu Ala Ala Glu Ala Thr Val Ala
    210                 215                 220

Leu Ser Asn Ala Glu Val Ala Val Asn Gln Ala Arg Asn Ala Gln Ala
225                 230                 235                 240

Thr Ala Ser Thr Gln Ala Ser Ala Ala Val Arg Val Asp Ser Gln Ala
                245                 250                 255

Ala Asn Ala Glu Ala Ala Ala Val Ala Gln Ala Glu Thr Leu Leu Val
            260                 265                 270
```

```
Thr Ala Glu Ala Ile Ala Ala Glu Ala Glu Ala Ala Ser Lys Ala
        275                 280                 285

Ala Ser Phe Ala Lys Lys Ile Val Asp Glu Lys Lys Ile His Val Glu
290                 295                 300

Lys Leu Glu
305

<210> SEQ ID NO 85
<211> LENGTH: 316
<212> TYPE: PRT
<213> ORGANISM: Apis cerana

<400> SEQUENCE: 85

Gly Val Glu Glu Phe Lys Ser Ser Thr Thr Glu Glu Val Ile Gly Lys
1               5                   10                  15

Asn Leu Glu Val Asp Leu Leu Lys Asn Val Asp Thr Ser Ala Lys Arg
            20                  25                  30

Arg Glu Asn Gly Ala Pro Val Leu Gly Lys Asn Val Phe Lys Ser Leu
        35                  40                  45

Glu Asn Ile Lys Ala Ser Ala Gly Ala Asp Ala Lys Ala Ser Ala Val
    50                  55                  60

Val Lys Ala Ser Ala Leu Ala Leu Ala Glu Ala Tyr Leu Arg Ala Ser
65                  70                  75                  80

Ala Leu Ser Ala Ala Ala Ser Ala Lys Ala Ala Ala Ala Leu Lys Asn
                85                  90                  95

Ala Gln Gln Ala Gln Leu Ile Ala Gln Glu Lys Ala Leu Ala Ala Leu
            100                 105                 110

Lys Ala Gln Ser Glu Glu Glu Ala Ala Ser Ala Arg Ala Asn Ala Ala
        115                 120                 125

Ala Ala Ala Thr Gln Ser Ala Val Glu Arg Ala Gln Ala Ser Ser Arg
    130                 135                 140

Thr Ala Thr Ala Ala Gln Asn Val Ala Ser Asn Leu Gln Lys Arg Thr
145                 150                 155                 160

Ser Thr Lys Ala Ala Ala Glu Ala Ala Ala Thr Leu Arg Gln Leu Gln
                165                 170                 175

Asp Ala Glu Gln Thr Lys Trp Ser Ala Asn Ala Ala Leu Glu Val Ser
            180                 185                 190

Ala Ala Ala Thr Ala Ala Glu Thr Lys Thr Thr Ala Ser Ser Glu Ala
        195                 200                 205

Ala Ser Ala Ala Ala Lys Lys Ala Ala Ala Ile Ala Ser Asp Ala Asp
    210                 215                 220

Gly Ala Glu Lys Ser Ala Ser Thr Glu Ala Gln Ser Ala Ala Lys Ile
225                 230                 235                 240

Glu Ser Val Ala Ala Ala Glu Gly Ser Ala Asn Ser Ala Ser Glu Asp
                245                 250                 255

Ser Gln Ala Ala Gln Leu Glu Ala Ser Thr Ala Ala Arg Ala Asn Val
            260                 265                 270

Ala Thr Ala Ile Gly Asp Gly Ala Ile Leu Gly Leu Gly Gln Asp Val
        275                 280                 285

Gly Ala Ala Ala Gln Leu Leu Ala Gln Ala Lys Ala Leu Ala Glu Val
    290                 295                 300

Ser Ser Lys Ser Glu Asn Ile Glu Asp Lys Lys Phe
305                 310                 315

<210> SEQ ID NO 86
```

```
<211> LENGTH: 335
<212> TYPE: PRT
<213> ORGANISM: Apis cerana

<400> SEQUENCE: 86

Met Gln Ile Pro Thr Phe Val Val Cys Leu Leu Thr Ser Gly Leu
1               5                   10                  15

Val His Ala Gly Val Glu Glu Phe Lys Ser Ser Thr Thr Glu Glu Val
        20                  25                  30

Ile Gly Lys Asn Leu Glu Val Asp Leu Leu Lys Asn Val Asp Thr Ser
        35                  40                  45

Ala Lys Arg Arg Glu Asn Gly Ala Pro Val Leu Gly Lys Asn Val Phe
50                  55                  60

Lys Ser Leu Glu Asn Ile Lys Ala Ser Ala Gly Ala Asp Ala Lys Ala
65                  70                  75                  80

Ser Ala Val Val Lys Ala Ser Ala Leu Ala Leu Ala Glu Ala Tyr Leu
                85                  90                  95

Arg Ala Ser Ala Leu Ser Ala Ala Ser Ala Lys Ala Ala Ala
            100                 105                 110

Leu Lys Asn Ala Gln Gln Ala Gln Leu Ile Ala Gln Glu Lys Ala Leu
            115                 120                 125

Ala Ala Leu Lys Ala Gln Ser Glu Glu Glu Ala Ala Ser Ala Arg Ala
130                 135                 140

Asn Ala Ala Ala Ala Thr Gln Ser Ala Val Glu Arg Ala Gln Ala
145                 150                 155                 160

Ser Ser Arg Thr Ala Thr Ala Ala Gln Asn Val Ala Ser Asn Leu Gln
                165                 170                 175

Lys Arg Thr Ser Thr Lys Ala Ala Ala Glu Ala Ala Thr Leu Arg
            180                 185                 190

Gln Leu Gln Asp Ala Glu Gln Thr Lys Trp Ser Ala Asn Ala Ala Leu
            195                 200                 205

Glu Val Ser Ala Ala Ala Thr Ala Ala Glu Thr Lys Thr Thr Ala Ser
210                 215                 220

Ser Glu Ala Ala Ser Ala Ala Lys Lys Ala Ala Ala Ile Ala Ser
225                 230                 235                 240

Asp Ala Asp Gly Ala Glu Lys Ser Ala Ser Thr Glu Ala Gln Ser Ala
                245                 250                 255

Ala Lys Ile Glu Ser Val Ala Ala Glu Gly Ser Ala Asn Ser Ala
            260                 265                 270

Ser Glu Asp Ser Gln Ala Ala Gln Leu Glu Ala Ser Thr Ala Ala Arg
            275                 280                 285

Ala Asn Val Ala Thr Ala Ile Gly Asp Gly Ala Ile Leu Gly Leu Gly
            290                 295                 300

Gln Asp Val Gly Ala Ala Ala Gln Leu Leu Ala Gln Ala Lys Ala Leu
305                 310                 315                 320

Ala Glu Val Ser Ser Lys Ser Glu Asn Ile Glu Asp Lys Lys Phe
                325                 330                 335

<210> SEQ ID NO 87
<211> LENGTH: 320
<212> TYPE: PRT
<213> ORGANISM: Apis cerana

<400> SEQUENCE: 87

Ala Ser Glu Glu Val Glu Thr Arg Gly Lys Thr Lys Thr Ser Thr Val
1               5                   10                  15
```

```
Val Lys Ser Glu Lys Val Glu Val Pro Ala Lys Asp Glu Leu Lys
         20                  25                  30

Leu Thr Ser Glu Pro Ile Leu Gly Arg Arg Val Gly Thr Gly Ala Ser
         35                  40                  45

Glu Val Ala Ser Ser Ser Gly Glu Ile Ile Ala Ile Ser Leu Gly Thr
50                   55                  60

Gly Gln Ala Ala Ala Glu Ser Gln Ala Val Ala Ala Ser Gln Ser Lys
65                  70                  75                  80

Ser Ala Ala Ser Ala Ala Ile Ser Ala Ser Glu Leu Ala Asn Lys Val
                 85                  90                  95

Ala Ala Leu Val Val Gly Ala Thr Ala Ala Gln Ala Arg Ala Ala Ala
             100                 105                 110

Ala Ser Ser Gly Ala Leu Lys Ala Ser Leu Ala Thr Glu Glu Ser Ala
         115                 120                 125

Glu Glu Ala Glu Ala Ala Val Ala Val Ala Lys Ala Ala Ala Glu Lys
         130                 135                 140

Ala Glu Ser Leu Ala Arg Asn Leu Ala Ser Ala Ser Ala Arg Ala Ala
145                 150                 155                 160

Ile Ser Ser Glu Ser Ala Asn Glu Leu Ala Gln Ala Glu Ser Ala Ala
                 165                 170                 175

Ala Ala Glu Ala Gln Ala Lys Thr Ala Ala Ala Lys Ala Ala Glu
             180                 185                 190

Ile Ala Leu Lys Val Ala Glu Ile Ala Val Lys Ala Glu Ala Asp Ala
             195                 200                 205

Ala Ala Ala Ala Val Ala Ala Ala Lys Ala Arg Ala Val Ala Asp Ala
         210                 215                 220

Ala Ala Ala Arg Ala Ala Ala Val Asn Ala Ile Ala Lys Ala Glu Glu
225                 230                 235                 240

Glu Ala Ser Ala Gln Ala Glu Asn Thr Ala Gly Val Ser Gln Ala Ala
                 245                 250                 255

Ala Ser Ala Ala Ala Glu Ser Arg Ala Ala Ala Ala Ala Ala Ala
             260                 265                 270

Thr Ser Glu Thr Ala Ala Glu Ala Gly Pro Leu Ala Gly Glu Leu Lys
         275                 280                 285

Pro Pro Gln Trp Lys Arg Ile Pro Val Lys Lys Glu Glu Trp Lys Thr
290                 295                 300

Ser Thr Lys Glu Glu Trp Lys Thr Thr Asn Glu Glu Trp Glu Val Lys
305                 310                 315                 320

<210> SEQ ID NO 88
<211> LENGTH: 339
<212> TYPE: PRT
<213> ORGANISM: Apis cerana

<400> SEQUENCE: 88

Met Lys Ile Pro Ser Ile Leu Ala Val Ser Leu Leu Ile Trp Gly Leu
1               5                   10                  15

Ala Ser Gly Ala Ser Glu Glu Val Glu Thr Arg Gly Lys Thr Lys Thr
             20                  25                  30

Ser Thr Val Val Lys Ser Glu Lys Val Glu Val Pro Ala Lys Asp
         35                  40                  45

Glu Leu Lys Leu Thr Ser Glu Pro Ile Leu Gly Arg Arg Val Gly Thr
50                  55                  60

Gly Ala Ser Glu Val Ala Ser Ser Ser Gly Glu Ile Ile Ala Ile Ser
65                  70                  75                  80
```

-continued

```
Leu Gly Thr Gly Gln Ala Ala Glu Ser Gln Ala Val Ala Ala Ser
                85                  90                  95

Gln Ser Lys Ser Ala Ala Ser Ala Ala Ile Ser Ala Ser Glu Leu Ala
            100                 105                 110

Asn Lys Val Ala Ala Leu Val Val Gly Ala Thr Ala Ala Gln Ala Arg
        115                 120                 125

Ala Ala Ala Ala Ser Ser Gly Ala Leu Lys Ala Ser Leu Ala Thr Glu
    130                 135                 140

Glu Ser Ala Glu Glu Ala Gly Ala Ala Val Ala Val Ala Lys Ala Ala
145                 150                 155                 160

Ala Glu Lys Ala Glu Ser Leu Ala Arg Asn Leu Ala Ser Ala Ser Ala
                165                 170                 175

Arg Ala Ala Ile Ser Ser Glu Ser Ala Asn Glu Leu Ala Gln Ala Glu
            180                 185                 190

Ser Ala Ala Ala Glu Ala Gln Ala Lys Thr Ala Ala Ala Ala Lys
        195                 200                 205

Ala Ala Glu Ile Ala Leu Lys Val Ala Glu Ile Ala Val Lys Ala Glu
    210                 215                 220

Ala Asp Ala Ala Ala Ala Val Ala Ala Ala Lys Ala Arg Ala Val
225                 230                 235                 240

Ala Asp Ala Ala Ala Arg Ala Ala Val Asn Ala Ile Ala Lys
                245                 250                 255

Ala Glu Glu Glu Ala Ser Ala Gln Ala Glu Asn Thr Ala Gly Val Ser
            260                 265                 270

Gln Ala Ala Ala Ser Ala Ala Ala Glu Ser Arg Ala Ala Ala Ala Ala
        275                 280                 285

Ala Ala Ala Thr Ser Glu Thr Ala Ala Glu Ala Gly Pro Leu Ala Gly
    290                 295                 300

Glu Leu Lys Pro Pro Gln Trp Lys Arg Ile Pro Val Lys Lys Glu Glu
305                 310                 315                 320

Trp Lys Thr Ser Thr Lys Glu Glu Trp Lys Thr Thr Asn Glu Glu Trp
                325                 330                 335

Glu Val Lys
```

<210> SEQ ID NO 89
<211> LENGTH: 945
<212> TYPE: DNA
<213> ORGANISM: Apis cerana

<400> SEQUENCE: 89

```
ggtttggaag ggtcgggtaa cccattgccc gagctcgtga aaggtagcgc atcggccacc      60
gcgtcgactg ctgtgactgc tagatcgggg cttagagtcg acaagtagc tttagcttcg     120
cagaaggatg ccgtactcca agctgaagct gctgcatccg ccgcgtcaga ggcacgcgcc     180
gctgccgatc tgacggctaa acttagccaa gaatcggcat cagtgcaatc acaggccgcc     240
gccaagggaa ggaaacggaa ggaggcagcg gttggtcaag ctagagctgg tctcgagtcg     300
gtatccatcg ccgcatcggc cacttctgct gccaagaag catcaaccgc cgccagagcc     360
gcagcatccg cactatccac agccacggtg caagcgaaaa tagccgagag agcagccaag     420
gctgaagctg ttgcctcaga ggaagccaag gccaaggcga ttgcagcagc caacttggcg     480
gctgcggcta gtgaagccgc ggaaacagcc ctcaaggctg agaaagtggc cgaagaagct     540
atcgcaagag cggcctctgc aaaggctgct gcaagagctg ctgcggccgc tctagcctcc     600
tcgaaggaag cagccacggc cagcgcgaga aacgccgcgg aatccgaggc caggaacgaa     660
```

```
gtagctgtat tgatcgccga gattgataaa aagagtaggg aaatcgacgc agccacttcg    720
cttaatgcgc gtgccgctgc caaagcaagc tccaggaacg tagaaacggc gacaatcggg    780
gctaacatcg actcttcgaa acaagtcgta tcaattccag tggaaataaa gaaattcccg    840
gagccagaac tgtcaacatc atggagagaa gatgaagagg ttacgaaagg aaaaaaggag    900
gatataaatc tgaatagctt cgaattgaag agcaatgtat tttag                    945
```

<210> SEQ ID NO 90
<211> LENGTH: 1002
<212> TYPE: DNA
<213> ORGANISM: Apis cerana

<400> SEQUENCE: 90

```
atgaagattc cagtattgct tgcaacgtgc ctctaccttt gcggatttgc gtccgccggt     60
ttggaagggt cgggtaaccc attgcccgag ctcgtgaaag gtagcgcatc ggccaccgcg    120
tcgactgctg tgactgctag atcggggctt agagtcggac aagtagcttt agcttcgcag    180
aaggatgccg tactccaagc tgaagctgct gcatccgccg cgtcagaggc acgcgccgct    240
gccgatctga cggctaaact tagccaagaa tcggcatcag tgcaatcaca ggccgccgcc    300
aaagggaagg aaacggagga ggcagcggtt ggtcaagcta gagctggtct cgagtcggta    360
tccatcgccg catcggccac ttctgctgcc aaagaagcat caaccgccgc cagagccgca    420
gcatccgcac tatccacagc cacggtgcaa gcgaaaatag ccgagagagc agccaaggct    480
gaagctgttg cctcagagga agccaaggcc aaggcgattg cagcagccaa cttggcggct    540
gcggctagtg aagccgcgga aacagccctc aaggctgaga agtggccgga agaagctatc    600
gcaagagcgg cctctgcaaa ggctgctgca gagctgctg cggccgctct agcctcctcg    660
aaggaagcag ccacggccag cgcgagaaac gccgcggaat ccgaggccag gaacgaagta    720
gctgtattga tcgccgagat tgataaaaag agtagggaaa tcgacgcagc cacttcgctt    780
aatgcgcgtg ccgctgccaa agcaagctcc aggaacgtag aaacggcgac aatcggggct    840
aacatcgact cttcgaaaca agtcgtatca attccagtgg aaataaagaa attcccggag    900
ccagaactgt caacatcatg gagagaagat gaagaggtta cgaaaggaaa aaggaggat    960 ataaatctga atagcttcga attgaagagc aatgtatttt ag                      1002
```

<210> SEQ ID NO 91
<211> LENGTH: 867
<212> TYPE: DNA
<213> ORGANISM: Apis cerana

<400> SEQUENCE: 91

```
cgtgtgatta atcacgaatc cctgaagacg aacgtggata ttcaagtaac accaggacaa     60
gtcggtgatg gatctgacgc gactagctcc tccatagaaa acgccctaaa agtcgctcga    120
gcgtctgaga acgtgggcct gaatctggaa ttgaacgcag gcgcgcatgc tgccagtgtt    180
gccgctgctg cccaggccaa aaatacagag gctgcggaag taggagcaaa cgccgctctg    240
gccgccgcca ttgccaaacg agaggaagcg attaaagcca gcgagatagc aagccagtta    300
ttgaccaatg cagcaaaggc agcagaagcg actgtatcgg caacgaagag ggcagcacaa    360
ttgacggctg cagcgaaaga agcaaccaga gcttctgcag ccgctgctga agctgctacg    420
gaggcccagg taaaggctaa tgctgattcg attatcacga agaggactgc gattgctgag    480
gctcaagctg cggcagaagc tcaagttaag gcggcaatcg ctagaaaggc ggcagcgaat    540
tttttggcta aggctcaaat agcggctgcc gcggaatccg aggccacgaa actcgcggcc    600
```

| | |
|---|---|
| gaagccacag tggcattaag taacgccgaa gtcgccgtga accaggctag aaacgcacag | 660 |
| gcaaccgcct cgactcaagc ttccgcagct gttagggtag attctcaagc agcgaacgct | 720 |
| gaagcagccg ctgtagcaca agccgaaact ctcttggtta cggcagaagc catcgcagct | 780 |
| gcagaggctg aggctgcgag caaagccgcc tcatttgcaa aaaagatcgt cgatgagaag | 840 |
| aaaatacatg tagaaaagtt ggaataa | 867 |

<210> SEQ ID NO 92
<211> LENGTH: 924
<212> TYPE: DNA
<213> ORGANISM: Apis cerana

<400> SEQUENCE: 92

| | |
|---|---|
| atgaagattc cagcaatatt cgtcacatct ctgctggtct ggggattggc cgagggccgt | 60 |
| gtgattaatc acgaatccct gaagacgaac gtggatattc aagtaacacc aggacaagtc | 120 |
| ggtgatggat ctgacgcgac tagctcctcc atagaaaacg ccctaaaagt cgctcgagcg | 180 |
| tctgagaacg tgggcctgaa tctggaattg aacgcaggcg cgcatgctgc cagtgttgcc | 240 |
| gctgctgccc aggccaaaaa tacagaggct gcggaagtag agcaaacgc cgctctggcc | 300 |
| gccgccattg ccaaacgaga ggaagcgatt aaagccagcg agatagcaag ccagttattg | 360 |
| accaatgcag caaaggcagc agaagcgact gtatcggcaa cgaagagggc agcacaattg | 420 |
| acggctgcag cgaaagaagc aaccagagct tctgcagccg ctgctgaagc tgctacggag | 480 |
| gcccaggtaa aggctaatgc tgattcgatt atcacgaaga ggactgcgat tgctgaggct | 540 |
| caagctgcgg cagaagctca agttaaggcg gcaatcgcta aaaggcggc agcgaatttt | 600 |
| ttggctaagg ctcaaatagc ggctgccgcg gaatccgagg ccacgaaaact cgcggccgaa | 660 |
| gccacagtgg cattaagtaa cgccgaagtc gccgtgaacc aggctagaaa cgcacaggca | 720 |
| accgcctcga ctcaagcttc cgcagctgtt agggtagatt ctcaagcagc gaacgctgaa | 780 |
| gcagccgctg tagcacaagc cgaaactctc ttggttacgg cagaagccat cgcagctgca | 840 |
| gaggctgagg ctgcgagcaa agccgcctca tttgcaaaaa agatcgtcga tgagaagaaa | 900 |
| atacatgtag aaaagttgga ataa | 924 |

<210> SEQ ID NO 93
<211> LENGTH: 951
<212> TYPE: DNA
<213> ORGANISM: Apis cerana

<400> SEQUENCE: 93

| | |
|---|---|
| ggcgtcgagg aattcaagtc ctcgacaacc gaggaggtga tcggcaaaaa cttagaagtc | 60 |
| gacctattga aaatgtggga tactagcgcg aaacgaagag agaatggcgc cccagtgctc | 120 |
| ggcaagaacg tattcaaatc cctggagaac atcaaggcgt cggcgggcgc ggatgccaaa | 180 |
| gcatcagccg tggtgaaagc gtccgctctg gctcttgcag aagccatttt gcagagcgtct | 240 |
| gcattgtctg ccgccgcttc agccaaggca gccgctgccc tgaagaatgc gcaacaagcg | 300 |
| caattaatcg cccaggaaaa ggctttggcc gcgttgaaag ctcagtccga ggaagaggca | 360 |
| gcttctgctc gtgcgaacgc agcagccgct gcaacacagt cagcagtgga acgcgctcaa | 420 |
| gcctcctcca gaacagcaac ggcgcccaa acgtagcca gcaacttgca gaaacggacc | 480 |
| agcaccaagg ccgcggctga agccgctgct accctcagac aattacagga tgcggaacaa | 540 |
| accaaatgga gtgccaacgc tgcttttgaa gtctccgctg ctgcaactgc cgcagaaacg | 600 |
| aagaccactg cctcctcgga ggccgctagc gccgccgcca aaaaggcggc cgcgatagct | 660 |

| | |
|---|---|
| tctgacgcgg atggcgcaga aaagtcggca tctaccgaag cacaatcagc tgcgaagatc | 720 |
| gaaagtgtgg cagccgccga aggatccgcc aactcggcct ccgaggactc ccaggccgcg | 780 |
| caattggaag cttccaccgc ggcgagagcc aacgtggcca cagctatcgg ggatggagcg | 840 |
| attttaggac ttggacagga cgtgggtgcc gcggctcagt tgcttgcaca ggcgaaggca | 900 |
| ttggccgaag ttagctcgaa atccgaaaat attgaggata aaaattttg a | 951 |

<210> SEQ ID NO 94
<211> LENGTH: 1008
<212> TYPE: DNA
<213> ORGANISM: Apis cerana

<400> SEQUENCE: 94

| | |
|---|---|
| atgcagatcc caacgtttgt cgtcgtatgc ttgctcacat cgggcttggt gcacgcaggc | 60 |
| gtcgaggaat tcaagtcctc gacaaccgag gaggtgatcg gcaaaaactt agaagtcgac | 120 |
| ctattgaaaa atgtggatac tagcgcgaaa cgaagagaga atggcgcccc agtgctcggc | 180 |
| aagaacgtat tcaaatccct ggagaacatc aaggcgtcgg cgggcgcgga tgccaaagca | 240 |
| tcagccgtgg tgaaagcgtc cgctctggct cttgcagaag cctatttgcg agcgtctgca | 300 |
| ttgtctgccg ccgcttcagc caaggcagcc gctgccctga gaatgcgca acaagcgcaa | 360 |
| ttaatcgccc aggaaaaggc tttggccgcg ttgaaagctc agtccgagga gaggcagct | 420 |
| tctgctcgtg cgaacgcagc agccgctgca acacagtcag cagtggaacg cgctcaagcc | 480 |
| tcctccagaa cagcaacggc cgcccaaaac gtagccagca cttgcagaa acggaccagc | 540 |
| accaaggccg cggctgaagc cgctgctacc ctcagacaat tacaggatgc ggaacaaacc | 600 |
| aaatggagtg ccaacgctgc tttggaagtc tccgctgctg caactgccgc agaaacgaag | 660 |
| accactgcct cctcggaggc cgctagcgcc gccgccaaaa aggcggccgc gatagcttct | 720 |
| gacgcggatg gcgcagaaaa gtcggcatct accgaagcac aatcagctgc gaagatcgaa | 780 |
| agtgtggcag ccgccaaagg atccgccaac tcggcctccg aggactccca ggccgcgcaa | 840 |
| ttggaagctt ccaccgcggc gagagccaac gtggccacag ctatcgggga tggagcgatt | 900 |
| ttaggacttg gacaggacgt gggtgccgcg gctcagttgc ttgcacaggc gaaggcattg | 960 |
| gccgaagtta gctcgaaatc cgaaaatatt gaggataaaa attttga | 1008 |

<210> SEQ ID NO 95
<211> LENGTH: 963
<212> TYPE: DNA
<213> ORGANISM: Apis cerana

<400> SEQUENCE: 95

| | |
|---|---|
| gcaagcgaag aggtggagac acggggcaag accaagacct cgacagtggt gaaaagcgag | 60 |
| aaagtggaag tcgttcccgc taaggatgaa cttaaattaa cgagcgagcc catccttgga | 120 |
| agaagagtgg gaactggagc atccgaggtg gcatctagca gcggtgaaat catcgcaata | 180 |
| agtcttggaa cagggcaggc agcggcagaa tctcaggccg tggccgcctc gcaatccaaa | 240 |
| tcggcagcga gcgccgccat aagcgcaagc gagcttgcca caaagttgc tgctctagtt | 300 |
| gttggcgcga ctgcggcgca ggcgagagcg gccgccgcct cctcaggcgc gttgaaggcc | 360 |
| agcttggcga ccgaagaatc ggcggaagag gccgaggcgg ccgtggctgt cgccaaggct | 420 |
| gccgcggaaa aggccgaatc cctggcgaga atctcgcgt cggcgagcgc tcgtgcggct | 480 |
| atctcgtcgg aaagtgcgaa cgaattggct caagctgaga gcgcggcagc ggccgaagcg | 540 |
| caggccaaga cagccgccgc cgccaaagca gcggaaatcg cccttaaggt cgctgagata | 600 |

| gcggtgaaag cggaagcaga cgcggcagct gccgccgtgg cagctgcaaa ggcaagggcc | 660 |
| gtagcagacg cggccgctgc ccgtgctgca gccgtgaacg ccatcgccaa gcggaagag | 720 |
| gaggcctcgg cccaagcaga gaacaccgcc ggtgtttcgc aagctgccgc ctccgccgcg | 780 |
| gcggaatcgc gagccgctgc agcagccgcc gctgctactt cggagacagc ggctgaagct | 840 |
| ggcccgttag caggggagct gaaaccacca caatggaaac ggattcctgt taagaaggaa | 900 |
| gagtggaaaa catcaacgaa ggaagaatgg aaaacgacga atgaagaatg ggaggtgaag | 960 |
| taa | 963 |

<210> SEQ ID NO 96
<211> LENGTH: 1020
<212> TYPE: DNA
<213> ORGANISM: Apis cerana

<400> SEQUENCE: 96

| atgaagatcc catccatact cgcggtttcc ctgctgatct ggggtttggc aagcggcgca | 60 |
| agcgaagagg tggagacacg gggcaagacc aagacctcga cagtggtgaa agcgagaaa | 120 |
| gtggaagtcg ttcccgctaa ggatgaactt aaattaacga gcgagcccat ccttggaaga | 180 |
| agagtgggaa ctggagcatc cgaggtggca tctagcagcg gtgaaatcat cgcaataagt | 240 |
| cttggaacag gcaggcagc ggcagaatct caggccgtgg ccgcctcgca atccaaatcg | 300 |
| gcagcgagcg ccgccataag cgcaagcgag cttgccaaca agttgctgc tctagttgtt | 360 |
| ggcgcgactg cggcgcaggc gagagcggcc gccgcctcct caggcgcgtt gaaggccagc | 420 |
| ttggcgaccg aagaatcggc ggaagaggcc gaggcggccg tggctgtcgc caaggctgcc | 480 |
| gcggaaaagg ccgaatccct ggcgagaaat ctcgcgtcgg cgagcgctcg tgcggctatc | 540 |
| tcgtcggaaa gtgcgaacga attggctcaa gctgagagcg cggcagcggc cgaagcgcag | 600 |
| gccaagacag ccgccgccgc caaagcagcg gaaatcgccc ttaaggtcgc tgagatagcg | 660 |
| gtgaaagcgg aagcagacgc ggcagctgcc gccgtggcag ctgcaaaggc aagggccgta | 720 |
| gcagacgcgg ccgctgcccg tgctgcagcc gtgaacgcca tcgccaaggc ggaagaggag | 780 |
| gcctcggccc aagcagagaa caccgccggt gtttcgcaag ctgccgcctc cgccgcggcg | 840 |
| gaatcgcgag ccgctgcagc agccgccgct gctacttcgg agacagcggc tgaagctggc | 900 |
| ccgttagcag gggagctgaa accaccacaa tggaaacgga ttcctgttaa gaaggaagag | 960 |
| tggaaaacat caacgaagga agaatggaaa acgacgaatg aagaatggga ggtgaagtaa | 1020 |

<210> SEQ ID NO 97
<211> LENGTH: 562
<212> TYPE: PRT
<213> ORGANISM: Mallada signata

<400> SEQUENCE: 97

Ala Val Leu Ile Ser Gly Ser Ala Ala Gly Ala Ser Ser His Asn Ala
1               5                   10                  15

Ala Gly Ala Ala Ala Ala Ala Arg Ala Ala Leu Gly Ala Ser Gly Ala
            20                  25                  30

Ala Gly Leu Gly Ala Ala Ser Gly Ala Ala Arg Arg Asn Val Ala Val
        35                  40                  45

Gly Ala Asn Gly Ala Ala Ala Ala Ser Ala Ala Ala Ala Ala Ala Arg
    50                  55                  60

Arg Ala Gly Ala Ile Gly Leu Asn Gly Ala Ala Gly Ala Asn Val Ala
65                  70                  75                  80

Val Ala Gly Gly Lys Lys Gly Gly Ala Ala Gly Leu Asn Ala Gly Ala

```
                85                  90                  95
Gly Ala Ser Leu Val Ser Ala Ala Arg Arg Asn Gly Ala Leu Gly
            100                 105                 110
Leu Asn Gly Ala Ala Gly Ala Asn Leu Ala Ala Gly Gly Lys Lys
            115                 120                 125
Gly Gly Ala Ile Gly Leu Asn Ala Gly Ala Ser Ala Asn Val Gly Ala
            130                 135                 140
Ala Ala Ala Lys Lys Asn Gly Ala Ile Gly Leu Asn Ser Ala Ala Ser
145                 150                 155                 160
Ala Asn Ala Ala Ala Ala Ala Lys Lys Gly Gly Ala Ile Gly Leu
            165                 170                 175
Asn Ala Gly Ala Ser Ala Asn Ala Ala Ala Ala Ala Lys Lys Ser
            180                 185                 190
Gly Ala Val Gly Leu Asn Ala Gly Ala Ser Ala Asn Ala Ala Ala Ala
            195                 200                 205
Ala Ala Lys Lys Ser Gly Ala Val Ala Ala Asn Ser Ala Ala Ser Ala
            210                 215                 220
Asn Ala Ala Ala Ala Gln Lys Lys Ala Ala Ala Asp Ala Ala Asn
225                 230                 235                 240
Ala Ala Ala Ser Glu Ser Ala Ala Ala Ala Ala Lys Lys Ala Ala
            245                 250                 255
Ala Val Ala Glu Asn Ala Ala Ala Thr Ala Asn Ala Ala Ser Ala Leu
            260                 265                 270
Arg Lys Asn Ala Leu Ala Ile Ala Ser Asp Ala Ala Val Arg Ala
            275                 280                 285
Asp Ala Ala Ala Ala Ala Asp Asp Ala Ala Lys Ala Asn Asn Ala
            290                 295                 300
Ala Ser Arg Gly Ser Asp Gly Leu Thr Ala Arg Ala Asn Ala Ala Thr
305                 310                 315                 320
Leu Ala Ser Asp Ala Ala Arg Arg Ala Ser Asn Ala Ala Thr Ala Ala
            325                 330                 335
Ser Asp Ala Ala Thr Asp Arg Leu Asn Ala Ala Thr Ala Ala Ser Asn
            340                 345                 350
Ala Ala Thr Ala Arg Ala Asn Ala Ala Thr Arg Ala Asp Asp Ala Ala
            355                 360                 365
Thr Asp Ala Asp Asn Ala Ala Ser Lys Ala Ser Asp Val Ser Ala Ile
            370                 375                 380
Glu Ala Asp Asn Ala Ala Arg Ala Ala Asp Ala Asp Ala Ile Ala Thr
385                 390                 395                 400
Asn Arg Ala Ala Glu Ala Ser Asp Ala Ala Ile Ala Ala Asp Ala
            405                 410                 415
Ala Ala Asn Ala Ala Asp Ala Ala Ala Gln Cys Asn Asn Lys Val Ala
            420                 425                 430
Arg Val Ser Asp Ala Leu Ala Leu Ala Ala Asn Ala Ala Ala Arg Gly
            435                 440                 445
Ser Asp Ala Ala Ala Glu Ala Gln Asp Ala Val Ala Arg Ala Ser Asp
            450                 455                 460
Ala Ala Ala Ala Gln Ala Asp Gly Val Ala Ile Ala Val Asn Gly Ala
465                 470                 475                 480
Thr Ala Arg Asp Ser Ala Ile Glu Ala Ala Thr Ala Gly Ala Ala
            485                 490                 495
Gln Ala Lys Ala Ala Gly Arg Ala Gly Ala Ala Ala Gly Leu Arg
            500                 505                 510
```

-continued

```
Ala Gly Ala Ala Arg Gly Ala Ala Gly Ser Ala Arg Gly Leu Ala
            515                 520                 525
Gly Gly Leu Ala Ala Gly Ser Asn Ala Gly Ile Ala Ala Gly Ala Ala
530             535                 540
Ser Gly Leu Ala Arg Gly Ala Ala Glu Val Cys Ala Ala Arg Ile
545                 550                 555                 560
Ala Leu

<210> SEQ ID NO 98
<211> LENGTH: 588
<212> TYPE: PRT
<213> ORGANISM: Mallada signata

<400> SEQUENCE: 98

Met Ala Ala Ser Asn Lys Ile Ile Phe Ser Phe Leu Ala Ile Val Leu
1               5                   10                  15
Leu Gln Leu Ala Thr His Cys Ser Ser Thr Ala Val Leu Ile Ser Gly
            20                  25                  30
Ser Ala Ala Gly Ala Ser Ser His Asn Ala Gly Ala Ala Ala Ala
        35                  40                  45
Ala Arg Ala Ala Leu Gly Ala Ser Gly Ala Ala Gly Leu Gly Ala Ala
    50                  55                  60
Ser Gly Ala Ala Arg Arg Asn Val Ala Val Gly Ala Asn Gly Ala Ala
65                  70                  75                  80
Ala Ala Ser Ala Ala Ala Ala Ala Arg Arg Ala Gly Ala Ile Gly
                85                  90                  95
Leu Asn Gly Ala Ala Gly Ala Asn Val Ala Val Ala Gly Lys Lys
            100                 105                 110
Gly Gly Ala Ala Gly Leu Asn Ala Gly Ala Gly Ala Ser Leu Val Ser
        115                 120                 125
Ala Ala Ala Arg Arg Asn Gly Ala Leu Gly Leu Asn Gly Ala Ala Gly
    130                 135                 140
Ala Asn Leu Ala Ala Ala Gly Gly Lys Lys Gly Gly Ala Ile Gly Leu
145                 150                 155                 160
Asn Ala Gly Ala Ser Ala Asn Val Gly Ala Ala Ala Lys Lys Asn
                165                 170                 175
Gly Ala Ile Gly Leu Asn Ser Ala Ser Ala Asn Ala Ala Ala
            180                 185                 190
Ala Ala Lys Lys Gly Gly Ala Ile Gly Leu Asn Ala Gly Ala Ser Ala
    195                 200                 205
Asn Ala Ala Ala Ala Ala Lys Lys Ser Gly Ala Val Gly Leu Asn
210                 215                 220
Ala Gly Ala Ser Ala Asn Ala Ala Ala Ala Ala Lys Lys Ser Gly
225                 230                 235                 240
Ala Val Ala Ala Asn Ser Ala Ser Ala Asn Ala Ala Ala Ala
                245                 250                 255
Gln Lys Lys Ala Ala Asp Ala Ala Asn Ala Ala Ser Glu Ser
            260                 265                 270
Ala Ala Ala Ala Ala Lys Lys Ala Ala Val Ala Glu Asn Ala
        275                 280                 285
Ala Ala Thr Ala Asn Ala Ser Ala Leu Arg Lys Asn Ala Leu Ala
    290                 295                 300
Ile Ala Ser Asp Ala Ala Val Arg Ala Asp Ala Ala Ala Ala
305                 310                 315                 320
Ala Asp Asp Ala Ala Lys Ala Asn Asn Ala Ala Ser Arg Gly Ser Asp
```

|  | 325 |  |  |  | 330 |  |  |  | 335 |  |  |
|---|---|---|---|---|---|---|---|---|---|---|---|
| Gly | Leu | Thr | Ala | Arg | Ala | Asn | Ala | Ala | Thr | Leu | Ala |
|  |  |  | 340 |  |  |  | 345 |  |  |  | 350 |
| Ser | Asp | Ala | Ala |

| Arg | Arg | Ala | Ser | Asn | Ala | Ala | Thr | Ala | Ala | Ser | Asp |
|---|---|---|---|---|---|---|---|---|---|---|---|
|  |  |  | 355 |  |  |  | 360 |  |  |  | 365 |
| Ala | Ala | Thr | Asp |

| Arg | Leu | Asn | Ala | Ala | Thr | Ala | Ala | Ser | Asn | Ala | Ala |
|---|---|---|---|---|---|---|---|---|---|---|---|
|  | 370 |  |  |  | 375 |  |  |  | 380 |  |  |
| Thr | Ala | Arg | Ala |

| Asn | Ala | Ala | Thr | Arg | Ala | Asp | Asp | Ala | Ala | Thr | Asp |
|---|---|---|---|---|---|---|---|---|---|---|---|
| 385 |  |  |  |  | 390 |  |  |  |  | 395 |  |
| Ala | Asp | Asn | Ala | 400 |

| Ala | Ser | Lys | Ala | Ser | Asp | Val | Ser | Ala | Ile | Glu | Ala |
|---|---|---|---|---|---|---|---|---|---|---|---|
|  |  |  |  | 405 |  |  |  |  | 410 |  |  |
| Asp | Asn | Ala | Ala | 415 |

| Arg | Ala | Ala | Asp | Ala | Asp | Ala | Ile | Ala | Thr | Asn | Arg |
|---|---|---|---|---|---|---|---|---|---|---|---|
|  |  |  | 420 |  |  |  |  | 425 |  |  |  |
| Ala | Ala | Glu | Ala | 430 |

| Ser | Asp | Ala | Ala | Ala | Ile | Ala | Ala | Asp | Ala | Ala | Ala |
|---|---|---|---|---|---|---|---|---|---|---|---|
|  |  |  | 435 |  |  |  |  | 440 |  |  |  |
| Asn | Ala | Ala | Asp | 445 |

| Ala | Ala | Ala | Gln | Cys | Asn | Asn | Lys | Val | Ala | Arg | Val |
|---|---|---|---|---|---|---|---|---|---|---|---|
|  | 450 |  |  |  |  | 455 |  |  |  |  | 460 |
| Ser | Asp | Ala | Leu |

| Ala | Leu | Ala | Ala | Asn | Ala | Ala | Ala | Arg | Gly | Ser | Asp |
|---|---|---|---|---|---|---|---|---|---|---|---|
| 465 |  |  |  |  | 470 |  |  |  |  | 475 |  |
| Ala | Ala | Ala | Glu | 480 |

| Ala | Gln | Asp | Ala | Val | Ala | Arg | Ala | Ser | Asp | Ala | Ala |
|---|---|---|---|---|---|---|---|---|---|---|---|
|  |  |  |  | 485 |  |  |  |  | 490 |  |  |
| Ala | Ala | Gln | Ala | 495 |

| Asp | Gly | Val | Ala | Ile | Ala | Val | Asn | Gly | Ala | Thr | Ala |
|---|---|---|---|---|---|---|---|---|---|---|---|
|  |  |  | 500 |  |  |  |  | 505 |  |  |  |
| Arg | Asp | Ser | Ala | 510 |

| Ile | Glu | Ala | Ala | Ala | Thr | Ala | Gly | Ala | Ala | Gln | Ala |
|---|---|---|---|---|---|---|---|---|---|---|---|
|  |  |  | 515 |  |  |  |  | 520 |  |  |  |
| Lys | Ala | Ala | Gly | 525 |

| Arg | Ala | Gly | Ala | Ala | Ala | Ala | Gly | Leu | Arg | Ala | Gly |
|---|---|---|---|---|---|---|---|---|---|---|---|
|  | 530 |  |  |  |  | 535 |  |  |  |  | 540 |
| Ala | Ala | Arg | Gly |

| Ala | Ala | Ala | Gly | Ser | Ala | Arg | Gly | Leu | Ala | Gly | Gly |
|---|---|---|---|---|---|---|---|---|---|---|---|
| 545 |  |  |  |  | 550 |  |  |  |  | 555 |  |
| Leu | Ala | Ala | Gly | 560 |

| Ser | Asn | Ala | Gly | Ile | Ala | Ala | Gly | Ala | Ala | Ser | Gly |
|---|---|---|---|---|---|---|---|---|---|---|---|
|  |  |  | 565 |  |  |  |  | 570 |  |  |  |
| Leu | Ala | Arg | Gly | 575 |

| Ala | Ala | Ala | Glu | Val | Cys | Ala | Ala | Arg | Ile | Ala | Leu |
|---|---|---|---|---|---|---|---|---|---|---|---|
|  |  |  | 580 |  |  |  |  | 585 |  |  |  |

<210> SEQ ID NO 99
<211> LENGTH: 1689
<212> TYPE: DNA
<213> ORGANISM: Mallada signata

<400> SEQUENCE: 99

| gctgtattga | tttctggttc | ggctgctggt | gcttcctcac | acaatgctgc | tggtgcagct | 60 |
|---|---|---|---|---|---|---|
| gcagcagcca | gagctgcctt | aggcgcttct | ggggctgcag | gtttaggtgc | tgcatctggt | 120 |
| gctgcaagaa | gaaacgtagc | agttggtgct | aacggtgccg | ccgccgctag | tgctgcagct | 180 |
| gcagctgcca | gacgagctgg | cgctattggc | ctaaatggag | cagctggagc | taatgtagct | 240 |
| gtcgctggtg | gcaaaaaagg | aggtgctgct | ggattaaatg | ctggcgctgg | tgcttcttta | 300 |
| gtatctgcag | ctgcaagacg | aaatggagcc | cttggactta | acggtgcagc | tggagcaaat | 360 |
| ctcgcagcag | ctggtggcaa | aaaggaggt | gctattggat | taaacgctgg | agcatcagcc | 420 |
| aatgttggtg | ccgctgctgc | caagaaaaat | ggagccatag | gacttaactc | agctgcttca | 480 |
| gctaatgctg | ccgctgccgc | tgctaaaaaa | ggtggagcca | ttggattgaa | tgctggagct | 540 |
| tcagcaaatg | ctgctgctgc | cgctgccaag | aagagtggag | ctgttggatt | aaatgctgga | 600 |
| gcttctgcta | acgctgctgc | tgctgctgcc | aagaaaagtg | gagctgttgc | tgccaattcc | 660 |

```
gctgcttcag caaatgcagc tgctgctgca caaaagaaag ccgctgctga tgccgcaaat      720
gctgctgctt ctgaaagtgc tgctgctgct gcagccaaga aagccgccgc tgttgctgaa      780
aatgcagctg ccaccgccaa tgccgcttca gctttacgta aaaatgcatt agccattgcc      840
agtgatgcag cagctgtccg tgctgatgcc gctgccgccg ccgctgacga tgctgctaaa      900
gctaacaacg ctgcttcccg tggaagtgat ggtttaactg cccgcgccaa tgccgccact      960
ttagccagtg atgctgcccg tagagctagc aatgcagcaa cagctgccag cgatgctgcc     1020
actgaccgat tgaacgccgc caccgctgct agcaacgctg ccactgctcg tgcaaatgcc     1080
gccacacgtg ccgatgatgc cgccactgat gccgacaatg ctgcttcaaa ggccagtgat     1140
gtatcagcta ttgaagccga caacgctgca cgagctgctg atgctgatgc tatcgctacc     1200
aaccgtgccg ctgaagcaag cgatgctgct gctattgccg ctgatgccgc tgccaatgct     1260
gctgatgccg ctgcccaatg taataacaaa gttgcccgag taagtgatgc cttagctctc     1320
gccgctaatg ctgctgcccg aggatctgat gccgccgctg aagctcaaga tgctgttgcc     1380
agagcaagtg acgctgccgc tgcccaagct gatggtgttg ccattgccgt aaatggagct     1440
actgcgagag actcagcaat tgaagccgct gctactgctg gagctgccca agctaaagcc     1500
gctggacgtg ctggagctgc tgcagctggt ttaagagctg gtgccgctag aggtgctgcc     1560
gctggtagtg cccgcggtct agctggagga ttagctgcag gttccaatgc tggaatcgcg     1620
gctggtgcag cttctggatt agcaagaggc gcagctgctg aagtttgcgc agctagaata     1680
gcattgtaa                                                             1689

<210> SEQ ID NO 100
<211> LENGTH: 1767
<212> TYPE: DNA
<213> ORGANISM: Mallada signata

<400> SEQUENCE: 100
atggcagcgt cgaacaaaat catcttcagc tttttagcta ttgttctatt acaacttgcc       60
acacactgtt catcaacagc tgtattgatt tctggttcgg ctgctggtgc ttcctcacac      120
aatgctgctg tgcagctgc agcagccaga gctgccttag cgcttctgg ggctgcaggt        180 ttaggtgctg catctggtgc tgcaagaaga aacgtagcag ttggtgctaa cggtgccgcc      240
gccgctagtg ctgcagctgc agctgccaga cgagctggcg ctattggcct aaatggagca      300
gctggagcta atgtagctgt cgctggtggc aaaaaaggag gtgctgctgg attaaatgct      360
ggcgctggtg cttcttttagt atctgcagct gcaagacgaa atggagccct tggacttaac      420
ggtgcagctg gagcaaatct cgcagcagct ggtggcaaaa aaggaggtgc tattggatta      480
aacgctggag catcagccaa tgttggtgcc gctgctgcca gaaaaatgg agccatagga      540 cttaactcag ctgcttcagc taatgctgcc gctgccgctg ctaaaaaagg tggagccatt      600
ggattgaatg ctgagcttc agcaaatgct gctgctgccg ctgccaagaa gagtggagct      660
gttggattaa atgctggagc ttctgctaac gctgctgctg ctgctgccaa gaaagtggga      720
gctgttgctg ccaattccgc tgcttcagca aatgcagctg ctgctgcaca aaagaaagcc      780
gctgctgatg ccgcaaatgc tgctgcttct gaaagtgctg ctgctgctgc agccaagaaa      840
gccgccgctc ttgctgaaaa tgcagctgcc accgccaatg ccgcttcagc tttacgtaaa      900
aatgcattag ccattgccag tgatgcagca gctgtccgtg ctgatgccgc tgccgccgcc      960
gctgacgatg ctgctaaagc taacaacgct gcttcccgtg gaagtgatgg tttaactgcc     1020
cgcgccaatg ccgccacttt agccagtgat gctgcccgta gagctagcaa tgcagcaaca     1080
```

-continued

```
gctgccagcg atgctgccac tgaccgattg aacgccgcca ccgctgctag caacgctgcc    1140
actgctcgtg caaatgccgc cacacgtgcc gatgatgccg ccactgatgc cgacaatgct    1200
gcttcaaagg ccagtgatgt atcagctatt gaagccgaca acgctgcacg agctgctgat    1260
gctgatgcta tcgctaccaa ccgtgccgct gaagcaagcg atgctgctgc tattgccgct    1320
gatgccgctg ccaatgctgc tgatgccgct gcccaatgta ataacaaagt tgcccgagta    1380
agtgatgcct agctctcgc cgctaatgct gctgcccgag gatctgatgc cgccgctgaa    1440
gctcaagatg ctgttgccag agcaagtgac gctgccgctg cccaagctga tggtgttgcc    1500
attgccgtaa atggagctac tgcgagagac tcagcaattg aagccgctgc tactgctgga    1560
gctgcccaag ctaaagccgc tggacgtgct ggagctgctg cagctggttt aagagctggt    1620
gccgctagag gtgctgccgc tggtagtgcc cgcggtctag ctggaggatt agctgcaggt    1680
tccaatgctg gaatcgcggc tggtgcagct tctggattag caagaggcgc agctgctgaa    1740
gtttgcgcag ctagaatagc attgtaa                                       1767
```

<210> SEQ ID NO 101
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 101

```
ggaattctca tgagtttgga ggggccgggc aactcg                              36
```

<210> SEQ ID NO 102
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 102

```
cggcggatcc ttattaaaat acgttgctct tcaagt                              36
```

<210> SEQ ID NO 103
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 103

```
ggaattctca tgagccgcgt gattaatcac gagtccctg                           39
```

<210> SEQ ID NO 104
<211> LENGTH: 41
<212> TYPE: DNA
<213> ORGANISM: Artificial Sequence
<220> FEATURE:
<223> OTHER INFORMATION: Oligonucleotide primer

<400> SEQUENCE: 104

```
cggcggatcc ttattattcc aactttgcta catgtatttt c                        41
```

<210> SEQ ID NO 105
<211> LENGTH: 36
<212> TYPE: DNA
<213> ORGANISM: Artificial Sequence
<220> FEATURE:
<223> OTHER INFORMATION: Oligonucleotide primer -continued

```
<400> SEQUENCE: 105
ggaattccca tgggcgtcga ggaattcaag tcctcg                                36

<210> SEQ ID NO 106
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 106
cggcagatct ttattaaaat tttttatcct caata                                 35

<210> SEQ ID NO 107
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 107
ggaattccca tggcaaggga agaggtggag acacgg                                36

<210> SEQ ID NO 108
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 108
cggcggatcc ttattacttc acctcccatt cttcattc                              38
```

PROCESSES FOR PRODUCING SILK DOPE

FIELD OF THE INVENTION

The present invention relates to methods of producing silk dope comprising silk proteins with a coiled-coil structure such as honeybee silk proteins. The silk dope can be used for a variety of purposes such as in the production of personal care products, plastics, textiles, and biomedical products.

BACKGROUND OF THE INVENTION

Silks are protein fibres produced by a wide range of insect and spider species. The silk of the domesticated silkworm, *Bombyx mori*, has been used as a suture biomaterial for centuries. Numerous efforts to clone and express silkworm or spider silks in transgenic systems have found it a Herculean task. The large sizes and highly repetitive sequences of these silk genes make them recalcitrant to expression outside specialized silk glands, and lead to low protein yields.

Although silkworm cocoons and spider webs are the best known silks, other species may produce silks better suited to transgenic production. Honeybee larvae (*Apis mellifera*) spin silk cocoons in which they pupate. Honeybee silk is encoded by four small (~30 kDa each) and non-repetitive fibre genes (Sutherland et al., 2006). Homologous sets of four genes have also been found in bumblebees, bulldog ants, weaver ants, hornets and Asiatic honeybees (Sutherland et al., 2007; Sezutsu et al., 2007; Shi et al., 2008; WO 2007/038837).

Vintage x-ray fibre diffraction work demonstrated that honeybee silk contains α-helical proteins assembled into a coiled-coil conformation, most likely a tetrameric coiled-coil structure (Atkins, 1967), with the four strands likely corresponding to the four different silk proteins. Bioinformatics techniques predict that each of the honeybee silk protein sequences contains 60-68% coiled-coil (Sutherland et al., 2006).

Silk threads can be hand-drawn from the silk glands of honeybee larvae. These threads are less strong but more extensible and tougher than silkworm silk fibres (Hepburn et al., 1979).

Shi et al. (2008) recently reported recombinant production of Asiatic honeybee silk (*Apis cerana*). The four *A. cerana* silk proteins were expressed in a soluble form in *Escherichia coli* with yields of 10-60 mg per liter of ferment. A variety of experimental techniques were used to characterize the structure and interactions of the proteins at low concentration (0.03 to 0.2 wt %). These conclusively demonstrated that neither the individual proteins nor a mix of four proteins had tight tertiary packing in solution. The proteins existed as monomers or loosely associated dimers and had predominantly random-coil conformation with little α-helical structure.

There is a need for further methods to produce silk dope from recombinantly expressed coiled-coil silk proteins which can be used to manufacture a wide variety of products.

SUMMARY OF THE INVENTION

The present inventors have surprisingly found that surfactants and ionic liquids can be used in a process to produce silk dope comprising coiled-coil silk proteins.

In a first aspect, the present invention provides a method for producing silk dope, the method comprising
  i) lysing cells producing one or more silk proteins,
  ii) solubilising the silk proteins by contacting them with a surfactant or an ionic liquid, and
  iii) concentrating the silk proteins to produce silk dope, wherein the one or more silk proteins are capable of forming a tertiary structure which comprises a coiled-coil structure.

In one embodiment, the silk proteins are concentrated by
  a) reducing the amount of surfactant in solution by adding a compound which precipitates the surfactant, and
  b) separating the solution comprising the silk proteins from the precipitate formed in step a) to produce the silk dope.

Compounds which can be used to precipitate surfactants are known in the art and include a salt or a carbohydrate; or a combination of two or more thereof. Preferably, the salt is a potassium salt or a sodium salt. In an embodiment, the carbohydrate is α-cyclodextrin.

In another embodiment, the silk proteins are concentrated by filtration, more preferably membrane filtration, and even more preferably tangential flow filtration.

In an embodiment, the method further comprises increasing the concentration of silk proteins in the silk dope. This can be achieved by any method known in the art. For example, the silk dope is dialysed against a dehydrating solution such as solution comprising a hygroscopic polymer. Examples of hygroscopic polymers include, but are not limited to, polyethylene glycol, amylase and sericin, as well as a combination of two or more thereof.

In a preferred embodiment, the silk dope comprises at least about 0.5% w/v silk proteins. In a further embodiment, the silk dope comprises about 0.5% to about 15% silk proteins.

The cell can be any cell type, typically a recombinant cell comprising an exogenous polynucleotide(s) encoding, and capable of producing, the silk protein(s). Examples include, but are not limited, to bacterial cells, yeast cells, insect cells, plant cells or animal cells, or a combination of two or more thereof. In a preferred embodiment, the cell is a bacterial cell. In a particularly preferred embodiment, the bacterial cell is *Escherichia coli*.

In a preferred embodiment, step i) further comprises isolating inclusion bodies from the lysed cells.

The method may also comprise culturing the cells before step i).

In a preferred embodiment, the portion of the silk protein that is capable of forming a tertiary structure which comprises a coiled-coil structure comprises at least 10 copies of the heptad sequence abcdefg, and wherein at least 25% of the amino acids at positions a and d are alanine residues. More preferably, at least 25% of the amino acids at positions a, d and e are alanine residues.

In a further preferred embodiment, the silk protein comprises, more preferably consists essentially of, even more preferably consists of, a sequence selected from:
  a) an amino acid sequence as provided in any one of SEQ ID NOs 1 to 8, 17 to 24, 33 to 40, 49 to 56, 65 to 72, 81 to 88, 97 or 98,
  b) an amino acid sequence which is at least 30% identical to any one or more of SEQ ID NOs 1 to 8, 17 to 24, 33 to 40, 49 to 56, 65 to 72, 81 to 88, 97 or 98, and
  c) a biologically active fragment of a) or b).

In the above aspect it is preferred that as little as possible of the silk proteins are secreted from the cell. Accordingly, it is preferred that the silk proteins do not comprise an N-terminal signal sequence. Examples of silk proteins particularly useful for the above aspect include, but are not limited to, silk proteins comprising, more preferably consisting essentially of, and even more preferably consisting of, a sequence selected from:

a) an amino acid sequence as provided in any one of SEQ ID NOs 1, 3, 5, 7, 17, 19, 21, 23, 33, 35, 37, 39, 49, 51, 53, 55, 65, 67, 69, 71, 81, 83, 85, 87 or 97, b) an amino acid sequence which is at least 30% identical to any one or more of SEQ ID NOs 1, 3, 5, 7, 17, 19, 21, 23, 33, 35, 37, 39, 49, 51, 53, 55, 65, 67, 69, 71, 81, 83, 85, 87 or 97, and c) a biologically active fragment of a) or b).

In an embodiment, the silk proteins can be a plurality of the same silk protein or a combination of two or more different silk proteins. In a preferred embodiment, if different silk proteins are used there are four different silk proteins.

In a further embodiment, the silk proteins comprise a first silk protein which comprises, more preferably consists essentially of, even more preferably consists of, a) an amino acid sequence as provided in any one of SEQ ID NOs 1, 2, 17, 18, 33, 34, 49, 50, 65, 66, 81 or 82;

b) an amino acid sequence which is at least 30% identical to any one or more of SEQ ID NOs 1, 2, 17, 18, 33, 34, 49, 50, 65, 66, 81 or 82; and c) a biologically active fragment of a) or b), a second silk protein which comprises, more preferably consists essentially of, even more preferably consists of, d) an amino acid sequence as provided in any one of SEQ ID NOs 3, 4, 19, 20, 35, 36, 51, 52, 67, 68, 83 or 84;

e) an amino acid sequence which is at least 30% identical to any one or more of SEQ ID NOs 3, 4, 19, 20, 35, 36, 51, 52, 67, 68, 83 or 84; and f) a biologically active fragment of c) or d), a third silk protein which comprises, more preferably consists essentially of, even more preferably consists of, g) an amino acid sequence as provided in any one of SEQ ID NOs 5, 6, 21, 22, 37, 38, 53, 54, 69, 70, 85 or 86;

h) an amino acid sequence which is at least 30% identical to any one or more of SEQ ID NOs 5, 6, 21, 22, 37, 38, 53, 54, 69, 70, 85 or 86; and i) a biologically active fragment of g) or h), and/or a fourth silk protein which comprises, more preferably consists essentially of, even more preferably consists of, j) an amino acid sequence as provided in any one of SEQ ID NOs 7, 8, 23, 24, 39, 40, 55, 56, 71, 72, 87 or 88;

k) an amino acid sequence which is at least 30% identical to any one or more of SEQ ID NOs 7, 8, 23, 24, 39, 40, 55, 56, 71, 72, 87 or 88; and l) a biologically active fragment of j) or k). More preferably, in relation to above aspect the silk proteins comprise, or consist essentially of, a first silk protein which comprises, more preferably consists essentially of, even more preferably consists of, a) an amino acid sequence as provided in any one of SEQ ID NOs 1, 17, 33, 49, 65 or 81;

b) an amino acid sequence which is at least 30% identical to any one or more of SEQ ID NOs 1, 17, 33, 49, 65 or 81; and c) a biologically active fragment of a) or b), a second silk protein which comprises, more preferably consists essentially of, even more preferably consists of, d) an amino acid sequence as provided in any one of SEQ ID NOs 3, 19, 35, 51, 67 or 83;

e) an amino acid sequence which is at least 30% identical to any one or more of SEQ ID NOs 3, 19, 35, 51, 67 or 83; and f) a biologically active fragment of d) or e), a third silk protein which comprises, more preferably consists essentially of, even more preferably consists of, g) an amino acid sequence as provided in any one of SEQ ID NOs 5, 21, 37, 53, 69 or 85;

h) an amino acid sequence which is at least 30% identical to any one or more of SEQ ID NOs 5, 21, 37, 53, 69 or 85; and i) a biologically active fragment of g) or h), and/or a fourth silk protein which comprises, more preferably consists essentially of, even more preferably consists of, j) an amino acid sequence as provided in any one of SEQ ID NOs 7, 23, 39, 55, 71 or 87;

k) an amino acid sequence which is at least 30% identical to any one or more of SEQ ID NOs 7, 23, 39, 55, 71 or 87; and l) a biologically active fragment of j) or k).

In an embodiment, the first silk protein, second silk protein, third silk protein and/or fourth silk protein are produced by the same cells.

In an alternate embodiment, the first silk protein, second silk protein, third silk protein and/or fourth silk protein are produced by different cells. In this embodiment, it is preferred that step ii) comprises approximate equimolar amounts of the first silk protein, the second silk protein, the third silk protein and the fourth silk protein.

At any point up until and excluding step iii) the silk proteins processed according to the invention may be prepared independently and combined. The separately prepared silk proteins can be the same or different. For example, a first silk protein as defined herein is expressed in a first cell and processed as defined in steps i) and ii), a second silk protein as defined herein is expressed in a second cell and processed as defined in steps i) and ii), and then the two solutions combined before step iii) is performed.

The surfactant and ionic liquid solubilise precipitated protein and enables the silk protein to stay in solution whilst allowing the formation of a coiled-coil structure during later steps.

In a preferred embodiment, the surfactant is an anionic surfactant. Examples of anionic surfactants useful for the invention include, but are not limited to, sodium dodecyl sulfate (SDS), ammonium lauryl sulfate and other alkyl sulfate salts, sodium 1-octanesulfonate monohydrate, sodium lauroyl sarcosinate, sodium lauryl ether sulfate (SLES), sodium taurodeoxycholate hydrate, and alkyl benzene sulfonate; as well as a combination of two or more thereof. In a preferred embodiment, the anionic surfactant is SDS.

In an embodiment, the ionic liquid comprises
i) an anion selected from chloride, bromide, iodide, thiocyanate, acetate, $C_1$-$C_4$-alkylsulfates, methanesulfonates, tosylate, $C_1$-$C_4$-dialkylphosphates, hydrogensulfate and tetrachloroaluminate, and ii) a cation selected from 1,3-$C_1$-$C_4$-dialkylimidazolium, 3-chloropyridinium, 4-dimethylaminopyridinium, 2-ethyl-4-aminopyridinium, 2-methylpyridinium, 2-ethylpyridinium, 2-ethyl-6-methylpyridinium, quinolinium, isoquinolinium, pyridinium, 1-$C_1$-$C_4$-alkylimidazolium, 1-methylimidazolium, 1,2-dimethylimidazolium, 1-n-butyl-imidazolium, 1,4,5-trimethylimidazolium, 1,4-dimethylimidazolium, imidazolium, 2-methylimidazolium, 1-butyl-2-methylimidazolium, 4 methylimidazolium, 1-(2'-aminoethyl)imidazolium, 1-vinylimidazolium, 2-ethylimidazolium and benzotriazolium.

In a further preferred embodiment, the method yields at least about 0.1 g, more preferably at least about 1 g, more preferably at least about 1.5 g, more preferably at least about 2 g, even more preferably at least about 2.5 g. of silk protein(s) per liter of cultured cells.

In another aspect, the present invention provides a method for producing silk dope, the method comprising i) obtaining supernatant from cell cultures, or from a cell-free expression system, producing one or more silk proteins, ii) solubilising the silk proteins by contacting them with a surfactant or an ionic liquid, and iii) concentrating the silk proteins to produce the silk dope, wherein the one or more silk proteins are capable of forming a tertiary structure which comprises a coiled-coil structure.

In this aspect, instead of the silk proteins in the cell being used to produce the silk dope, silk proteins which are secreted from the cells are used. As the skilled addressee will appreciate, step i) of the first aspect and step i) of the above aspect may be performed simultaneously or sequentially. Furthermore, at any corresponding step silk proteins derived from the cell and the supernatant could be combined and from thereon processed together. For example, step ii) of the first aspect and step ii) of the above aspect can be performed separately and the silk proteins combined for further processing including steps iii) and iv).

In a particularly preferred embodiment of the above aspect, step i) further comprises increasing the concentration of silk proteins from the supernatant. This can be achieved by any method known in the art, for example by contacting the supernatant with an agent which precipitates the silk proteins such as, but not limited to, ammonium sulfate, trichloroacetic acid, perchloric acid and acetone.

In relation to the above aspect it is preferred that as much as possible of the silk proteins are secreted from the cell. Accordingly, it is preferred that the silk proteins comprise an N-terminal signal sequence. Examples of silk proteins particularly useful for the above aspect include, but are not limited to, silk proteins comprising, more preferably consisting essentially of, and even more preferably consisting of, a sequence selected from:

a) an amino acid sequence as provided in any one of SEQ ID NOs 2, 4, 6, 8, 18, 20, 22, 24, 34, 36, 38, 40, 50, 52, 54, 56, 66, 68, 70, 72, 82, 84, 86, 88 or 98, b) an amino acid sequence which is at least 30% identical to any one or more of SEQ ID NOs 2, 4, 6, 8, 18, 20, 22, 24, 34, 36, 38, 40, 50, 52, 54, 56, 66, 68, 70, 72, 82, 84, 86, 88 or 98, and c) a biologically active fragment of a) or b).

In a further embodiment, the silk proteins comprise a first silk protein which comprises, more preferably consists essentially of, even more preferably consists of, a) an amino acid sequence as provided in any one of SEQ ID NOs 2, 18, 34, 50, 66 or 82;

b) an amino acid sequence which is at least 30% identical to any one or more of SEQ ID NOs 2, 18, 34, 50, 66 or 82; and c) a biologically active fragment of a) or b), a second silk protein which comprises, more preferably consists essentially of, even more preferably consists of, d) an amino acid sequence as provided in any one of SEQ ID NOs 4, 20, 36, 52, 68 or 84;

e) an amino acid sequence which is at least 30% identical to any one or more of SEQ ID NOs 4, 20, 36, 52, 68 or 84; and f) a biologically active fragment of c) or d), a third silk protein which comprises, more preferably consists essentially of, even more preferably consists of, g) an amino acid sequence as provided in any one of SEQ ID NOs 6, 22, 38, 54, 70 or 86;

h) an amino acid sequence which is at least 30% identical to any one or more of SEQ ID NOs 6, 22, 38, 54, 70 or 86; and i) a biologically active fragment of g) or h), and/or a fourth silk protein which comprises, more preferably consists essentially of, even more preferably consists of, j) an amino acid sequence as provided in any one of SEQ ID NOs 8, 24, 40, 56, 72 or 88;

k) an amino acid sequence which is at least 30% identical to any one or more of SEQ ID NOs 8, 24, 40, 56, 72 or 88; and l) a biologically active fragment of j) or k).

In a further aspect, the present invention provides a method for producing a silk fibre, the method comprising extruding and/or drawing silk dope produced by a method of the invention.

In an embodiment, the extruding comprises passing the silk dope through an about 5 µm to about 500 µm capillary tube.

In a particularly preferred embodiment, the method comprises i) lysing cells producing one or more silk proteins and isolating inclusion bodies from the cells, ii) solubilising the silk proteins in the inclusion bodies by contacting them with a surfactant or an ionic liquid, iii) concentrating the silk proteins to produce silk dope, iv) increasing the concentration of silk proteins in the silk dope to about 2% to about 10% wt (%) silk proteins, more preferably about 3% to about 6% wt (%) silk proteins, and vi) extruding the silk dope in a dehydrating solution.

In relation to the above embodiment, the dehydrating solution preferably comprises an alcohol such as methanol or ethanol, or a high concentration of salt such as $MgCl_2$ or NaCl. Extruding silk fibres under these conditions is generally known in the art as wet spinning.

Preferably, the alcohol is methanol and the concentration of the methanol in the solution is about 40% to about 80% v/v, more preferably about 50% to about 70% v/v. In this embodiment, the silk dope may comprise a single type of silk polypeptide as defined herein, or two, or more different types such as four different types.

In another aspect, the present invention provides a method for producing a silk film, wherein the method comprising casting silk dope produced by a method of the invention.

In another aspect, the present invention provides silk dope produced by a method of the invention.

In a further aspect, the present invention provides a silk fibre produced by a method of the invention.

Also provided is a silk film produced by a method of the invention.

In yet another aspect, the present invention provides a product comprising a silk fibre and/or silk film of the invention.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. SDS-PAGE of purified inclusion bodies solubilised in SDS. Lanes correspond to recombinant proteins AmelF1-4; scale is protein weight in kDa.

Figure 2:
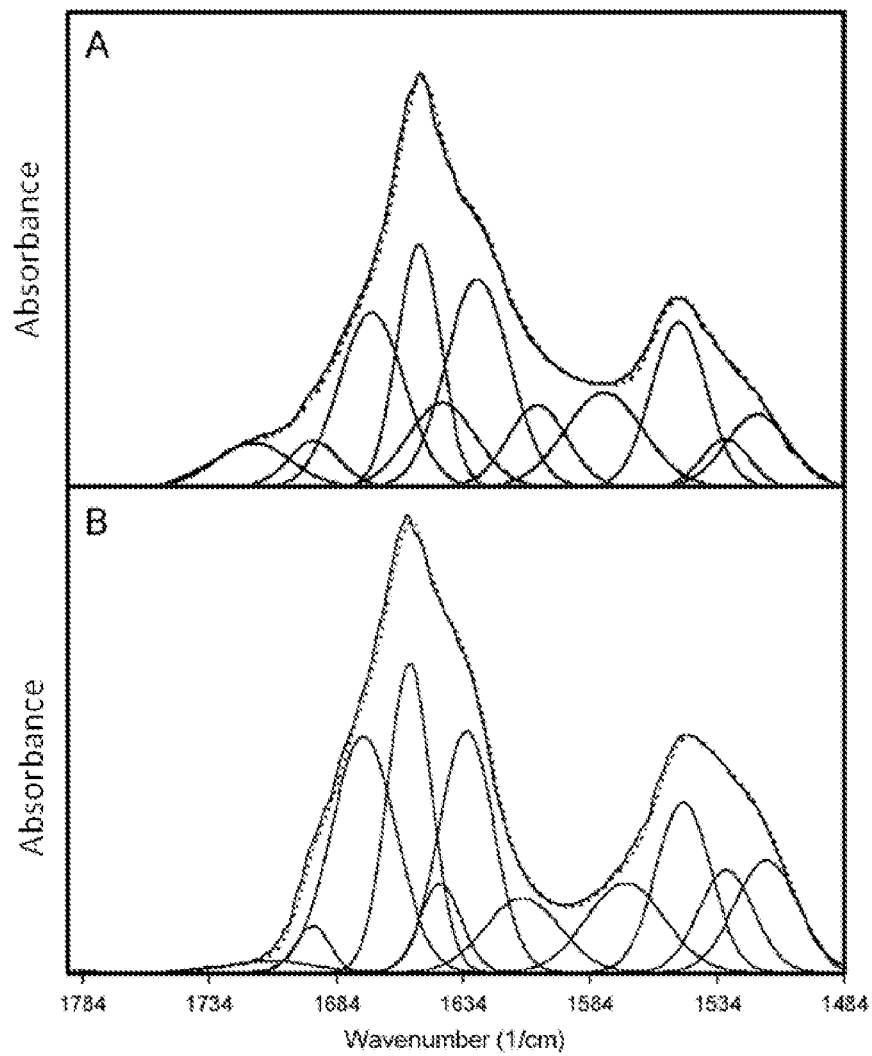

FIG. 2. Fourier self deconvolution of the amide I and II regions of the infrared spectra of native honeybee silk (A) and recombinant honeybee silk (B). Assignments of bands to structures are found in Table 2.

Figure 3:
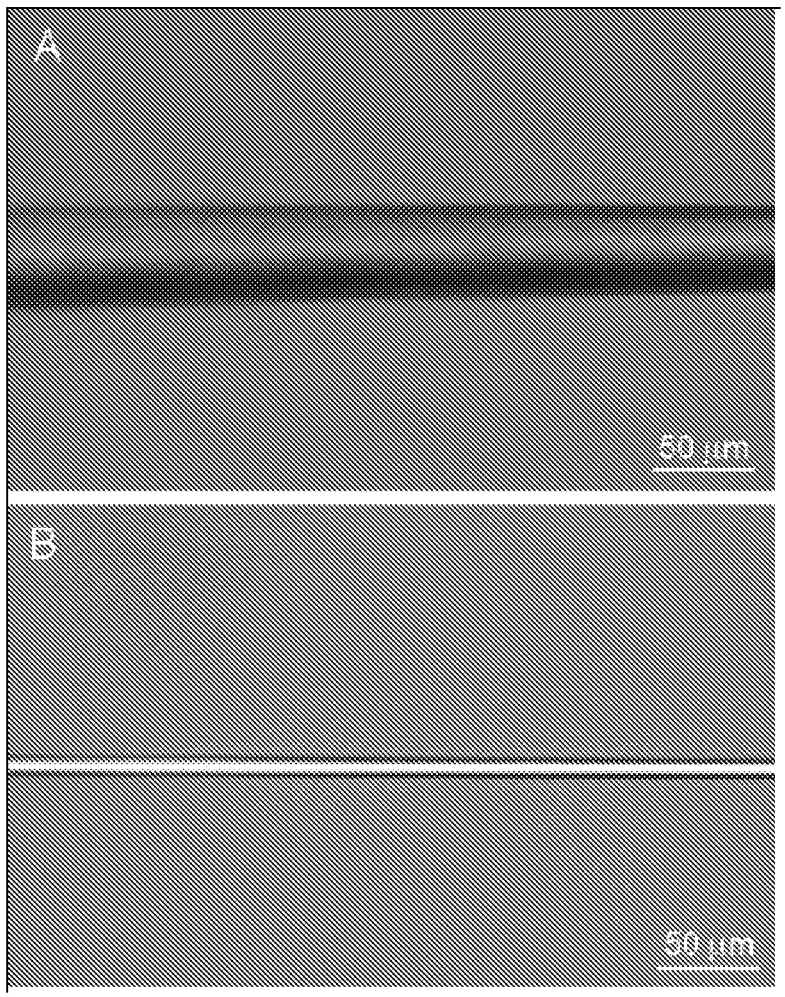

FIG. 3. Cross-polarized microscopy of recombinant honeybee silk fibres (A) drawn in air, and (B) drawn in air then drawn a second time in methanol.

Figure 4:
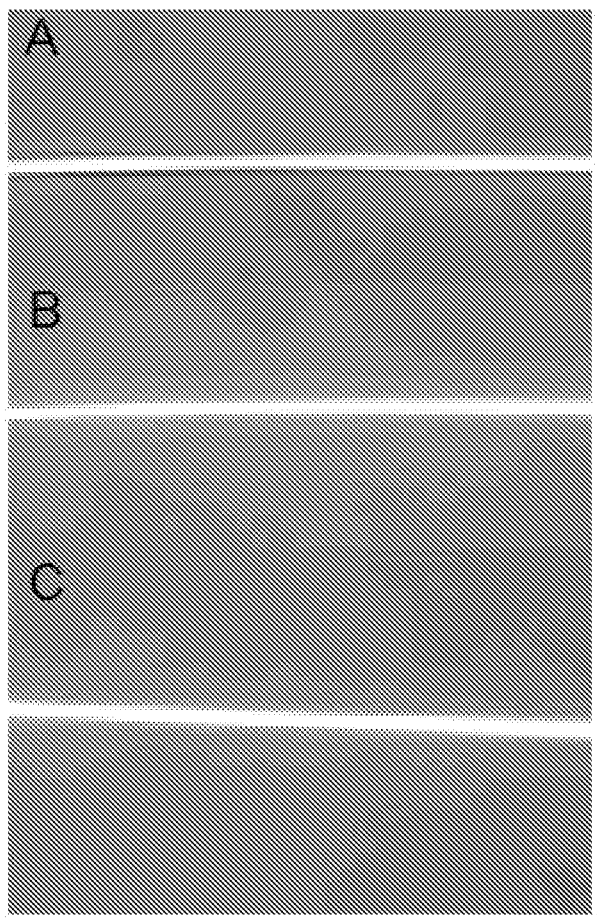

FIG. 4. Cross-polarized microscopy of recombinant honeybee silk fibres (A) extruded into methanol bath, and (B) air dried then drawn a second time in a methanol bath to x2 length or (C) air dried then drawn a second time in a methanol bath to x4 length.

KEY TO THE SEQUENCE LISTING

SEQ ID NO:1—Honeybee silk protein termed herein Xenospira1 (also termed herein AmelF1) (minus signal peptide).
SEQ ID NO:2—Honeybee silk protein termed herein Xenospira1.
SEQ ID NO:3—Honeybee silk protein termed herein Xenospira2 (also termed herein AmelF2) (minus signal peptide).
SEQ ID NO:4—Honeybee silk protein termed herein Xenospira2.
SEQ ID NO:5—Honeybee silk protein termed herein Xenospira3 (also termed herein AmelF3) (minus signal peptide).
SEQ ID NO:6—Honeybee silk protein termed herein Xenospira3.
SEQ ID NO:7—Honeybee silk protein termed herein Xenospira4 (also termed herein AmelF4) (minus signal peptide).
SEQ ID NO:8—Honeybee silk protein termed herein Xenospira4.
SEQ ID NO:9—Nucleotide sequence encoding honeybee silk protein Xenospira1 (minus region encoding signal peptide).
SEQ ID NO:10—Nucleotide sequence encoding honeybee silk protein Xenospira1.
SEQ ID NO:11—Nucleotide sequence encoding honeybee silk protein Xenospira2 (minus region encoding signal peptide).
SEQ ID NO:12—Nucleotide sequence encoding honeybee silk protein Xenospira2.
SEQ ID NO:13—Nucleotide sequence encoding honeybee silk protein Xenospira3 (minus region encoding signal peptide).
SEQ ID NO:14—Nucleotide sequence encoding honeybee silk protein Xenospira3.
SEQ ID NO:15—Nucleotide sequence encoding honeybee silk protein Xenospira4 (minus region encoding signal peptide).
SEQ ID NO:16—Nucleotide sequence encoding honeybee silk protein Xenospira4.
SEQ ID NO:17—Bumblebee silk protein termed herein BBF1 (minus signal peptide).
SEQ ID NO:18—Bumblebee silk protein termed herein BBF1.
SEQ ID NO:19—Bumblebee silk protein termed herein BBF2 (minus signal peptide).
SEQ ID NO:20—Bumblebee silk protein termed herein BBF2.
SEQ ID NO:21—Bumblebee silk protein termed herein BBF3 (minus signal peptide).
SEQ ID NO:22—Bumblebee silk protein termed herein BBF3.
SEQ ID NO:23—Bumblebee silk protein termed herein BBF4 (minus signal peptide).
SEQ ID NO:24—Bumblebee silk protein termed herein BBF4.
SEQ ID NO:25—Nucleotide sequence encoding bumblebee silk protein BBF1 (minus region encoding signal peptide).
SEQ ID NO:26—Nucleotide sequence encoding bumblebee silk protein BBF1.
SEQ ID NO:27—Nucleotide sequence encoding bumblebee silk protein BBF2 (minus region encoding signal peptide).
SEQ ID NO:28—Nucleotide sequence encoding bumblebee silk protein BBF2.
SEQ ID NO:29—Nucleotide sequence encoding bumblebee silk protein BBF3 (minus region encoding signal peptide).
SEQ ID NO:30—Nucleotide sequence encoding bumblebee silk protein BBF3.
SEQ ID NO:31—Nucleotide sequence encoding bumblebee silk protein BBF4 (minus region encoding signal peptide).
SEQ ID NO:32—Nucleotide sequence encoding bumblebee silk protein BBF4.
SEQ ID NO:33—Bulldog ant silk protein termed herein BAF1 (minus signal peptide).
SEQ ID NO:34—Bulldog ant silk protein termed herein BAF1.
SEQ ID NO:35—Bulldog ant silk protein termed herein BAF2 (minus signal peptide).
SEQ ID NO:36—Bulldog ant silk protein termed herein BAF2.
SEQ ID NO:37—Bulldog ant silk protein termed herein BAF3 (minus signal peptide).
SEQ ID NO:38—Bulldog ant silk protein termed herein BAF3.
SEQ ID NO:39—Bulldog ant silk protein termed herein BAF4 (minus signal peptide).
SEQ ID NO:40—Bulldog ant silk protein termed herein BAF4.
SEQ ID NO:41—Nucleotide sequence encoding bulldog ant silk protein BAF1 (minus region encoding signal peptide).
SEQ ID NO:42—Nucleotide sequence encoding bulldog ant silk protein BAF1.
SEQ ID NO:43—Nucleotide sequence encoding bulldog ant silk protein BAF2 (minus region encoding signal peptide).
SEQ ID NO:44—Nucleotide sequence encoding bulldog ant silk protein BAF2.
SEQ ID NO:45—Nucleotide sequence encoding bulldog ant silk protein BAF3 (minus region encoding signal peptide).
SEQ ID NO:46—Nucleotide sequence encoding bulldog ant silk protein BAF3.
SEQ ID NO:47—Nucleotide sequence encoding bulldog ant silk protein BAF4 (minus region encoding signal peptide).
SEQ ID NO:48—Nucleotide sequence encoding bulldog ant silk protein BAF4.
SEQ ID NO:49—Weaver ant silk protein termed herein GAF1 (minus signal peptide).
SEQ ID NO:50—Weaver ant silk protein termed herein GAF1.
SEQ ID NO:51—Weaver ant silk protein termed herein GAF2 (minus signal peptide).
SEQ ID NO:52—Weaver ant silk protein termed herein GAF2.
SEQ ID NO:53—Weaver ant silk protein termed herein GAF3 (minus signal peptide).
SEQ ID NO:54—Weaver ant silk protein termed herein GAF3.
SEQ ID NO:55—Weaver ant silk protein termed herein GAF4 (minus signal peptide).
SEQ ID NO:56—Weaver ant silk protein termed herein GAF4.
SEQ ID NO:57—Nucleotide sequence encoding weaver ant silk protein GAF1 (minus region encoding signal peptide).
SEQ ID NO:58—Nucleotide sequence encoding weaver ant silk protein GAF1.

SEQ ID NO:59—Nucleotide sequence encoding weaver ant silk protein GAF2 (minus region encoding signal peptide).
SEQ ID NO:60—Nucleotide sequence encoding weaver ant silk protein GAF2.
SEQ ID NO:61—Nucleotide sequence encoding weaver ant silk protein GAF3 (minus region encoding signal peptide).
SEQ ID NO:62—Nucleotide sequence encoding weaver ant silk protein GAF3.
SEQ ID NO:63—Nucleotide sequence encoding weaver ant silk protein GAF4 (minus region encoding signal peptide).
SEQ ID NO:64—Nucleotide sequence encoding weaver ant silk protein GAF4.
SEQ ID NO:65—Hornet silk protein termed herein Vssilk3 (minus signal peptide).
SEQ ID NO:66—Hornet silk protein termed herein Vssilk3.
SEQ ID NO:67—Hornet silk protein termed herein Vssilk4 (minus signal peptide).
SEQ ID NO:68—Hornet silk protein termed herein Vssilk4.
SEQ ID NO:69—Hornet silk protein termed herein Vssilk2 (minus signal peptide).
SEQ ID NO:70—Hornet silk protein termed herein Vssilk2.
SEQ ID NO:71—Hornet silk protein termed herein Vssilk1 (minus signal peptide).
SEQ ID NO:72—Hornet silk protein termed herein Vssilk1.
SEQ ID NO:73—Nucleotide sequence encoding hornet silk protein Vssilk3 (minus region encoding signal peptide).
SEQ ID NO:74—Nucleotide sequence encoding hornet silk protein Vssilk3.
SEQ ID NO:75—Nucleotide sequence encoding hornet silk protein Vssilk4 (minus region encoding signal peptide).
SEQ ID NO:76—Nucleotide sequence encoding hornet silk protein Vssilk4.
SEQ ID NO:77—Nucleotide sequence encoding hornet silk protein Vssilk2 (minus region encoding signal peptide).
SEQ ID NO:78—Nucleotide sequence encoding hornet silk protein Vssilk2.
SEQ ID NO:79—Nucleotide sequence encoding hornet silk protein Vssilk1 (minus region encoding signal peptide).
SEQ ID NO:80—Nucleotide sequence encoding hornet silk protein Vssilk1.
SEQ ID NO:81—Asiatic honeybee silk protein termed silk protein 1 (also termed ABS1) (minus signal peptide).
SEQ ID NO:82—Asiatic honeybee silk protein termed silk protein 1 (also termed ABS1).
SEQ ID NO:83—Asiatic honeybee silk protein termed silk protein 2 (also termed ABS2) (minus signal peptide).
SEQ ID NO:84—Asiatic honeybee silk protein termed silk protein 2 (also termed ABS2).
SEQ ID NO:85—Asiatic honeybee silk protein termed silk protein 3 (also termed ABS3) (minus signal peptide).
SEQ ID NO:86—Asiatic honeybee silk protein termed silk protein 3 (also termed ABS3).
SEQ ID NO:87—Asiatic honeybee silk protein termed silk protein 4 (also termed ABS4) (minus signal peptide).
SEQ ID NO:88—Asiatic honeybee silk protein termed silk protein 4 (also termed ABS4).
SEQ ID NO:89—Nucleotide sequence encoding asiatic honeybee silk protein ABS1 (minus region encoding signal peptide).
SEQ ID NO:90—Nucleotide sequence encoding asiatic honeybee silk protein ABS1.
SEQ ID NO:91—Nucleotide sequence encoding asiatic honeybee silk protein ABS2 (minus region encoding signal peptide).
SEQ ID NO:92—Nucleotide sequence encoding asiatic honeybee silk protein ABS2.
SEQ ID NO:93—Nucleotide sequence encoding asiatic honeybee silk protein ABS3 (minus region encoding signal peptide).
SEQ ID NO:94—Nucleotide sequence encoding asiatic honeybee silk protein ABS3.
SEQ ID NO:95—Nucleotide sequence encoding asiatic honeybee silk protein ABS4 (minus region encoding signal peptide).
SEQ ID NO:96—Nucleotide sequence encoding asiatic honeybee silk protein ABS4.
SEQ ID NO:97—Lacewing silk protein termed herein MalF1 (minus signal peptide).
SEQ ID NO:98—Lacewing silk protein termed herein MalF1.
SEQ ID NO:99—Nucleotide sequence encoding lacewing silk protein MalF1 (minus region encoding signal peptide).
SEQ ID NO:100—Nucleotide sequence encoding lacewing silk protein MalF1.
SEQ ID NOs 101 to 108—Oligonucleotide primers.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, silk processing, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the terms "silk protein" and "silk polypeptide" refer to a fibrous protein/polypeptide that can be used to produce a silk fibre, and/or a fibrous protein complex.

As used herein, the term "one or more silk proteins" refers to the process possibly using two or more different types of silk proteins such as a first silk protein, second silk protein, etc, as defined herein. Thus, in this context one silk protein means a population of identical silk protein molecules sufficient to produce silk dope.

As used herein, the term "capable of forming a tertiary structure which comprises a coiled-coil structure" refers to the ability of the proteins to form said structures under suitable conditions. For example, when processed to produce silk fibres the proteins form said structures. Furthermore, this term does not mean that the entire protein is capable of forming a coiled-coil structure, just a portion thereof. In an embodiment, about 45% to about 90%, more preferably about 55% to about 70%, and even more preferably about 60% to about 66%, of the silk protein is capable of forming a tertiary structure which comprises a coiled-coil structure.

As used herein, the term "silk dope" refers to an aqueous solution comprising silk proteins. Preferably, the silk dope comprises at least 0.05% w/v, more preferably at least 0.1% w/v, and even more preferably at least 0.5% w/v, of a silk protein as defined herein. In an embodiment, silk dope produced by a method of the invention comprises about 0.5% to about 15% (wt %) silk protein. However, if the further step of increasing the concentration of silk proteins in the silk dope is not performed the more typical yield is about 0.5% to about 4% (wt %) silk protein. Silk dope produced using a method of the invention is amenable to extrusion for the formation of a fibre and/or film casting.

As used herein, a "silk fibre" refers to filaments comprising silk proteins which can be woven into various items such as textiles.

As used herein, the term "reducing the amount of surfactant solution", or variations thereof including reducing the amount of ionic liquid, means that the total amount of surfactant or ionic liquid is decreased. In an embodiment, the concentration of surfactant or ionic liquid following the reduction is less than about 10 mM, more preferably less than 5 mM and even more preferably less than 1 mM, prior to any step involving further concentration of the solution.

As used herein, a "dehydrating solution" is any solution, preferably an aqueous solution, that has a lower water concentration in solution than the silk dope that is to be concentrated.

As used herein, the term "solubilising" when referring to the silk proteins being contacted with a surfactant or ionic liquid means that the surfactant or ionic liquid associates with the silk proteins and maintains them in solution by preventing their aggregation. This is contrast to silk proteins seen in the cells, especially in the inclusion bodies.

The term "signal peptide", "N-terminal signal sequence" and variations thereof refers to an amino terminal protein/peptide preceding a secreted mature protein. The signal peptide is cleaved from and is therefore not present in the mature protein. Signal peptides have the function of directing and trans-locating secreted proteins across cell membranes. The signal peptide is also referred to as signal sequence, and are well known in the art Coiled-Coil Silk Proteins The terms "polypeptide" and "protein" are generally used interchangeably and refer to a single polypeptide chain which may or may not be modified by addition of non-amino acid groups. The terms "proteins" and "polypeptides" as used herein also include variants, mutants, modifications, analogous and/or derivatives of the silk proteins described herein. In a preferred embodiment, a silk protein used in the invention is only comprised of naturally occurring amino acids.

The % identity of a protein is determined by GAP (Needleman and Wunsch, 1970) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

As used herein a "biologically active" fragment is a portion of a protein of the invention which maintains a defined activity of the full-length protein, namely the ability to be used to produce silk. Biologically active fragments can be any size as long as they maintain the defined activity.

The term "consisting essentially of", or variations thereof, means that the defined amino acid sequence may have a few, such as one, two, three or four, additional amino acids compared to that defined. For example, when absent from the defined sequence an N-terminal methionine may be added. The term "consists of", or variations thereof, means that the defined sequence does not have additional or less amino acids when compared to the defined sequence, particularly at the N- and C-termini.

With regard to a defined protein, it will be appreciated that % identity figures higher than those provided above will encompass preferred embodiments. Thus, where applicable, in light of the minimum % identity figures, it is preferred that the protein comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the naturally occurring silk proteins described herein can be prepared by introducing appropriate nucleotide changes into a nucleic acid encoding the silk protein, or by in vitro synthesis of the desired protein. Such mutants include, for example, deletions, insertions or substitutions of residues within the amino acid sequence. A combination of deletion, insertion and substitution can be made to arrive at the final construct, provided that the final protein product possesses the desired characteristics.

Mutant (altered) proteins can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides of the invention are subjected to DNA shuffling techniques as broadly described by Harayama (1998). These DNA shuffling techniques may include genes of the invention possibly in addition to genes related to those of the present invention, such as silk genes from Hymenopteran or Neuroptean species other than the specific species characterized herein. Products derived from mutated/altered DNA can readily be screened using techniques described herein to determine if they can be used as silk proteins.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions or insertions generally range from about 1 to 15 residues, more preferably about 1 to 10 residues and typically about 1 to 5 contiguous residues.

Substitution mutants have at least one amino acid residue in the protein molecule removed and a different residue inserted in its place. The sites of greatest interest for substitutional mutagenesis include sites identified as important for function. Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

TABLE 1

Exemplary substitutions

| Original Residue | Exemplary Substitutions |
| --- | --- |
| Ala (A) | val; leu; ile; gly; cys; ser; thr |
| Arg (R) | lys |
| Asn (N) | gln; his |
| Asp (D) | glu |
| Cys (C) | ser; thr; ala; gly; val |
| Gln (Q) | asn; his |
| Glu (E) | asp |
| Gly (G) | pro; ala; ser; val; thr; cyc |
| His (H) | asn; gln |
| Ile (I) | leu; val; ala; met |
| Leu (L) | ile; val; met; ala; phe |
| Lys (K) | arg |
| Met (M) | leu; phe |
| Phe (F) | leu; val; ala |
| Pro (P) | gly |
| Ser (S) | thr; ala; gly; val; gln; cys |
| Thr (T) | ser; gln; ala; cys |
| Trp (W) | tyr |
| Tyr (Y) | trp; phe |
| Val (V) | ile; leu; met; phe; ala; ser; thr |

Coiled-coil structures of silk proteins are characterized by heptad repeats represented by the consensus sequence (abcdefg)$_n$. In a preferred embodiment, the portion of the protein that has a coiled-coil structure comprises at least 10 copies of the heptad sequence abcdefg, and at least 25% of the amino acids at positions a and d are alanine residues.

In a preferred embodiment, the protein that has a coiled-coil structure comprises at least 12 consecutive copies, more preferably at least 15 consecutive copies, and even more preferably at least 18 consecutive copies of the heptad. In further embodiments, the protein that has a coiled-coil structure can have up to at least 28 copies of the heptad. Typically, the copies of the heptad will be tandemly repeated. However, they do not necessarily have to be perfect tandem repeats, for example, as shown in FIGS. 5 and 6 of WO 2007/038837 a few amino acids may be found between two heptads, or a few truncated heptads may be found (see, for example, Xenospira1 in FIG. 5 of WO 2007/038837).

Guidance regarding amino acid substitutions which can be made to the silk proteins which have a coiled-coil structure is provided in FIGS. 5 and 6, as well as Tables 6 to 10, of WO 2007/038837. Where a predicted useful amino acid substitution based on the experimental data provided herein is in anyway in conflict with the exemplary substitutions provided in Table 1 of WO 2007/038837 it is preferred that a substitution based on the experimental data is used.

Coiled-coil structures of the silk proteins have a high content of alanine residues, particularly at amino acid positions a, d and e of the heptad. However, positions b, c, f and g also have a high frequency of alanine residues. In a preferred embodiment, at least 15% of the amino acids at positions a, d and/or e of the heptads are alanine residues, more preferably at least 25%, more preferably at least 30%, more preferably at least 40%, and even more preferably at least 50%. In a further preferred embodiment, at least 25% of the amino acids at both positions a and d of the heptads are alanine residues, more preferably at least 30%, more preferably at least 40%, and even more preferably at least 50%. Furthermore, it is preferred that at least 15% of the amino acids at positions b, c, f and g of the heptads are alanine residues, more preferably at least 20%, and even more preferably at least 25%.

Typically, the heptads will not comprise any proline or histidine residues. Furthermore, the heptads will comprise few (1 or 2), if any, phenylalanine, methionine, tyrosine, cysteine, glycine or tryptophan residues. Apart from alanine, common (for example greater than 5%, more preferably greater than 10%) amino acids in the heptads include leucine (particularly at positions b and d), serine (particularly at positions b, e and f), glutamic acid (particularly at positions c, e and f), lysine (particularly at positions b, c, d, f and g) as well as arginine at position g.

In a preferred embodiment, the heptads are determined by using the pattern recognition program MARCOIL (Delorenzi and Speed, 2002).

Proteins (and polynucleotides) useful for the methods of the invention can be purified (isolated) from a wide variety of Hymenopteran and Neuropteran species. Examples of Hymenopterans include, but are not limited to, any species of the Suborder Apocrita (bees, ants and wasps), which include the following Families of insects; Chrysididae (cuckoo wasps), Formicidae (ants), Mutillidae (velvet ants), Pompilidae (spider wasps), Scoliidae, Vespidae (paper wasps, potter wasps, hornets), Agaonidae (fig wasps), Chalcididae (chalcidids), Eucharitidae (eucharitids), Eupelmidae (eupelmids), Pteromalidae (pteromalids), Evamidae (ensign wasps), Braconidae, Ichneumonidae (ichneumons), Megachilidae, Apidae, Colletidae, Halictidae, and Melittidae (oil collecting bees). Examples of Neuropterans include species from the following insect Families: Mantispidae, Chrysopidae (lacewings), Myrmeleontidae (antlions), and Ascalaphidae (owlflies). Such further proteins (and polynucleotides) can be characterized using the same procedures described herein for silks from *Bombus terrestris, Myrmecia forficata, Oecophylla smaragdina* and *Mallada signata*.

Also included within the scope of the invention are proteins which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the protein.

Polynucleotides

The term "polynucleotide" is used interchangeably herein with the term "nucleic acid".

The term "exogenous" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded protein. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components.

The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

With regard to the defined polynucleotides, it will be appreciated that % identity figures higher than those provided above will encompass preferred embodiments. Thus, where applicable, in light of the minimum % identity figures, it is preferred that a polynucleotide of the invention comprises a sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In an embodiment, a polynucleotide which encodes a silk protein useful for the invention comprises, more preferably consists essentially of, even more preferably consists of, a sequence selected from:

a) a nucleotide sequence as provided in any one of SEQ ID NOs 9 to 16, 25 to 32, 41 to 48, 57 to 64, 73 to 80, 89 to 96, 99 or 100, b) a nucleotide sequence which is at least 30% identical to any one or more of SEQ ID NOs 9 to 16, 25 to 32, 41 to 48, 57 to 64, 73 to 80, 89 to 96, 99 or 100, and c) a biologically active fragment encoding portion of a) or b).

When it is preferred that as little as possible of the silk proteins is secreted from the cell, the encoded silk proteins do not comprise an N-terminal signal sequence. Examples of polynucleotides encoding such silk proteins include those comprising, more preferably consisting essentially of, even more preferably consisting of, a sequence selected from:

a) a nucleotide sequence as provided in any one of SEQ ID NOs 9, 11, 13, 15, 25, 27, 29, 31, 41, 43, 45, 47, 57, 59, 61, 63, 73, 75, 77, 79, 89, 91, 93, 95 or 97, b) a nucleotide sequence which is at least 30% identical to any one or more of SEQ ID NOs 9, 11, 13, 15, 25, 27, 29, 31, 41, 43, 45, 47, 57, 59, 61, 63, 73, 75, 77, 79, 89, 91, 93, 95 or 97, and c) a biologically active fragment of a) or b).

Other embodiments of the invention rely on the expression of silk proteins with an N-terminal signal sequence, and/or the co-production (in the same or different cells) of a first silk protein, second silk protein, third silk protein and/or fourth silk protein as defined herein. Based on the sequence information provided in the Sequence Listing, the skilled person could readily identifying representative polynucleotides for expression for each embodiment of the invention.

Polynucleotides for use in the methods of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

Polynucleotides for use in the invention can also hybridize to a silk protein encoding nucleotide sequence as provided herein, such as one or more of SEQ ID NOs 9 to 16, 25 to 32, 41 to 48, 57 to 64, 73 to 80, 89 to 96, 99 and 100, under stringent conditions. The term "stringent hybridization conditions" and the like as used herein refers to parameters with which the art is familiar, including the variation of the hybridization temperature with length of an oligonucleotide. Nucleic acid hybridization parameters may be found in references which compile such methods, Sambrook, et al. (supra), and Ausubel, et al. (supra). For example, stringent hybridization conditions, as used herein, can refer to hybridization at 65° C. in hybridization buffer (3.5×SSC, 0.02% Ficoll, 0.02% polyvinyl pyrrolidone, 0.02% Bovine Serum Albumin (BSA), 2.5 mM $NaH_2PO_4$ (pH7), 0.5% SDS, 2 mM EDTA), followed by one or more washes in 0.2.×SSC, 0.01% BSA at 50° C.

Nucleic Acid Constructs

Cells for use in the methods of the invention will typically comprise a nucleic acid construct(s) encoding the silk protein(s). The construct may be integrated into the genome of the cell, or be extrachromosal such as be a recombinant vector. Such a vector contains heterologous polynucleotide sequences, that is polynucleotide sequences that are not naturally found adjacent to the polynucleotide molecule encoding the silk protein, and that preferably are derived from a species other than the species from which the polynucleotide molecule(s) are derived. The vector can be either RNA or DNA, either prokaryotic or eukaryotic, and typically is a transposon (such as described in U.S. Pat. No. 5,792,294), a virus or a plasmid.

One type of recombinant vector comprises a polynucleotide molecule encoding the silk protein operatively linked to an expression vector. The phrase operatively linked refers to insertion of a polynucleotide molecule into an expression vector in a manner such that the molecule is able to be expressed when transformed into a host cell. As used herein, an expression vector is a DNA or RNA vector that is capable of transforming a host cell and of effecting expression of a specified polynucleotide molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, arthropod, insect, animal, and plant cells. Particularly preferred expression vectors of the present invention can direct gene expression in plants cells. Vectors of the invention can also be used to produce the protein in a cell-free expression system, such systems are well known in the art.

In particular, the nucleic acid construct contains regulatory sequences such as transcription control sequences, translation control sequences, origins of replication, and other regulatory sequences that are compatible with the recombinant cell and that control the expression of the polynucleotide molecules. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, arthropod, plant or mammalian cells, such as, but not limited to, tac, lac, trp, trc, oxy-pro, omp/lpp, rrnB, bacteriophage lambda, bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells.

As outlined above, an aspect of the invention relies on the silk protein being secreted from the cell, typically due to the presence of an N-termnal signal sequence. Examples of suitable signal segments include, but are not limited to, tissue plasminogen activator (t-PA), interferon, interleukin, growth hormone, viral envelope glycoprotein signal segments, *Nicotiana nectarin* signal peptide (U.S. Pat. No. 5,939,288), tobacco extensin signal, the soy oleosin oil body binding protein signal, *Arabidopsis thaliana* vacuolar basic chitinase signal peptide, as well as native signal sequences of the silk polypeptides defined herein.

Cells

Most of the methods of the invention rely on the use of cells producing the one or more silk proteins as defined herein. Transformation of a polynucleotide molecule into a cell can be accomplished by any method by which a polynucleotide molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed polynucleotide molecules can remain extrachromosomal or can integrate into one or more sites within a chromosome of the transformed (i.e., recombinant) cell in such a manner that their ability to be expressed is retained.

Suitable host cells to transform include any cell that can be transformed with a polynucleotide encoding a silk polypeptide as defined herein. Host cells either can be endogenously (i.e., naturally) capable of producing the silk polypeptides or can be capable of producing such polypeptides after being transformed with at least one polynucleotide molecule as defined herein. Host cells can be any cell capable of producing at least one silk protein as defined herein, and include bacterial, fungal (including yeast), parasite, arthropod, animal and plant cells. Examples of host cells include *Salmonella, Escherichia, Bacillus, Listeria, Saccharomyces, Spodoptera, Mycobacteria, Trichoplusia*, BHK (baby hamster kidney) cells, MDCK cells, CRFK cells, CV-1 cells, COS (e.g., COS-7) cells, and Vero cells. Further examples of host cells are *E. coli*, including *E. coli* K-12 derivatives; *Salmonella typhi; Salmonella typhimurium*, including attenuated strains; *Spodoptera frugiperda; Trichoplusia ni*; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK cells and/or HeLa cells. Particularly preferred host cells are bacterial cells.

The skilled person can readily determine suitable culture conditions such as media, temperature and time for a particular cell type. For example, in an embodiment the cells are *Escherichia coli* cultered at about 30° C. to about 37° C. for a period of about 24 h to about 48 h.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules include, but are not limited to, operatively linking polynucleotide molecules to high-copy number plasmids, integration of the polynucleotide molecule into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules to correspond to the codon usage of the host cell, and the deletion of sequences that destabilize transcripts.

Production of Silk Dope

The present invention relates to methods of producing silk dope which can then be used for a wide variety of applications.

One step of an aspect of the invention relates to lysing cells to liberate silk proteins produced and contained within the cells. This step can be performed by any means known in the art. For example, the cell suspension is typically centrifuged to pellet the cells and the cells resuspended into a more concentrated solution ready for lysis. Cells can be lysed, for example, by passages through a French Press, homogenized using a Polytron (Brinkman Instruments) or sonicated on ice. Alternate methods of lysing cells, such as bacterial cells, are well known to those of skill in the art (see, e.g., Sambrook et al., supra). Various kits are available for cell lysis and are well known in the art, for example the Bugbuster kit (Novagen) and the ProteaPrep kit (Protea Biosciences, Inc.).

The present inventors have identified that silk proteins as defined herein expressed in bacteria form insoluble aggregates ("inclusion bodies"). In a preferred embodiment, the method includes the isolation of these inclusion bodies. Several protocols are suitable for purification of protein inclusion bodies. For example, purification of inclusion bodies typically involves the extraction, separation and/or purification of inclusion bodies by disruption of bacterial cells by the methods discussed above. In an embodiment, the cells are lysed, the cell membranes solubilised, and the insoluble fraction comprising the inclusion bodies is isolated for further processing.

An aspect of the invention relies on increasing the concentration of silk proteins from the supernatant. Again, this can be achieved by any method known in the art. In one embodiment, this is achieved by contacting the supernatant with an agent which precipitates the silk proteins such as, but not limited to, ammonium sulfate, trichloroacetic acid, perchloric acid and acetone, or commercial precipitant cocktails such as PlusOne (Amersham Biosciences), or Perfect-Focus (Geno Technology Inc.).

An optional step of the invention for producing silk dope, but nonetheless preferred in cases where the yield of silk protein is not sufficiently high, comprises increasing the concentration of silk proteins in the silk dope. Again, the can be achieved by any method known in the art for increasing the concentration of a protein an aqueous solution. In a particularly useful embodiment, the silk dope is concentrated by dialysing against a dehydrating solution such as a solution comprising a hygroscopic polymer. Examples suitable hygroscopic polymers include, but are not limited to, polyethylene glycol (PEG), amylase, and sericin, or a combination of two or more thereof. PEG molecules are available in a range of molecular sizes and the selection of the PEG will be determined by the membrane chosen for dialysis and the rate of concentration required. Preferably, the PEG is of a molecular weight of about 8,000 to about 10,000 g/mol and has a concentration of about 25% to about 50%.

Surfactants

In one embodiment, a step of producing silk dope as defined herein involves the use of a surfactant. The present inventors were surprised to find that surfactants, such as SDS, enables the silk proteins as defined herein to stay in solution whilst allowing the formation of a coiled-coil structure when the concentration of the surfactant is lowered.

In an embodiment, the surfactant is an anionic surfactant. Examples of anionic surfactants useful for the invention include, but are not limited to, sodium dodecyl sulfate (SDS), ammonium lauryl sulfate and other alkyl sulfate salts, sodium 1-octanesulfonate monohydrate, sodium lauroyl sarcosinate, sodium lauryl ether sulfate (SLES), sodium taurodeoxycholate hydrate, and alkyl benzene sulfonate; or a combination of two or more thereof. In a preferred embodiment, the anionic surfactant is SDS.

Any concentration of the surfactant can be used which increases the solubility of the silk proteins can be used. For example, at least about 0.1% v/v of the surfactant is used. In an embodiment, about 0.1% to about 10% v/v, more preferably, about 0.5% to about 2% v/v or about 0.5% to about 5% v/v, of the surfactant is used.

A further step of the methods of the invention for producing silk dope comprises reducing the amount of surfactant in solution by adding a compound which precipitates the surfactant to assist in the correct folding of the silk proteins. Any compound may be used which associates which, and reduces the solubility of, the surfactant. Examples include, but are not limited to, a salt or a carbohydrate such as α-cyclodextrin; or a combination of two or more thereof. Preferably, the salt is a potassium salt or a sodium salt. Preferably, the potassium salt is potassium chloride and the sodium salt is sodium acetate. Any concentration of the compound can be used which results in a reduction in the amount of surfactant in solution. For example, the compound is added to a final concentration of about 1 mM to about 1M, more preferably about 40 mM to about 100 mM, or about 40 mM to 400 mM.

A further step of the methods of the invention for producing silk dope comprises separating the solution from the precipitate formed following the addition of the compound. This can be achieved by any method known in the art such as using centrifugation, for example at 16000 g for 5 minutes, and removing the supernatant (solution) comprising (which is) the silk dope. Preferably, after this step the silk proteins constitute at least 75%, more preferably at least 80%, more preferably at least 85%, more preferably at least 90%, more preferably at least 95%, more preferably at least 97%, more preferably at least 99%, and even more preferably 100% of the protein in solution.

Ionic Liquids

Generally, ionic liquids can be defined as compounds that are comprised entirely of ions and are liquids at temperatures of less than about 100° C., preferably less than about 85° C. As used in the present invention, ionic liquids generally comprise one or more anions and one or more cations. In preferred embodiments, the ionic liquids comprise organic cations created by derivatizing one or more compounds to include substituents, such as alkyl, alkenyl, alkynyl, alkoxy, alkenoxy, alkynoxy, a variety of aromatics, such as (substituted or unsubstituted) phenyl, (substituted or unsubstituted) benzyl, (substituted or unsubstituted) phenoxy, and (substituted or unsubstituted) benzoxy, and a variety of heterocyclic aromatics having one, two, or three heteroatoms in the ring portion thereof, said heterocyclics being substituted or unsubstituted. The derivatized compounds include, but are not limited to, imidazoles, pyrazoles, thiazoles, isothiazoles, azathiozoles, oxothiazoles, oxazines, oxazolines, oxazaboroles, dithiozoles, triazoles, delenozoles, oxaphospholes, pyrroles, boroles, furans, thiophenes, phospholes, pentazoles, indoles, indolines, oxazoles, isoxazoles, isotetrazoles, tetrazoles, benzofurans, dibenzofurans, benzothiophenes, dibenzothiophenes, thiadiazoles, pyridines, pyrimidines, pyrazines, pyridazines, piperazines, piperidines, morpholones, pyrans, annolines, phthalazines, quinazolines, guanidiniums, quinxalines, choline-based analogues, and combinations thereof. The basic cation structure can be singly or multiply substituted or unsubstituted.

The anionic portion of the ionic liquid can comprise an inorganic moiety, an organic moiety, or combinations thereof. In preferred embodiments, the anionic portion comprises one or more moieties selected from halogens, phosphates, alkylphosphates, alkenylphosphates, bis(trifluoromethylsulfonyl)imide ($NTf_2^-$), $BF_4^-$, $PF_6^-$, $AsF_6^-$, $NO_3^-$, $N(CN)_2^-$, $N(SO_3CF_3)_2^-$, amino acids, substituted or unsubstituted carboranes, perchlorates, pseudohalogens such as thiocyanate and cyanate, metal chloride-based Lewis acids (e.g., zinc chlorides and aluminum chlorides), or $C_{1-6}$ carboxylates. Pseudohalides are monovalent and have properties similar to those of halides. Examples of pseudohalides useful according to the invention include cyanides, thiocyanates, cyanates, fulminates, and azides. Exemplary carboxylates that contain 1-6 carbon atoms are formate, acetate, propionate, butyrate, hexanoate, maleate, fumarate, oxalate, lactate, pyruvate and the like.

A variety of ionic liquids can be prepared and used according to the present invention. In particular, any combination of the cations and anions noted above could be used. It is only necessary to combine one or more cations (such as those described above) with one or more anions (such as those described above) to form a material that is liquid under the conditions described herein. For example, a cation imidazolium moiety could be combined with an anionic halogen moiety to form a material that is liquid under the requisite conditions (e.g., 1-butyl-3-methyl-imidazolium chloride)

and that is formed substantially completely of ionic moieties. Thus, it is clear that the present invention encompasses the use of a great diversity of ionic liquids. Specific, non-limiting examples of ionic liquids for use according to the invention include 1-butyl-3-methyl-imidazolium chloride ("BmimCl"); 1-allyl-3-methyl-imidazolium chloride ("AmimCl"); 1-ethyl-3-methyl-imidazolium chloride; 1-hydrogen-3-methyl-imidazolium chloride; 1-benzyl-3-methyl-imidazolium chloride ("BenzylmimCl"); 1-isopropyl-3-methyl-imidazolium chloride; 1-m-methoxybenzyl-3-methyl-imidazolium chloride ("MethoxylBenzylmimCl"); 1-m-methylbenzyl-3-methyl-imidazolium chloride ("MethylBenzylmimCl"); 1-benzyl-3-methyl-imidazolium chloride, and 1-methyl-3-benzyl-imidazolium dicyanamide ("BenzylmimDca").

The invention also encompasses the use of various mixtures of ionic liquids. In fact, ionic liquid mixtures can be useful for providing ionic liquids having customized properties, such as viscosity. For example, BenzylmimCl is a relatively viscous ionic liquid; however, it viscosity can be significantly reduced by mixing with AmimCl. The viscosity of the ionic liquid mixture can thus be adjusted by varying the ratio between the more viscous component and the less viscous component.

Ionic liquids for use according to the invention can be synthesized according to the literature. Preferably, the ionic liquids are dried (e.g., at 100° C.) in a vacuum oven over a period of time, such as about 48 hours, prior to use. In one embodiment, the ionic liquid is formed of a material that is solid (e.g., crystalline) at ambient conditions but is liquid at increased temperature (such as greater than about 30° C., greater than about 50° C., greater than about 75° C., or greater than about 100° C.). Generally, the crystalline material can be placed in an appropriate container and heated to dissolution (see, for example, Ionic Liquids in Synthesis, Wasserscheid, P. and Weldon, T. (Eds.), Wiley Pub.). Of course, the ionic liquid can also comprise a material that is liquid at ambient conditions (e.g., at a temperature around 20-25° C.).

Filtration and/or Chromatography

The solubilised silk proteins may be concentrated and separated from impurities, such as the surfactant, ionic liquid and other cellular components based on charge, hydrophilicity, affinity, solubility or stability, or size. Non-limiting examples of separation techniques include ammonium sulfate precipitation, chromatography, and membrane-filtration (including tangential flow membrane filtration). In embodiments utilizing chromatography for separation, exemplary methods include ion-exchange (cationic or anionic), affinity chromatography, hydrophilic-interaction, hydrophobic-interaction, size-exclusion and gel-permeation (see U.S. Pat. No. 6,248,570).

In some embodiments, the separation can be conducted by membrane-filtration, which includes, but is not limited to, methods such as single pass, dead-end, direct flow filtration (DFF), and crossflow or tangential flow filtration (TFF). According to the invention, filtration is based on the principle of separating molecules according to size using a semi-permeable membrane of a defined range of pore sizes. It is known to those skilled in the art that combinations of filtration methods and membrane types may be used in separation.

According to the invention, membrane-filtration is the separation of cellular components effected by polymeric or inorganic membranes. Within the art, there are four commonly accepted categories of membranes defined by the size of the material they remove from the carrier liquid. Methods of sequentially filtering through membranes from the smallest to largest pore size are Reverse Osmosis (RO), Nanofiltration (NF), Ultrafiltration (UF), and Microfiltration (MF).

Filtration with the above-mentioned membranes separates molecules according to their molecular weight by using membranes with specific pore sizes. For example, separation with RO membranes that have pore sizes less than 0.001 micrometers is intended to separate molecules that have a molecular weight less than 200 Daltons. Filtration with NF membranes that have pore sizes from 0.001-0.008 micrometers, inclusive, is intended to separate molecules that have a molecular weight from 200 Daltons to 15 kilodaltons (kDa) inclusive. Filtration with UF membranes that have pore sizes from 0.005-0.1 micrometers, inclusive, is intended to separate molecules that have a molecular weight from 5 kDa-300 kDa, inclusive. Filtration with microfiltration membranes that have pore sizes from 0.05-3.0 micrometers, inclusive, is intended to separate molecules that have a molecular weight from 100 kDa-3000 kDa and larger.

According to this invention, membrane-filtration can separate the solubilised silk proteins from other components based on size exclusion by utilizing membranes that have a particular Molecular Weight Cut-Off (MQWCO) that is determined by the pore size of the membrane. The MWCO, also called Nominal Molecular Weight Limit (NMWL) or Nominal Molecular Weight Cut-Off (NMWCO), is the kilodalton size designation for the filtration by membranes. The MWCO is defined as the molecular weight of the molecule that is 90% retained by the membrane. Because, for example, molecules of the same molecular weight can have significantly different shapes, the MWCO is not an exact metric, but is nevertheless a useful metric and is commonly employed by filter manufacturers. Both hydrophobic as well as hydrophilic membranes may be used in the present invention. Such membranes may be used as flat sheets or in a spirally wound configuration. Hollow fibers may also be used. In relation to compositions of UF membranes, any number of potential membrane materials may be used including, but not limited to, regenerated cellulose, polyether sulfone (which may or may not be modified to alter its inherent hydrophobicity), polyvinylidene fluoride, and ceramic and metal oxide aggregates. Many polyether sulfone UF membranes can withstand a pH range of 0.5-13, and temperatures ranging up to 85° C. Materials for MF membranes include everything used for UF membranes, as well as polycarbonate, polypropylene, polyethylene and PTFE (TEFLON™).

In some embodiments, the solubilised silk proteins can be filtered for the separation of large cellular debris from smaller cellular components to prevent the cellular debris from interfering with the proceeding separation and purification steps that involve the use of membranes or chromatography. In these embodiments, the permeate comprises the silk proteins and is recovered.

In some embodiments, a membrane can be used in a separation step having a suitable MWCO. For example, typical silks proteins used in the methods of the invention have a MW of about 30 kDa. In these embodiments, the retentate comprises the silk protein and can be recovered.

In a preferred embodiment, tangential flow filtration acts to both diafilter and concentrate the silk proteins. In TFF, typically, the solution flows parallel to the filter membrane. A pressure differential across the membrane causes fluid and filterable solutes (whose molecular weight is smaller than that of the membranes or behaves like so, such as globular proteins) to flow through the filter. In HPTFF (high performance tangential flow filtration) the membrane is charged, therefore using both size and charge of molecules to separate contaminants (see US 20030229212). According to the invention, diafiltration can be either discontinuous or continuous diafiltration. In discontinuous diafiltration, the solution is concentrated, and the lost volume is replaced by a new buffer. In continuous diafiltration, the solution volume is maintained by the inflow of new buffer solution while the old buffer solution is removed. In some embodiments, the separation and purification of the silk proteins can be performed by tangential flow filtration methods using ultrafiltration membranes.

Uses

The silk dope produced using the methods of the invention can be used for a broad and diverse array of medical, military, industrial and commercial applications. For example, the silk dope is used to produce silk fibres which in turn can be used in the manufacture of medical devices such as sutures, skin grafts, cellular growth matrices, replacement ligaments, and surgical mesh, and in a wide range of industrial and commercial products, such as, for example, cable, rope, netting, fishing line, clothing fabric, bullet-proof vest lining, container fabric, backpacks, knapsacks, bag or purse straps, adhesive binding material, non-adhesive binding material, strapping material, tent fabric, tarpaulins, pool covers, vehicle covers, fencing material, sealant, construction material, weatherproofing material, flexible partition material, sports equipment; and, in fact, in nearly any use of fibre or fabric for which high tensile strength and elasticity are desired characteristics. The silk dope also have applications for use in the production of compositions for personal care products such as cosmetics, skin care, hair care and hair colouring; and in coating of particles, such as pigments.

The silks may be used in their native form or they may be modified to form derivatives, which provide a more beneficial effect. For example, the silks may be modified by conjugation to a polymer to reduce allergenicity as described in U.S. Pat. No. 5,981,718 and U.S. Pat. No. 5,856,451. Suitable modifying polymers include, but are not limited to, polyalkylene oxides, polyvinyl alcohol, poly-carboxylates, poly(vinylpyrolidone), and dextrans. In another example, the silks may be modified by selective digestion and splicing of other protein modifiers. For example, the silk proteins may be cleaved into smaller peptide units by treatment with acid at an elevated temperature of about 60° C. The useful acids include, but are not limited to, dilute hydrochloric, sulfuric or phosphoric acids. Alternatively, digestion of the silk proteins may be done by treatment with a base, such as sodium hydroxide, or enzymatic digestion using a suitable protease may be used.

The proteins may be further modified to provide performance characteristics that are beneficial in specific applications for personal care products. The modification of proteins for use in personal care products is well known in the art. For example, commonly used methods are described in U.S. Pat. No. 6,303,752, U.S. Pat. No. 6,284,246, and U.S. Pat. No. 6,358,501. Examples of modifications include, but are not limited to, ethoxylation to promote water-oil emulsion enhancement, siloxylation to provide lipophilic compatibility, and esterification to aid in compatibility with soap and detergent compositions. Additionally, the silk proteins may be derivatized with functional groups including, but not limited to, amines, oxiranes, cyanates, carboxylic acid esters, silicone copolyols, siloxane esters, quaternized amine aliphatics, urethanes, polyacrylamides, dicarboxylic acid esters, and halogenated esters. The silk proteins may also be derivatized by reaction with diimines and by the formation of metal salts.

Consistent with the above definitions of "polypeptide" (and "protein"), such derivatized and/or modified molecules are also referred to herein broadly as "polypeptides" and "proteins".

The silk dope can be spun together and/or bundled or braided with other fibre types. Examples include, but are not limited to, polymeric fibres (e.g., polypropylene, nylon, polyester), fibres and silks of other plant and animal sources (e.g., cotton, wool, *Bombyx mori* or spider silk), and glass fibres. A preferred embodiment is silk fibre braided with 10% polypropylene fibre. The present invention contemplates that the production of such combinations of fibres can be readily practiced to enhance any desired characteristics, e.g., appearance, softness, weight, durability, water-repellant properties, improved cost-of-manufacture, that may be generally sought in the manufacture and production of fibres for medical, industrial, or commercial applications.

Personal Care Products

Cosmetic and skin care compositions may be anhydrous compositions comprising an effective amount of silk in a cosmetically acceptable medium. The uses of these compositions include, but are not limited to, skin care, skin cleansing, make-up, and anti-wrinkle products. An effective amount of a silk for cosmetic and skin care compositions is herein defined as a proportion of from about $10^{-4}$ to about 30% by weight, but preferably from about $10^{-3}$ to 15% by weight, relative to the total weight of the composition. This proportion may vary as a function of the type of cosmetic or skin care composition. Suitable compositions for a cosmetically acceptable medium are described in U.S. Pat. No. 6,280,747. For example, the cosmetically acceptable medium may contain a fatty substance in a proportion generally of from about 10 to about 90% by weight relative to the total weight of the composition, where the fatty phase containing at least one liquid, solid or semi-solid fatty substance. The fatty substance includes, but is not limited to, oils, waxes, gums, and so-called pasty fatty substances. Alternatively, the compositions may be in the form of a stable dispersion such as a water-in-oil or oil-in-water emulsion. Additionally, the compositions may contain one or more conventional cosmetic or dermatological additives or adjuvants, including but not limited to, antioxidants, preserving agents, fillers, surfactants, UVA and/or UVB sunscreens, fragrances, thickeners, wetting agents and anionic, nonionic or amphoteric polymers, and dyes or pigments.

Emulsified cosmetics and quasi drugs which are producible with the use of emulsified materials comprising silk produced by a method of the invention, for example, cleansing cosmetics (beauty soap, facial wash, shampoo, rinse, and the like), hair care products (hair dye, hair cosmetics, and the like), basic cosmetics (general cream, emulsion, shaving cream, conditioner, cologne, shaving lotion, cosmetic oil, facial mask, and the like), make-up cosmetics (foundation, eyebrow pencil, eye cream, eye shadow, mascara, and the like), aromatic cosmetics (perfume and the like), tanning and sunscreen cosmetics (tanning and sunscreen cream, tanning and sunscreen lotion, tanning and sunscreen oil, and the like), nail cosmetics (nail cream and the like), eyeliner cosmetics (eyeliner and the like), lip cosmetics (lipstick, lip cream, and the like), oral care products (tooth paste and the like) bath cosmetics (bath products and the like), and the like.

The cosmetic composition may also be in the form of products for nail care, such as a nail varnish. Nail varnishes are herein defined as compositions for the treatment and colouring of nails, comprising an effective amount of silk in a cosmetically acceptable medium. An effective amount of a silk for use in a nail varnish composition is herein defined as a proportion of from about $10^{-4}$ to about 30% by weight relative to the total weight of the varnish. Components of a cosmetically acceptable medium for nail varnishes are described in U.S. Pat. No. 6,280,747. The nail varnish typically contains a solvent and a film forming substance, such as cellulose derivatives, polyvinyl derivatives, acrylic polymers or copolymers, vinyl copolymers and polyester polymers. The composition may also contain an organic or inorganic pigment.

Hair care compositions are herein defined as compositions for the treatment of hair, including but not limited to shampoos, conditioners, lotions, aerosols, gels, and mousses, comprising an effective amount of silk in a cosmetically acceptable medium. An effective amount of a silk for use in a hair care composition is herein defined as a proportion of from about $10^{-2}$ to about 90% by weight relative to the total weight of the composition. Components of a cosmetically acceptable medium for hair care compositions are described in US 2004/0170590, U.S. Pat. No. 6,280,747, U.S. Pat. No. 6,139,851, and U.S. Pat. No. 6,013,250. For example, these hair care compositions can be aqueous, alcoholic or aqueous-alcoholic solutions, the alcohol preferably being ethanol or isopropanol, in a proportion of from about 1 to about 75% by weight relative to the total weight, for the aqueous-alcoholic solutions. Additionally, the hair care compositions may contain one or more conventional cosmetic or dermatological additives or adjuvants, as given above.

Hair colouring compositions are herein defined as compositions for the colouring, dyeing, or bleaching of hair, comprising an effective amount of silk in a cosmetically acceptable medium. An effective amount of a silk for use in a hair colouring composition is herein defined as a proportion of from about $10^{-4}$ to about 60% by weight relative to the total weight of the composition. Components of a cosmetically acceptable medium for hair colouring compositions are described in US 2004/0170590, U.S. Pat. No. 6,398,821 and U.S. Pat. No. 6,129,770. For example, hair colouring compositions generally contain a mixture of inorganic peroxygen-based dye oxidizing agent and an oxidizable coloring agent. The peroxygen-based dye oxidizing agent is most commonly hydrogen peroxide. The oxidative hair coloring agents are formed by oxidative coupling of primary intermediates (for example p-phenylenediamines, p-aminophenols, p-diaminopyridines, hydroxyindoles, aminoindoles, aminothymidines, or cyanophenols) with secondary intermediates (for example phenols, resorcinols, m-aminophenols, m-phenylenediamines, naphthols, pyrazolones, hydroxyindoles, catechols or pyrazoles). Additionally, hair colouring compositions may contain oxidizing acids, sequestrants, stabilizers, thickeners, buffers carriers, surfactants, solvents, antioxidants, polymers, non-oxidative dyes and conditioners.

The silks can also be used to coat pigments and cosmetic particles in order to improve dispersibility of the particles for use in cosmetics and coating compositions. Cosmetic particles are herein defined as particulate materials such as pigments or inert particles that are used in cosmetic compositions. Suitable pigments and cosmetic particles; include, but are not limited to, inorganic color pigments, organic pigments, and inert particles. The inorganic color pigments include, but are not limited to, titanium dioxide, zinc oxide, and oxides of iron, magnesium, cobalt; and aluminium. Organic pigments include, but are not limited to, D&C Red No. 36, D&C Orange No. 17, the calcium lakes of D&C Red Nos. 7, 11, 31 and 34, the barium lake of D&C Red No. 12, the strontium lake D&C Red No. 13, the aluminium lake of FD&C Yellow No. 5 and carbon black particles. Inert particles include, but are not limited to, calcium carbonate, aluminium silicate, calcium silicate, magnesium silicate, mica, talc, barium sulfate, calcium sulfate, powdered NYLON™, perfluorinated alkanes, and other inert plastics.

The silks may also be used in dental floss (see, for example, US 2005/0161058). The floss may be monofilament yarn or multifilament yarn, and the fibres may or may not be twisted. The dental floss may be packaged as individual pieces or in a roll with a cutter for cutting pieces to any desired length. The dental floss may be provided in a variety of shapes other than filaments, such as but not limited to, strips and sheets and the like. The floss may be coated with different materials, such as but not limited to, wax, polytetrafluoroethylene monofilament yarn for floss.

The silks may also be used in soap (see, for example, US 2005/0130857).

Pigment and Cosmetic Particle Coating

The effective amount of a silk for use in pigment and cosmetic particle coating is herein defined as a proportion of from about $10^{-4}$ to about 50%, but preferably from about 0.25 to about 15% by weight relative to the dry weight of particle. The optimum amount of the silk to be used depends on the type of pigment or cosmetic particle being coated. For example, the amount of silk used with inorganic color pigments is preferably between about 0.01% and 20% by weight. In the case of organic pigments, the preferred amount of silk is between about 1% to about 15% by weight, while for inert particles, the preferred amount is between about 0.25% to about 3% by weight. Methods for the preparation of coated pigments and particles are described in U.S. Pat. No. 5,643,672. These methods include: adding an aqueous solution of the silk to the particles while tumbling or mixing, forming a slurry of the silk and the particles and drying, spray drying a solution of the silk onto the particles or lyophilizing a slurry of the silk and the particles. These coated pigments and cosmetic particles may be used in cosmetic formulations, paints, inks and the like.

Biomedical

The silks may be used as a coating on a bandage to promote wound healing. For this application, the bandage material is coated with an effective amount of the silk. For the purpose of a wound-healing bandage, an effective amount of silk is herein defined as a proportion of from about $10^{-4}$ to about 30% by weight relative to the weight of the bandage material. The material to be coated may be any soft, biologically inert, porous cloth or fibre. Examples include, but are not limited to, cotton, silk, rayon, acetate, acrylic, polyethylene, polyester, and combinations thereof. The coating of the cloth or fibre may be accomplished by a number of methods known in the art. For example, the material to be coated may be dipped into an aqueous solution containing the silk. Alternatively, the solution containing the silk may be sprayed onto the surface of the material to be coated using a spray gun. Additionally, the solution containing the silk may be coated onto the surface using a roller coat printing process. The wound bandage may include other additives including, but not limited to, disinfectants such as iodine, potassium iodide, povidon iodine, acrinol, hydrogen peroxide, benzalkonium chloride, and chlorohexidine; cure accelerating agents such as allantoin, dibucaine hydrochloride, and chlorophenylamine malate; vasoconstrictor agents such as naphazoline hydrochloride; astringent agents such as zinc oxide; and crust generating agents such as boric acid.

The silk dope may also be used in the form of a film as a wound dressing material. The use of silk, in the form of an amorphous film, as a wound dressing material is described in U.S. Pat. No. 6,175,053. The amorphous film comprises a dense and nonporous film of a crystallinity below 10% which contains an effective amount of silk. For a film for wound care, an effective amount of silk is herein defined as between about 1 to 99% by weight. The film may also contain other components including but not limited to other proteins such as sericin, and disinfectants, cure accelerating agents, vasoconstrictor agents, astringent agents, and crust generating agents, as described above. Other proteins such as sericin may comprise 1 to 99% by weight of the composition. The amount of the other ingredients listed is preferably below a total of about 30% by weight, more preferably between about 0.5 to 20% by weight of the composition. The wound dressing film may be prepared by dissolving the above mentioned materials in an aqueous solution, removing insolubles by filtration or centrifugation, and casting the solution on a smooth solid surface such as an acrylic plate, followed by drying.

The silk dope may also be used to produce sutures (see, for example, US 2005/0055051). Such sutures can feature a braided jacket made of ultrahigh molecular weight fibres and silk fibres. The polyethylene provides strength. Polyester fibres may be woven with the high molecular weight polyethylene to provide improved tie down properties. The silk may be provided in a contrasting color to provide a trace for improved suture recognition and identification. Silk also is more tissue compliant than other fibres, allowing the ends to be cut close to the knot without concern for deleterious interaction between the ends of the suture and surrounding tissue. Handling properties of the high strength suture also can be enhanced using various materials to coat the suture. The suture advantageously has the strength of Ethibond No. 5 suture, yet has the diameter, feel and tie-ability of No. 2 suture. As a result, the suture is ideal for most orthopedic procedures such as rotator cuff repair, Achilles tendon repair, patellar tendon repair, ACL/PCL reconstruction, hip and shoulder reconstruction procedures, and replacement for suture used in or with suture anchors. The suture can be uncoated, or coated with wax (beeswax, petroleum wax, polyethylene wax, or others), silicone (Dow Corning silicone fluid 202 A or others), silicone rubbers, PBA (polybutylate acid), ethyl cellulose (Filodel) or other coatings, to improve lubricity of the braid, knot security, or abrasion resistance, for example.

The silk dope may also be used to produce stents (see, for example, US 2004/0199241). For example, a stent graft is provided that includes an endoluminal stent and a graft, wherein the stent graft includes silk. The silk induces a response in a host who receives the stent graft, where the response can lead to enhanced adhesion between the silk stent graft and the host's tissue that is adjacent to the silk of the silk stent graft. The silk may be attached to the graft by any of various means, e.g., by interweaving the silk into the graft or by adhering the silk to the graft (e.g., by means of an adhesive or by means of suture). The silk may be in the form of a thread, a braid, a sheet, powder, etc. As for the location of the silk on the stent graft; the silk may be attached only the exterior of the stent, and/or the silk may be attached to distal regions of the stent graft, in order to assist in securing those distal regions to neighbouring tissue in the host. A wide variety of stent grafts may be utilized within the context of the present invention, depending on the site and nature of treatment desired. Stent grafts may be, for example, bifurcated or tube grafts, cylindrical or tapered, self-expandable or balloon-expandable, unibody or, modular, etc.

In addition to silk, the stent graft may contain a coating on some or all of the silk, where the coating degrades upon insertion of the stent graft into a host, the coating thereby delaying contact between the silk and the host. Suitable coatings include, without limitation, gelatin, degradable polyesters (e.g., PLGA, PLA, MePEG-PLGA, PLGA-PEG-PLGA, and copolymers and blends thereof), cellulose and cellulose derivatives (e.g., hydroxypropyl cellulose), polysaccharides (e.g., hyaluronic acid, dextran, dextran sulfate, chitosan), lipids, fatty acids, sugar esters, nucleic acid esters, polyanhydrides, polyorthoesters and polyvinylalcohol (PVA). The silk-containing stent grafts may contain a biologically active agent (drug), where the agent is released from the stent graft and then induces an enhanced cellular response (e.g., cellular or extracellular matrix deposition) and/or fibrotic response in a host into which the stent graft has been inserted.

The silk dope may also be used to produce a matrix for producing ligaments and tendons ex vivo (see, for example, US 2005/0089552). A silk-fibre-based matrix can be seeded with pluripotent cells, such as bone marrow stromal cells (BMSCs). The bioengineered ligament or tendon is advantageously characterized by a cellular orientation and/or matrix crimp pattern in the direction of applied mechanical forces, and also by the production of ligament and tendon specific markers including collagen type I, collagen type III, and fibronectin proteins along the axis of mechanical load produced by the mechanical forces or stimulation, if such forces are applied. In a preferred embodiment, the ligament or tendon is characterized by the presence of fibre bundles which are arranged into a helical organization. Some examples of ligaments or tendons that can be produced include anterior cruciate ligament, posterior cruciate ligament, rotator cuff tendons, medial collateral ligament of the elbow and knee, flexor tendons of the hand, lateral ligaments of the ankle and tendons and ligaments of the jaw or temporomandibular joint. Other tissues that may be produced by methods of the present invention include cartilage (both articular and meniscal), bone, muscle, skin and blood vessels.

The silk dope may also be used to produce hydrogels (see, for example, US 2005/0266992). Silk fibroin hydrogels can be characterized by an open pore structure which allows their use as tissue engineering scaffolds, substrate for cell culture, wound and burn dressing, soft tissue substitutes, bone filler, and as well as support for pharmaceutical or biologically active compounds.

The silk dope may also be used to produce dermatological compositions (see, for example, US 2005/0019297). Furthermore, the dope may also be used to produce sustained release compositions (see, for example, US 2004/0005363).

Textiles

The silk dope may also be used to produce a coating for the surface of fibres for subsequent use in textiles. This provides a monolayer of the protein film on the fibre, resulting in a smooth finish. U.S. Pat. No. 6,416,558 and U.S. Pat. No. 5,232,611 describe the addition of a finishing coat to fibres. The methods described in these disclosures provide examples of the versatility of finishing the fibre to provide a good feel and a smooth surface. For this application, the fibre is coated with an effective amount of the silk. For the purpose of fibre coating for use in textiles, an effective amount of silk is herein defined as a proportion of from about 1 to about 99% by weight relative to the weight of the fibre material. The fibre materials include, but are not limited to textile fibres of cotton, polyesters such as rayon and LYCRA™, nylon, wool, and other natural fibres including native silk. Compositions suitable for applying the silk onto the fibre may include co-solvents such as ethanol, isopropanol, hexafluoranols, isothiocyanouranates, and other polar solvents that can be mixed with water to form solutions or microemulsions. The silk containing solution may be sprayed onto the fibre or the fibre may be dipped into the solution. While not necessary, flash drying of the coated material is preferred. An alternative protocol is to apply the silk composition onto woven fibres. An ideal embodiment of this application is the use of silks to coat stretchable weaves such as used for stockings.

Composite Materials

Silk fibres can be added to polyurethane, other resins or thermoplastic fillers to prepare panel boards and other construction material or as moulded furniture and benchtops that replace wood and particle board. The composites can be also be used in building and automotive construction especially rooftops and door panels. The silk fibres re-enforce the resin making the material much stronger and allowing lighter-weight construction which is of equal or superior strength to other particle boards and composite materials. Silk fibres may be isolated and added to a synthetic composite-forming resin or be used in combination with plant-derived proteins, starch and oils to produce a biologically-based composite materials. Processes for the production of such materials are described in JP 2004284246, US 2005175825, U.S. Pat. No. 4,515,737, JP 47020312 and WO 2005/017004.

Paper Additives

The fibre properties of the silk can add strength and quality texture to paper making. Silk papers are made by mottling silk threads in cotton pulp to prepare extra smooth handmade papers is used for gift wrapping, notebook covers, carry bags. Processes for production of paper products from silk dope are generally described in JP 2000139755.

Advanced Materials

Silks produced from silk dope of the invention have considerable toughness and stands out among other silks in maintaining these properties when wet (Hepburn et al., 1979).

Areas of substantial growth in the clothing textile industry are the technical and intelligent textiles. There is a rising demand for healthy, high value functional, environmentally friendly and personalized textile products. Fibres, such as those of the invention, that do not change properties when wet and in particular maintain their strength and extensibility are useful for functional clothing for sports and leisure wear as well as work wear and protective clothing.

Developments in the weapons and surveillance technologies are prompting innovations in individual protection equipments and battle-field related systems and structures. Besides conventional requirements such as material durability to prolonged exposure, heavy wear and protection from external environment, silk textiles produced from silk dope of the invention can be processed to resist ballistic projectiles, fire and chemicals. Processes for the production of such materials are described in WO 2005/045122 and US 2005268443.

EXAMPLES

Example 1

Recombinant Production and Purification of Honeybee Silk Proteins

To create recombinant expression constructs, the four honeybee silk gene sequences (Genbank Accession Nos: FJ235088; FJ235089, FJ235090, FJ235091) without signal peptides were amplified by PCR from the cDNA clones described in Sutherland et al. (2006) using the following oligonucleotide primer sets:

AmelF1:
(SEQ ID NO: 101)
GGAATT CTC ATG AGT *TTG GAG GGG CCG GGC AAC TCG*
and (SEQ ID NO: 102)
CGGC GGATCC TTA TTA *AAA TAC GTT GCT CTT CAA GT*;

AmelF2:
(SEQ ID NO: 103)
GGAATT CTC ATG AGC *CGC GTG ATT AAT CAC GAG TCC CTG*
and (SEQ ID NO: 104)
CGGC GGATCC TTA TTA *TTC CAA CTT TGC TAC ATG TAT TTT C*;

AmelF3:
(SEQ ID NO: 105)
GGAATT CCC ATG GGC *GTC GAG GAA TTC AAG TCC TCG*
and (SEQ ID NO: 106)
CGGC AGATCT TTA TTA *AAA TTT TIT ATC CTC AAT A*;

AmelF4:
(SEQ ID NO: 107)
GGAATT CCC ATG GCA *AGG GAA GAG GTG GAG ACA CGG*
and (SEQ ID NO: 108)
CGGC GGATCC TTA TTA *CTT CAC CTC CCA TTC TTC ATT C*
(cloning restriction enzyme sites are underlined and in bold and sequences that match the cDNA sequence are shown in italics).

The PCR amplicons were cloned into restriction enzyme sites (AmelF1 and AmelF2: BspH1 and Bam HI; AmelF3: Ncol and Bgl II; AmelF4: Ncol and Bam HI) of the pET14b expression vector (Novagen) and the sequences verified by DNA sequencing before expression.

The constructs were transformed into Rosetta 2 (DE3) competent cells (Novagen) and the silk proteins were initially expressed in 50 mL overnight express instant TB medium (Novagen) in shake flasks. The four honeybee silk proteins, AmelF1-4, were synthesized in *E. coli* cells in the soluble form at 20° C. and insoluble form at 30° C. and 37° C. The highest yields of protein, as judged by comparative protein band intensity after SDS-PAGE (FIG. 1), were obtained when expression was conducted for extended periods (24-36 h) at temperatures ≥30° C. with the proteins recovered from the inclusion bodies. Quantitative gel band intensity analysis, with protein identities confirmed by mass spectroscopy, indicated that protein recovered from the inclusion bodies was essentially pure (>95%) silk protein. Subsequent analysis found that proteins solubilised from inclusion bodies self assembled into native-like structure. Thus, all subsequent expression was conducted under conditions such that recombinant proteins were recovered from the inclusion bodies.

In order to increase protein yield a large-scale batch fed fermentation process was developed and optimised for AmelF3. Fermentations were carried out in 2-liter Biostat B culture vessels (Sartorius Stedim, Melsungen, Germany) using minimal medium (starting volume 1.6 liters). Glucose was used as initial carbon source, switching to a glycerol feed following induction of silk protein expression with IPTG. The initial medium contained (per liter): $KH_2PO_4$, 13.3 g; $(NH_4)_2HPO_4$, 4 g and citric acid 1.7 g. The pH of the medium was adjusted to a final value of 7.0 using 2 M NaOH. The following components were sterilized separately, then added (per liter of final medium): 40 ml of 50% (w/v) glucose; 5 ml of 1M $MgSO_4$; 130 µl of 0.1M thiamine hydrochloride; 1 ml of 100 mg/ml ampicillin and 5 ml of a vitamin/trace metal solution containing (per liter of solution): biotin, 0.2 g;

CuSO$_4$.5H$_2$O, 2.0 g; NaI, 0.08 g; MnSO$_4$.H$_2$O, 3.0 g; Na$_2$MoO$_4$.2H$_2$O, 0.2 g; boric acid 0.02 g; CoCl$_2$.6H$_2$O, 0.5 g; ZnCl$_2$, 7.0 g; FeSO$_4$.7H$_2$O, 22.0 g; CaSO$_4$.2H$_2$O, 0.5 g and H$_2$SO$_4$, 1 ml.

The fermentation inocula for the four strains were cultured for 20 h at 37° C. in the same medium as used in the fermenter. Once the inocula were transferred to the fermentation vessels, the pH of the medium was adjusted and controlled at 7.0 through the addition of 10% (w/v) NH$_4$OH or 10% (w/v) H$_3$PO$_4$. The temperature was controlled at 37° C., and dissolved oxygen (DO) concentration was maintained above 40% air saturation by manipulating the agitation speed up to 1100 rpm and enriching the air supply with pure oxygen when required.

When the cultures had grown to an optical density at 600 nm (OD$_{600nm}$) value of approximately 20 (~10 h after inoculation), IPTG was added to a final concentration of 1 mM. The fermenters were operated in batch mode until all of the glucose was consumed, as indicated by a sharp rise in DO (~12 h after inoculation). In the glycerol fed-batch phase, 400 ml of 62% (v/v) glycerol solution was fed into the fermenter at a rate of 50 ml/h. Cultures were grown for 24 h, after which the cells were harvested by centrifugation and stored at −80° C. Under these conditions the OD$_{600nm}$ value of the ferment was 34 and the yield of purified recombinant AmelF3 after solubilisation was approximately 2.5 grams per liter of ferment. The same fermentation conditions were used to express the other honeybee silk proteins. The strains expressing silk proteins AmelF1, 2 and 4 grew to OD$_{600nm}$ values of 30, 67, and 57 respectively. The yields of purified recombinant proteins AmelF1, 2 and 4 after solubilisation were approximately 0.2, 1.5 and 1.9 grams per liter of ferment respectively.

The yield of 2.5 g/L purified protein from the optimised batch fed fermentation system is by far the highest reported expression levels for any recombinant silk protein. Factors contributing to this high yield include the size and nature of the honeybee fibroin genes and the structural properties of the silk proteins. In contrast to the large size (>10 kbp) and highly repetitive nature of the genes encoding the well-studied dragline silk of spiders and cocoon silk of silkworms, the honeybee silk genes are small (approximately 1 kbp) with far less repetition in their DNA sequences (Sutherland et al., 2006). The smaller size and reduced level of repetition means that the honeybee genes are not prone to the genetic instabilities including premature translation termination and truncation that result from transgenic expression of highly repetitive nucleotide sequences.

The silk proteins in inclusion bodies were purified from the E. coli cells after repeatedly treating with BugBuster Master Mix (Novagen), according to manufacturer's protocol for soluble or inclusion body preparation. Protein solutions were analyzed by SDS polyacrylamide gel electrophoresis (SDS-PAGE) with 4-12% gradient (Invitrogen). Recombinant silk protein identification was verified by tandem mass spectrometry as previously described (Sutherland et al., 2006).

Silk proteins in inclusion bodies were solubilised in 3% sodium dodecyl sulfate (SDS) with 2 h incubation at 60° C. Protein concentration in solution was measured using a QuantiPro BCA assay kit (Sigma). Where required, solutions of the each of the four recombinant honeybee silk proteins were mixed at equimolar ratios. Excess SDS was removed from protein solutions by dialysis against 5 g/L KCl solution causing KDS precipitation. The precipitate was removed by centrifugation at 16000 g for 5 min.

Example 2

Fourier Transform Infrared Spectroscopy (FTIR)

Fourier transform infrared spectroscopy was used to compare the protein structure of native and recombinant honeybee silks. Native honeybee silk sheets were obtained from a commercial hive, washed extensively in chloroform to remove wax and washed extensively in warm water to remove water-soluble contaminants. Solutions of each of the four recombinant honeybee silk proteins were mixed at equimolar ratios, cast and dried into a film. Infrared spectra from these samples were obtained in transmission mode using a Perkin-Elmer System 2000 Fourier transform spectrometer fitted with an i-series imaging infrared microscope accessory. Spectra were collected using Spectrum software (version 5.3.1) and represent the average of 256 scans collected at a resolution of 4 cm$^{-1}$. Post-collection data manipulation and analysis was carried out using Grams/AI software v5.05. The deconvolution of the amide I region for each silk spectrum is shown in FIG. 2. A summary of the results and the component secondary structure assignments is presented in Table 2.

TABLE 2

FTIR curve fitting summary.

| Native honeybee silk | | Recombinant silk | | |
|---|---|---|---|---|
| Frequency (cm$^{-1}$) | Amide I area (%) | Frequency (cm$^{-1}$) | Amide I area (%) | Assignment |
| 1717 | | 1710 | | COOH |
| 1693 | | 1693 | | side chains |
| 1670 | 25 | 1673 | 30 | β-sheet and side chains |
| 1651 | 23 | 1655 | 26 | coiled-coil |
| 1642 | 13 | 1643 | 7 | coiled-coil |
| 1628 | 29 | 1632 | 26 | coiled-coil |
| 1604 | 10 | 1610 | 11 | β-sheet |

The FTIR results suggest that the native honeybee silk contains approximately 65% coiled-coil structure, which is consistent with previous sequence-based predictions (Sutherland et al., 2006). The recombinant silk spectrum is very similar to the native silk spectrum, and the recombinant silk is estimated to contain 59% coiled-coil structure.

Example 3

Dry Spinning

The inclusion bodies were solubilised in 3% SDS to give soluble honeybee fibroin solutions of generally between 0.5-2 wt % protein and up to 3 wt % protein. The excess SDS was removed from silk protein solutions by KCl precipitation. The potassium precipitation removed up to 95%, such as 70-80%, of SDS (by weighing the precipitate) but <10% of protein (by measuring protein concentrations in solution). The silk solutions were concentrated by extended dialysis against 20 wt % polyethylene glycol (PEG, MW 8000, Sigma) or Slide-A-Lyzer concentrating solution (Pierce), until a honey-like viscosity was obtained (around 10-15 wt % protein). A droplet of concentrated silk dope was suspended between the prongs of a pair of tweezers in air and the tweezers were opened to form a fine thread (FIG. 3A). These single-drawn threads were stable in air but dissolved in water. Fibres were then submerged in a 90% methanol 10% water bath, drawn a second time to approximately 2× length, and air-dried FIG. 3B). The double-drawn threads were not soluble in water. Single-drawn and double-drawn fibres were examined by a light microscope with polarizing lenses, and by a Zeiss EVO LS15 environmental scanning electron microscope.

Recombinant silk threads imaged by ESEM (not shown) were circular in cross-section and fairly uniform in diameter along their length. Single-drawn fibres had small bodies adhering to their surface that could be salt crystals, however double-drawn fibres had smooth surfaces. Polarized light microscopy showed that single-drawn fibres are not birefringent, but that double-drawn fibres are strongly birefringent (FIG. 3).

Single-drawn and double-drawn fibres and recombinant silk films were analysed by wide-angle x-ray scattering at the SAXS/WAXS beamline of the Australian Synchrotron. A wavelength of 0.886 Å and camera length of 0.558 m provided a q-range of approximately 0.07 to 1.4 Å$^{-1}$, which was calibrated using a silver behenate standard. The WAXS patterns for the film and for single-drawn fibres were dominated by a strong signal from SDS crystals, but this was not detectable in the double-drawn fibres. The present inventors therefore calculate that double-drawn threads contain <0.1% of the SDS crystals per unit length found in the single-drawn threads. The protein scattering patterns from recombinant silk could not be analysed due to either the strong SDS diffraction limiting the sensitivity of the technique, or to low signal-to-noise ratio in the case of the very fine double-drawn fibres.

The strength and extensibility of recombinant honeybee silk threads were measured on an Instron Tensile Tester model 4501 at a rate of 2.5 mm/min. Tests were conducted in air at 21° C. and 65% relative humidity. Prior to testing each fibre was placed across a 3 mm slot in a plastic frame and fixed with epoxy glue. The gauge length ($L_0$) and diameter of each fibre were measured on an optical microscope. Table 3 compares the mechanical properties of recombinant silk fibres to the properties of native fibres drawn from the honeybee silk gland.

TABLE 3

Tensile properties of recombinant honeybee silk fibres compared to native fibres.

| | Diameter (μm) | Breaking stress (MPa) | Breaking strain (%) | True breaking stress (MPa) |
|---|---|---|---|---|
| Single-drawn fibres | 30 ± 5 | 15 ± 3 | 225 ± 10 | 50 ± 12 |
| Double-drawn fibres | 13 ± 7 | 150 ± 39 | 47 ± 26 | 213 ± 63 |
| Native fibres (Hepburn, 1979) | 9 | 132 | 204 | 400 |

Example 4

Wet Spinning

Silk proteins were generally prepared as described in Example 1. Generally protein concentration after SDS solubilisation was around 3% silk protein. If protein solutions had lower concentration they were concentrated by extended dialysis against 20 wt % polyethylene glycol (PEG, MW 8000, Sigma) or Slide-A-Lyzer concentrating solution (Pierce), until solutions were 3-6% silk protein.

The concentrated protein solutions of either equimolar mixtures of AmelF1-4 or AmelF3 alone were extruded through 10 cm 100 μm capillary tubing at a rate of 10 m/min into methanol solution (50-90% methanol) which caused a fine and continuous thread to form. The threads were dried in the air and examined by a light microscope with polarizing lenses. The threads showed significant birefringence indicating that the proteins within the threads were directionally aligned (FIG. 4A). Air dried fibres were submerged in a 90% methanol 10% water bath and drawn a second time to approximately 2× length (FIG. 4B) or 4× length (FIG. 4C), and air-dried. The strength and extensibility of recombinant honeybee silk threads were measured on an Instron Tensile Tester model 4501 at a rate of 2.5 mm/min. Tests were conducted in air at 21° C. and 65% relative humidity. Prior to testing each fibre was placed across a 3 mm slot in a plastic frame and fixed with epoxy glue. The gauge length ($L_0$) and diameter of each fibre were measured on an optical microscope.

Tables 4 and 5 describes the mechanical properties of undrawn recombinant silk fibres. Drawing resulted in threads that were stronger and insoluble in water, and highly birefringent.

TABLE 4

Tensile properties of recombinant honeybee silk fibres after extrusion of concentrated silk protein dope into methanol with and without drawing.

| | Diameter (μm) | Breaking stress (MPa) | Breaking strain (%) |
|---|---|---|---|
| Undrawn fibres (equimolar mixture of 4 proteins) | 22-39 | 70-78 | 200-250 |
| Fibres drawn X2 length (equimolar mixture of 4 proteins) | 17-22 | 50-92 | 80-160 |
| Fibres drawn x4 length (equimolar mixture of 4 proteins) | 19-21 | 150-161 | 38-91 |
| Undrawn fibres (AmelF3) | 39-41 | 39-53 | 256-275 |
| Fibres drawn X2 length (AmelF3) | 32-42 | 68-80 | 88-211 |
| Fibres drawn X4 length (AmelF3) | 28-30 | 99-117 | 131-154 |

TABLE 5

Mechanical properties of honeybee silk fibers.

| Method of fabrication | Constituent proteins | Diameter (μm) | Breaking stress (MPa) | Breaking strain (%) | Toughness (MPa) |
|---|---|---|---|---|---|
| Extruded into 70% MeOH | AmelF1-4 | 31 ± 2 | 70 ± 4 | 190 ± 11 | 91 ± 7 |
| | AmelF3 | 45 ± 2 | 50 ± 3 | 243 ± 10 | 105 ± 6 |
| Extruded into 70% MeOH then drawn ≈100% in 90% MeOH | AmelF1-4 | 21 ± 1 | 133 ± 11 | 94 ± 11 | 85 ± 9 |
| | AmelF3 | 34 ± 2 | 97 ± 7 | 129 ± 15 | 97 ± 10 |
| Extruded into 70% MeOH then drawn ≈300% in 90% MeOH | AmelF1-4 | 17 ± 1 | 203 ± 10 | 51 ± 5 | 70 ± 8 |
| | AmelF3 | 23 ± 1 | 178 ± 20 | 68 ± 9 | 85 ± 18 |
| Natural[3] | Native | 9 | 132 | 204 | NG |

[1]Calculated as $(d_0/d_1)^2$ where $d_0$ and $d_1$ are the diameters of the initial and drawn fibres

Example 5

Circular Dichroism (CD)

The AmelF3 honeybee silk protein was expressed into the inclusion bodies of E. coli. AmelF3 inclusion bodies were unfolded using equivalent dry weight of the detergent sodium dodecyl sulphate (SDS) to generate 2-4% monomeric protein solutions. Dynamic light scattering (DLS) measured the hydrodynamic diameter of particles in the protein-detergent solution diluted ten-fold in 100 mM NaCl as 9.2+/−0.1 nm (peak containing 98.2% of particle volume). The diameter of SDS micelles in 3% SDS solutions without protein under the same experimental conditions was a single peak at 5.5+/−0.2 nm. No SDS micelles were detected in the SDS—protein solutions confirming that the majority of the SDS was bound to the protein.

Proteins were refolded by removing SDS using KCl. Potassium dodecyl sulfate has significantly lower solubility than SDS and precipitates out of solution where it can be removed by centrifugation. The protein solutions were dialysed against water to reduce salt levels then concentrated by dialysis against PEG8000, resulting in 3-4% protein and 0.2-0.4% SDS concentration. When AmelF3 solutions were diluted ten-fold in 100 mM NaCl (comparable to physiological salt levels) the particle diameter increased to 20.3+/−0.7 nm (peak containing 86.8% of particle volume), in agreement with the approximate particle diameter calculated for an AmelF3 coiled coil.

CD spectra of honeybee AmelF3 solutions (0.12%) held in 0.01 mm path length sandwich quartz cell (Nova Biotech, El Cajon, Calif.) were collected using a AVIV Model 410 spectrophotometer (AVIV Biomedical, Inc., Lakewood, N.J.) with a temperature controller. All samples were scanned at 25° C.) with a 1 nm bandwidth from 260 nm to 180 nm, and the results were averaged from four repeated experiments. The CD spectra of AmelF3 solutions showed strong spectral minima at 220 and 209 nm and a 220 nm/209 nm ratio of 1.02 supporting a coiled coil structure. A 220 nm/209 nm ratio of one or more is indicative of coiled coils whereas a ratio of less than 0.86 is indicative of isolated helices. DLS measurements indicated that after addition of SDS back to the AmelF3 solutions the hydrodynamic particle diameter was reduced to the size observed in the original monomeric solutions, confirming that the removal of most SDS is a prerequisite for the protein to fold into a native-like silk protein conformation. In contrast to the AmelF3 protein, His-tagged recombinant versions of the homologous protein from Apis cerana remained monomeric and predominantly random coil at comparable concentrations (Shi et al., 2008). This result shows that AmelF3 alone, when prepared in the presence of low levels of SDS, folds to adopt a native like silk molecular structure.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/237,156 filed 26 Aug. 2009, and U.S. 61/315,812 filed 19 Mar. 2010, the entire contents of both of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Atkins (1967) J. Mol. Biol. 24: 139-41.
Delorenzi and Speed (2002) Bioinformatics 18:617-625.
Harayama (1998) Trends Biotech. 16: 76-82.
Hepburn et al. (1979) Insect Biochem. 9: 69-77.
Needleman and Wunsch (1970) J. Mol. Biol. 48: 443-453.
Sezutzu et al. (2007) Biosci. Biotechnol. Biochem. 71: 2725-34.
Shi et al. (2008) Biomaterials 29: 2820-8.
Sutherland et al. (2006) Genome Res 16: 1414-21.
Sutherland et al. (2007) Mol Biol Evol 24: 2424-32.

The invention claimed is:

1. A method for producing silk dope comprising silk proteins which have a coiled coil tertiary structure, the method comprising
   i) lysing cells producing one or more silk proteins capable of forming a coiled coil tertiary structure,
   ii) solubilising the silk proteins by contacting them with an amount of anionic surfactant sufficient to solubilize the silk proteins, and
   iii) concentrating the silk proteins while reducing the amount of the anionic surfactant to produce the silk dope, wherein the silk dope comprises the anionic surfactant and silk proteins which have a coiled coil tertiary structure.

2. The method of claim 1, wherein the silk proteins are concentrated by
   a) reducing the amount of surfactant in solution by adding a compound which precipitates the surfactant, and
   b) separating the solution comprising the silk proteins from the precipitate formed in step a) to produce the silk dope.

3. The method of claim 1, wherein the compound which precipitates the surfactant is a salt or a carbohydrate; or a combination of two or more thereof.

4. The method of claim 3, wherein the salt is a potassium salt or a sodium salt.

5. The method of claim 1, wherein the silk proteins are concentrated by filtration.

6. The method of claim 1 which further comprises increasing the concentration of silk proteins in the silk dope.

7. The method of claim 6 which comprises dialysing the silk dope against a dehydrating solution.

8. The method of claim 7, wherein the dehydrating solution comprises a hygroscopic polymer.

9. The method of claim 1, wherein the silk dope comprises at least about 0.5% w/v silk proteins.

10. The method of claim 9, wherein the silk dope comprises about 0.5% to about 15% w/v silk proteins.

11. The method of claim 1, wherein the cells are bacterial cells, yeast cells, insect cells, plant cells or animal cells, or a combination of two or more thereof.

12. The method of claim 11, wherein the cells are bacterial cells.

13. The method of claim 1, wherein step i) further comprises isolating inclusion bodies from the lysed cells.

14. The method of claim 1 which further comprises culturing the cells before step i).

15. The method of claim 1, wherein the portion of the silk protein that is capable of forming a tertiary structure which comprises a coiled-coil structure comprises at least 10 copies of the heptad sequence abcdefg, and wherein at least 25% of the amino acids at positions a and d in the at least 10 copies of the heptad are alanine residues.

16. The method of claim 1, wherein the anionic surfactant is sodium dodecyl sulfate (SDS), ammonium lauryl sulfate or other alkyl sulfate salts, sodium 1-octanesulfonate monohydrate, sodium lauroyl sarcosinate, sodium lauryl ether sulfate (SLES), sodium taurodeoxycholate hydrate, alkyl benzene sulfonate; or a combination of two or more thereof.

17. A method for producing silk dope comprising silk proteins which have a coiled coil tertiary structure, the method comprising
   i) obtaining supernatant from cell cultures, or from a cell-free expression system, producing one or more silk proteins capable of forming a coiled coil tertiary structure, ii) solubilising the silk proteins by contacting them with an amount of anionic surfactant sufficient to solubilize the silk proteins, and iii) concentrating the silk proteins while reducing the amount of the anionic surfactant to produce the silk dope, wherein the silk dope comprises the anionic surfactant and silk proteins which have a coiled coil tertiary structure.

18. A method for producing a silk fibre, the method comprising extruding and/or drawing silk dope produced by the method of claim 1.

19. A method for producing a silk film, the method comprising casting silk dope produced by the method of claim 1.

20. The method of claim 16, wherein the anionic surfactant is sodium dodecyl sulfate (SDS).

21. The method of claim 17, wherein the anionic surfactant is sodium dodecyl sulfate (SDS).

* * * * *